(12) United States Patent
Bonutti et al.

(10) Patent No.: US 11,129,645 B2
(45) Date of Patent: Sep. 28, 2021

(54) METHODS OF SECURING A FASTENER

(71) Applicant: P Tech, LLC, Effingham, IL (US)

(72) Inventors: Peter M Bonutti, Delray Beach, FL (US); Justin E Beyers, Effingham, IL (US); Matthew J Cremens, Effingham, IL (US)

(73) Assignee: P TECH, LLC, Effingham, IL (US)

( * ) Notice: Subject to any disclaimer, the term of this patent is extended or adjusted under 35 U.S.C. 154(b) by 0 days.

(21) Appl. No.: 13/953,652

(22) Filed: Jul. 29, 2013

(65) Prior Publication Data

US 2014/0039495 A1 Feb. 6, 2014

Related U.S. Application Data

(63) Continuation of application No. 12/202,210, filed on Aug. 29, 2008, now Pat. No. 8,496,657, and a
(Continued)

(51) Int. Cl.
*A61B 17/72* (2006.01)
*A61B 17/68* (2006.01)
(Continued)

(52) U.S. Cl.
CPC .......... *A61B 17/68* (2013.01); *A61B 17/0401* (2013.01); *A61B 17/7058* (2013.01);
(Continued)

(58) Field of Classification Search
CPC ............ A61F 2002/30065–30067; A61B 17/84–8695; A61B 17/80–8095;
(Continued)

(56) References Cited

U.S. PATENT DOCUMENTS

| 319,296 A | 6/1885 | Molesworth |
|---|---|---|
| 668,878 A | 2/1901 | Jensen |

(Continued)

FOREIGN PATENT DOCUMENTS

| CA | 2641580 | 8/2007 |
|---|---|---|
| CA | 2680827 | 9/2008 |

(Continued)

OTHER PUBLICATIONS

The Search for the Holy Grail: A Centrury of Anterior Cruciate Ligament Reconstruction, R. John Naranja, American Journal of Orthopedics, Nov. 1997.
(Continued)

*Primary Examiner* — Eduardo C Robert
*Assistant Examiner* — Steven J Cotroneo
(74) *Attorney, Agent, or Firm* — Stinson LLP

(57) ABSTRACT

Embodiments may include an attachable fastener, which may include a bondable material that may be secured to the end of an end effector. Vibration may be tuned to occur at a distal end of the fastener. Accordingly, the fastener may be used to generate heat at a distal point of contact. If the contact surface contains bondable material, that material may be softened. If the fastener includes bondable material at the point of contact, that material may also be softened by heat produced by vibration at the contact area. A hard implant or another polymeric material may function as the anvil.

21 Claims, 58 Drawing Sheets

Related U.S. Application Data continuation-in-part of application No. 11/689,670, filed on Mar. 22, 2007, and a continuation-in-part of application No. 11/671,556, filed on Feb. 6, 2007, and a continuation-in-part of application No. 11/416,618, filed on May 3, 2006, now Pat. No. 7,967,820.

(60) Provisional application No. 60/968,969, filed on Aug. 30, 2007, provisional application No. 60/810,080, filed on Jun. 1, 2006, provisional application No. 60/784,186, filed on Mar. 21, 2006, provisional application No. 60/765,857, filed on Feb. 7, 2006.

(51) Int. Cl.

| | |
|---|---|
| *A61B 17/70* | (2006.01) |
| *A61B 17/04* | (2006.01) |
| *A61B 17/86* | (2006.01) |
| *A61F 2/90* | (2013.01) |
| *A61F 2/30* | (2006.01) |
| *A61F 2/82* | (2013.01) |
| *A61B 17/88* | (2006.01) |
| *A61B 17/80* | (2006.01) |
| *A61F 2/46* | (2006.01) |
| *A61B 17/11* | (2006.01) |
| *A61F 2/34* | (2006.01) |
| *A61F 2/44* | (2006.01) |
| *A61F 2/32* | (2006.01) |
| *A61F 2/36* | (2006.01) |
| *A61F 2/06* | (2013.01) |
| *A61F 2/38* | (2006.01) |
| *A61F 2/28* | (2006.01) |
| *A61F 2/42* | (2006.01) |
| *A61F 2/08* | (2006.01) |
| *A61F 2/40* | (2006.01) |
| *A61B 17/00* | (2006.01) |

(52) U.S. Cl.
CPC ...... *A61B 17/7059* (2013.01); *A61B 17/7225* (2013.01); *A61B 17/7233* (2013.01); *A61B 17/80* (2013.01); *A61B 17/866* (2013.01); *A61B 17/8685* (2013.01); *A61B 17/8802* (2013.01); *A61B 17/8872* (2013.01); *A61F 2/30* (2013.01); *A61F 2/46* (2013.01); *A61F 2/82* (2013.01); *A61F 2/90* (2013.01); *A61B 17/0487* (2013.01); *A61B 17/11* (2013.01); *A61B 17/1128* (2013.01); *A61B 17/1146* (2013.01); *A61B 17/7098* (2013.01); *A61B 17/7258* (2013.01); *A61B 17/8822* (2013.01); *A61B 2017/005* (2013.01); *A61B 2017/044* (2013.01); *A61B 2017/0409* (2013.01); *A61B 2017/1107* (2013.01); *A61F 2/0811* (2013.01); *A61F 2/3094* (2013.01); *A61F 2/30721* (2013.01); *A61F 2/30756* (2013.01); *A61F 2/32* (2013.01); *A61F 2/34* (2013.01); *A61F 2/36* (2013.01); *A61F 2/3603* (2013.01); *A61F 2/38* (2013.01); *A61F 2/3804* (2013.01); *A61F 2/389* (2013.01); *A61F 2/3859* (2013.01); *A61F 2/40* (2013.01); *A61F 2/4081* (2013.01); *A61F 2/4202* (2013.01); *A61F 2/44* (2013.01); *A61F 2/4455* (2013.01); *A61F 2/468* (2013.01); *A61F 2002/067* (2013.01); *A61F 2002/2817* (2013.01); *A61F 2002/30062* (2013.01); *A61F 2002/30065* (2013.01); *A61F 2002/30067* (2013.01); *A61F 2002/3068* (2013.01); *A61F 2002/30133* (2013.01); *A61F 2002/30451* (2013.01); *A61F 2002/30576* (2013.01); *A61F 2002/30604* (2013.01); *A61F 2002/30677* (2013.01); *A61F 2002/30785* (2013.01); *A61F 2002/30787* (2013.01); *A61F 2002/30878* (2013.01); *A61F 2002/30892* (2013.01); *A61F 2002/30894* (2013.01); *A61F 2002/30971* (2013.01); *A61F 2002/30973* (2013.01); *A61F 2002/3401* (2013.01); *A61F 2002/3403* (2013.01); *A61F 2002/444* (2013.01); *A61F 2002/4619* (2013.01); *A61F 2002/4683* (2013.01); *A61F 2002/828* (2013.01); *A61F 2210/0004* (2013.01); *A61F 2210/0071* (2013.01); *A61F 2220/0008* (2013.01); *A61F 2220/0058* (2013.01); *A61F 2230/0015* (2013.01); *A61F 2250/0068* (2013.01); *A61F 2310/00011* (2013.01); *A61F 2310/00365* (2013.01); *A61F 2310/00383* (2013.01); *A61F 2310/00952* (2013.01)

(58) Field of Classification Search
CPC ...... A61B 17/72–7291; A61B 17/0401; A61B 2017/0403–0464
USPC ...... 606/280–331, 86 B
See application file for complete search history.

(56) References Cited

U.S. PATENT DOCUMENTS

| | | |
|---|---|---|
| 668,879 A | 2/1901 | Miller |
| 702,789 A | 6/1902 | Gibson |
| 862,712 A | 8/1907 | Collins |
| 2,121,193 A | 12/1932 | Hanicke |
| 2,187,852 A | 8/1936 | Friddle |
| 2,178,840 A | 11/1939 | Libarid |
| 2,199,025 A | 4/1940 | Conn |
| 2,235,419 A | 3/1941 | Callahan |
| 2,248,054 A | 7/1941 | Becker |
| 2,270,188 A | 1/1942 | Longfellow |
| 2,518,276 A | 8/1950 | Braward |
| 2,557,669 A | 6/1951 | Lloyd |
| 2,566,499 A | 9/1951 | Richter |
| 2,621,653 A | 12/1952 | Briggs |
| 2,725,053 A | 11/1955 | Bambara |
| 2,830,587 A | 4/1958 | Everett |
| 3,204,635 A | 9/1965 | Voss |
| 3,347,234 A | 10/1967 | Voss |
| 3,367,809 A | 2/1968 | Soloff |
| 3,391,690 A | 7/1968 | Armao |
| 3,477,429 A | 11/1969 | Sampson |
| 3,513,848 A | 5/1970 | Winston et al. |
| 3,518,993 A | 7/1970 | Blake |
| 3,577,991 A | 5/1971 | Wilkinson |
| 3,596,292 A | 8/1971 | Erb et al. |
| 3,608,539 A | 9/1971 | Miller |
| 3,625,220 A | 12/1971 | Engelsher |
| 3,648,705 A | 3/1972 | Lary |
| 3,653,388 A | 4/1972 | Tenckhoff |
| 3,656,476 A | 4/1972 | Swinney |
| 3,657,056 A | 4/1972 | Winston et al. |
| 3,678,980 A | 7/1972 | Gutshall |
| 3,709,218 A | 1/1973 | Halloran |
| 3,711,347 A | 1/1973 | Wagner et al. |
| 3,760,808 A | 9/1973 | Bleuer |
| 3,788,318 A | 1/1974 | Kim et al. |
| 3,789,852 A | 2/1974 | Kim et al. |
| 3,802,438 A | 4/1974 | Wolvek |
| 3,807,394 A | 4/1974 | Attenborough |
| 3,809,075 A | 5/1974 | Matles |
| 3,811,449 A | 5/1974 | Gravlee et al. |
| 3,825,010 A | 7/1974 | McDonald |
| 3,833,003 A | 9/1974 | Taricco |
| 3,835,849 A | 9/1974 | McGuire |
| 3,842,824 A | 10/1974 | Neufeld |
| 3,857,396 A | 12/1974 | Hardwick |
| 3,867,932 A | 2/1975 | Huene |

(56) References Cited

U.S. PATENT DOCUMENTS

| | | |
|---|---|---|
| 3,875,652 A | 4/1975 | Arnold |
| 3,888,405 A | 6/1975 | Jones et al. |
| 3,898,992 A | 8/1975 | Balamuth |
| 3,918,442 A | 11/1975 | Nikolaev et al. |
| 3,968,800 A | 7/1976 | Vilasi |
| 4,023,559 A | 5/1977 | Gaskell |
| 4,064,566 A | 12/1977 | Fletcher et al. |
| 4,089,071 A | 5/1978 | Kainberz et al. |
| 4,156,574 A | 5/1979 | Boben |
| 4,164,794 A | 8/1979 | Spector et al. |
| 4,171,544 A | 10/1979 | Hench et al. |
| 4,183,102 A | 1/1980 | Guiset |
| 4,199,864 A | 4/1980 | Ashman |
| 4,200,939 A | 5/1980 | Oser |
| 4,210,148 A | 7/1980 | Stivala |
| 4,213,816 A | 7/1980 | Morris |
| 4,235,233 A | 11/1980 | Mouwen |
| 4,235,238 A | 11/1980 | Ogiu et al. |
| 4,257,411 A | 3/1981 | Cho |
| 4,265,231 A | 5/1981 | Scheller, Jr. |
| 4,281,649 A | 8/1981 | Derweduwen |
| 4,291,698 A | 9/1981 | Fuchs |
| 4,309,488 A | 1/1982 | Heide et al. |
| 4,320,762 A | 3/1982 | Bentov |
| 4,351,069 A | 9/1982 | Ballintyn et al. |
| 4,364,381 A | 12/1982 | Sher et al. |
| 4,365,356 A | 12/1982 | Broemer et al. |
| 4,388,921 A | 6/1983 | Sutter et al. |
| 4,395,798 A | 8/1983 | McVey |
| 4,409,974 A | 10/1983 | Freedland |
| 4,414,166 A | 11/1983 | Charlson et al. |
| 4,437,191 A | 3/1984 | Van der Zat et al. |
| 4,437,362 A | 3/1984 | Hurst |
| 4,444,180 A | 4/1984 | Schneider et al. |
| 4,448,194 A | 5/1984 | DiGiovanni et al. |
| 4,456,005 A | 6/1984 | Lichty |
| 4,461,281 A | 7/1984 | Carson |
| 4,493,317 A | 1/1985 | Klaue |
| 4,495,664 A | 1/1985 | Bianquaert |
| 4,501,031 A | 2/1985 | McDaniel et al. |
| 4,504,268 A | 3/1985 | Herlitze |
| 4,506,681 A | 3/1985 | Mundell |
| 4,514,125 A | 4/1985 | Stol |
| 4,526,173 A | 7/1985 | Sheehan |
| 4,532,926 A | 8/1985 | O'Holla |
| 4,535,772 A | 8/1985 | Sheehan |
| 4,547,327 A | 10/1985 | Bruins et al. |
| 4,556,350 A | 12/1985 | Bernhardt et al. |
| 4,566,138 A | 1/1986 | Lewis et al. |
| 4,589,868 A | 5/1986 | Dretler |
| 4,590,928 A | 5/1986 | Hunt et al. |
| 4,597,379 A | 7/1986 | Kihn et al. |
| 4,599,085 A | 7/1986 | Riess et al. |
| 4,601,893 A | 7/1986 | Cardinal |
| 4,606,335 A | 8/1986 | Wedeen |
| 4,621,640 A | 11/1986 | Mulhollan |
| 4,630,609 A | 12/1986 | Chin |
| 4,632,101 A | 12/1986 | Freedland |
| 4,645,503 A | 2/1987 | Lin et al. |
| 4,653,487 A | 3/1987 | Maale |
| 4,657,460 A | 4/1987 | Bien |
| 4,659,268 A | 4/1987 | Del Mundo et al. |
| 4,662,063 A | 5/1987 | Collins et al. |
| 4,662,068 A | 5/1987 | Polonsky |
| 4,662,887 A | 5/1987 | Turner et al. |
| 4,669,473 A | 6/1987 | Richards et al. |
| 4,685,458 A | 8/1987 | Leckrone |
| 4,691,741 A | 9/1987 | Affa et al. |
| 4,705,040 A | 11/1987 | Mueller et al. |
| 4,706,670 A | 11/1987 | Andersen |
| 4,708,139 A | 11/1987 | Dunbar |
| 4,713,077 A | 12/1987 | Small |
| 4,716,901 A | 1/1988 | Jackson |
| 4,718,909 A | 1/1988 | Brown |
| 4,722,331 A | 2/1988 | Fox |
| 4,722,948 A | 2/1988 | Sanderson |
| 4,724,584 A | 2/1988 | Kasai |
| 4,738,255 A | 4/1988 | Goble |
| 4,739,751 A | 4/1988 | Sapega |
| 4,741,330 A | 5/1988 | Hayhurst |
| 4,749,585 A | 6/1988 | Greco |
| 4,750,492 A | 6/1988 | Jacobs |
| 4,768,507 A | 6/1988 | Fischell |
| 4,772,286 A | 9/1988 | Goble |
| 4,773,406 A | 9/1988 | Spector et al. |
| 4,776,328 A | 10/1988 | Frey |
| 4,776,738 A | 10/1988 | Winston |
| 4,776,851 A | 10/1988 | Bruchman |
| 4,781,182 A | 11/1988 | Purnell |
| 4,790,303 A | 12/1988 | Steffee |
| 4,792,336 A | 12/1988 | Hiavacek et al. |
| 4,817,591 A | 4/1989 | Klause |
| 4,822,224 A | 4/1989 | Carl et al. |
| 4,823,794 A | 4/1989 | Pierce |
| 4,832,025 A | 5/1989 | Coates |
| 4,832,026 A | 5/1989 | Jones |
| 4,834,752 A | 5/1989 | Van Kampen |
| 4,841,960 A | 6/1989 | Garner |
| 4,843,112 A | 6/1989 | Gerhart |
| 4,846,812 A | 7/1989 | Walker |
| 4,862,882 A | 9/1989 | Venturi |
| 4,869,242 A | 9/1989 | Galluzzo |
| 4,870,957 A | 10/1989 | Goble |
| 4,883,048 A | 11/1989 | Purnell |
| 4,890,612 A | 1/1990 | Kensey |
| 4,895,148 A | 1/1990 | Bays |
| 4,898,156 A | 2/1990 | Gattuma |
| 4,899,729 A | 2/1990 | Gill |
| 4,899,744 A | 2/1990 | Fujitsuka |
| 4,901,721 A | 2/1990 | Hakki |
| 4,911,718 A | 3/1990 | Lee et al. |
| 4,921,479 A | 5/1990 | Grayzel |
| 4,922,897 A | 5/1990 | Sapega |
| 4,924,866 A | 5/1990 | Yoon |
| 4,932,960 A | 6/1990 | Green et al. |
| 4,935,026 A | 6/1990 | Drews |
| 4,935,028 A | 6/1990 | Drews |
| 4,945,625 A | 8/1990 | Winston |
| 4,946,468 A | 8/1990 | Li |
| 4,954,126 A | 9/1990 | Wallsten |
| 4,955,910 A | 9/1990 | Bolesky |
| 4,957,498 A | 9/1990 | Caspari |
| 4,963,151 A | 10/1990 | Ducheyne et al. |
| 4,966,583 A | 10/1990 | Debbas |
| 4,968,315 A | 11/1990 | Gatturna |
| 4,969,888 A | 11/1990 | Scholten et al. |
| 4,969,892 A | 11/1990 | Burton et al. |
| 4,990,161 A | 2/1991 | Kampner |
| 4,994,071 A | 2/1991 | MacGregor |
| 4,997,445 A | 3/1991 | Hodorek |
| 4,998,539 A | 3/1991 | Delsanti |
| 5,002,550 A | 3/1991 | Li |
| 5,002,563 A | 3/1991 | Pyka et al. |
| 5,009,652 A | 4/1991 | Morgan et al. |
| 5,009,663 A | 4/1991 | Broome |
| 5,009,664 A | 4/1991 | Sievers |
| 5,013,316 A * | 5/1991 | Goble ............... A61B 17/8875 606/75 |
| 5,019,090 A | 5/1991 | Pinchuk |
| 5,021,059 A | 6/1991 | Kensey et al. |
| 5,035,713 A | 7/1991 | Friis |
| 5,037,404 A | 8/1991 | Gold |
| 5,037,422 A | 8/1991 | Hayhurst et al. |
| 5,041,093 A | 8/1991 | Chu |
| 5,041,114 A | 8/1991 | Chapman et al. |
| 5,041,129 A | 8/1991 | Hayhurst et al. |
| 5,046,513 A | 9/1991 | Gatturna et al. |
| 5,047,055 A | 9/1991 | Bao et al. |
| 5,051,049 A | 9/1991 | Wills |
| 5,053,046 A | 10/1991 | Janese |
| 5,053,047 A | 10/1991 | Yoon |
| 5,059,193 A | 10/1991 | Kuslich |
| 5,059,206 A | 10/1991 | Winters |
| 5,061,274 A | 10/1991 | Kensey |

(56) References Cited

U.S. PATENT DOCUMENTS

| | | |
|---|---|---|
| 5,061,286 A | 10/1991 | Lyle |
| 5,064,286 A | 10/1991 | Lyle |
| 5,069,674 A | 12/1991 | Fearnot et al. |
| 5,078,731 A | 1/1992 | Hayhurst |
| 5,078,744 A | 1/1992 | Chvapil |
| 5,078,745 A | 1/1992 | Rhenter et al. |
| 5,084,050 A | 1/1992 | Draenert |
| 5,084,051 A | 1/1992 | Tormala et al. |
| 5,085,660 A | 2/1992 | Lin |
| 5,085,661 A | 2/1992 | Moss |
| 5,098,433 A | 3/1992 | Freedland |
| 5,098,434 A | 3/1992 | Serbousek |
| 5,098,436 A | 3/1992 | Ferrante et al. |
| 5,100,405 A | 3/1992 | McLaren |
| 5,100,417 A | 3/1992 | Cerier et al. |
| 5,102,417 A | 4/1992 | Palmaz |
| 5,102,421 A | 4/1992 | Anspach, Jr. |
| 5,108,399 A | 4/1992 | Eitenmuller et al. |
| 5,120,175 A | 6/1992 | Arbegast et al. |
| 5,123,520 A | 6/1992 | Schmid et al. |
| 5,123,914 A | 6/1992 | Cope |
| 5,123,941 A | 6/1992 | Lauren et al. |
| 5,133,732 A | 7/1992 | Wiktor |
| RE34,021 E | 8/1992 | Mueller |
| 5,141,520 A | 8/1992 | Goble et al. |
| 5,147,362 A | 9/1992 | Goble |
| 5,154,720 A | 10/1992 | Trott et al. |
| 5,156,613 A | 10/1992 | Sawyer |
| 5,156,616 A | 10/1992 | Meadows et al. |
| 5,158,566 A | 10/1992 | Pianetti |
| 5,158,934 A | 10/1992 | Ammann et al. |
| 5,163,960 A | 11/1992 | Bonutti |
| 5,171,251 A | 12/1992 | Bregen et al. |
| 5,176,682 A | 1/1993 | Chow |
| 5,179,964 A | 1/1993 | Cook |
| 5,180,388 A | 1/1993 | DiCarlo |
| 5,183,464 A | 2/1993 | Dubrul et al. |
| 5,192,287 A | 3/1993 | Fournier et al. |
| 5,192,326 A | 3/1993 | Bao et al. |
| 5,197,166 A | 3/1993 | Meier et al. |
| 5,197,971 A | 3/1993 | Bonutti |
| 5,203,784 A | 4/1993 | Ross et al. |
| 5,203,787 A | 4/1993 | Noblitt et al. |
| 5,208,950 A | 5/1993 | Merritt |
| 5,209,776 A | 5/1993 | Bass et al. |
| 5,217,493 A | 6/1993 | Raad et al. |
| 5,219,359 A | 6/1993 | McQuilkin et al. |
| 5,226,899 A | 7/1993 | Lee et al. |
| 5,234,006 A | 8/1993 | Eaton et al. |
| 5,234,425 A | 8/1993 | Fogarty et al. |
| 5,236,438 A | 8/1993 | Wilk |
| 5,236,445 A | 8/1993 | Hayhurst |
| 5,242,902 A | 9/1993 | Murphy et al. |
| 5,254,113 A | 10/1993 | Wilk |
| 5,258,007 A | 11/1993 | Spetzler et al. |
| 5,258,015 A | 11/1993 | Li et al. |
| 5,258,016 A | 11/1993 | DiPoto et al. |
| 5,266,325 A | 11/1993 | Kuzma et al. |
| 5,269,783 A | 12/1993 | Sander |
| 5,269,785 A | 12/1993 | Bonutti |
| 5,269,809 A | 12/1993 | Hayhurst et al. |
| 5,281,235 A | 1/1994 | Haber et al. |
| 5,282,832 A | 2/1994 | Toso et al. |
| 5,290,281 A * | 3/1994 | Tschakaloff .................. 606/28 |
| 5,304,119 A | 4/1994 | Balaban et al. |
| 5,306,280 A | 4/1994 | Bregen et al. |
| 5,306,301 A | 4/1994 | Graf et al. |
| 5,306,309 A | 4/1994 | Wagner et al. |
| 5,315,741 A | 5/1994 | Dubberke |
| 5,318,570 A | 6/1994 | Hood |
| 5,318,588 A | 6/1994 | Horzewski et al. |
| 5,320,611 A | 6/1994 | Bonutti |
| 5,324,308 A | 6/1994 | Pierce |
| 5,328,480 A | 7/1994 | Melker et al. |
| 5,329,846 A | 7/1994 | Bonutti |
| 5,329,924 A | 7/1994 | Bonutti |
| 5,330,446 A | 7/1994 | Weldon et al. |
| 5,330,468 A | 7/1994 | Burkhart |
| 5,330,476 A | 7/1994 | Hiot et al. |
| 5,330,486 A | 7/1994 | Wilk |
| 5,336,231 A | 8/1994 | Adair |
| 5,336,240 A | 8/1994 | Metzler et al. |
| 5,339,799 A | 8/1994 | Kami et al. |
| 5,349,956 A | 9/1994 | Bonutti |
| 5,352,229 A | 10/1994 | Goble et al. |
| 5,354,298 A | 10/1994 | Lee et al. |
| 5,354,302 A | 10/1994 | Ko |
| 5,366,480 A | 11/1994 | Corriveaau et al. |
| 5,370,646 A | 12/1994 | Reese et al. |
| 5,370,660 A | 12/1994 | Weinstein et al. |
| 5,372,146 A | 12/1994 | Branch |
| 5,374,235 A * | 12/1994 | Ahrens ............... A61B 17/7233 606/101 |
| 5,376,126 A | 12/1994 | Lin |
| 5,382,254 A | 1/1995 | McGarry et al. |
| 5,383,883 A | 1/1995 | Wilk et al. |
| 5,383,905 A | 1/1995 | Golds et al. |
| 5,391,173 A | 2/1995 | Wilk |
| 5,395,308 A | 3/1995 | Fox et al. |
| 5,397,311 A | 3/1995 | Walker |
| 5,400,805 A | 3/1995 | Warren |
| 5,403,312 A | 4/1995 | Yates et al. |
| 5,403,348 A | 4/1995 | Bonutti |
| 5,405,359 A | 4/1995 | Pierce |
| 5,411,523 A | 5/1995 | Goble |
| 5,413,585 A | 5/1995 | Pagedas |
| 5,417,691 A | 5/1995 | Hayhurst |
| 5,417,701 A | 5/1995 | Holmes |
| 5,417,712 A * | 5/1995 | Whittaker .......... A61B 17/0401 606/232 |
| 5,423,796 A | 6/1995 | Shikhman et al. |
| 5,431,670 A | 7/1995 | Holmes |
| 5,439,470 A | 8/1995 | Li |
| 5,441,538 A | 8/1995 | Bonutti |
| 5,443,512 A | 8/1995 | Parr et al. |
| 5,447,503 A | 9/1995 | Miller |
| 5,449,372 A | 9/1995 | Schmaltz et al. |
| 5,449,382 A | 9/1995 | Dayton |
| 5,451,235 A | 9/1995 | Lock |
| 5,453,090 A | 9/1995 | Martinez |
| 5,456,722 A | 10/1995 | McLeod et al. |
| 5,458,653 A | 10/1995 | Davison |
| 5,462,561 A | 10/1995 | Voda |
| 5,464,424 A | 11/1995 | O'Donnell, Jr. |
| 5,464,426 A | 11/1995 | Bonutti |
| 5,464,427 A | 11/1995 | Curtis et al. |
| 5,470,337 A | 11/1995 | Moss |
| 5,472,444 A | 12/1995 | Huebner et al. |
| 5,474,554 A | 12/1995 | Ku |
| 5,478,351 A | 12/1995 | Meade et al. |
| 5,478,353 A | 12/1995 | Yoon |
| 5,480,403 A | 1/1996 | Lee et al. |
| 5,486,197 A | 1/1996 | Le et al. |
| 5,487,844 A | 1/1996 | Fujita |
| 5,488,958 A | 2/1996 | Topel et al. |
| 5,496,292 A | 3/1996 | Burnham |
| 5,496,335 A | 3/1996 | Thomason et al. |
| 5,496,348 A | 3/1996 | Bonutti |
| 5,499,382 A | 3/1996 | Nusinov et al. |
| 5,500,000 A | 3/1996 | Feagin et al. |
| 5,501,700 A | 3/1996 | Hirata |
| 5,504,977 A | 4/1996 | Weppner |
| 5,505,735 A | 4/1996 | Li |
| 5,507,754 A | 4/1996 | Green et al. |
| 5,522,844 A | 6/1996 | Johnson |
| 5,522,845 A | 6/1996 | Wenstrom, Jr. |
| 5,522,846 A | 6/1996 | Bonutti |
| 5,527,341 A | 6/1996 | Gogolewski et al. |
| 5,527,342 A | 6/1996 | Pietrzak et al. |
| 5,527,343 A | 6/1996 | Bonutti |
| 5,529,075 A | 6/1996 | Clark |
| 5,531,759 A | 7/1996 | Kensey et al. |
| 5,534,012 A | 7/1996 | Bonutti |
| 5,534,028 A | 7/1996 | Bao et al. |

(56) References Cited

U.S. PATENT DOCUMENTS

| | | |
|---|---|---|
| 5,540,718 A | 7/1996 | Bartlett |
| 5,542,423 A | 8/1996 | Bonutti |
| 5,545,178 A | 8/1996 | Kensey et al. |
| 5,545,180 A | 8/1996 | Le et al. |
| 5,545,206 A | 8/1996 | Carson |
| 5,549,630 A | 8/1996 | Bonutti |
| 5,549,631 A | 8/1996 | Bonutti |
| 5,556,402 A | 9/1996 | Xu |
| 5,569,252 A | 10/1996 | Justin et al. |
| 5,569,305 A | 10/1996 | Bonutti |
| 5,569,306 A | 10/1996 | Thal |
| 5,571,190 A | 11/1996 | Ulrich et al. |
| 5,573,517 A | 11/1996 | Bonutti et al. |
| 5,573,538 A | 11/1996 | Laboureau |
| 5,573,542 A | 11/1996 | Stevens |
| 5,575,801 A | 11/1996 | Habermeyer |
| 5,580,344 A | 12/1996 | Hasson |
| 5,584,835 A | 12/1996 | Greenfield |
| 5,584,860 A | 12/1996 | Goble et al. |
| 5,584,862 A | 12/1996 | Bonutti |
| 5,591,206 A | 1/1997 | Moufarrege |
| 5,593,422 A | 1/1997 | Muijs Van De Moer et al. |
| 5,593,425 A | 1/1997 | Bonutti et al. |
| 5,593,625 A | 1/1997 | Riebel et al. |
| 5,601,557 A | 2/1997 | Hayhurst |
| 5,601,558 A | 2/1997 | Torrie et al. |
| 5,601,595 A | 2/1997 | Schwartz |
| 5,607,427 A | 3/1997 | Tschakaloff |
| 5,609,595 A | 3/1997 | Pennig |
| 5,618,314 A | 4/1997 | Harwin et al. |
| 5,620,461 A | 4/1997 | Muijs Van De Moer et al. |
| 5,626,612 A | 5/1997 | Bartlett |
| 5,626,614 A | 5/1997 | Hart |
| 5,626,718 A | 5/1997 | Philippe et al. |
| 5,630,824 A | 5/1997 | Hart |
| 5,634,926 A | 6/1997 | Jobe |
| 5,635,784 A | 6/1997 | Seale |
| 5,628,751 A | 7/1997 | Sander et al. |
| 5,643,274 A | 7/1997 | Sander et al. |
| 5,643,293 A | 7/1997 | Kogasaka et al. |
| 5,643,295 A | 7/1997 | Yoon |
| 5,643,321 A | 7/1997 | McDevitt |
| 5,645,553 A | 7/1997 | Kolesa et al. |
| 5,645,597 A | 7/1997 | Krapiva |
| 5,645,599 A | 7/1997 | Samani |
| 5,649,955 A | 7/1997 | Hashimoto et al. |
| 5,649,963 A | 7/1997 | McDevitt |
| 5,651,377 A | 7/1997 | O'Donnell, Jr. |
| 5,658,313 A | 8/1997 | Thal |
| 5,660,225 A | 8/1997 | Saffran |
| 5,662,658 A | 9/1997 | Wenstrom, Jr. |
| 5,665,089 A | 9/1997 | Dall et al. |
| 5,665,109 A | 9/1997 | Yoon |
| 5,667,513 A | 9/1997 | Torrie et al. |
| 5,669,917 A | 9/1997 | Sauer et al. |
| 5,674,240 A | 10/1997 | Bonutti |
| 5,681,310 A | 10/1997 | Yuan et al. |
| 5,681,333 A | 10/1997 | Burkhart et al. |
| 5,681,351 A | 10/1997 | Jamiolkowski et al. |
| 5,681,352 A | 10/1997 | Clancy, III et al. |
| 5,685,820 A | 11/1997 | Riek et al. |
| 5,688,283 A | 11/1997 | Knapp |
| 5,690,654 A | 11/1997 | Ovil |
| 5,690,655 A | 11/1997 | Hart et al. |
| 5,690,676 A | 11/1997 | DiPoto et al. |
| 5,693,055 A | 12/1997 | Zahiri et al. |
| 5,697,950 A | 12/1997 | Fucci et al. |
| 5,702,397 A | 12/1997 | Gonle et al. |
| 5,702,462 A | 12/1997 | Oberlander |
| 5,707,395 A | 1/1998 | Li |
| 5,713,903 A | 2/1998 | Sander et al. |
| 5,713,921 A | 2/1998 | Bonutti |
| 5,718,717 A | 2/1998 | Bonutti |
| 5,720,747 A | 2/1998 | Burke |
| 5,725,541 A | 3/1998 | Anspach, III et al. |
| 5,725,556 A | 3/1998 | Moser et al. |
| 5,725,582 A | 3/1998 | Bevan |
| 5,730,747 A | 3/1998 | Ek et al. |
| 5,733,306 A | 3/1998 | Bonutti |
| 5,720,753 A | 4/1998 | Sander et al. |
| 5,735,875 A | 4/1998 | Bonutti et al. |
| 5,735,877 A | 4/1998 | Pagedas |
| 5,735,899 A | 4/1998 | Schwartz et al. |
| 5,741,282 A | 4/1998 | Anspach, III et al. |
| 5,752,952 A | 5/1998 | Adamson |
| 5,752,974 A | 5/1998 | Rhee et al. |
| 5,755,809 A | 5/1998 | Cohen et al. |
| 5,762,458 A | 6/1998 | Wang et al. |
| 5,766,221 A | 6/1998 | Benderev et al. |
| 5,769,894 A | 6/1998 | Ferragamo |
| 5,772,672 A | 6/1998 | Toy et al. |
| 5,776,151 A | 7/1998 | Chan |
| 5,779,706 A * | 7/1998 | Tschakaloff .................. 606/281 |
| 5,782,862 A | 7/1998 | Bonutti |
| 5,785,713 A | 7/1998 | Jobe |
| 5,792,096 A | 8/1998 | Rentmeester et al. |
| 5,797,931 A | 8/1998 | Bito et al. |
| 5,800,537 A | 9/1998 | Bell |
| 5,807,403 A | 9/1998 | Beyar et al. |
| 5,810,849 A | 9/1998 | Kontos |
| 5,810,853 A | 9/1998 | Yoon |
| 5,810,884 A | 9/1998 | Kim |
| 5,814,072 A | 9/1998 | Bonutti |
| 5,814,073 A | 9/1998 | Bonutti |
| 5,817,107 A | 10/1998 | Schaller |
| 5,823,994 A | 10/1998 | Sharkey et al. |
| 5,824,009 A | 10/1998 | Fukuda et al. |
| 5,830,125 A | 11/1998 | Scribner et al. |
| 5,836,897 A | 11/1998 | Sakural et al. |
| 5,839,899 A | 11/1998 | Robinson |
| 5,843,178 A | 12/1998 | Vanney et al. |
| 5,845,645 A | 12/1998 | Bonutti |
| 5,851,185 A | 12/1998 | Berns |
| 5,865,834 A | 2/1999 | McGuire |
| 5,866,634 A | 2/1999 | Tokushige |
| 5,868,749 A | 2/1999 | Reed |
| 5,874,235 A | 2/1999 | Chan |
| 5,879,372 A | 3/1999 | Bartlett |
| 5,891,166 A | 4/1999 | Schervinsky |
| 5,891,168 A | 4/1999 | Thal |
| 5,893,880 A | 4/1999 | Egan et al. |
| 5,897,574 A | 4/1999 | Bonutti |
| 5,899,911 A | 5/1999 | Carter |
| 5,899,921 A | 5/1999 | Caspari et al. |
| 5,906,579 A | 5/1999 | Vander Salm et al. |
| 5,906,625 A | 5/1999 | Bito et al. |
| 5,908,429 A | 6/1999 | Yoon |
| 5,911,721 A | 6/1999 | Nicholson et al. |
| 5,918,604 A | 7/1999 | Whelan |
| 5,919,193 A | 7/1999 | Slavitt |
| 5,919,194 A | 7/1999 | Anderson |
| 5,919,208 A | 7/1999 | Valenti |
| 5,919,215 A | 7/1999 | Wiklund et al. |
| 5,921,986 A | 7/1999 | Bonutti |
| 5,925,064 A | 7/1999 | Meyers et al. |
| 5,928,244 A | 7/1999 | Tovey et al. |
| 5,928,267 A | 7/1999 | Bonutti et al. |
| 5,931,838 A | 8/1999 | Vito |
| 5,931,869 A | 8/1999 | Boucher et al. |
| 5,940,942 A | 8/1999 | Fong |
| 5,941,900 A | 8/1999 | Bonutti |
| 5,941,901 A | 8/1999 | Egan |
| 5,945,002 A | 9/1999 | Bonutti |
| 5,947,982 A | 9/1999 | Duran |
| 5,948,000 A | 9/1999 | Larsen et al. |
| 5,948,001 A | 9/1999 | Larsen |
| 5,951,590 A | 9/1999 | Goldfarb |
| 5,957,953 A | 9/1999 | DiPoto et al. |
| 5,961,499 A | 10/1999 | Bonutti |
| 5,961,521 A | 10/1999 | Roger |
| 5,961,554 A | 10/1999 | Janson et al. |
| 5,964,765 A | 10/1999 | Fenton, Jr. et al. |
| 5,964,769 A | 10/1999 | Wagner et al. |
| 5,968,046 A | 10/1999 | Castleman |

(56) References Cited

U.S. PATENT DOCUMENTS

| | | |
|---|---|---|
| 5,968,047 A | 10/1999 | Reed |
| 5,948,002 A | 11/1999 | Bonutti |
| 5,980,520 A | 11/1999 | Vancaillie |
| 5,980,559 A | 11/1999 | Bonutti |
| 5,984,929 A | 11/1999 | Bashiri et al. |
| 5,989,282 A | 11/1999 | Bonutti |
| 5,993,458 A | 11/1999 | Vaitekunas et al. |
| 5,993,477 A | 11/1999 | Vaitekunas et al. |
| 6,007,567 A | 12/1999 | Bonutti |
| 6,007,580 A | 12/1999 | Lehto et al. |
| 6,010,525 A | 1/2000 | Bonutti |
| 6,010,526 A | 1/2000 | Sandstrom et al. |
| 6,017,321 A | 1/2000 | Boone |
| 6,033,429 A | 3/2000 | Magovern |
| 6,033,430 A | 3/2000 | Bonutti |
| 6,045,551 A | 4/2000 | Bonutti |
| 6,050,998 A | 4/2000 | Fletcher et al. |
| 6,056,751 A * | 5/2000 | Fenton, Jr. .......... A61B 17/0401 606/151 |
| 6,056,772 A | 5/2000 | Bonutti |
| 6,056,773 A | 5/2000 | Bonutti |
| 6,059,797 A | 5/2000 | Mears |
| 6,059,817 A | 5/2000 | Bonutti et al. |
| 6,059,827 A | 5/2000 | Fenton |
| 6,063,095 A | 5/2000 | Wang et al. |
| 6,066,151 A | 5/2000 | Miyawaki et al. |
| 6,066,160 A | 5/2000 | Colvin et al. |
| 6,066,166 A | 5/2000 | Bischoff et al. |
| 6,068,637 A | 5/2000 | Popov et al. |
| 6,077,277 A | 6/2000 | Mollenauer et al. |
| 6,077,292 A | 6/2000 | Bonutti |
| 6,080,161 A * | 6/2000 | Eaves et al. .................... 606/76 |
| 6,083,522 A | 7/2000 | Chu et al. |
| 6,086,593 A | 7/2000 | Bonutti |
| 6,086,608 A | 7/2000 | Ek et al. |
| 6,090,072 A | 7/2000 | Kratoska |
| 6,099,531 A | 8/2000 | Bonutti |
| 6,099,537 A | 8/2000 | Sugai et al. |
| 6,099,550 A | 8/2000 | Yoon |
| 6,099,552 A | 8/2000 | Adams |
| 6,102,850 A | 8/2000 | Wang et al. |
| 6,106,545 A | 8/2000 | Egan |
| 6,117,160 A | 9/2000 | Bonutti |
| 6,120,536 A | 9/2000 | Ding et al. |
| 6,125,574 A | 10/2000 | Ganaja et al. |
| 6,126,677 A | 10/2000 | Ganaja et al. |
| 6,139,320 A | 10/2000 | Hahn |
| RE36,974 E | 11/2000 | Bonutti |
| 6,149,669 A | 11/2000 | Li |
| 6,152,949 A | 11/2000 | Bonutti |
| 6,155,756 A | 12/2000 | Mericle et al. |
| 6,159,224 A | 12/2000 | Yoon |
| 6,159,234 A | 12/2000 | Bonutti et al. |
| 6,171,307 B1 | 1/2001 | Bonutti |
| 6,174,324 B1 | 1/2001 | Egan et al. |
| 6,179,840 B1 | 1/2001 | Bowman |
| 6,179,850 B1 | 1/2001 | Goradia |
| 6,187,008 B1 | 2/2001 | Hamman |
| 6,190,400 B1 | 2/2001 | Van De Moer et al. |
| 6,190,401 B1 | 2/2001 | Green |
| 6,200,322 B1 | 3/2001 | Branch et al. |
| 6,214,049 B1 | 4/2001 | Gayer et al. |
| 6,217,591 B1 | 4/2001 | Egan et al. |
| 6,224,593 B1 | 5/2001 | Ryan |
| 6,224,630 B1 | 5/2001 | Bao et al. |
| 6,228,086 B1 | 5/2001 | Wahl et al. |
| 6,231,592 B1 | 5/2001 | Bonutti et al. |
| 6,238,395 B1 | 5/2001 | Bonutti |
| 6,238,396 B1 | 5/2001 | Bonutti |
| 6,258,091 B1 | 7/2001 | Sevrain et al. |
| 6,264,675 B1 | 7/2001 | Brotz |
| 6,267,761 B1 | 7/2001 | Ryan |
| 6,273,717 B1 | 8/2001 | Hahn et al. |
| 6,280,474 B1 | 8/2001 | Cassidy et al. |
| 6,286,746 B1 | 9/2001 | Egan et al. |
| 6,287,325 B1 | 9/2001 | Bonutti |
| 6,293,961 B2 | 9/2001 | Schwartz et al. |
| 6,306,159 B1 | 10/2001 | Schwartz et al. |
| 6,309,405 B1 | 10/2001 | Bonutti |
| 6,312,448 B1 | 11/2001 | Bonutti |
| 6,338,730 B1 | 1/2002 | Bonutti |
| 6,340,365 B2 | 1/2002 | Dittrich et al. |
| 6,348,056 B1 | 2/2002 | Bates et al. |
| 6,358,271 B1 | 3/2002 | Egan et al. |
| 6,364,897 B1 | 4/2002 | Bonutti |
| 6,368,325 B1 | 4/2002 | McKinley et al. |
| 6,368,343 B1 | 4/2002 | Bonutti |
| 6,371,957 B1 | 4/2002 | Amrein et al. |
| 6,409,716 B1 | 6/2002 | Sahatjian et al. |
| 6,409,742 B1 | 6/2002 | Fulton, III |
| 6,409,743 B1 | 6/2002 | Fenton, Jr. |
| 6,409,768 B1 * | 6/2002 | Tepic .................. A61B 17/1753 606/64 |
| 6,419,704 B1 | 7/2002 | Ferree |
| 6,423,088 B1 | 7/2002 | Fenton |
| 6,425,919 B1 | 7/2002 | Lambrecht |
| 6,428,562 B2 | 8/2002 | Bonutti |
| 6,432,115 B1 | 8/2002 | Mollenauer et al. |
| 6,447,516 B1 | 9/2002 | Bonutti |
| 6,450,985 B1 | 9/2002 | Schoelling et al. |
| 6,461,360 B1 | 10/2002 | Adam |
| 6,468,293 B2 | 10/2002 | Bonutti |
| 6,475,230 B1 | 11/2002 | Bonutti |
| 6,488,196 B1 | 12/2002 | Fenton |
| 6,500,195 B2 | 12/2002 | Bonutti |
| 6,503,259 B2 | 1/2003 | Huxel et al. |
| 6,530,933 B1 | 3/2003 | Yeung et al. |
| 6,535,764 B2 | 3/2003 | Imran et al. |
| 6,544,267 B1 | 4/2003 | Cole et al. |
| 6,545,390 B1 | 4/2003 | Hahn et al. |
| 6,547,792 B1 | 4/2003 | Tsuji et al. |
| 6,551,304 B1 | 4/2003 | Whalen et al. |
| 6,554,852 B1 | 4/2003 | Oberlander |
| 6,527,774 B2 | 5/2003 | Lieberman |
| 6,558,390 B2 | 5/2003 | Cragg |
| 6,568,313 B2 | 5/2003 | Fukui et al. |
| 6,569,187 B1 | 5/2003 | Bonutti |
| 6,572,635 B1 | 6/2003 | Bonutti |
| D477,776 S | 7/2003 | Pontaoe |
| 6,557,426 B2 | 7/2003 | Reinemann et al. |
| 6,585,750 B2 | 7/2003 | Bonutti |
| 6,592,609 B1 | 7/2003 | Bonutti |
| 6,594,517 B1 | 7/2003 | Nevo |
| 6,585,764 B2 | 8/2003 | Wright et al. |
| 6,605,090 B1 * | 8/2003 | Trieu et al. .................... 606/281 |
| 6,610,080 B2 | 8/2003 | Morgan |
| 6,618,910 B1 | 9/2003 | Pontaoe |
| 6,623,487 B1 * | 9/2003 | Goshert .......................... 606/329 |
| 6,626,944 B1 | 9/2003 | Taylor |
| 6,623,486 B1 | 10/2003 | Weaver |
| 6,632,245 B2 | 10/2003 | Kim |
| 6,635,073 B2 | 10/2003 | Bonutti |
| 6,638,279 B2 | 10/2003 | Bonutti |
| 6,641,592 B1 | 11/2003 | Sauer et al. |
| 6,645,227 B2 | 11/2003 | Fallin et al. |
| 6,652,585 B2 | 11/2003 | Lange |
| 6,666,877 B2 | 12/2003 | Morgan et al. |
| 6,669,705 B2 | 12/2003 | Westhaver et al. |
| 6,679,888 B2 | 1/2004 | Green et al. |
| 6,685,750 B1 | 2/2004 | Plos et al. |
| 6,699,240 B2 | 3/2004 | Francischelli |
| 6,702,821 B2 | 3/2004 | Bonutti |
| 6,705,179 B1 | 3/2004 | Mohtasham |
| 6,709,436 B1 | 3/2004 | Hover et al. |
| 6,709,457 B1 | 3/2004 | Otte |
| 6,719,765 B2 | 4/2004 | Bonutti |
| 6,719,797 B1 | 4/2004 | Ferree |
| 6,722,552 B2 | 4/2004 | Fenton |
| 6,733,531 B1 | 5/2004 | Trieu |
| 6,764,514 B1 | 7/2004 | Li et al. |
| 6,770,078 B2 | 8/2004 | Bonutti |
| 6,780,198 B1 | 8/2004 | Gregoire et al. |
| 6,786,989 B2 | 9/2004 | Torriani et al. |
| 6,796,003 B1 | 9/2004 | Marvel |

(56) References Cited

U.S. PATENT DOCUMENTS

| | | |
|---|---|---|
| 6,818,010 B2 | 11/2004 | Eichhorn et al. |
| 6,823,871 B2 | 11/2004 | Schmieding |
| 6,860,885 B2 | 3/2005 | Bonutti |
| 6,878,167 B2 | 4/2005 | Ferree |
| 6,893,434 B2 | 5/2005 | Fenton et al. |
| 6,899,722 B2 | 5/2005 | Bonutti |
| 6,890,334 B2 | 7/2005 | Brace et al. |
| 6,913,666 B1 | 7/2005 | Aeschlimann et al. |
| 6,916,321 B2 | 7/2005 | TenHuisen |
| 6,921,264 B2 | 7/2005 | Mayer et al. |
| 6,923,824 B2 | 8/2005 | Morgan et al. |
| 6,932,835 B2 | 8/2005 | Bonutti |
| 6,942,684 B2 | 9/2005 | Bonutti |
| 6,944,111 B2 | 9/2005 | Nakamura et al. |
| 6,955,540 B2 | 10/2005 | Mayer et al. |
| 6,955,683 B2 | 10/2005 | Bonutti |
| 6,958,077 B2 | 10/2005 | Suddaby |
| 6,981,983 B1 | 1/2006 | Rosenblatt et al. |
| 6,997,940 B2 | 2/2006 | Bonutti |
| 7,001,411 B1 | 2/2006 | Dean |
| 7,004,959 B2 | 2/2006 | Bonutti |
| 7,008,226 B2 | 3/2006 | Mayer et al. |
| 7,033,379 B2 | 4/2006 | Peterson |
| 7,048,755 B2 | 5/2006 | Bonutti |
| 7,066,960 B1 | 6/2006 | Dickman |
| 7,087,073 B2 | 8/2006 | Bonutti |
| 7,090,111 B2 | 8/2006 | Egan et al. |
| 7,094,251 B2 | 8/2006 | Bonutti |
| 7,104,996 B2 | 9/2006 | Bonutti |
| 7,128,761 B2 | 10/2006 | Kuras et al. |
| 7,128,763 B1 | 10/2006 | Blatt |
| 7,018,380 B2 | 12/2006 | Cole |
| 7,147,652 B2 | 12/2006 | Bonutti et al. |
| 7,160,405 B2 | 1/2007 | Aeschlimann et al. |
| 7,179,259 B1 | 2/2007 | Gibbs |
| 7,192,448 B2 | 3/2007 | Ferree |
| 7,217,279 B2 | 5/2007 | Reese |
| 7,217,290 B2 | 5/2007 | Bonutti |
| 7,241,297 B2 | 7/2007 | Shaolian et al. |
| 7,250,051 B2 | 7/2007 | Francischelli |
| 7,252,685 B2 | 8/2007 | Bindseil et al. |
| 7,273,497 B2 | 9/2007 | Ferree |
| 7,329,263 B2 | 2/2008 | Bonutti |
| 7,335,205 B2 * | 2/2008 | Aeschlimann et al. ...... 606/232 |
| 7,429,266 B2 | 9/2008 | Bonutti |
| 7,445,634 B2 | 11/2008 | Trieu |
| 7,481,825 B2 | 1/2009 | Bonutti |
| 7,481,831 B2 | 1/2009 | Bonutti |
| 7,510,895 B2 * | 3/2009 | Raterman ...................... 438/54 |
| 7,632,272 B2 | 12/2009 | Munro et al. |
| 7,854,750 B2 | 12/2010 | Bonutti |
| 7,879,072 B2 * | 2/2011 | Bonutti .............. A61B 17/0487 606/232 |
| 7,891,691 B2 | 2/2011 | Bearey |
| 7,967,820 B2 | 6/2011 | Bonutti |
| 8,128,669 B2 | 3/2012 | Bonutti |
| 8,140,982 B2 | 3/2012 | Hamilton, II et al. |
| 8,147,514 B2 | 4/2012 | Bonutti |
| 8,162,977 B2 | 4/2012 | Bonutti et al. |
| 8,487,844 B2 | 7/2013 | Koyama |
| 2001/0002440 A1 | 5/2001 | Bonutti |
| 2001/0009250 A1 | 7/2001 | Herman et al. |
| 2001/0041916 A1 | 11/2001 | Bonutti |
| 2002/0016593 A1 | 2/2002 | Hearn et al. |
| 2002/0016633 A1 | 2/2002 | Lin et al. |
| 2002/0019649 A1 | 2/2002 | Sikora |
| 2002/0026244 A1 | 2/2002 | Trieu |
| 2002/0029083 A1 | 3/2002 | Zucherman et al. |
| 2002/0029084 A1 | 3/2002 | Paul et al. |
| 2002/0045902 A1 | 4/2002 | Bonutti |
| 2002/0062153 A1 | 5/2002 | Paul et al. |
| 2002/0082529 A1 | 6/2002 | Suorsa |
| 2002/0099379 A1 | 7/2002 | Adam |
| 2002/0103495 A1 | 8/2002 | Cole |
| 2002/0120336 A1 | 8/2002 | Santilli |
| 2002/0123750 A1 | 9/2002 | Eisermann et al. |
| 2002/0183762 A1 | 12/2002 | Anderson et al. |
| 2002/0188301 A1 | 12/2002 | Dallara et al. |
| 2003/0009224 A1 | 1/2003 | Kuras |
| 2003/0039196 A1 | 2/2003 | Nakamura et al. |
| 2003/0040758 A1 | 2/2003 | Wang et al. |
| 2003/0065361 A1 | 4/2003 | Dreyfuss |
| 2003/0105474 A1 | 6/2003 | Bonutti |
| 2003/0158582 A1 | 8/2003 | Bonutti et al. |
| 2003/0167072 A1 | 8/2003 | Oberlander |
| 2003/0118518 A1 | 9/2003 | Hahn et al. |
| 2003/0181800 A1 | 9/2003 | Bonutti |
| 2003/0187506 A1 | 10/2003 | Ross et al. |
| 2003/0195530 A1 | 10/2003 | Thill |
| 2003/0195565 A1 | 10/2003 | Bonutti |
| 2003/0204204 A1 | 10/2003 | Bonutti |
| 2003/0216742 A1 | 11/2003 | Wetzler et al. |
| 2003/0225438 A1 | 12/2003 | Bonutti et al. |
| 2003/0229361 A1 | 12/2003 | Jackson |
| 2004/0010287 A1 | 1/2004 | Bonutti |
| 2004/0030341 A1 * | 2/2004 | Aeschlimann ........ B29C 66/727 606/232 |
| 2004/0034357 A1 | 2/2004 | Beane et al. |
| 2004/0220616 A1 | 2/2004 | Bonutti |
| 2004/0230223 A1 | 2/2004 | Bonutti |
| 2004/0068320 A1 | 4/2004 | Robie et al. |
| 2004/0087902 A1 | 5/2004 | Richter |
| 2004/0097939 A1 | 5/2004 | Bonutti |
| 2004/0098050 A1 | 5/2004 | Foerster et al. |
| 2004/0138703 A1 | 7/2004 | Alleyne |
| 2004/0143334 A1 | 7/2004 | Ferree |
| 2004/0167548 A1 | 8/2004 | Bonutti |
| 2004/0215111 A1 | 10/2004 | Bonutti et al. |
| 2004/0225325 A1 | 11/2004 | Bonutti |
| 2004/0225371 A1 * | 11/2004 | Roger ...................... A61F 2/34 623/22.28 |
| 2004/0236374 A1 | 11/2004 | Bonutti et al. |
| 2004/0243241 A1 | 12/2004 | Istephanous et al. |
| 2005/0033366 A1 | 2/2005 | Cole |
| 2005/0038514 A1 | 2/2005 | Helm et al. |
| 2005/0043796 A1 | 2/2005 | Grant et al. |
| 2005/0071012 A1 | 3/2005 | Serhan et al. |
| 2005/0085817 A1 | 4/2005 | Ringeisen |
| 2005/0090827 A1 | 4/2005 | Gedebou |
| 2005/0096699 A1 | 5/2005 | Wixey et al. |
| 2005/0113928 A1 | 5/2005 | Cragg et al. |
| 2005/0126680 A1 | 6/2005 | Aeschlimann et al. |
| 2005/0143826 A1 | 6/2005 | Zucherman et al. |
| 2005/0240227 A1 | 6/2005 | Bonutti |
| 2005/0149024 A1 | 7/2005 | Ferrante et al. |
| 2005/0149029 A1 | 7/2005 | Bonutti |
| 2005/0177162 A1 | 8/2005 | McLeod et al. |
| 2005/0203521 A1 | 9/2005 | Bonutti |
| 2005/0216008 A1 | 9/2005 | Zwimmann et al. |
| 2005/0216059 A1 | 9/2005 | Bonutti |
| 2005/0216087 A1 | 9/2005 | Zucherman et al. |
| 2005/0222620 A1 | 10/2005 | Bonutti |
| 2005/0240190 A1 | 10/2005 | Gall et al. |
| 2005/0246021 A1 | 11/2005 | Ringeisen et al. |
| 2005/0261684 A1 | 11/2005 | Shaolian et al. |
| 2005/0267481 A1 | 12/2005 | Carl et al. |
| 2005/0267534 A1 | 12/2005 | Bonutti |
| 2006/0009855 A1 | 1/2006 | Goble et al. |
| 2006/0015101 A1 | 1/2006 | Warburton et al. |
| 2006/0015108 A1 | 1/2006 | Bonutti |
| 2006/0024357 A1 | 2/2006 | Carpenter et al. |
| 2006/0026244 A1 | 2/2006 | Watson |
| 2006/0036203 A1 | 2/2006 | Ouchene et al. |
| 2006/0142799 A1 | 2/2006 | Bonutti |
| 2006/0200199 A1 | 2/2006 | Bonutti |
| 2006/0229623 A1 | 2/2006 | Bonutti |
| 2006/0064095 A1 | 3/2006 | Senn et al. |
| 2006/0167495 A1 | 3/2006 | Bonutti |
| 2006/0089646 A1 | 4/2006 | Bonutti |
| 2006/0122600 A1 | 6/2006 | Cole |
| 2006/0122704 A1 | 6/2006 | Vresilovic et al. |
| 2006/0235470 A1 | 7/2006 | Bonutti |
| 2006/0241695 A1 | 7/2006 | Bonutti |
| 2006/0265009 A1 | 7/2006 | Bonutti |

(56) References Cited

U.S. PATENT DOCUMENTS

| | | |
|---|---|---|
| 2006/0265011 A1 | 7/2006 | Bonutti |
| 2006/0212073 A1 | 9/2006 | Bonutti |
| 2006/0217765 A1 | 9/2006 | Bonutti |
| 2006/0229715 A1 | 10/2006 | Istephanous et al. |
| 2006/0264950 A1 | 11/2006 | Nelson |
| 2007/0032825 A1 | 2/2007 | Bonutti et al. |
| 2007/0088362 A1 | 4/2007 | Bonutti et al. |
| 2007/0118129 A1* | 5/2007 | Fraser et al. ............ 606/71 |
| 2007/0123878 A1 | 5/2007 | Shaver |
| 2007/0198555 A1 | 8/2007 | Friedman et al. |
| 2007/0265561 A1 | 11/2007 | Yeung |
| 2007/0270833 A1 | 11/2007 | Bonutti |
| 2008/0021474 A1 | 1/2008 | Bonutti |
| 2008/0039845 A1 | 2/2008 | Bonutti |
| 2008/0039873 A1 | 2/2008 | Bonutti |
| 2008/0046090 A1 | 2/2008 | Paul et al. |
| 2008/0195145 A1 | 2/2008 | Bonutti |
| 2008/0097448 A1 | 4/2008 | Binder et al. |
| 2008/0108897 A1 | 5/2008 | Bonutti et al. |
| 2008/0108916 A1 | 5/2008 | Bonutti |
| 2008/0114399 A1 | 5/2008 | Bonutti |
| 2008/0132950 A1* | 6/2008 | Lange ................ 606/246 |
| 2008/0140116 A1 | 6/2008 | Bonutti |
| 2008/0140117 A1 | 6/2008 | Bonutti |
| 2008/0269753 A1* | 10/2008 | Cannestra ............ 606/70 |
| 2008/0269808 A1* | 10/2008 | Gall et al. ............ 606/299 |
| 2009/0024161 A1 | 1/2009 | Bonutti |
| 2009/0138014 A1 | 1/2009 | Bonutti |
| 2009/0093684 A1 | 4/2009 | Schorer |
| 2009/0194969 A1 | 8/2009 | Bearey |
| 2010/0211120 A1 | 2/2010 | Bonutti |
| 2011/0060375 A1 | 3/2011 | Bonutti |
| 2011/0295253 A1 | 12/2011 | Bonutti et al. |
| 2012/0165841 A1 | 6/2012 | Bonutti |
| 2012/0191140 A1 | 7/2012 | Bonutti |
| 2012/0197316 A1* | 8/2012 | Mayer et al. .......... 606/328 |
| 2012/0215233 A1 | 8/2012 | Bonutti et al. |

FOREIGN PATENT DOCUMENTS

| | | |
|---|---|---|
| CA | 2698057 | 3/2009 |
| DE | 1903016 | 10/1964 |
| DE | 1903316 | 10/1964 |
| DE | 1903016 | 8/1970 |
| DE | 3517204 | 11/1986 |
| DE | 3722538 | 1/1989 |
| DE | 9002844 U1 | 1/1991 |
| EP | 784454 | 5/1996 |
| EP | 773004 | 5/1997 |
| EP | 1614525 | 1/2006 |
| EP | 1988837 | 8/2007 |
| EP | 2134294 | 12/2009 |
| FR | 2717368 | 3/1994 |
| FR | 2696338 | 4/1994 |
| FR | 2728779 | 1/1995 |
| FR | 2736257 | 7/1995 |
| FR | 2750031 | 6/1996 |
| FR | 2771621 | 11/1997 |
| FR | 2785171 | 10/1998 |
| GB | 2093701 A | 9/1982 |
| GB | 2306110 A | 4/1997 |
| JP | 8140982 | 6/1996 |
| SU | 184396 | 7/1966 |
| WO | 91/12779 | 9/1991 |
| WO | 93/23094 | 11/1993 |
| WO | WO1994008642 | 4/1994 |
| WO | 95/16398 | 6/1995 |
| WO | WO 95/31941 | 11/1995 |
| WO | WO1996014802 | 5/1996 |
| WO | WO1997012779 | 4/1997 |
| WO | WO 97/49347 | 12/1997 |
| WO | WO1998011838 | 3/1998 |
| WO | WO1998026720 | 6/1998 |
| WO | WO2002053011 | 7/2002 |
| WO | 2007/092869 | 8/2007 |
| WO | 2007/092869 A2 | 8/2007 |
| WO | 2008/116203 | 9/2008 |
| WO | 2009/029908 | 3/2009 |
| WO | WO2010099222 | 2/2010 |

OTHER PUBLICATIONS

Femoral Bone Plug Recession in Endoscope Anterior Cruciate Ligament Reconstruction, David E. Taylor, Arthroscopy: The Journal of Arthroscopic and Related Surgery, Aug. 1996.
Meniscus Replacement with Bone Anchors: A Surgical Technique, Arthroscopy: The Journal of Arthroscopic and Related Surgery, 1994.
Problem Solving Report Question No. 1014984.066, Ultrasonic Welding, (c) 1999.
Guide to Ultrasound Plastic Assembly, Ultrasonic Division Publication, (c) 1995.
Branson, Polymers: Characteristics and Compatibility for Ultrasonic Assembly, Applied Technologies Group, Publication unknown.
Enabling Local Drug Delivery-Implant Device Combination Therapies, Surmodics, Inc., (c) 2003.
Stent Based Delivery of Sirolimus Reduces Neointimal Formation in a Porcine Coronary Model, Takeshi Suzuki, American Heart Association, Inc. (c) 2001.
Why Tie a Knot When You Can Use Y-Knot?, Innovasive Devices Inc., (c) 1998.
Ask Oxford, compact Oxford English dictionary: projection, Mar. 30, 2009.
Ask Oxford, compact Oxford English dictionary: slit, Mar. 30, 2009.
Textured Surface Technology, Branson Technolog, Branson Ultrasonics Copr., (c) 1992.
IPR—International Publication WO/2007/092869, publishedAug. 16, 2007 for PCT/US2007/061730.
ISR—International Search Report WO/2007/092869, published Dec. 13, 2007 for PCT/US2007/061730.
Intl Prelim Report on Patentability, WO/2007/092869, published Aug. 12, 2008 for PCT/US2007/061730.
Written Opinion WO/2007/092869 dated Aug. 7, 2008 for PCT/US2007/061730.
010-3 Copending U.S. Appl. No. 11/932,907—RCE Response Sep. 15, 2011.
027 Copending U.S. Appl. No. 11/258,795 Non-Final Office Action dated Apr. 26, 2011.
046 Copending U.S. Appl. No. 11/689,670, RCE Response Sep. 19, 2011.
European Search Report dated Sep. 10, 2012 for EP08732724.3 (046).
003-1 Copending U.S. Appl. No. 10/614,352, Final Office Action dated Jul. 12, 2010.
007-2 Copending U.S. Appl. No. 11/932,602 Final Response to Office Action dated Jun. 10, 2011.
039 Copending U.S. Appl. No. 11/671,556 Response filed Aug. 23, 2010.
Co-pending U.S. Appl. No. 11/438,537, Supplemental Final Rejection dated Sep. 25, 2009.
IPR—International Publication WO/2008/116203, published Sep. 22, 2009 for PCT/US08/57948.
ISR—International Search Report WO/2008/116203, published Dec. 24, 2008 for PCT/US08/57948.
IPER—Internation Preliminary Report on Patentability, WO/2008/116203, published Sep. 22, 2009 for PCT/US08/57948.
Written Opinion WO/2008/116203 dated Oct. 23, 2008 for PCT/US08/57948.
IPR—International Publication WO2009/029908, published May 3, 2009 for PCT/US08/74941.
ISR—International Search Report, WO2009/029908, published May 3, 2009 for PCT/US08/74941.
IPER—Internation Preliminary Report on Patentability, WO2009/029908, published Mar. 2, 2010 for PCT/US08/74941.
Written Opinion WO2009/029908 dated Feb. 28, 2010 for PCT/US08/74941.

(56) References Cited

OTHER PUBLICATIONS

International Search Report PCT/US2010/025263 completed Apr. 13, 2010.
Written Opinion for PCT/US2010/025263 completed Apr. 13, 2010.
Arthrex, Protect your graft, Am J Sports Med, vol. 22, No. 4, Jul.-Aug. 1994.
Barrett et al, T-Fix endoscopic meniscal repair: technique and approach to different types of tears, Apr. 1995, Arthroscopy vol. 11 No. 2 p. 245-51.
Cope, Suture Anchor for Visceral Drainage, AJR, vol. 148 p. 160-162, Jan. 1986.
Gabriel, Arthroscopic Fixation Devices, Wiley Enc. of Biomed Eng., 2006.
Innovasive, We've got you covered, Am J Sports Med, vol. 26, No. 1, Jan.-Feb. 1998.
510k—TranSet Fracture Fixation System, Feb. 24, 2004, k033717.
510k—Linvatec Biomaterials modification of Duet and impact Suture Anchor, Nov. 19, 2004, k042966.
510k, arthrex pushlock, Jun. 29, 2005, K051219.
510k, mitek micro anchor, Nov. 6, 1996, K962511.
510k, Multitak Suture System, Jan. 10, 1997, K964324.
510k, Modified Mitek 3.5mm Absorbable Suture Anchor System, Jun. 9, 1997, K970896.
510K, Summary for Arthrex Inc.'s Bio-Interference Screw, Jul. 9, 1997, K971358.
510k, Surgicraft Bone Tie, Sep. 25, 1998, K982719.
Karlsson et al, Repair of Bankart lesions with a suture anchor in recurrent dislocation of the shoulder, Scand. j. of Med & Science in Sports, 1995, 5:170-174.
Madjar et al, Minimally Invasive Pervaginam Procedures, for the Treatment of Female Stress Incontinence . . . , Artificial Organs, 22 (10) 879-885, 1998.
Nowak et al, Comparative Study of Fixation Techniques in the Open Bankart Operation Using Either a Cannulated Screw or Suture-Anchors, Acta Orthopcedica Belgica, vol. 64—2—1998.
Packer et al, Repair of Acute Scapho-Lunate Dissociation Facilitated by the "Tag"* Suture Anchor, Journal of Hand Surgery (British and European vol. 1994) 19B: 5: 563-564.
Richmond, Modificatio of the Bankart reconstruction with a suture anchor, Am J Sports Med, vol. 19, No. 4, p. 343-346, 1991.
Shea et al, Technical Note: Arthroscopic Rotator Cuff Repair Using a Transhumeral Approach to Fixation, Arthroscopy: The Journal of Arthroscopic and Related Surgery, vol. 14, No. 1 (Jan.-Feb. 1998), pp. 118-122.
Tfix, Acufex just tied the knot . . . , Am. J. Sports Med., vol. 22, No. 3, May-Jun. 1994.
Wong et al, Case Report: Proper Insertion Angle Is Essential to Prevent Intra-Articular Protrusion of a Knotless Suture Anchor in Shoulder Rotator Cuff Repair, Arthroscopy: The Journal of Arthroscopic and Related Surgery, vol. 26, No. 2 (Feb. 2010), pp. 286-290.
Cobb et al, Late Correction of Malunited Intercondylar Humeral Fractures Intra-Articular Osteotomy and Tricortical Bone Grafting, J BoneJointSurg [Br] 1994; 76-B:622-6.
Fellinger, et al, Radial avulsion of the triangular fibrocartilage complex in acute wrist trauma: a new technique for arthroscopic repair, Jun. 1997, Arthroscopy vol. 13 No. 3 p. 370-4.
Hecker et al , Pull-out strength of suture anchors for rotator cuff and Bankart lesion repairs, Nov.-Dec. 1993 , The American Journal of Sports Medicine, vol. 21 No. 6 p. 874-9.
Hernigou et al , Proximal Tibial Osteotomy for Osteoarthritis with Varus Deformity a Ten to Thirteen-Year Follow-Up Study, J Bone Joint Surg, vol. 69-A, No. 3. Mar. 1987, p. 332-354.
Ibarra et al, Glenoid Replacement in Total Shoulder Arthroplasty, The Orthopedic Clinics of Northamerica: Total Shoulder Arthroplasty, vol. 29 No. 3, Jul. 1998 p. 403-413.
Mosca et al, Calcaneal Lengthening for Valgus Deformity of the Hindfoot: Results in Children Who Had Severe, Symptomatic flatfoot and Skewfoot, J Bone Joint Surg,, 1195—p. 499-512.

Murphycet al , Radial Opening Wedge Osteotomy in Madelung's Deformity, J. Hand Surg, vol. 21 A No. 6 Nov. 1996, p. 1035-44.
Biomet, Stanmore Modular Hip, J. Bone Joint Surg., vol. 76-B : No. Two, Mar. 1994.
Intl Prelim Rep on Patentability and Written Opinion for PCT/US10/25263 dated Aug. 30, 2011.
Declaration of David Kaplan, Ph.D. Regarding U.S. Pat. No. 5,980,559, IPR 2013-00603, Sep. 24, 2013.
Petition for Inter Partes Review of U.S. Pat. No. 7,087,073, IPR 2013-00604, Filing Date Sep. 24, 2013.
Declaration of Wayne J. Sebastianelli, MD Regarding U.S. Pat. No. 7,087,073, Sep. 24, 2013, IPR 2013-00604.
Petition for Inter Partes Review of U.S. Pat. No. 6,500,195, IPR 2013-00624, Filing Date Oct. 2, 2013.
Declaration of Dr. Philip Hardy in Support of Petition for Inter Partes Review of U.S. Pat. No. 6,500,195, IPR 2013-00624, Sep. 25, 2013.
Petition for Inter Partes Review of U.S. Pat. No. 5,527,343, IPR 2013-00628, Filing Date Sep. 26, 2013, Sep. 25, 2013.
Declaration of Dr. Philip Hardy in Support of Petition for Inter Partes Review of U.S. Pat. No. 5,527,343, IPR 2013-00628, Sep. 25, 2013.
Corrected Petition for Inter Partes Review of U.S. Pat. No. 5,921,986, IPR 2013-00631, Filing Date Sep. 27, 2013.
Expert Declaration of Steve E. Jordan, MD, for Inter Partes Review of U.S. Pat. No. 5,921,986, IPR 2013-00631, Sep. 24, 2013.
Corrected Petition for Inter Partes Review of U.S. Pat. No. 8,147,514, IPR 2013-00632, Filing Date Sep. 27, 2013.
Declaration of Steve Jordan for U.S. Pat. No. 8,147,514, from IPR 2013-00632, dated Sep. 23, 2013 (exhibit 1009).
Corrected Petition for Inter Partes Review of U.S. Pat. No. 8,147,514, IPR 2013-00633, Filing Date Sep. 27, 2013.
Declaration of Steve Jordan for U.S. Pat. No. 8,147,514, from IPR 2013-00633, dated Sep. 23, 2013 (exhibit 1006).
Flory, Principles of Polymer Chemistry, 1953, selected pages (cited in IPR 2013-00603, exhibit 1012).
Grizzi, Hydrolytic degradation of devices based on poly(DL-lactic acid) size-dependence, Biomaterials, 1995, vol. 16, No. 4, p. 305-11 (cited in IPR 2013-00603, exhibit 1006).
Gopferich, Mechanisms of polymer degradation and erosion, Biomaterials, 1996, vol. 17, No. 2, p. 103-114 (cited in IPR 2013-00603, exhibit 1013).
Gao et el, Swelling of Hydroxypropyl Methylcellulose Matrix Tablets . . . , J. of Pharmaceutical Sciences, vol. 85, No. 7, Jul. 1996, p. 732-740 (cited in IPR 2013-00603, exhibit 1014).
Linvatec, Impact Suture Anchor brochure, 2004 (cited in IPR 2013-00628, exhibit 1010).
Seitz et al, Repair of the Tibiofibular Syndesmosis with a Flexible Implant, J. of Orthopaedic Trauma, vol. 5, No. 1, p. 78-82, 1991 (cited in IPR 2013-00631, exhibit 1007) (cited in 2013-00632).
Translation of FR2696338 with translator's certificate dated Sep. 17, 2013 (cited in IPR 2013-00631, 2013-00632).
Translation of DE9002844.9 with translator's certificate dated Sep. 26, 2013 (cited in IPR 2013-00631, 2013-00632).
Declaration of Steve Jordan for U.S. Pat. No. 5,921,986, from IPR 2013-00632, dated Sep. 24, 2013 (exhibit 1010).
Declaration of Steve Jordan for U.S. Pat. No. 5,921,986, from IPR 2013-00633, dated Sep. 24, 2013 (exhibit 1007).
Declaration of Dr. Steve E. Jordan for U.S. Pat. No. 8,147,514, from IPR 2013-00631, dated Sep. 23, 2013.
Petition for Inter Partes Review of U.S. Pat. No. 5,980,559, IPR 2013-00603, Filing Date Sep. 24, 2013.
Non-Final Office Action dated Jun. 25, 2015 relating to U.S. Appl. No. 11/671,556, 11 pages.
Non-Final Office Action dated Jul. 22, 2015 relating to U.S. Appl. No. 12/711,540, 8 pages.
Non-Final Office action for U.S. Appl. No. 15/436,168, dated Jun. 4, 2018, 12 pages.

* cited by examiner

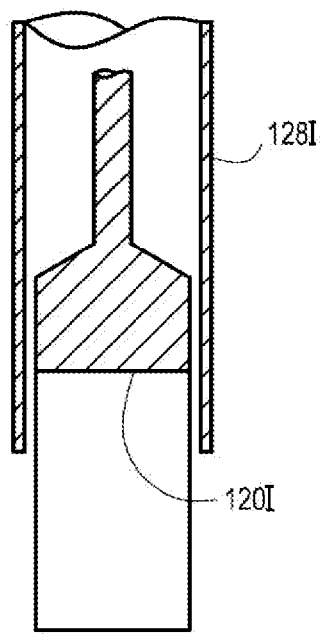
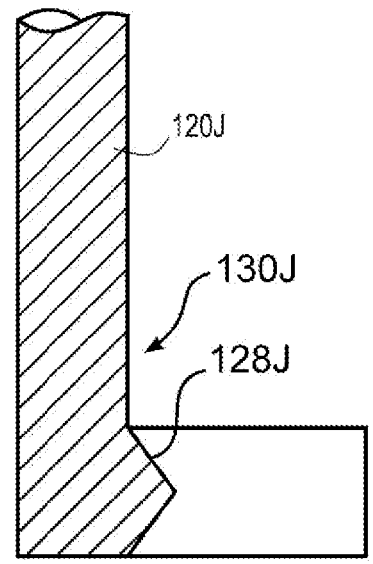
FIG. 3I    FIG. 3J
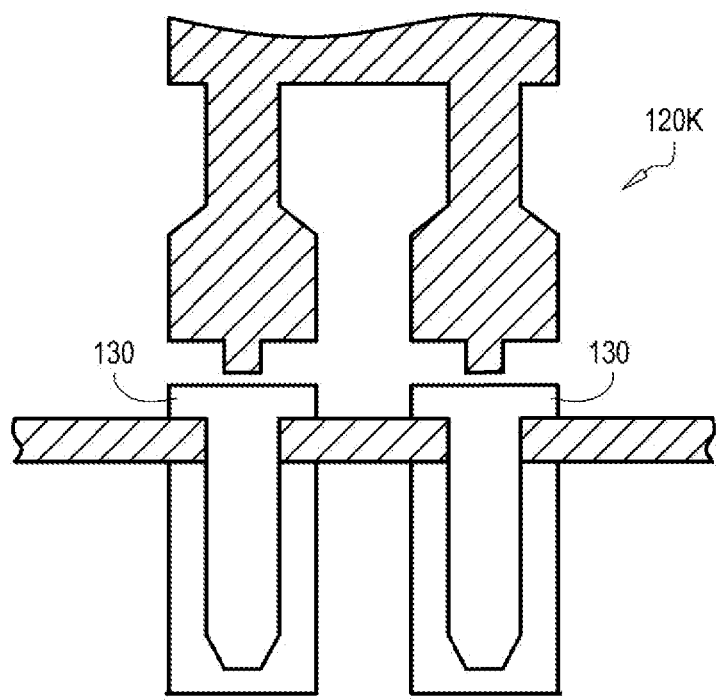
FIG. 3K

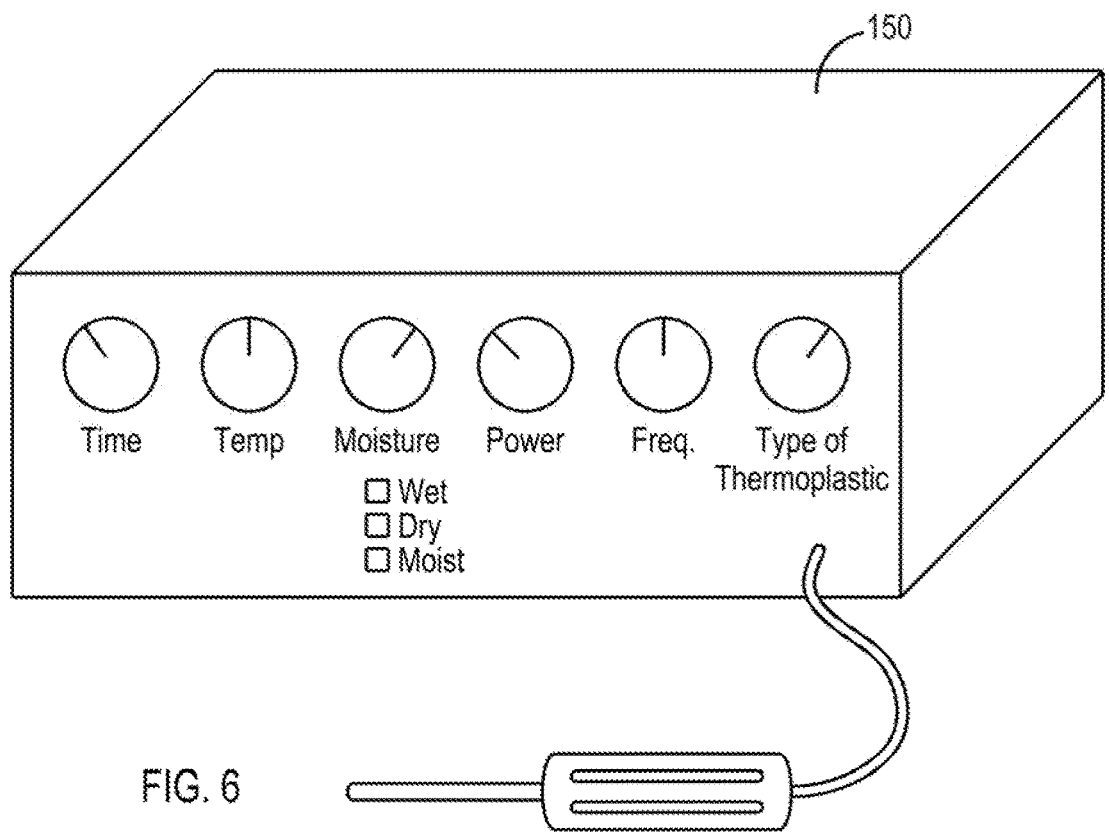
FIG. 6
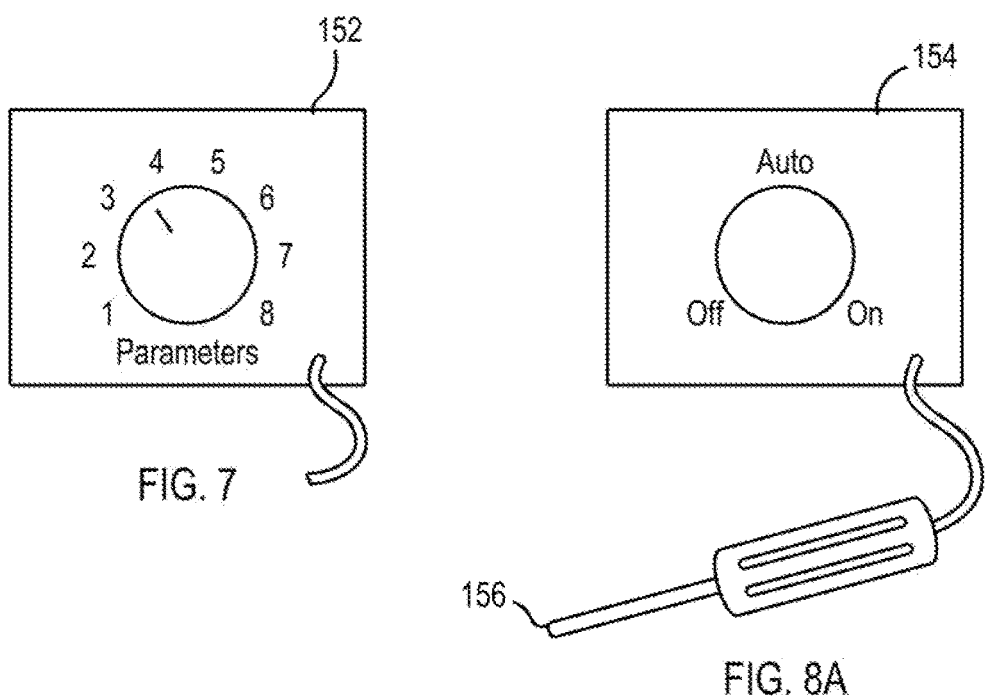
FIG. 7
FIG. 8A

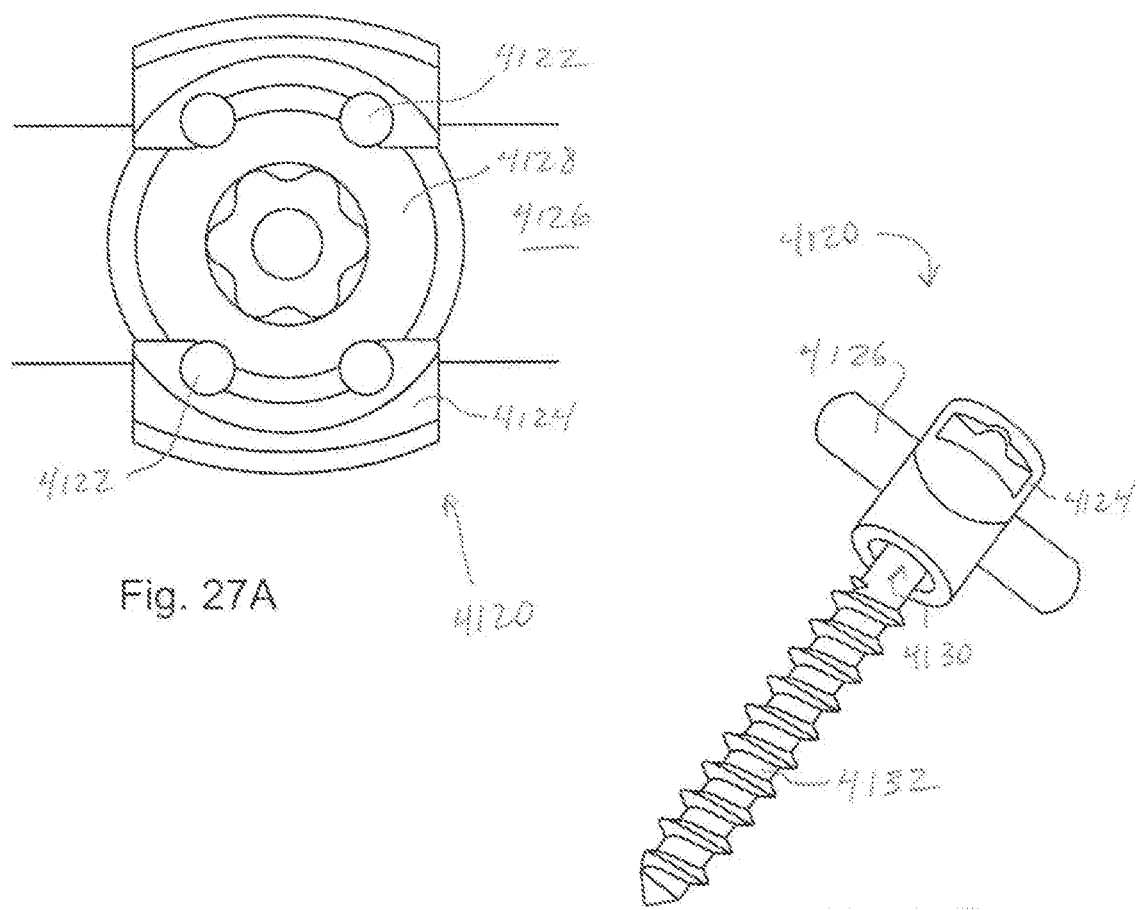

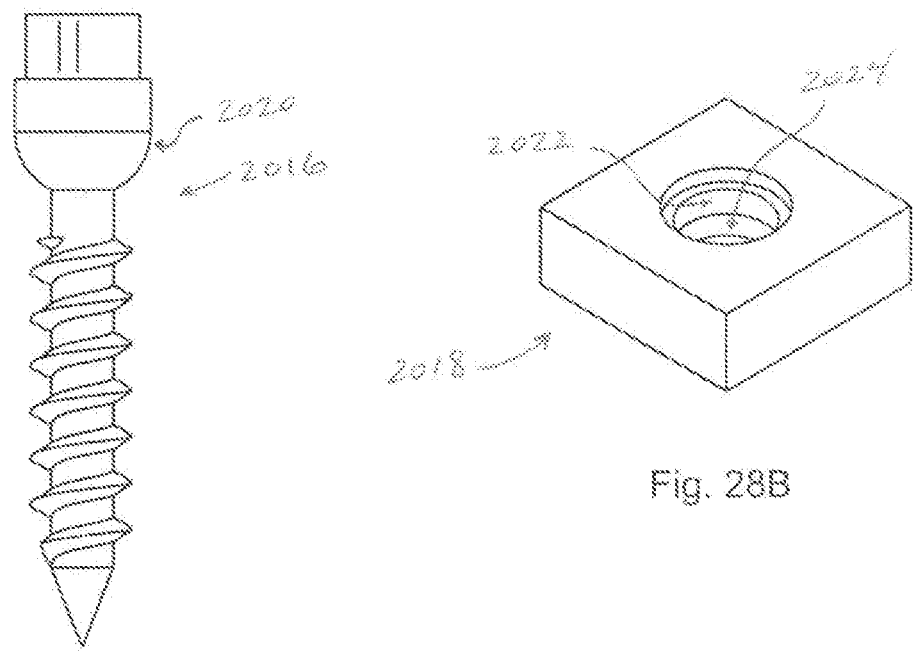
Fig. 28A
Fig. 28B
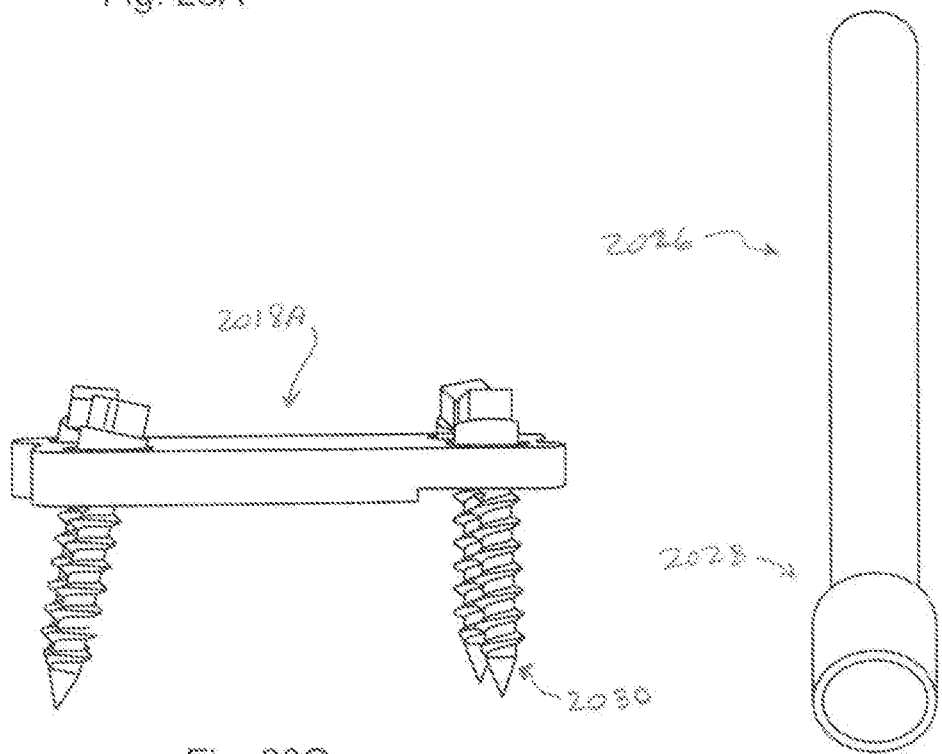
Fig. 28C
Fig. 29

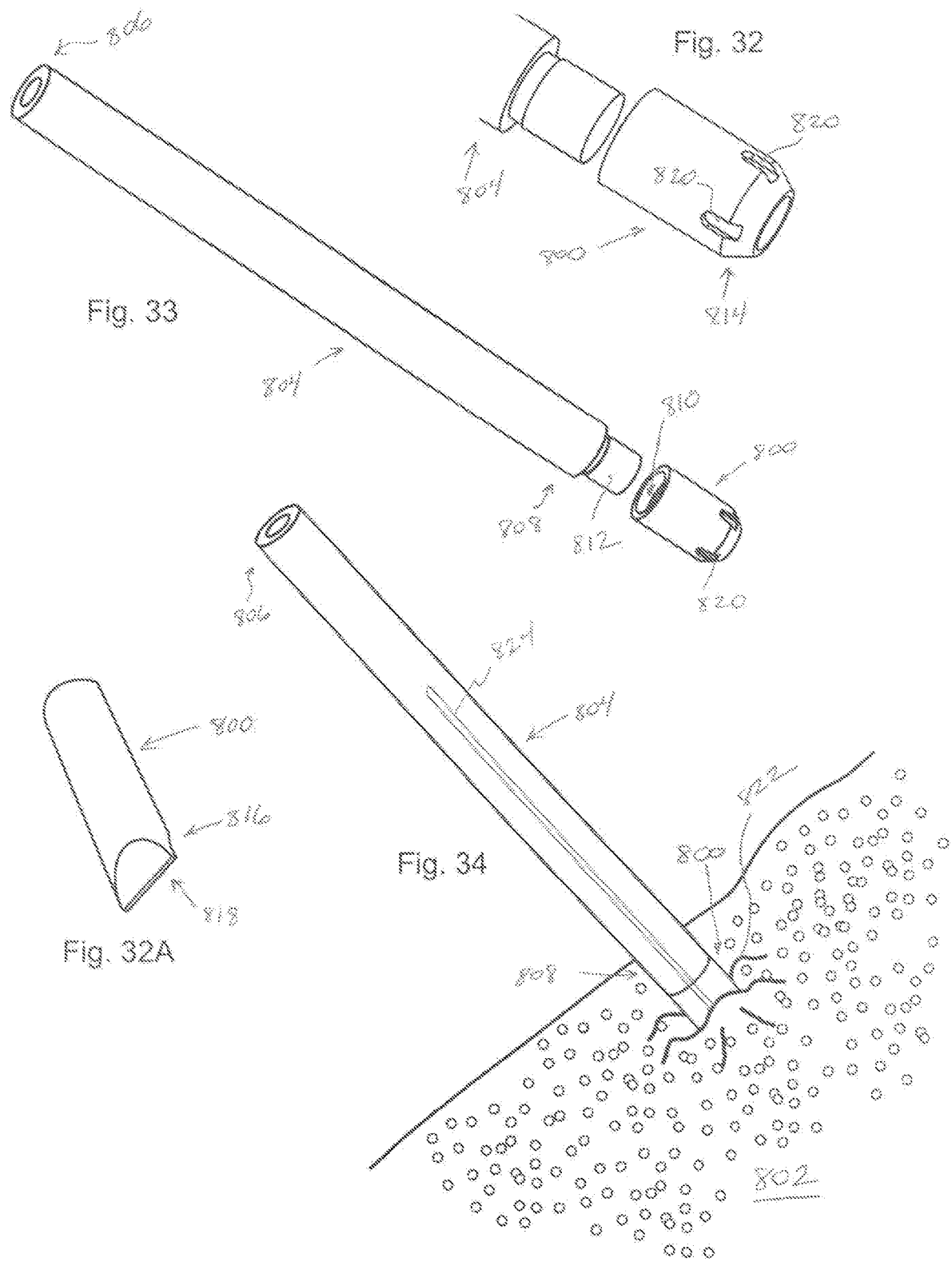

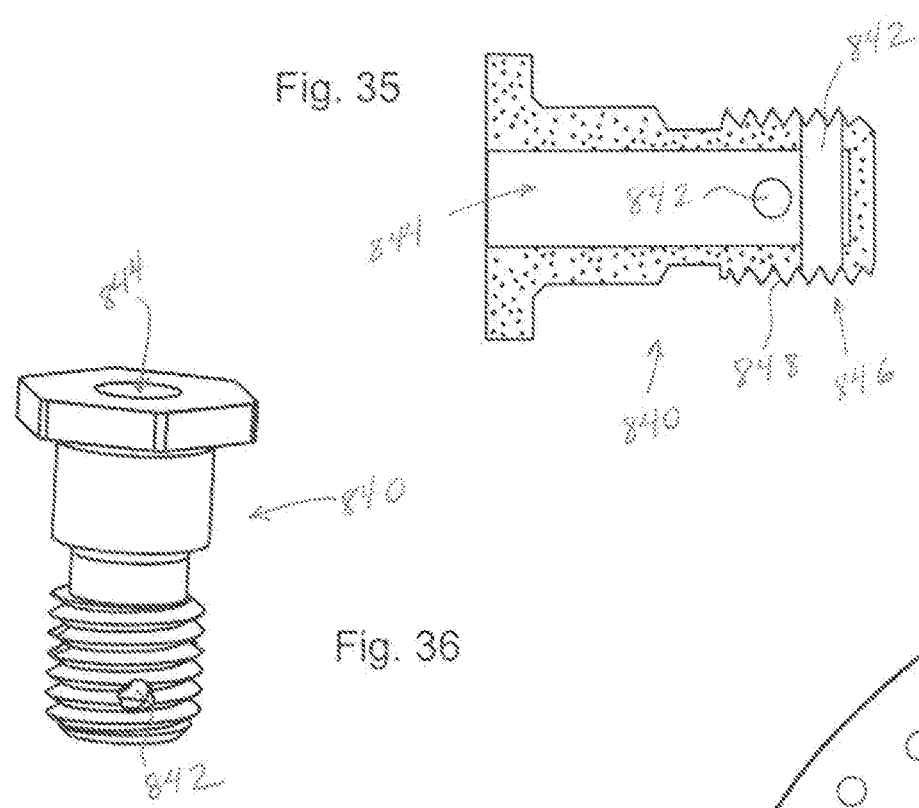

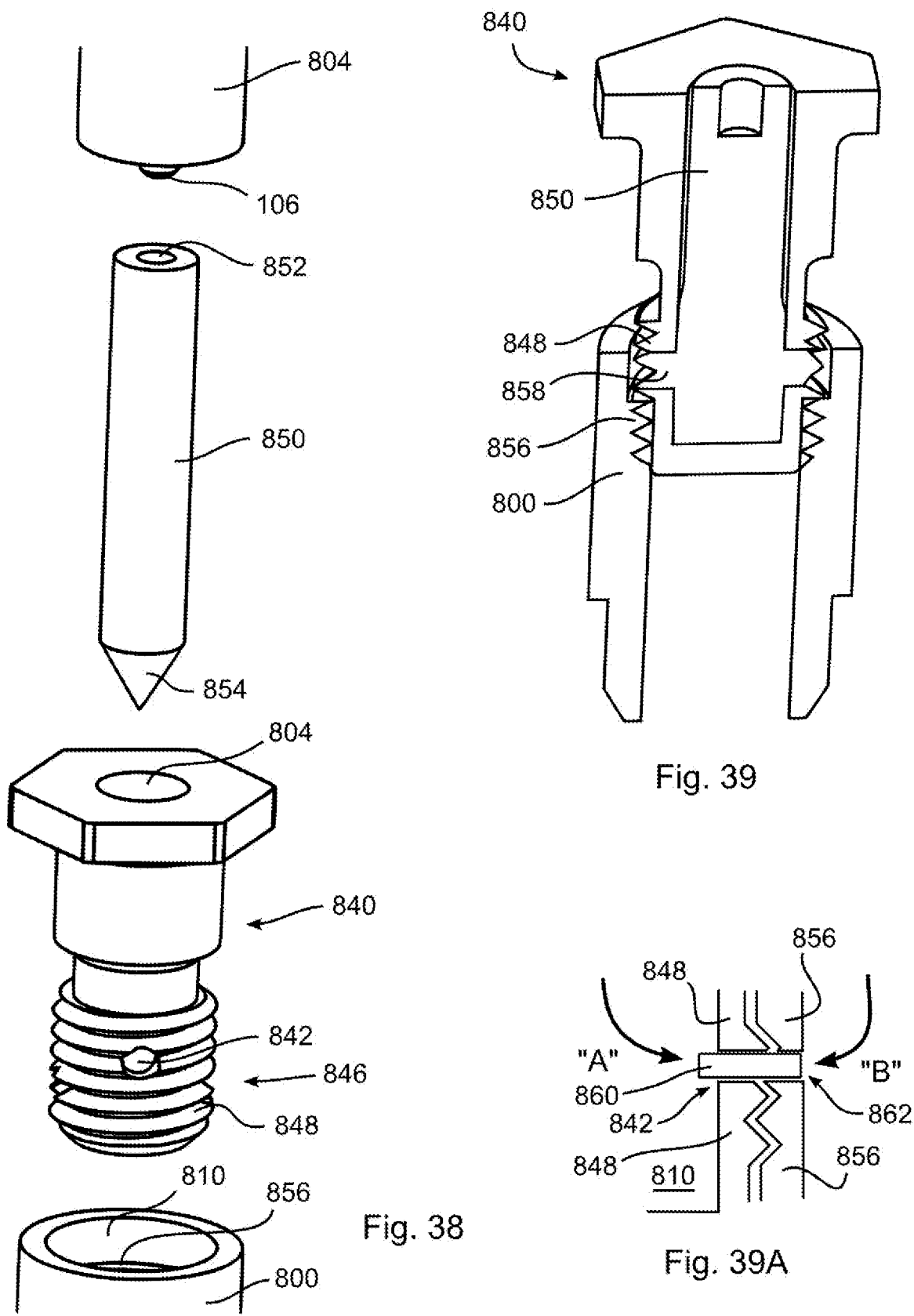

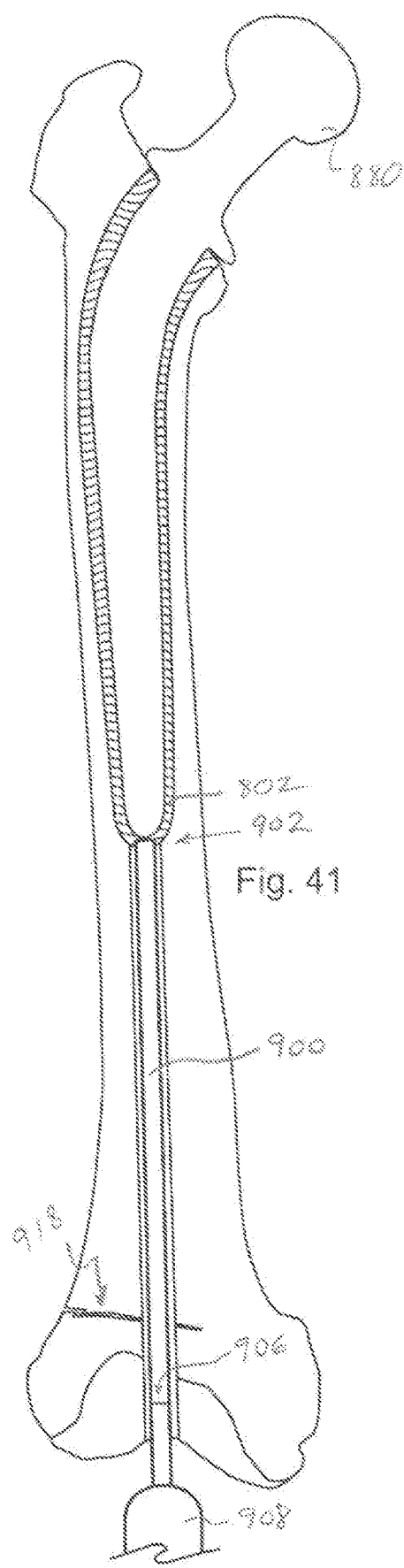
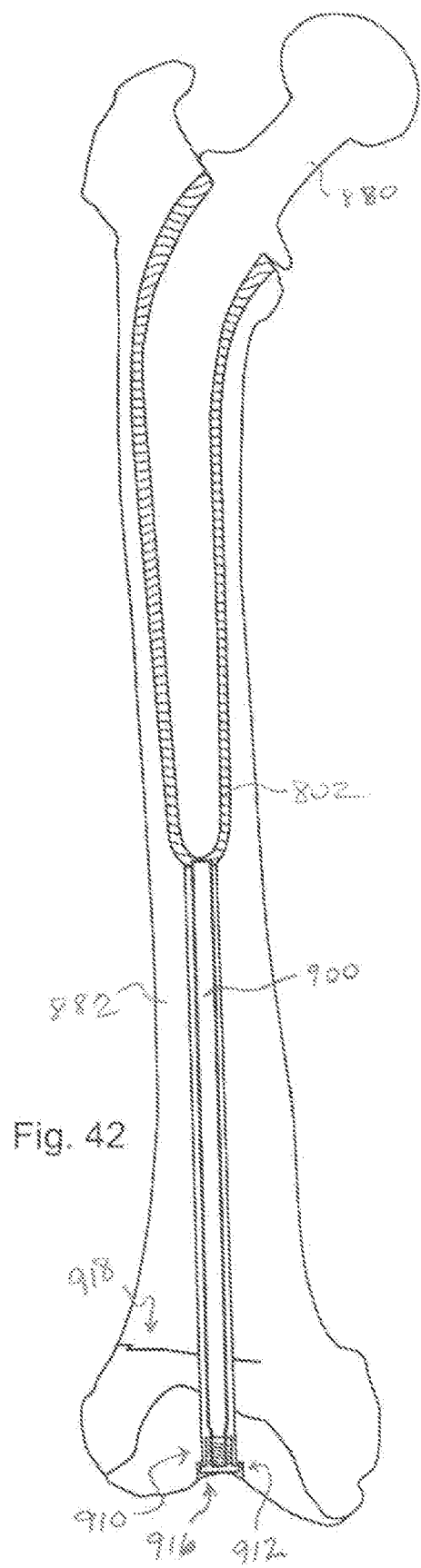

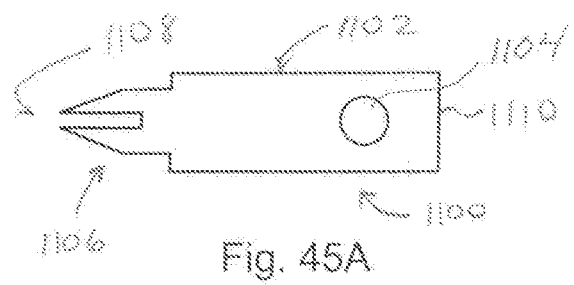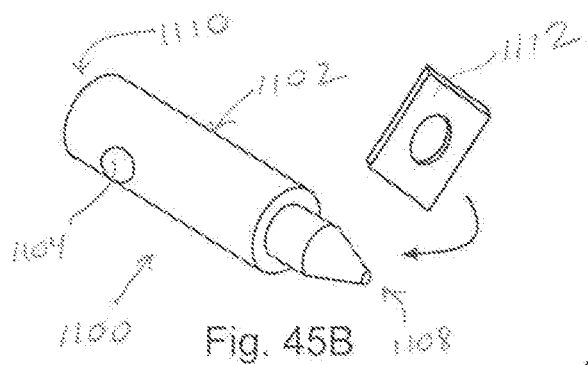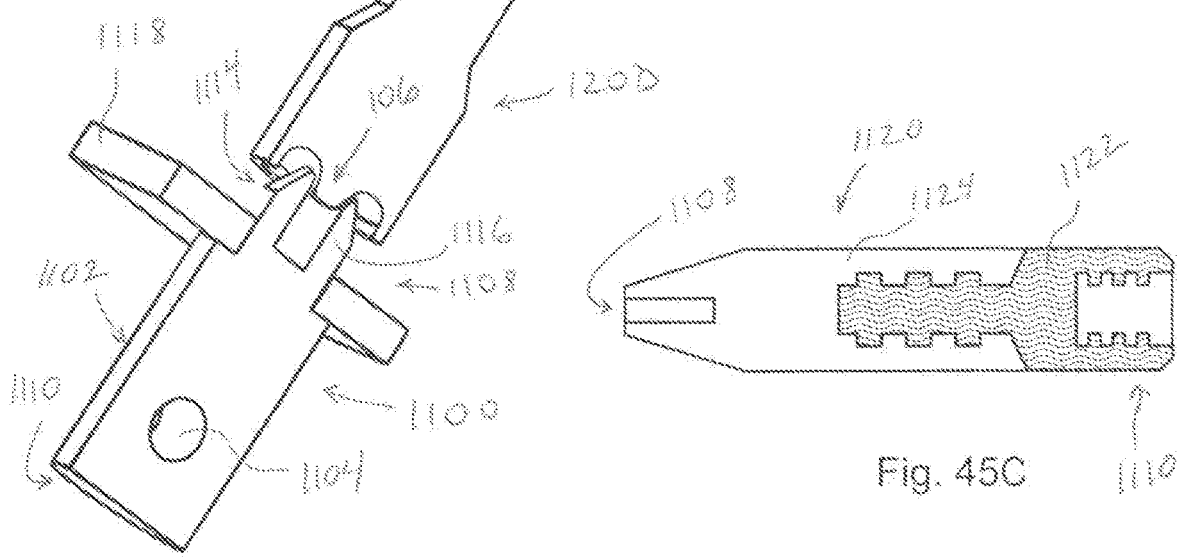

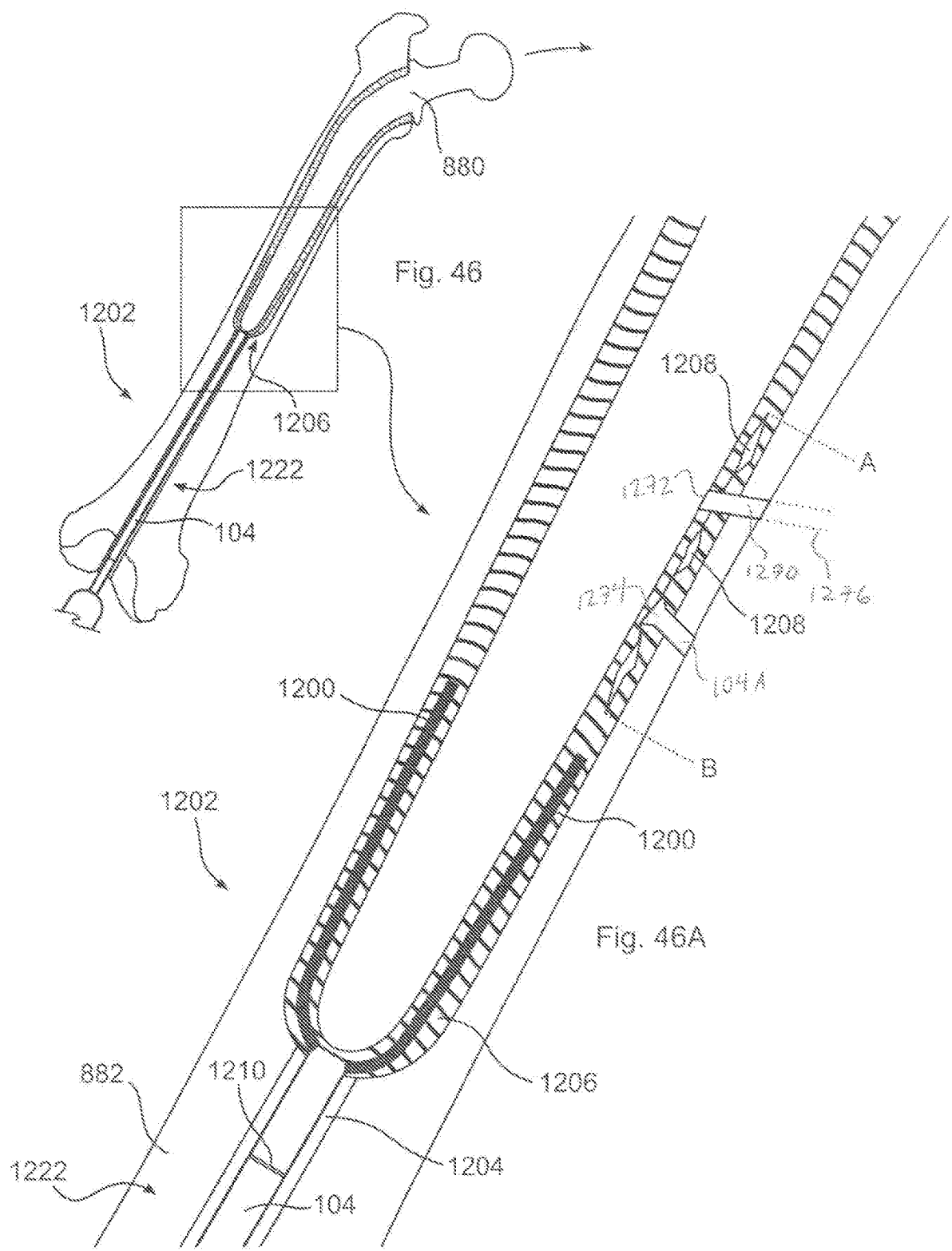

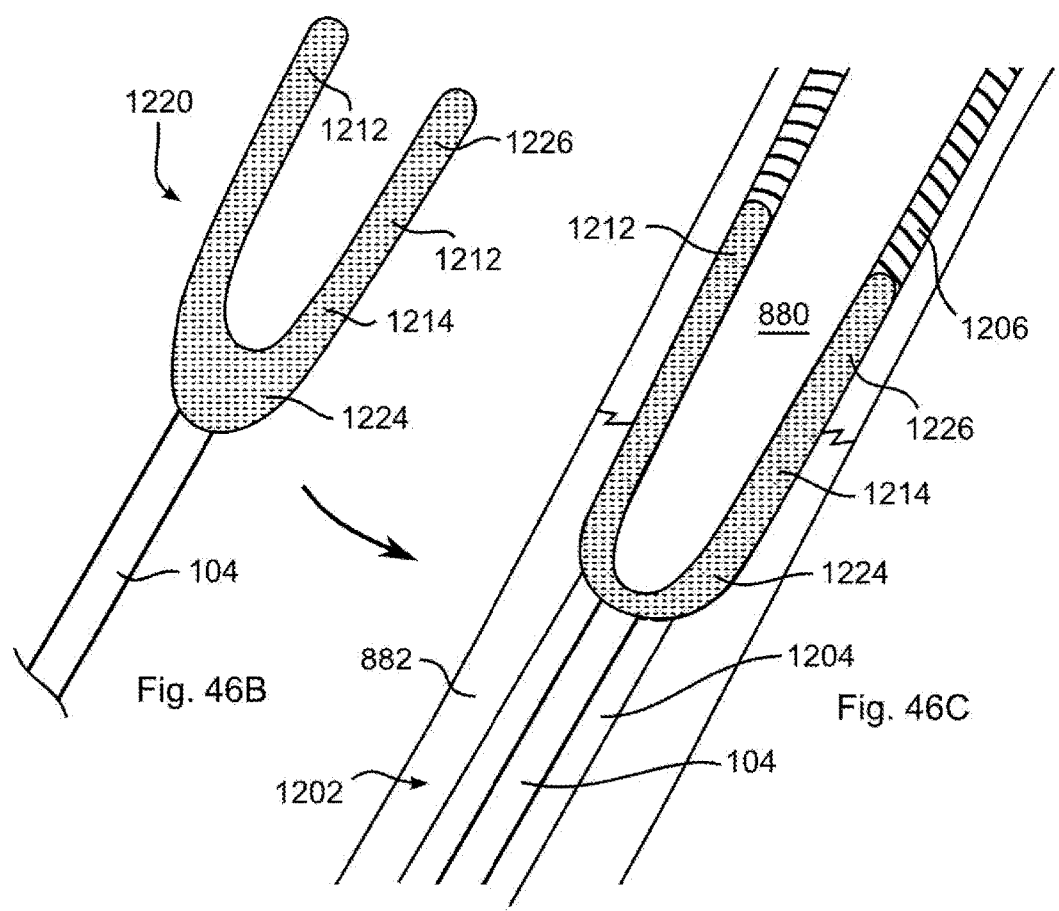
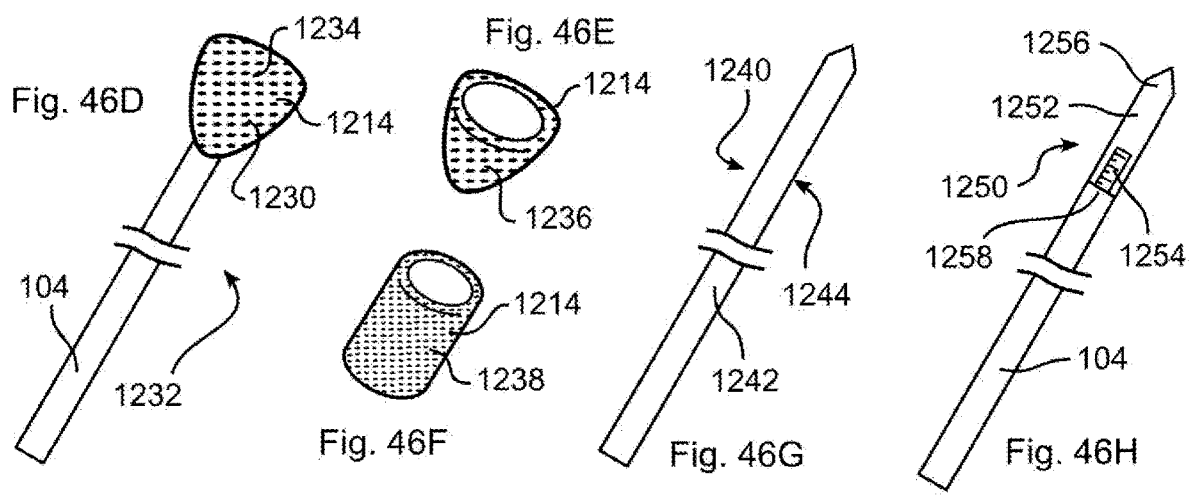

Fig. 47B - Prior Art

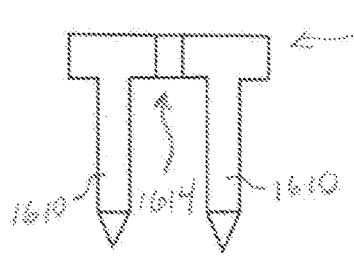
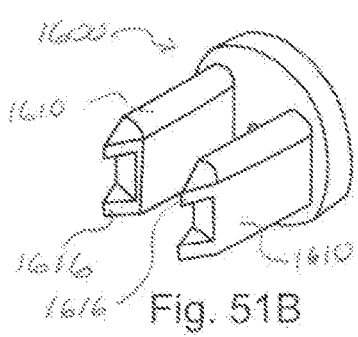
Fig. 51A    Fig. 51B
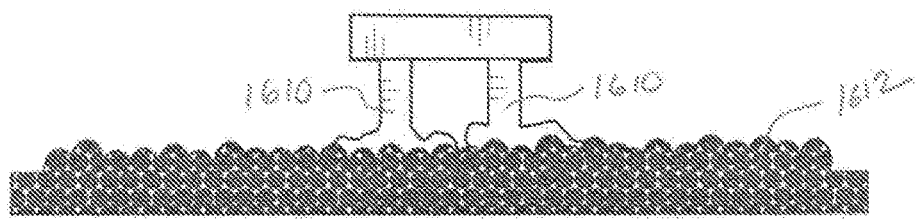
Fig. 51
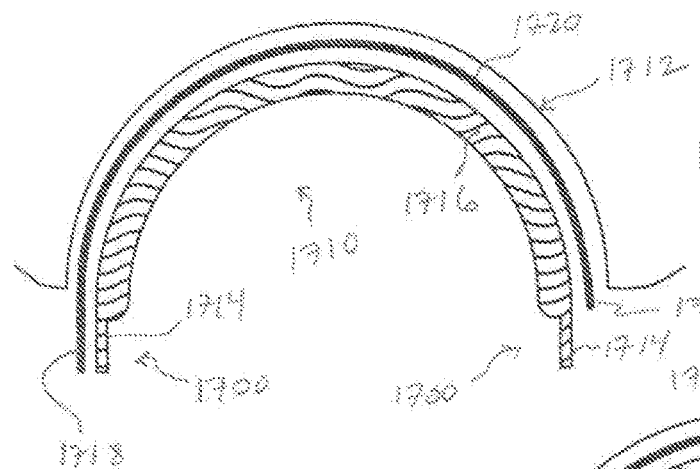
Fig. 52A
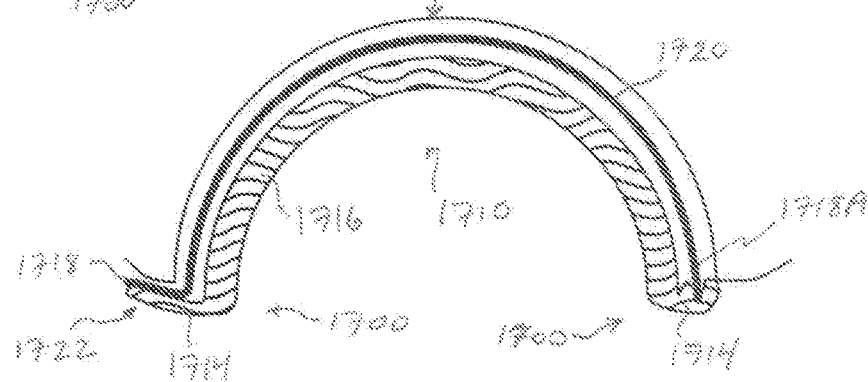
Fig. 52B

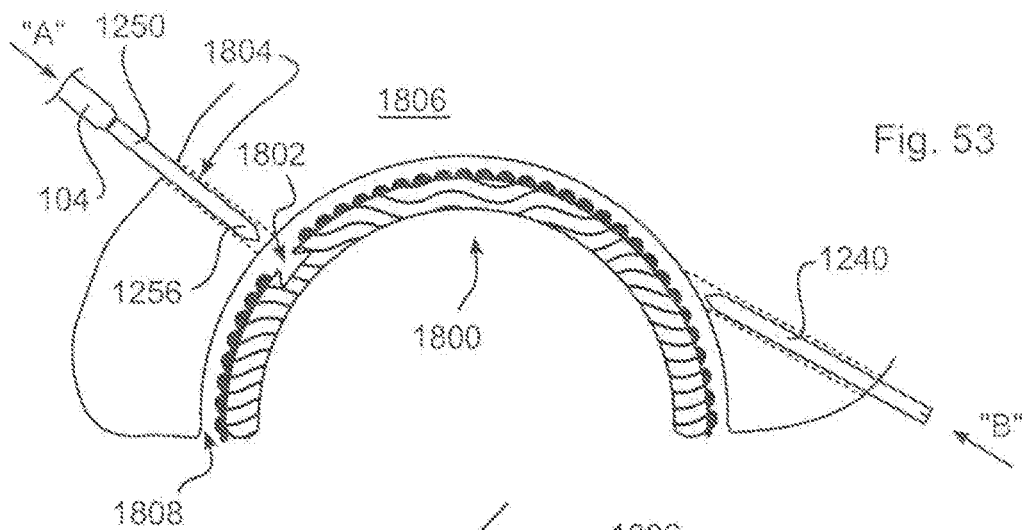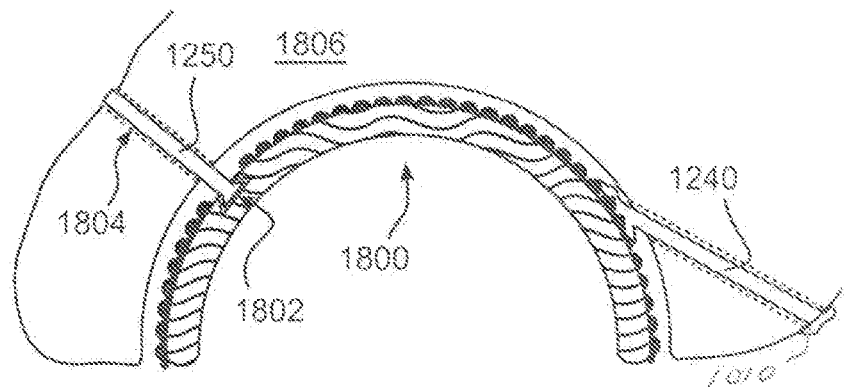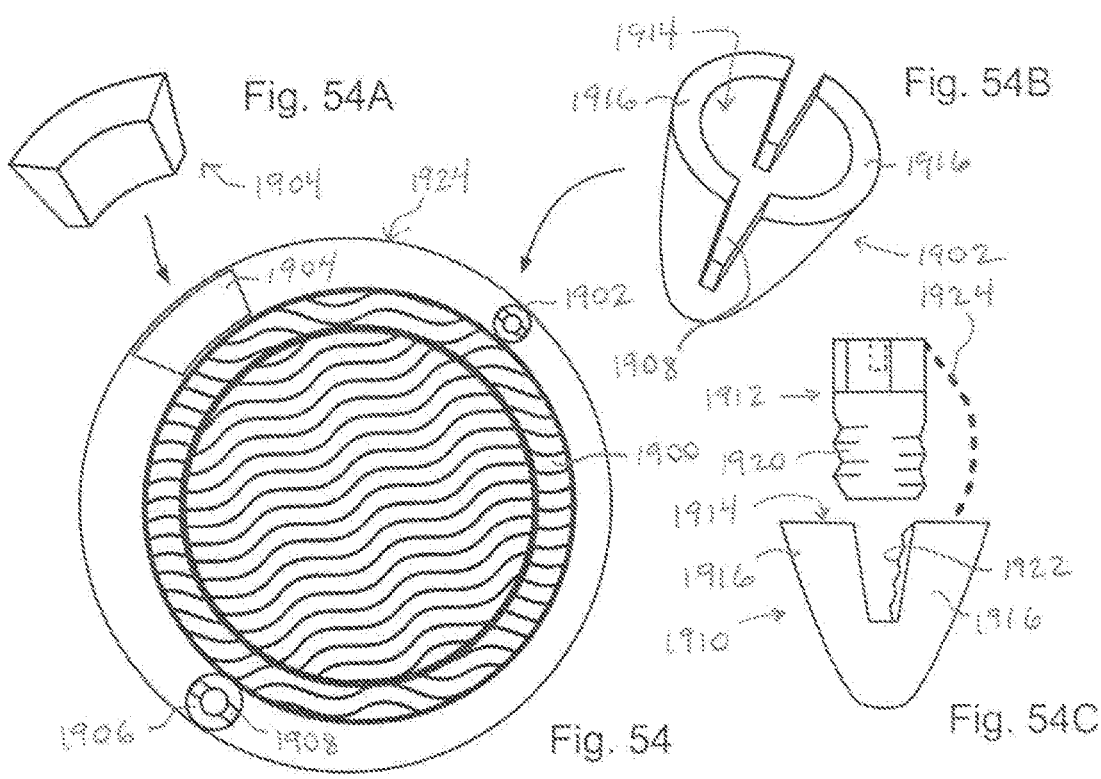

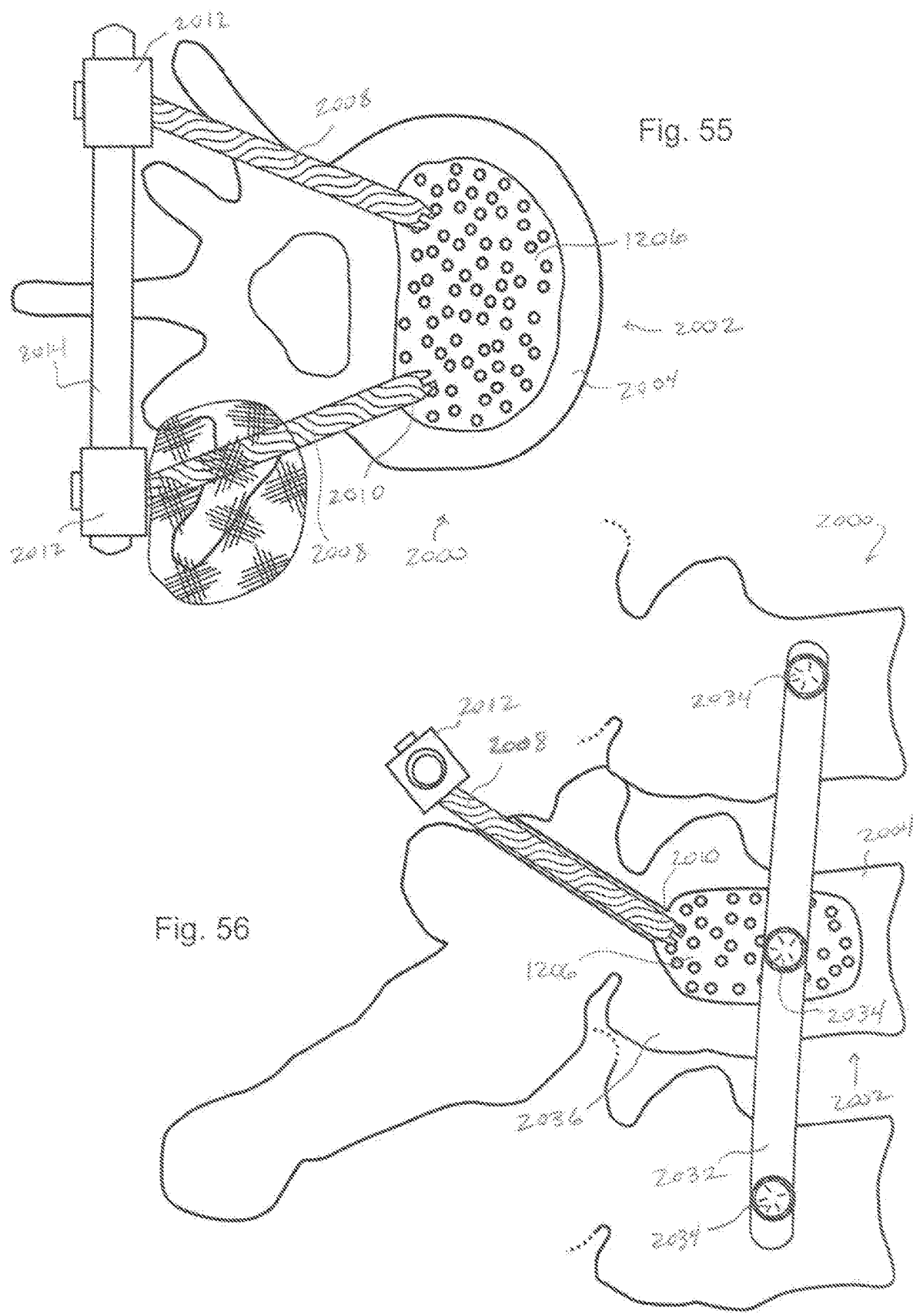

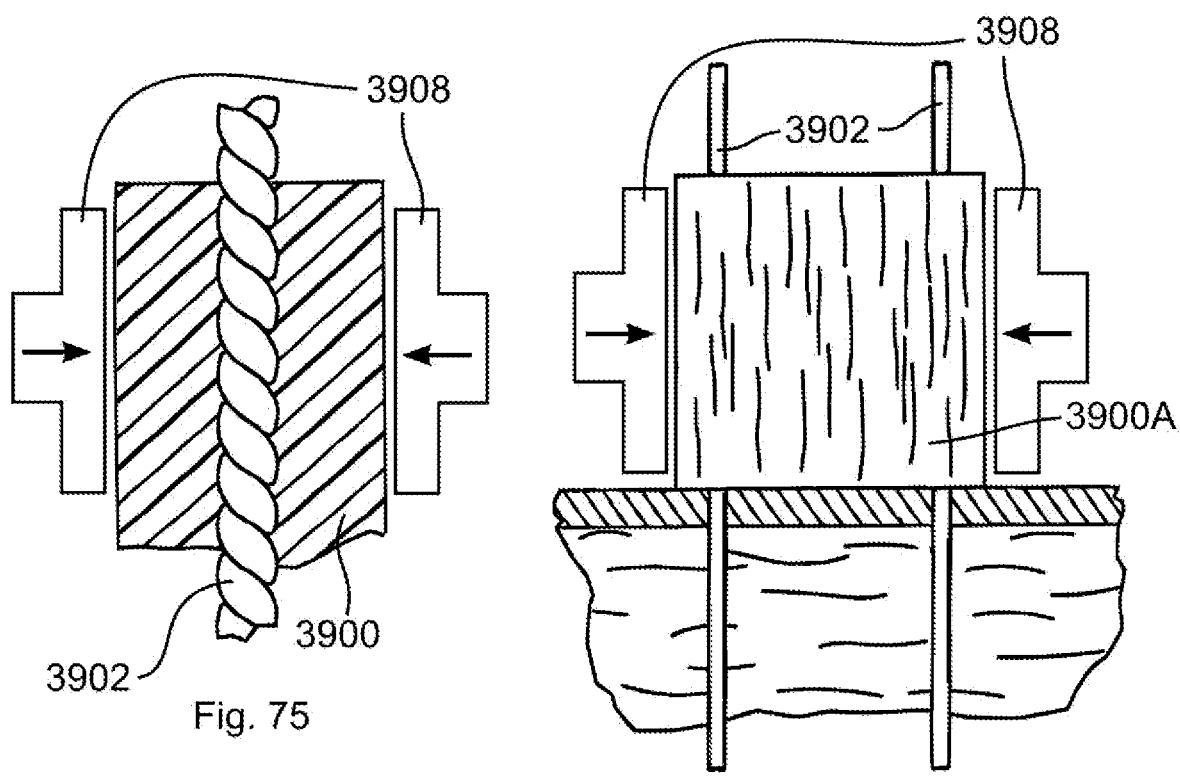
Fig. 75
Fig. 76
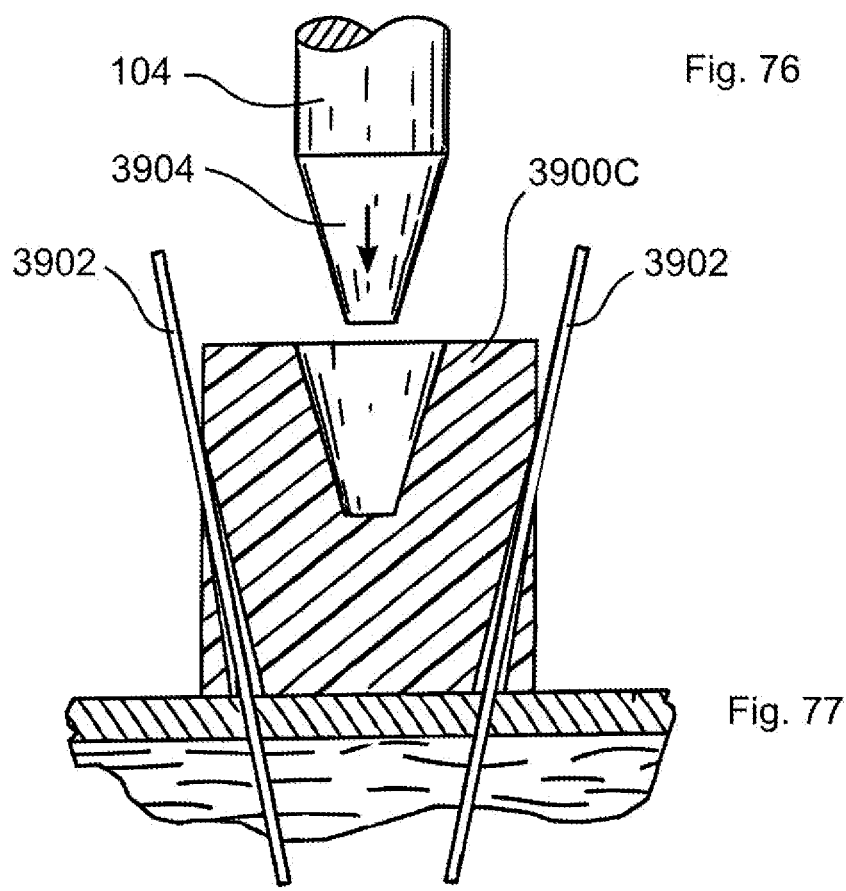
Fig. 77

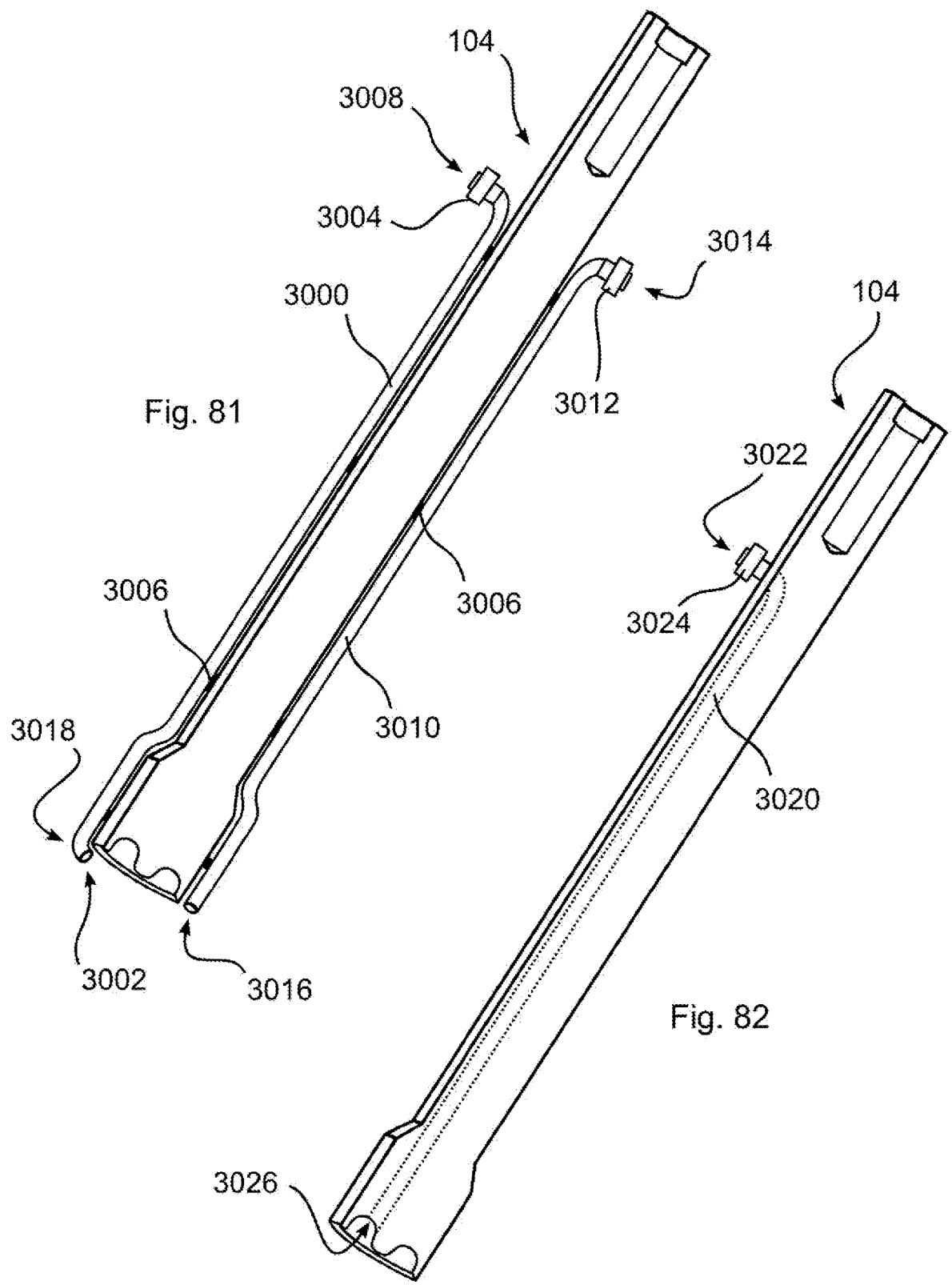

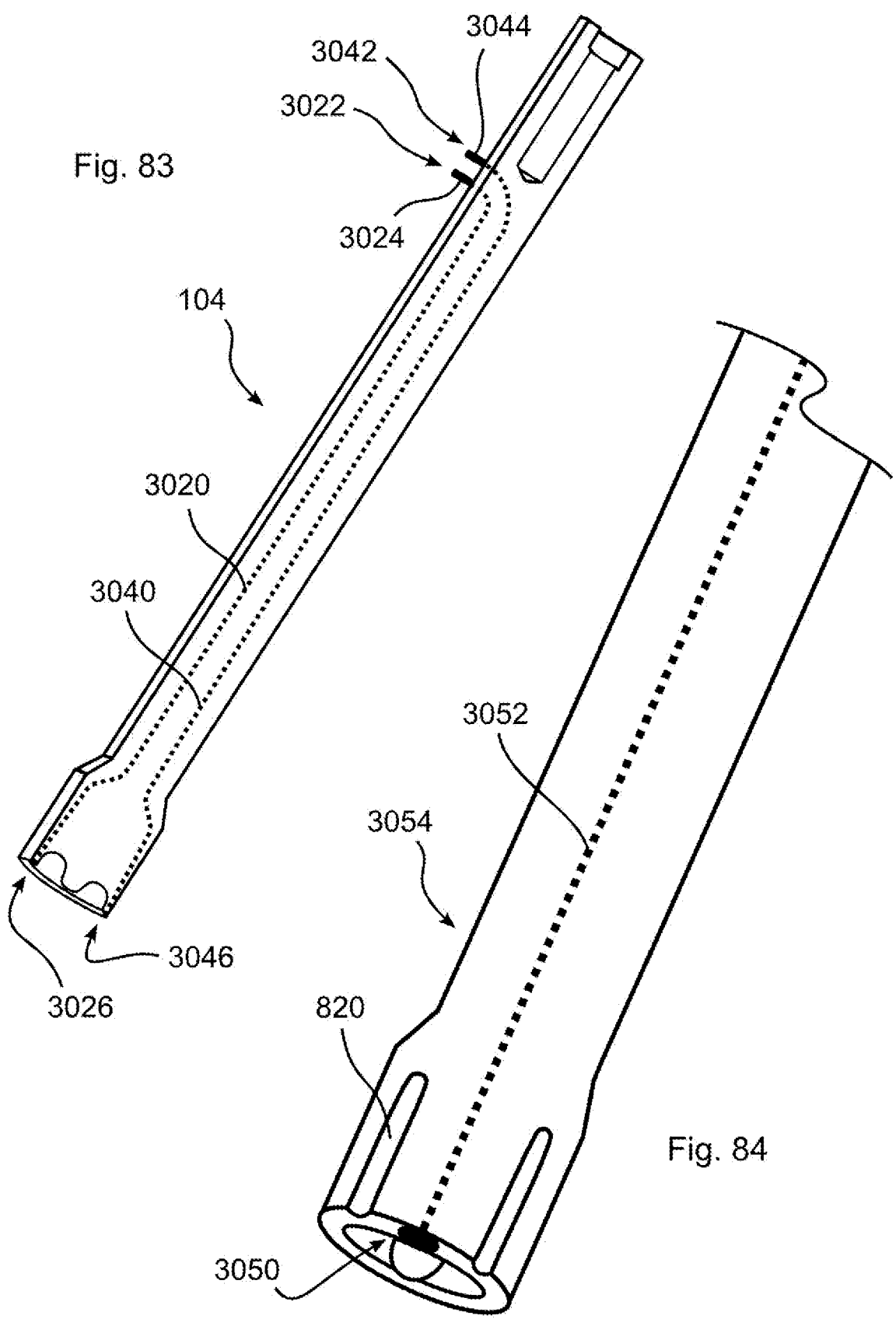

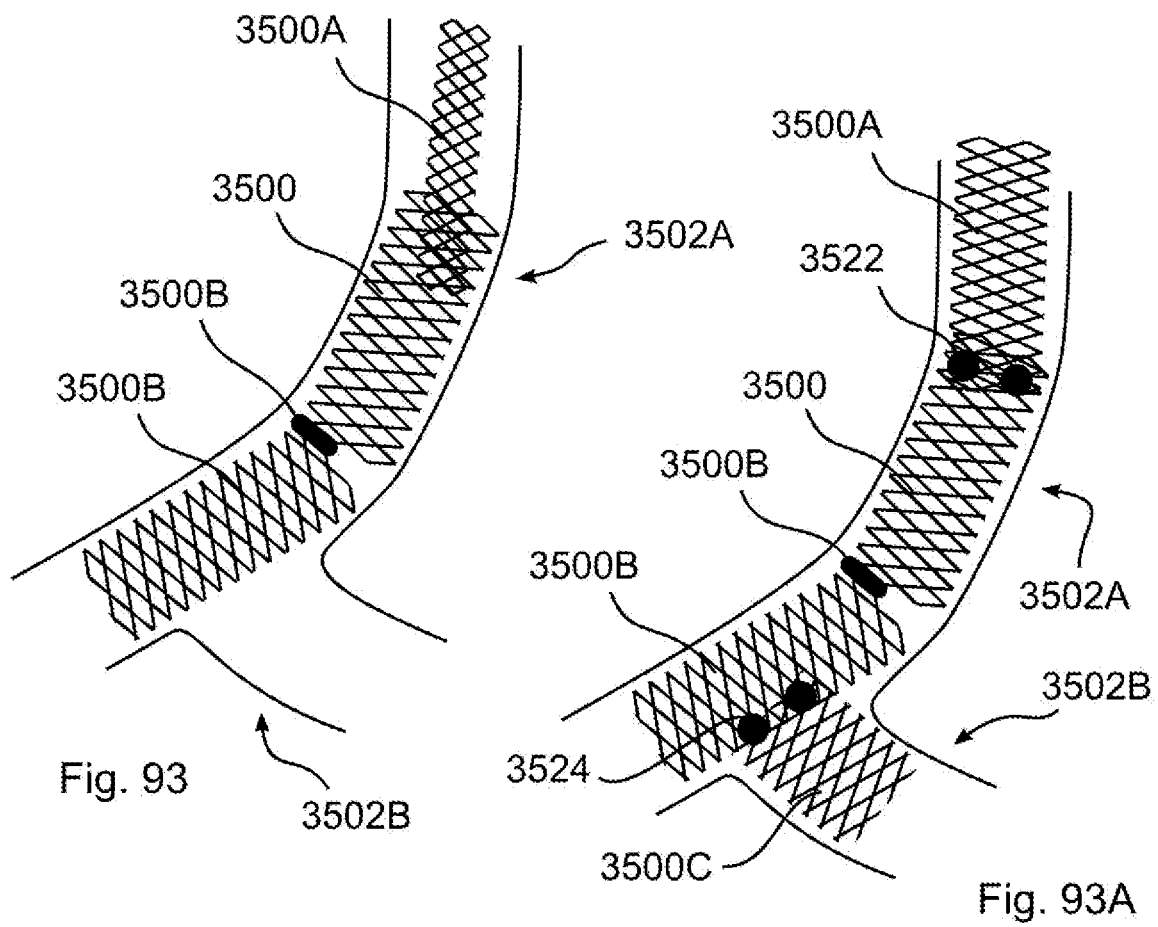
Fig. 93
Fig. 93A
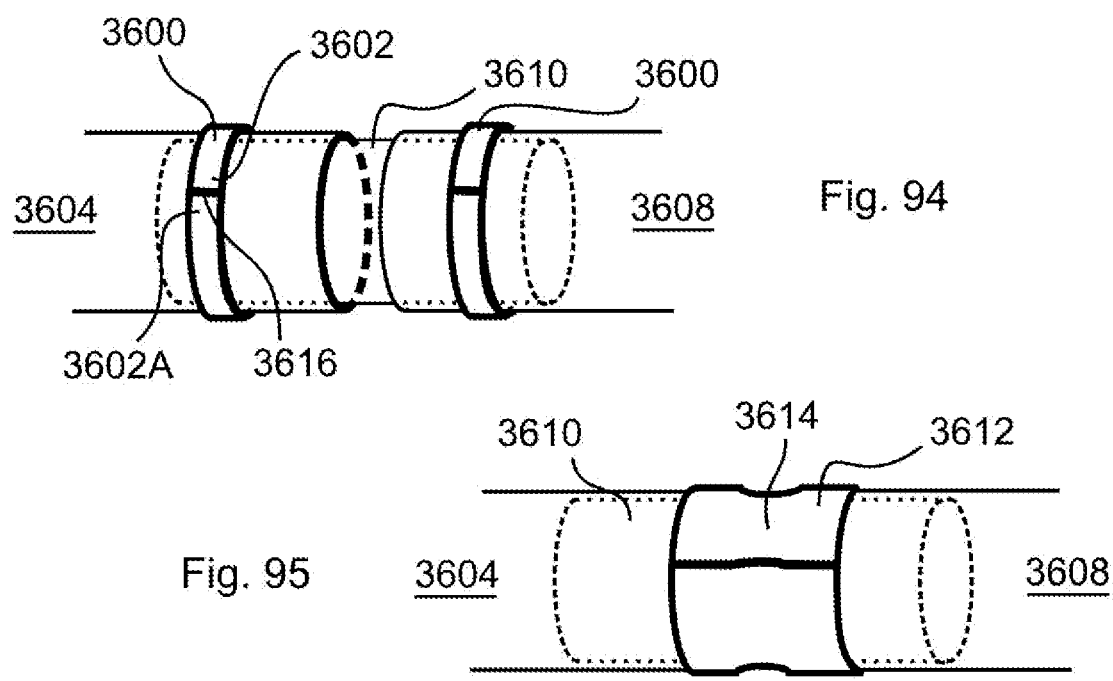
Fig. 94
Fig. 95

METHODS OF SECURING A FASTENER

CROSS REFERENCE TO RELATED APPLICATIONS

This application is a continuation of U.S. patent application Ser. No. 12/202,210, filed Aug. 29, 2008, which is a non-provisional patent application claiming benefit under 35 U.S.C. § 119(e) of U.S. Provisional Application No. 60/968,969, filed Aug. 30, 2007, the entire contents of which are hereby expressly incorporated by reference into this disclosure as if set forth fully herein. This application is also a continuation-in-part application of: U.S. patent application Ser. No. 11/416,618 filed May 3, 2006; U.S. patent application Ser. No. 11/689,670, filed Mar. 22, 2007; and U.S. patent application Ser. No. 11/671,556, filed Feb. 6, 2007. The '556 application claimed the benefit of the following U.S. Provisional Applications: 60/765,857 filed Feb. 7, 2006; 60/784,186 filed Mar. 21, 2006; and 60/810,080 filed Jun. 1, 2006. The entire contents of each of the aforementioned applications are hereby expressly incorporated by reference into this disclosure as if set forth fully herein.

FIELD

The invention relates to fixation or fastening of tissues and implants within the body, such as the fastening of two different tissue types, the fastening of an implant to tissue, or the fastening of an implant to another implant. This may involve using an energy source to bond and/or mechanically interlock biocompatible materials intracorporeally to stabilize tissue within a patient's body, such as a fractured bone. The present invention also relates to the use of an energy source to remove an implant.

BACKGROUND

Body tissue often requires repair and stabilization following trauma such as a fractured bone, torn ligament or tendon, ripped muscle, or the separation of soft tissue from bone. For example, trauma to the rotator cuff usually results in a portion, if not all, of the ligament being torn away from bone. To repair such an injury, the rotator cuff must be repositioned to its anatomically correct location and secured to the bone.

One method of repairing a damaged rotator cuff is through the use of a bone anchor and a suture. A hole is drilled in the bone near where the rotator cuff will be reattached to the bone. Then, an instrument is used to place a mattress stitch with a suture in the detached portion of the rotator cuff. The suture is slideably positioned through the anchor, and the anchor is placed in the bone hole using an insertion instrument. This instrument includes an anvil and mandrel placed in contact with the anchor so that when the anvil and mandrel are moved in opposite directions relative to each other, the anchor is deformed. The deformation locks the anchor within the bone. Thereafter, the suture is tensioned drawing the rotator cuff toward the anchor. A suture lock is then activated by the insertion instrument to thereby pinch the suture between the anchor and suture lock.

In another example, fractured bones are a common injury seen in trauma centers. Sports activities, vehicle accidents, industrial-type incidents, and slip and fall cases are just a few examples of how bones may become fractured. Surgeons in trauma centers frequently encounter many different types of fractures with a variety of different bones. Each bone and each fracture type may require unique procedures and devices for repairing the bone. Currently, a one-solution-fixes-all device is not available to repair fractured bones. Instead, surgeons may use a combination of bone screws, bone plates, and intramedullary rods.

Bone plates may be positioned internal to the skin, i.e. positioned against the fractured bone, or may be positioned external to the skin with rods connecting the bone and plate. Conventional bone plates are particularly well-suited to promote healing of the fracture by compressing the fracture ends together and drawing the bone into close apposition with other fragments and the bone plate. However, one drawback with plates and screws is that with the dynamic loading placed on the plate, loosening of the screws and loss of stored compression can result.

To reduce the potential of loosening, locking screws and a locking bone plate may be used. U.S. Pat. No. 5,085,660 to Lin discloses a locking plate system. The system has multiple locking pins, each with one end formed as a screw to lock in the pending fastening bones or vertebral tubercles, with another end defining rectangular or similarly shaped locking post having a threaded locking end. Near the locking post end, there is formed a stopping protrusion. A plate defines multiple locking bores disposed at one side to be placed over the locking post end until the plate reaches the stopping protrusion on the locking pin. The plate defines multiple threaded screwing bores near the other side to receive locking pin screw. Multiple locking devices fix the side of the plate having locking bores to the locking post end of its locking pins. Multiple screwing pins each have one end formed as a pin to be used for penetrating the threaded screwing bore to lock into the bone or the vertebral tubercle. Another end which forms a head is for holding against the threaded screwing bore of the plate. Threads are provided near the head for the screwing pins to be screwed within the threaded screwing bore of the plate.

An example of an external bone plate system is disclosed in U.S. Pat. No. 6,171,307 to Orlich. Orlich teaches an apparatus and procedure for the external unilateral fracture fastening, fracture compression or enlargement of osseous tissue with a metal or equivalent material slotted forked stick to hold and position the threaded pins in its length, inserted in the bone with multiple fastening slidable screws and their bolts to attach the pins to the slotted forked stick, a solid slidable cube to hold and position the slotted forked stick, a supporting axial bar, and an axial threaded bar. A preferred embodiment includes at least three slotted forked sticks that hold and fix, with the use of compression screws and their bolts, threaded pins that penetrate the proximal and distal fragments of the bone through both corticals. Another preferred embodiment includes slotted forked sticks that adapt to the threaded pins, introduced in the bone, at any degree of inclination or orientation that these pins might have with respect to the bone.

In addition to internal or external bone plates, surgeons sometimes use intramedullary rods to repair long bone fractures, such as fractures of the femur, radius, ulna, humerus, fibula, and tibia. The rod or nail is inserted into the medullary canal of the bone and affixed therein by screws or bolts. After complete healing of the bone at the fracture site, the rod may be removed through a hole drilled in the end of the bone. One problem associated with the use of today's intramedullary rods is that it is often difficult to treat fractures at the end of the long bone. Fastener members, such as bolts, are positioned through the cortical bone and into threaded openings in the rod. However, the number and positioning of the bolt/screw openings are limited at the tip of the rod because of the decreased surface area of the rod and the reduced strength at the tip of the rod. Therefore, fractured bone sections at the distal end of a femur, for example, may not be properly fastened to the intramedullary rod.

Various inventions have been disclosed to repair tissue and fasten implants to tissue. U.S. Pat. No. 5,120,175 to Arbegast et al. discloses a fastener having an elongated shank formed of a shape memory alloy, a head at the upper end of the shank, and an annular segment at the lower end of said shank having a deformed cross-sectional shape suitable for insertion into an opening extending through adjacent workpieces. The annular segment has a frusto-conical trained shape that is larger than this opening. The annular segment radially flares from the deformed shape to an approximation of the trained shape when heated above a critical transformation temperature, thereby securing the fastener in place with respect to the workpieces. Alternatively, a sleeve made of a different material (e.g. aluminum) extending over a portion or the entire length of the fastener can be added for improved deformational characteristics, by providing the same frusto-conical shape through axial contraction of the shank.

U.S. Pat. No. 5,290,281 to Tschakaloff teaches a surgical system including a thermoplastic, body absorbable, bodily tissue fixation plate having a plurality of formations and a plurality of through-bores arranged in alternating relation along with plate. The body absorbable fasteners are adapted for insertion into the through-bores to secure the plate to underlying bodily tissue. The heating apparatus includes a wand having a heating tip of a configuration adapted to substantially matingly cooperate with the formations to facilitate heating and bending of the plate into conformance with the underlying bodily tissue.

U.S. Pat. No. 5,941,901 to Egan discloses an expandable soft tissue fastening assembly for use in anchoring soft tissue to bone. The assembly includes a tab connected to an anchor, a sleeve adapted to surround the anchor, and a flange adapted to hold a soft tissue segment next to a bone. The sleeve is inserted into a blind hole in a bone, and a section of soft tissue is placed over the hole next to the bone. Energy is applied to the flange while a predetermined axial tension is applied to the tab to compress a flared portion of the anchor against the sleeve. An upper tube portion of the anchor and the flange are bonded together, and the applied axial force on the tab separates it from the anchor, leaving the assembly anchored in the bone and the soft tissue section anchored in place between the flange and the bone.

U.S. Pat. No. 7,018,380 to Cole discloses a femoral intramedullary rod system. The rod system is capable of treating a variety of femoral bone fractures using a uniform intramedullary rod design. The system generally comprises an intramedullary rod defining an opening having an upper surface and a transverse member including a bone engaging portion and a connection portion defining a thru-hole with the nail sized to pass therethrough. A pin is selectively coupled to the transverse member to rigidly assemble the transverse member to the nail when the nail is passed through the thru-hole and the pin is received within the opening. In an alternative design, an epiphyseal stabilizer is joined to the nail by a locking member.

Also, U.S. Pat. No. 6,228,086 to Wahl et al. discloses a modular intramedullary nail. The intramedullary nail apparatus comprises a nail having a proximal portion, a middle portion and a distal portion. The proximal portion has a longitudinal slot adapted to receive at least one fixing element and the distal portion has at least one transverse bore. The proximal portion has a longitudinal axial bore. The apparatus further includes a set of inserts, each of which is adapted to be inserted in the longitudinal bore. Each insert has at least one guiding bore, the orientation and position of which is different for each of the inserts.

Another assembly and method to fasten tissue is disclosed in U.S. Pat. No. 6,056,751 to Fenton et al. Fenton teaches a soft tissue fastening assembly comprising an anchor element which is installed in a bone or other tissue, and a joiner element which mates with the anchor element to define a tissue capture region between them. A section of soft tissue is held within the tissue capture region, and energy is transmitted into the joiner element to cause relative vibratory motion between the respective components and localized melting of the contacting portions of the respective components to establish a welded joint. The soft tissue segment is thus fixed to the bone without sutures or other fasteners.

U.S. Pat. No. 6,080,161 to Eaves, III et al. teaches a fastener for securing an osteosynthesis plate to a plurality of bone segments is provided. The fastener in the form of a fastener blank includes an elongated shank adapted for insertion through an opening in the plate and into a hole formed in the bone. The upper end of the shank forms a head that serves to secure the plate to the bone. The elongated shank is constructed of a material which when heated will deform to form a tight fit within the hole drilled in the bone. The fastener is preferably made of a resorbable material. The invention also provides a method for securing a plate to a bone using the fasteners of the invention. A fastener blank is positioned into the hole so that a portion of the blank extends into the hole provided in the bone and another portion overlies the plate. The blank is heated to raise the temperature of the blank above the transition temperature of the material from which it is made and deform the blank into a tight fit within the hole.

U.S. Pat. No. 6,605,090 to Trieu et al. discloses orthopedic implants and methods of treating bone defects. More specifically, but not exclusively, the present invention is directed to non-metallic implants and to methods for intra-operative assembly and fastening of orthopedic implants to facilitate medical treatment. The non-metallic implant assembly can be secured to underlying tissue by a fastener, such as a bone screw, that is capable of swelling on contact with fluid in the underlying tissue. Alternatively, the non-metallic implant assembly can be assembled intra-operatively using a fastener that is adhesively bonded to a bone plate or the bone plate can be deformed using heat, force or solvents to inhibit withdrawal of the fastener. In preferred embodiments, both the fastener and the bone plate are formed of biodegradable material.

Also, U.S. Patent Publication No. 2004/0030341 to Aeschlimann et al. teaches implants at least partially consist of a material that can be liquefied by means of mechanical energy. Particularly suitable materials of this type are thermoplastics (e.g. resorbable thermoplastics) or thixotropic materials. The implants are brought into contact with the tissue part, are subjected to the action of vibratory energy and are simultaneously pressed against the tissue part. The liquefiable material then liquefies and is pressed into openings or surface asperities of the tissue part so that, once solidified, it is positively joined thereto. The implantation involves the use of an implantation device comprising a generator, an oscillating element and a resonator, whereby the generator causes the oscillating element to mechanically oscillate, and the element transmits the oscillations to the resonator. The resonator is used to press the implant against the tissue part whereby causing oscillations to be transmitted to the implant. The implants are, for example, pin-shaped or dowel-shaped and are used in lieu of screws for forming connections with bone tissue, whereby the bone tissue is optionally pre-bored for positioning the implant. By virtue of the fact that it is unnecessary to transmit any torsional forces to the implants, these implants can be provided with a design that is weaker, i.e. slimmer than that of known screws made of the same material, and they can be implanted more quickly.

Existing systems and techniques for repairing tissue, like the ones previously described, can be complex, time consuming, lack the characteristic of being employed with precision, be damaging to tissue, and/or fail to provide a robust fastening of tissue. Therefore, there is a need for an apparatus and method for the fastening of tissue that involves reduced technical ability, fewer medical instruments, less time to complete, greater strength and precision, and preservation of living tissue. There is a need for a system that involves the precise application of energy to thermoplastic material to affix tissue and implants within the body. There also exists a need to be able to remove previously joined thermoplastic materials should the clinical situation dictate this.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIGS. 3A-3K show exemplary embodiments of a bonding horn;

FIG. 6 illustrates a manual bonding control box;

FIG. 7 shows a control box having pre-set bonding parameters;

FIG. 8A is an illustration of another embodiment of a bonding control unit;

FIGS. 27A-27C show a PEEK pin used to prevent loosening of a polyaxial pedicle screw/rod construct;

FIGS. 28A-28C show bone screws and plates that can be angulated;

FIG. 29 shows a dome shaped end effector;

FIG. 32 illustrates a fastener and end effector of the invention, wherein the fastener is embedded within bondable material;

FIG. 32A illustrates an alternative welding horn or fastener of the invention, with a chiseled end profile;

FIG. 33 illustrates an alternative view of the fastener and end effector of FIG. 32;

FIG. 34 shows the fastener of FIG. 32 embedded within bondable material;

FIG. 35 illustrates a cross section through the center of a long axis of the fastener of FIG. 36;

FIG. 36 illustrates a fastener of the invention, engageable with the fastener of FIG. 32;

FIG. 37 illustrates the fastener of FIG. 32 embedded, with the fastener of FIG. 36 engaged;

FIG. 38 illustrates a method of locking a position of the fastener of FIG. 36, in accordance with the invention, within the embedded fastener of FIG. 32;

FIG. 39 is a cross section through the center of the long axis of fastener of FIG. 38, after the locking step of FIG. 38;

FIG. 39A is a cross section through the locking aperture of the fastener of FIG. 38, after locking;

FIG. 41 is a cross section through the center of a long axis of a femur, illustrating an embeddable end effector of the invention;

FIG. 42 illustrates the end effector of FIG. 41, secured within the femur;

FIG. 45 illustrates a longitudinal cross section through the center of an end effector in accordance with the invention, and the fastener of FIG. 45A, illustrating the relationship therebetween for forming a cap;

FIG. 45A illustrates a cross section through the center of a longitudinal axis of a fastener in accordance with the invention, adapted to secure a plate, and form a cap;

FIG. 45B illustrates the fastener of FIG. 45A, together with a plate or load spreading device to be fastened;

FIG. 45C illustrates a fastener of the invention formed of two dissimilar materials at least mechanically interlocked to each other to form the fastener;

FIG. 46 illustrates a cross section through the center of a longitudinal axis of a femur, hip implant, and end effector of the invention;

FIG. 46A illustrates an enlarged view of a portion of FIG. 46, illustrating methods of repairing loosened bondable material within the body;

FIG. 46B illustrates an end effector and projections of the invention, for introducing bondable material within the body;

FIG. 46C illustrates the end effector and projections of FIG. 46B, positioned within the body, illustrated in a cross section through the center of a longitudinal axis of a bone within the body;

FIG. 46D-H illustrates various fasteners in accordance with the invention;

FIG. 47B illustrates fastening in accordance with the prior art;

FIG. 51 illustrates a fastener having two prongs, in accordance with the invention, fastened to a roughened or porous surface, or a surface having at least one cavity or projection into or upon which bondable material may become connected;

FIG. 51A illustrates a cross section view of the fastener shown in FIG. 51;

FIG. 51B illustrates a perspective view of the fastener shown in FIG. 51;

FIGS. 52A and 52B illustrate a device and method in accordance with the invention of securing a layer using heat meltable flanges;

FIG. 53 illustrates a method of securing an implant through fastening into a porous or roughened surface, or a surface with a cavity or projection, using a fastener of the invention inserted through a retrograde approach;

FIG. 53A illustrates the fastener and methods of FIG. 53, after fastening;

FIG. 54 illustrates an implant positioned and secured within an offset location using fasteners in accordance with the invention FIG. 54A illustrates a wedge shaped fastener in accordance with the invention;

FIG. 54B illustrates an enlarged view of a cone shaped fastener illustrated in FIG. 54;

FIG. 54C illustrates a cone shaped fastener provided with an expansion member that may be provided in an attached form;

FIG. 55 illustrates a cross section through a vertebra and fixation device in accordance with the invention, illustrating spinal fixation through embedding into bondable material, and additionally illustrates positioning of a sack containing therapeutic material in conjunction with the device of the invention;

FIG. 56 illustrates a partial cross section through a series of vertebrae, illustrating the embedded fastener of FIG. 55, and further illustrating a strap stabilizing successive vertebrae, fastened in accordance with the invention;

FIG. 75 illustrates a stranded suture bound within an anchor using vibratory energy in accordance with the invention;

FIG. 76 illustrates a device and method in accordance with the invention for securing one or more suture strands within an anchor which binds the strands upon the application of vibratory energy and or compression;

FIG. 77 illustrates an anchor in accordance with the invention, operable to secure one or more suture strands through the use of vibratory energy applied by a horn within an interior space of the anchor;

FIG. 81 illustrates an end effector and one or more tubes in accordance with the invention, the tubes operative to introduce or remove material proximate a bonding site;

FIG. 82 illustrates an alternative to the device of FIG. 81, wherein the tubes are located within the end effector;

FIG. 83 illustrates an alternative to the device of FIG. 82, wherein two tubes are internally located;

FIG. 84 illustrates an end effector in accordance with the invention, provided with a radio frequency transmitter at an end proximate a bonding site;

FIG. 93 illustrates various methods of the invention for fastening stents or implants together within the body;

FIG. 93A illustrates an alternative method of the invention for fastening stents or implants together within the body;

FIG. 94 illustrates a method of the invention for fastening two tubular body structures together;

FIG. 95 illustrates an alternative method of the invention for fastening tubular body structures together;

SUMMARY

Figure 1:
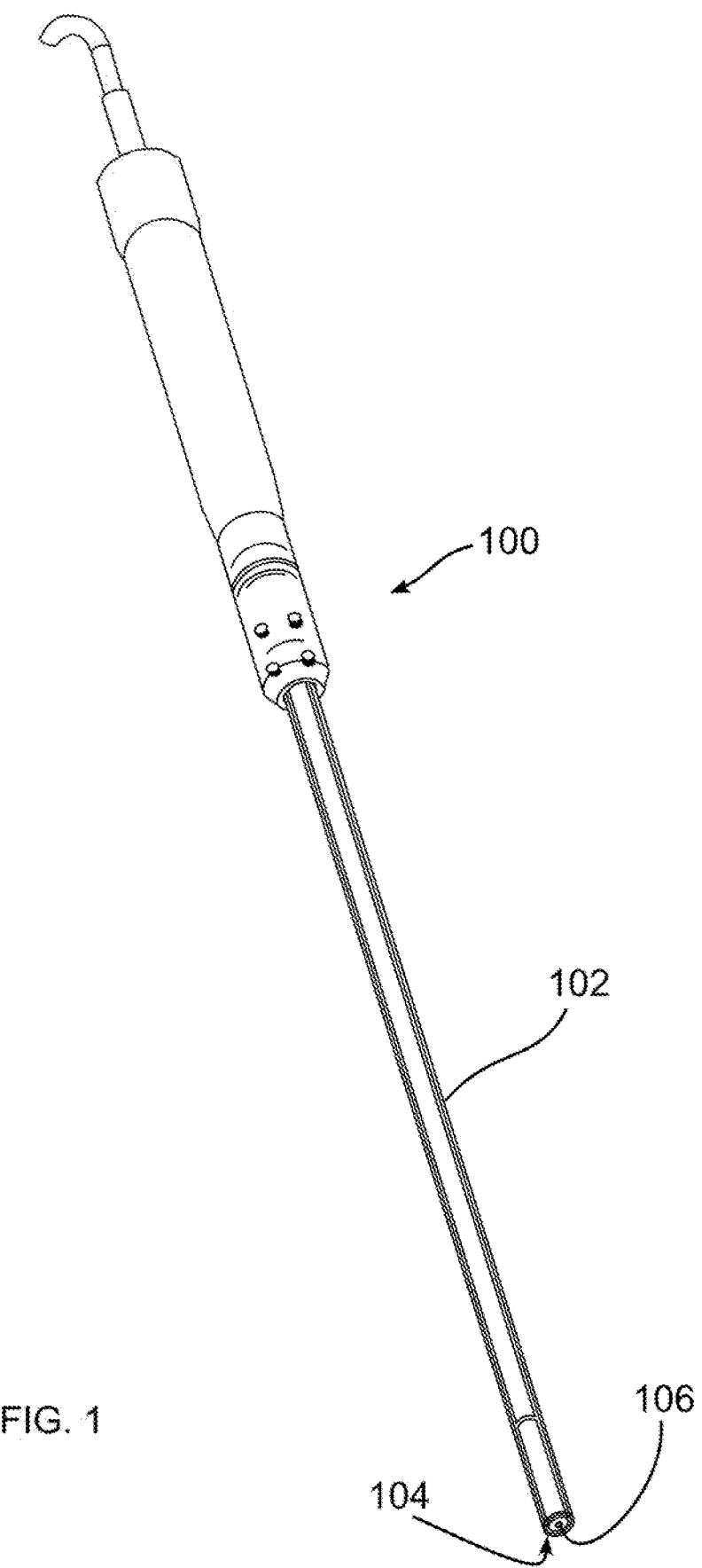
FIG. 1 is a perspective view of an exemplary vibratory bonding device.

For the convenience of the reader, text is organized generally into the following headings and order, although it should be understood that content within a heading does not necessarily stand on its own, and all of the content is intended to be understood and interpreted as a whole. Thus, headings or captions are not intended, and should not be construed, to limit or modify the scope of the accompanying text.

Fastening Materials
Sulfonation
Metals
Therapeutic Substances
Naturally Occurring Materials
Polymethylmethacrylate
Vibratory Mixing
Manufacturing with Vibratory Energy
Bonding Parts
Tissue Harvesting
Fasteners
Staking Fasteners
Embedded Bone Cement Fastener
Ported Embedded Fastener
Offset Shaft Collar
Knotless Suture Fastening
Bonded Flange Fastener
Headless Fastener
Spacer
End Effector with Cartridge Heater
Configurable End Effector Face
Coated Fastening Base
Expanding Fastener
Parameters and Additives
Additives
Energy Type
Pressure
Collapse
Instrumentation and Controls
Microprocessor Control
User Interface
Frequency Sweep Tuning
Impedance Feedback
Controlled Pressure Handpiece
Battery Powered Vibratory Energy Generator
SONAR Measurement of Collapse
Booster/Attenuator
Thermal Staking
Color Change Combined Therapeutic/Diagnostic Vibratory Generator
Irrigation/Suction End Effector
Radio Frequency End Effector
Testing
Fastening Procedures
Staking
Fastening into Existing Cement/Adhesives
End Effector for Fastening into Adhesives
Fastening into Implanted Device
Distal Fastening/Retrograde Approach
Spinal Fixation
Locking Screw Fastening
Resecuring or Removing an Implant
Fastening Dissimilar Materials
Fastening Combinations and Applications
Focal Defect Correction
Chain of Fastening As indicated above, the invention relates to devices and methods that help stabilize tissue or implanted materials in a patient's body, including the fastening of two different tissue types, the fastening of an implant to tissue, or the fastening of an implant to another implant. The invention additionally relates to removing and anchoring implants into bone cement, anchoring implants using previously implanted and hardened bone cement and adhesives, locking implants to body tissue, for example cartilage grafts, or other implants using vibratory energy, connecting implants to porous surfaces using vibratory energy, devices for generating and controlling delivery of vibratory energy, and mixing materials using vibratory energy.

The methods and devices disclosed herein may be used in conjunction with any surgical procedure of the body. In this specification, bonding or welding refers to the joining of parts wherein at least one part includes a bondable material, as defined herein. Welding herein generally indicates joining two similar materials, whereas bonding herein generally indicates they may or may not be the same material. Thus, the invention may be utilized as a trauma bonding system for the stabilization of damaged tissue, such as fractured bones. In this application, the system may include devices and methods for intracorporeal thermal bonding or mechanically interlocking of thermoplastic material. An energy source can be used to bond or lock the material in place. The energy source may be resistive heating, radiofrequency, ultrasound (vibratory), microwave, laser, electromagnetic, electro shockwave therapy, plasma energy (hot or cold), and other suitable sources. Likewise, the energy source may enable a portion of material to be foamed or expanded such that two components of the system are secured together. Other energy sources, surgical procedures, and medical instruments which may be used with the present invention are disclosed in U.S. Provisional Patent Application No. 60/968,969, filed Aug. 30, 2007, U.S. patent application Ser. No. 11/689,670, filed Mar. 22, 2007, U.S. patent application Ser. No. 11/671,556, filed Feb. 6, 2007, U.S. Provisional Patent Applications Nos. 60/765,857 filed Feb. 7, 2006; 60/784,186 filed Mar. 21, 2006; and 60/810,080 filed Jun. 1, 2006, as well as U.S. patent application Ser. No. 11/416,618 filed May 3, 2006; Ser. No. 11/689,670, filed Mar. 22, 2007; and Ser. No. 11/671,556, filed Feb. 6, 2007. The contents of these documents are incorporated by reference herein in their entirety.

Fastening Materials

The trauma bonding and staking system and other embodiments of the present invention contemplates the use of any biocompatible material bondable and/or stakable within the human body. Preferably, this material can melt with the application of energy, becoming gel-like, tacky, or soft. The energy source and the technique used to bond and/or stake the material within the body can be selected to minimize or avoid damage to surrounding body tissue. Exemplary materials that may be used may include polymers, ceramics, composites, and metals, although other materials may also be suitable for use with the invention. Generally, there are two types of polymers: thermoset and thermoplastic. Thermoplastics may be used with the present invention because they can be softened, reheated, molded and remolded.

Some semi crystalline materials have an amorphous structure or an amorphous region within them. These materials are particularly suitable for surgical bonding and/or staking, especially vibratory bonding and staking Examples of such materials include PAEK (polyaryletherketone), including PEEK (polyetheretherketone) and PEKK (polyetherketoneketone). With these special semi crystalline materials, the amorphous content of the polymer makes the material more conducive to vibratory energy, and therefore a better bond or mechanical interlock is achieved. Also, a lower amount of energy is needed for these materials.

The semi crystalline materials without an amorphous structure or region have a rigid or fixed melting point. A high level of energy is required to breakdown the crystalline structure before the melting occurs. Once the melting starts, the material very rapidly moves through the transition area from a solid to a flowable substance, i.e. a liquid. Also, the molecular structure of semi crystalline materials absorbs vibrational energy making it more difficult to transmit the vibrational energy from an energy-producing instrument to the interface of the parts being joined. When this material is used in surgical screws, plates, rods, etc., care must be taken to avoid over melting and weakening of the implant. The temperature, time, and pressure must be closely monitored and controlled with semi crystalline materials or the implant will fail.

The polymers used in the present invention, such as PEEK and PLLA, have randomly arranged molecules allowing vibrational energy to pass through the material with little attenuation. As such, the material requires relatively little vibratory energy to make the material soften and become tacky. This small amount of energy or heat needed to bond or stake PEEK and PLLA helps avoid or minimize the likelihood of tissue necrosis.

Dissimilar materials can also be mechanically interlocked. Staking is defined herein as the process of melting and reforming a piece, such as a stud, to mechanically lock a material in place. It provides an alternative to bonding when two parts to be joined are made of dissimilar materials that cannot be bonded, or when simple mechanical retention of one part relative to another is adequate.

In this application, the term "bondable" or "bondable material" is used to refer to the materials discussed above, as well as any material, suitable for use in in vivo applications, which can be softened and made flowable by the application of heat (such as heat produced with vibratory energy such as ultrasonic energy), and which, when softened, may become tacky and will bond to other materials and will flow to fill available space. Thus, the material may be thermoplastic, but it may also exhibit tackiness or bonding ability when in its plastic form. Many materials suitable for in vivo applications are made of or incorporate such bondable materials. Generally speaking, the amount of heat needed to be softened and make flowable should be within a temperature range that does not produce substantial thermal tissue necrosis. Alternatively stated, the amount of heat required to soften the bondable material during vibratory bonding is substantially confinable, due to the thermal properties of the bondable material, to an area of contact between two objects which are being bonded, thereby protecting living body tissue near the contact between the two objects from substantial thermal tissue necrosis. Selection of such material is within the ordinary skill of the art.

Sulfonation

Polymers used in methods and devices of the invention may be sulfonated to be wettable, or hydrophilic, using any of a variety of known methods, including a method of exposure to sulfur dioxide, an oxygen donating gas, and a free radical producing energy, as described in U.S. Pat. No. 6,066,286, the contents of which are hereby incorporated by reference. A hydrophilic surface presents the opportunity for improved bio-integration of implanted devices, including an enhanced surface structure for tissue ingrowth, should that be an objective. Moreover, therapeutic substances may be readily incorporated into the sulfonated surface layer, and may more readily transfer a target therapeutic dose into the body. Through sulfonation of bioabsorbable polymers, fasteners may be formed to elute therapeutic substances, with the aforementioned desirable benefits.

Further, a wettable surface may be used to reduce friction on one or more bearing surfaces, such as articulating bearing surfaces in joints, creating a more optimal and longer lasting replacement or repair. The wettable surface can be inlaid into the bone surface, including an inlaid articular surface. One mechanism of operation for the implant containing hydrophilic materials is the formation of a molecular linkage with body fluid, thereby promoting lubrication, tissue ingrowth, and biocompatibility.

Metals

In accordance with the invention, metals are advantageously connected with fasteners incorporating polymeric materials. Any of a variety of metals may be used, either smooth or formed with at least portions of foam metal, or a roughened or porous surface, or formed with cavities or other shapes upon which polymeric material may mold, enter, adhere, or otherwise affix. The polymer is softened in accordance with the invention through the application of heat, including heat created using vibratory energy, to become tacky, or sufficiently softened in order to bond on a microscopic level, or a macroscopic level through adaptation to the surface structure of the metal. For use in vivo, biocompatible metals are used, including stainless steel, nitinol or other SMA (shape metal alloy), tantalum, porous tantalum, titanium, cobalt-chrome alloys, and other metals such as are known to those skilled in the art. Additional related information, including bonding polymers and metals, and polymer to polymer bonding of implant materials, may be found in U.S. Pat. No. 5,163,960 entitled "Surgical devices assembled using bondable materials", and U.S. Pat. No. 7,104,996 entitled "Method of performing surgery", the contents of each of which being incorporated herein by reference.

Therapeutic Substances

The fastening device of the present invention may include therapeutic substances to promote healing. These therapeutic substances may be combined with the materials used to make the device. Alternatively, the therapeutic substances may be impregnated or coated on the device. Time-released therapeutic substances and drugs may also be incorporated into or coated on the surface of the device. The therapeutic substances may also be placed in a bioabsorbable, degradable, or biodegradable polymer layer or layers, or in cavities disposed in a fastening device of the present invention.

Naturally Occurring Materials

In addition to PEEK and the other polymers described herein, the implants, devices, and methods of the present invention may use keratin, a naturally occurring polymer. Keratin may be vibratory bonded or staked to itself, to other implants, or within tissue. This may be performed in the operating room or intracorporeally. Keratin may be bonded to collagen or to other known polymers.

Another polymer that can be used with the present invention is a class of natural materials, called polyhydroxyalkanoates- or PHA polymers.

Polymethylmethacrylate

Fasteners of the invention may be coated with polymethylmethacrylate (PMMA), in order to promote bonding with PMMA used in the body, or PMMA could be incorporated into polymer of the fastener, or deposited within cavities or shapes formed in the fastener surface, including threaded, roughened, porous, or nano textures. A fastener may be thus coated with PMMA, or formed entirely of PMMA, and may be heat bonded, advantageously using ultrasound, to another PMMA surface or an adhesive surface, otherwise as described herein with respect to bone cement.

Vibratory Mixing

In accordance with the invention, vibratory energy, for example ultrasound, is used to mix materials to be used in formulating implants of the invention, for mixing adhesives and cements, and for admixing therapeutic substances into implants and substances. Materials may be mixed in a production or laboratory setting, or in the operating room immediately before implantation. Vibratory energy is applied to the mixing bowl or chamber, to promote even distribution of materials, and the release of gases, gaps and voids, resulting in a denser, more even mixture. In addition, the temperature or pressure, as well as other parameters, may be applied along with vibratory energy, to produce an optimal result for the mixture.

To improve mixing, the energy level and frequency may be tailored to the particular mix constituents. For example, low energy or longer wavelengths may be used for polymeric materials mixing, particularly amorphous polymers, and shorter wavelengths may be advantageously used for metallic materials and denser polymers, and PMMA. Other frequencies may be used, both lower and higher than the frequencies commonly used in ultrasonics, for example within the audible range, or in the megahertz range.

Polymer, adhesive, binding material or grouting agents, including bone cement, may be maintained or converted to a liquid or viscous form within the mixer, therapeutic substances, including pharmaceuticals, may optionally be admixed, and an implant may be dipped into the mixture for coating. The dipped implant can include any material to be implanted, including metals and polymers. It is advantageous for the dipped implant to maintain its shape until the coated polymer cools and hardens. In this manner, an implant such as a stent or arthroplasty component may be coated to elute a therapeutic substance, while maintaining appropriate physical dimensions and properties. Further, the coated implant may then be fastened within the body using the methods and devices described in this specification, the coating forming a substrate for proximal and or distal heat fastening, including ultrasonic fastening. Vibratory energy imparted to the mixing chamber during coating further serves to improve interdigitation and a close, conforming coating of the implant.

Vibratory mixing as described, advantageously combined with changes in mixing parameters, such as temperature and pressure, may be used to alter the polymerization characteristics of polymers within the mixing chamber. Accordingly, the resultant polymer may have properties best suited to the procedure contemplated. Properties affected may vary, but may include changes in density, porosity, flexibility, hardness, color, and smoothness.

Manufacturing with Vibratory Energy

In addition to mixing, as described herein, vibratory energy may be advantageously employed in manufacturing requiring a mixing step. Operating parameters such as temperature and pressure may be varied, in combination with the application of vibratory energy to mixing or staging apparatus. With respect to injection molding, in particular, vibratory energy is applied to the injection molding equipment, to improve performance of the injection molding process, as well as to potentially improving the resulting injection molded parts.

Vibratory mixing and packing of the invention is particularly useful in mold filling and fabrication of precision parts requiring a tortuous fill path, having delicate structures, or having features on the nanometer scale.

A biologic matrix including fibers, such as collagen fibers, can be more uniformly mixed and formed into a polymer or biologic collagen scaffold in combination with vibratory energy as described. The matrix may include cells or pharmaceutical agents, including chemotherapeutic agents, antibiotics, cell growth agents, growth inducing factors, and proteins. Moreover, manufactured or harvesting tissue, cells, or cell products may be integrated into a mixture that is molded to conform to a body surface or cavity, including epithelial surfaces, or to an implant.

Bonding Parts

When bonding parts with adhesive, it can be a challenge to evenly distribute adhesive between the parts to be fastened. In accordance with the invention, vibratory energy, for example ultrasonic energy, is applied to either or both parts, and or the adhesive or grouting layer, to promote movement of the adhesive throughout the interstitial space between the parts, whereby a more uniform, reliable and predictable bond is formed.

In a medical context, it is often necessary to use an adhesive, binding material or grouting agent, for example PMMA or bone cement, to secure an implant, particularly an arthroplasty component, within the body. The implant may have a projection which enters a space within the body, for example the medullary canal of a bone, or may lie upon the surface of body tissue. In either application, it is advantageous to create uniform contact between the implant, adhesive, and body tissue, in order to avoid the formation of gaps or voids, appearing as lucencies in radiography.

In accordance with the invention, vibratory energy, advantageously ultrasonic energy, is applied to the implant, body tissue, adhesive layer, or a combination of same, to improve movement of the adhesive throughout the interface between the implant and the body tissue to be adhered. This is particularly effective when combined with pressure, applied to the interface, as by applying pressure to push the implant against a bone surface. An example includes the implantation of a tibial insert, including insertion of an implant stem into the tibial medullary canal. Vibratory energy is applied to the upper portion of the tibial implant, near or on the bearing surface, or along the sides of the implant, as the stem is inserted into the canal. Vibratory energy may be continued for a period of time thereafter, until an even distribution of adhesive is achieved. In this example, adhesive enters the small cancellous bone interstices, as well as surface formations of the implant, to improve the bond between the implant and the body.

Tissue Harvesting

In accordance with the invention, tissue is harvested by placing a harvesting tool with a holding area or chamber, such as a hollow coring drill, upon or within body tissue and applying vibratory energy to the harvesting tool, tissue, or both. Vibration, such as ultrasonic vibration, is applied to cause cells to become dislodged, freely mobile, or movable, whereupon they may be collected in the holding area. Cells may be further removed by applying lavage, pressure, suction, or abrasion. In a reverse process, vibratory energy aids in the implantation of cells, through modification of the body tissue surface, rendering the surface more conducive to implantation, and improves transfer of cells from the holding area to the implantation site. The use of vibratory energy is advantageously applied in the harvesting or implantation of fetal cells, for example.

The application of heat or other environmental change, or the addition of therapeutic elements, may be used to improve performance of harvesting or implantation. For example, including injectable polymers may improve bonding, the addition of nutrients may improve cell viability, or the addition of pharmaceutical agents may improve compatibility.

Fasteners

Fasteners of the invention may be configured to matingly engage other implants, being urged or locked into an advantageous orientation through a molded or otherwise formed three dimensional configuration. Alternatively, fasteners of the invention may be formed to maximize bonding surface, or to modify strength in designated locations.

Staking Fasteners

In another embodiment of the invention, a tackable fastener is sized to be insertable through a stab wound, drilled portal, or other focused aperture. The body of the fastener may be provided with an aperture or passageway through which another fastener may pass, for example a suture, cable, or another similar fastener. The fastener may further be provided with a ramped or angled face which advantageously is provided with a pointed or constricted end, operative to pierce material to be held thereon. The distal, or non-pointed end of the fastener may be secure using the distal fastening method described in this specification, or alternatively by any known means, including a press fit into a bore, or attachment using the aperture described above. If materials are to be held on the fastener, they are passed over the pointed end of the fastener, pierced by the fastener if needed, and are optionally followed by a load spreading device, such as a washer. When all materials have are held, a cap is placed upon or formed on the pointed end of the fastener. In one embodiment, and end effector is placed upon the pointed end, the pointed end advantageously formed with an alignment bore or other surface which mates and aligns with the end effector. Vibratory energy, such as ultrasonic energy, is then used to melt the tip and form the melted material into a cap which retains and thus stake the held materials.

Embedded Bone Cement Fastener

As is described in further detail, below, fasteners may be embedded within previously solidified bone cement, for example PMMA or other acrylic based material. In an embodiment in accordance with the invention, an anchor is connected to an end effector of a vibratory energy generator. The anchor is adapted to enter and engage cement or adhesive that has been locally melted by vibratory energy, and to be securely retained therein once the cement has cooled and hardened.

The end effector may be provided in any of a variety of shapes, one example being an elongated rod or shaft, connectable to a hand piece at a proximal end, and operative to transmit vibratory energy at a distal end. The fastener is adapted to connect to the distal end of the end effector by mechanical interlocking, as by a bore on either device sized to receive a post on the other, optionally with threading. Other mechanical connections are contemplated, including twist lock configurations, friction fitting, or adhesive attachment. The mechanical connection must be operative, however, to communicate the vibratory energy from the end effector to the fastener.

The fastener is adapted to be securely retained within the grouting agent or adhesive, in one embodiment, by being provided with a shaped or contoured surface upon which the adhesive may grip once hardened. A roughened or porous surface may be provided alone or in combination with a shaped surface, the adhesive obtaining purchase thereupon.

The fastener may further be provided with a taper at a leading end which first enters the adhesive. The taper improves performance, at least, by promoting accurate tracking and movement of the fastener into the adhesive, piercing tissue, and facilitating initial melting by concentrating vibratory energy over a smaller surface region.

Once anchored, the end effector and embedded fastener may remain connected, or the end effector may be removed and another fastener may be connected to the embedded fastener, connecting by mechanical means as described, including threading. In a further embodiment, a fastener such as described in the related references cited and incorporated herein may be fastened to the embedded fastener of the instant invention, then secured in its respective manner. For example, a pointed polymeric fastener may pierce tissue and enter the embedded fastener, then connecting by, for example, press fitting or threading into a bore within the embedded fastener. The fastener may be distally fastened into the bore using vibratory energy as detailed in this specification. Once secured within the embedded fastener, a head portion of the polymeric fastener may then be formed to cap and secure the tissue, using a vibratory end effector, including an ultrasonic end effector.

Ported Embedded Fastener

In a further embodiment of the invention, the embedded bone cement fastener described above is provided with one or more radial gaps, chambers, or ports, extending from a central bore. A polymeric fastener is inserted within the central bore, and vibratory energy is applied to the polymeric fastener, whereby polymer at the interface between the embedded fastener and the polymeric fastener melts. When the polymer melts, and particularly as pressure is applied to the polymeric fastener in the direction of insertion, polymer enters the ports, flowing in a direction away from the central bore. When vibratory energy is discontinued, the polymer solidifies, and the polymer faster is thereafter secured within the embedded fastener.

Offset Shaft Collar

In one embodiment, a fastener has a shaft, which may or may not be threaded, which terminates in a tip, and a head that is provided with a recess into which a pin of an end effector may be matingly engaged. The head and or shaft has a lip or flange or collar extending partially around the circumference of shaft. This flange corresponds with a channel formed in a typical spinal implant. In this manner, fasteners of the present invention may be adapted to be used in applications where traditional bone screws are used.

Knotless Suture Fastening

Although the present invention includes fastener concepts that eliminate the need for sutures (so-called "sutureless fastening"). The present invention also includes fastener concepts that use suture, but without the need for knots (so-called "knotless fastening"). In one embodiment, a system includes an anchor, having a bore configured and dimensioned to receive a shaft of the tack. A channel created by the forked end of the shaft extends through the tack such that one or more sutures can extend through both the anchor and tack. When the tack is partially inserted in the anchor, the suture can freely move; however, as the tack is further inserted in the anchor, channels misalign and trap the suture. When bonding of the anchor and tack occur, knotless fastening of the suture is achieved.

In a further embodiment, a suture is passed through body tissue, and one or more strands pass through a gap or aperture in an anchor comprising bondable material. An end effector of the invention is applied to the anchor to cause melting of the bondable material, trapping the suture strands therein. If the anchor and sutures are of the same material, the anchor and sutures may become welded. Alternatively, the anchor may be provided with a tortuous pathway for the strands, such that as vibratory energy is applied to the anchor, the anchor is deformed and the suture strands are mechanically locked within the anchor.

Figure 30:
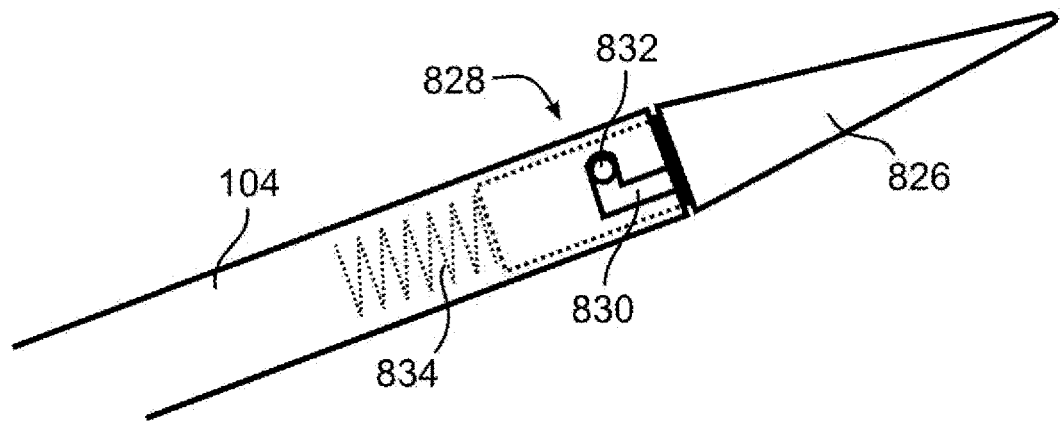
FIG. 30 shows an end effector with a removal metallic pin that can be implanted.

Further, the end effector may be driven into the anchor with vibratory energy, thus displacing material of the anchor to cause compression of the suture strands, binding the suture strands within the anchor. The end effector is thus advantageously shaped to penetrate and displace material along a predetermined path and direction. For example, fastener 826 of FIG. 30 is well adapted to penetrate a monolithic anchor, particularly where there is no established entry portal.

In an additional embodiment, more than one end effector may be applied to an anchor from opposing sides, whereupon vibratory energy and pressure caused by pinching of the anchor between the end effectors operates to compress the anchor and thereby bind one or more suture strands within the anchor. The end effectors may further be shaped to have contact the anchor along an increased surface area, improving the transmission of vibratory energy in the anchor.

Bonded Flange Fastener

In a further embodiment of the invention, a fastener is provided adapted to bond an implant to body tissue, the fastener having the form of one or more flanges or tabs projecting from the implant, and being formed of a heat softenable and bondable material. This fastener is advantageously used where the implant has the form of a liner, surface layer, or shell, and thus is advantageously formed without projecting mounting posts, or holes through which a fastener may pass. Examples include replacements for articulating surfaces of a joint, including the acetabular and condylar surfaces.

In one embodiment, a first implant component is fastened to body tissue at a location beneath or adjacent to the intended implantation site for the liner implant. The first implant may be attached to body tissue in accordance with any known manner, or in a manner disclosed herein. The first implant has mounting projections positioned to cooperate with the flanges of the liner. After the first implant is secured, the liner is positioned in the body, and the flanges are attached to the mounting projections using vibratory energy. The flanges and mounting projections may be provided in the form of mating flanges, flange and posts, mating posts, or any other cooperating projections which may be heat bonded together upon the application of vibratory energy. When heated the cooperating flanges and projections soften and bond together, and are further driven before hardening to lie in a position which will not interfere with proper functioning of the body.

In another embodiment, the flange is fastened directly to bone or body tissue adjacent to the site of implantation.

To further secure the liner, adhesive may be applied to an inner surface of the liner before mounting and attachment.

Headless Fastener

In another embodiment of the invention, a fastener is fastened in a manner described herein, the fastener passing, for example, through an aperture or bore; however, the fastener is not provided with a head or widened portion operative to prevent the fastener from passing completely through the aperture. For distally secured fasteners, described herein, there is a reduced possibility for the fastener to pass completely through the aperture, as the distal end of the fastener is securely fixed. Where the point of fastening is fixed relative to the location of the entry of the bore, a fastener head can be avoided. In this manner, the fastener may have an excess length, and be trimmed flush after being secured. Alternatively, the fastener may be provided with a length predetermined to lie flush with a surface through which the fastener is passed.

In a further alternative, a head portion may be bonded using vibratory energy, as described herein, after the fastener has been distally secured and trimmed.

Spacer

Implants may be positioned and secured in a precise location, in accordance with the invention, through the use of a progressively widening spacer, such as a spacer having a conical, ramp or wedge shape, affixed in a predetermined location, through the use of vibratory energy, for example ultrasonic energy. The implants include a bondable material as described herein, or alternatively, fasten to a surface including bondable material. One or both of the surfaces may be provided with a roughened, porous, or shaped surface, to which melted material may enter or surround, thereby becoming affixed after cooling.

Due to the ramped shape of the implant, a progressive insertion of the device produces a concomitant displacement of the implant to be affixed, relative to the body tissue proximate the implantation site. Spacers may be placed at different locations, so that they may cooperatively displace the implant, and offer greater strength when affixed.

End Effector with Cartridge Heater

A small cartridge heater may be used to deliver thermal energy, disposed within the end effector. To prevent heat build up on the outside shaft, an insulating region may be formed between the heater and the shaft.

Configurable End Effector Face

Further in accordance with the invention, an instrument may include different horn or end effector configurations within one design, retractable to alter the surface configuration of the tool. The instrument can be configured to have a bonding-surface face, a bonding face, and a contouring face.

Coated Fastening Base

In accordance with the invention, an implant is coated with a bondable material, and placed in the body as a point of attachment for other implants. The coated implant is advantageously shaped to provide a surface for attachment of numerous fasteners, or one or more fasteners at a variety of possible locations. Fasteners may be bonded to the coated implant using proximal or distal vibratory fastening, as described herein, or a combination of vibratory and mechanical fastening.

Expanding Fastener

In accordance with a further embodiment of the invention, an expanding anchor is provided, adapted to pass through an opening into a hollow space, and expand within the hollow space thereby resisting withdrawal through the opening. The anchor is fastened using vibratory fastening in accordance with the invention.

Parameters and Additives

Monitoring and controlling bonding parameters ensures proper bonding of thermoplastics. Parameters include, but are not limited to, the type of energy to emit, type of thermoplastic material, the size and configuration of the implant, the thickness of the implant, implant surface geometry, the aqueous environment, energy time, energy power, and frequency of the energy, amount of pressure applied to the implant during and after application of the energy, the geometry of the horn, the boost or attenuation of the end effector, the density of the implant, the amount of collapse of the thermoplastic material, the depth into tissue the implant is to be inserted, and the type and amount of any therapeutic agent that may be delivered.

There are several factors commonly encountered in vivo that effect bonding or staking of thermoplastic materials. One is how hydrophilic a material is, or the tendency of a material to absorb moisture. If too much fluid gets between the parts it can decrease the bond or create foam which prevents proper bonding of the materials. Therefore, the bonding of thermoplastics may be performed under vacuum/suction, or a hermetic seal may be placed around the thermoplastic during the bonding process.

Additives

In addition to or in place of reducing moisture from the bonding area, certain agents can be used to aid in the bonding process. Such agents may include filler material, glass filler, glass fiber, talc, and carbon. The agents may be placed at the bond site as a temporary bonding enhancement means or may be a permanent agent to enhance the bonding.

In addition to avoiding release agents, pigments, and moisture, the staking and/or bonding of thermoplastic materials may be further enhanced by adding minute metallic material to the polymer. The metallic material may be metal flakes or metal dust. Examples of such metal include iron particles, chromium, cobalt, or other suitable metals. The metal may be embedded within the polymeric material to enhance the thermal properties. Alternatively, or in addition, the metal may be applied to the surfaces of the polymeric material. Energy applied to the polymer would heat both the polymeric and metallic material providing a faster and more uniform thermal profile. It is contemplated that glass fillers, carbon fillers, talc, or combination thereof may also be used in addition to or in lieu of the metallic material.

Energy Type

Other factors affecting the thermal characteristics of thermoplastics include size, thickness, surface geometry, material properties of the thermoplastic, and the type of host tissue involved in the bond or staking, i.e. soft, hard, dry, wet, or moist tissue.

Furthermore, how the thermoplastic is staked, welded or bonded is an important characteristic of obtaining a robust mechanical interlock or thermal bond. The type of energy used is one way to control the process. As previously mentioned, various energy sources may be used to bond and/or stake polymers. In an exemplary embodiment, two or more different types of energy may also be used. For example, vibratory energy may be used to bond a polymeric component to another component, while resistive heating may be used to contour the surface or change the geometry of the materials. The surface of the component may be smoothed out or sculpted using resistive heating.

The intensity and duration of the energy source impacts the quality of the bond or mechanical interlock. For instance, the amount of energy used affects the thermal properties. Therefore, the energy may be controlled by the operator depending on the component to be bonded or staked. A switch, dial, or other control may be placed in connection with the energy source to vary the intensity of the energy applied. For example, the amount of current supplied to the instrument may be varied or controlled. It is also contemplated that the amount of time that energy is applied may be controlled not only by the operator but also via radiofrequency, optical, radiowave, etc. A computer or other microprocessor may send signals to the energy emitter to turn the energy on and off.

Pressure

Controlling the pressure applied to the thermoplastic material also may be used to affect the process. During bonding or staking, a handpiece, an anvil, a horn, end effector, or combinations thereof may be used to apply controlled force against the component. After completion, while the material is cooling, the force may continue to be applied to ensure proper bonding and/or mechanical interlock of the materials.

Collapse

Controlling collapse is another factor in achieving an effective thermoplastic bond or staking. For instance, the time and material collapse may be monitored to ensure a proper effect. A measurement of the change of the material being bonded or staked may be made to determine when complete. This may be accomplished by using microswitches to provide precise, binary control of the mold. Also, by using a linear variable displacement transducer (LVDT), the control system can monitor the bond more precisely.

Furthermore, collapse may be controlled or monitored through the use of a mechanical stop on the fastening device itself or on the instrumentation. The mechanical stop would prevent collapse after a predetermined point. It is also contemplated that the collapse could be monitored by other methods such as optics, laser, or even a hall-effect sensor. All of the above-mentioned parameters may be monitored and controlled by a computer.

Instrumentation and Controls

Any known energy emitting instrument may be used with the surgical system of the present invention. The instrument may produce energy such as resistive heating, radiofrequency, ultrasound, microwave, laser, electromagnetic, electro shockwave therapy, plasma energy (hot or cold), and other suitable energy. The instrument may be a vibratory energy handpiece with a sheath to cover and protect an end effector and hold a fastener. The sheath may have a small counter bore at its tip to cover a portion of the cap. The tip of the end effector may have a small post protruding from the bonding face, operative to press into a bore in the cap of the fastener, to align the fastener post into the anchor bore and keep the cap tight against the end effector face.

Microprocessor Control

In accordance with the invention, a digital signal processor (DSP) simplifies additional modes for fastening control. Whether or not analysis is performed by a DSP, other processor type, mechanical means, or by the practitioner, modes may include any or all of the following:

monitoring the phase angle differential between voltage and current during use, and making changes to the signal, including the frequency, to maintain a resonant frequency;

varying the output voltage while monitoring the bond power;

monitoring the stroke using a sensor in the handpiece or end effector;

varying the drive voltage while monitoring the current and voltage, in order to calculate the minimum impedance;

calculating the total power/energy applied to the bond; and monitoring the Eddy or Foucault currents created by movement of the end effector, wherein as the end effector vibrates, a magnetic field is changed, whereby the movement of the end effector can be tracked, the movement indicative of melting activity;

calculating the amount to which the fastener has collapsed or shrunk.

The methods may be combined, and further, the total time during which vibratory energy has been applied may be monitored, with a set minimum or maximum time being applied. The methods enable adjustment of the signal for variations in the environment and loading during a surgical procedure.

The control modes described above may be combined with input or measured parameters automatically by processor control, or at the election of the surgical practitioner. In this manner a matrix for overall control is created by the selected parameters, and selected control modality.

User Interface

The surgeon may manually control the parameters, or the parameters may be controlled using automation, including using a microprocessor or computer. In accordance with the invention, a generator control unit is provided having connections for grounding and a signal. The generator advantageously includes a user interface comprising gauges or indicators, and in one embodiment an LCD or similar output screen. A user keypad is provided to move a cursor or indicator on the output screen, whereby parameters can be selected and entered. A footswitch may be provided to enable the surgical practitioner to more easily activate the generator.

A staking or fastening process of the invention begins by either pushing the generator footswitch or by using a control on the hand piece, or by operating two or more controls together, if it is desired to render inadvertent activation less likely. Upon starting, the generator may first perform a system check. The software may also check for proper grounding, ground offset issues, as well as other vital circuits. If there are errors with the system or the grounding, the generator can give a visual or audible indication that an error has occurred, and the vibratory signal generator may be disabled to prevent inadvertent use.

In accordance with a further embodiment of the invention, the surgical practitioner enters information pertaining to the surgical procedure through interaction with the user interface, which includes a cursor keypad and output screen on the generator. It should be understood that an alternative and potentially more sophisticated and complete interface may be obtained by connecting a computer (not shown) to the generator, via a known method including USB, Bluetooth or network connection. Moreover, the generator interface may be programmed for the various types of surgeries and surgical operating parameters expected to be encountered, and the generator may thereafter be disconnected from the computer during the procedure.

Once programmed, the output screen contains menus offering the surgical practitioner options relevant to the procedure to be performed, including the type of procedure, and any or all of the parameters described in this specification. In this manner, the practitioner has the ability to input the correct procedure and real-time parameters, in order to enable precise control in the use of the generator. Further, the generator can perform a sophisticated analysis in order to determine the correct operating parameters, including for example frequency, wattage, and pulsing, and the generator may further independently vary one or more parameters over time. Accordingly, the practitioner need not make the complex calculations necessary in order to achieve a secure and reliable fastening, and thus time is saved, and the potential for error is reduced.

Frequency Sweep Tuning

If no errors are detected, the system may then sweep a frequency range, such as from about 38.5 kHz to about 43.5 kHz, to tune the circuit. Current measurements may be used to find the resonate frequency of the system, which in some embodiments may be close to 41 kHz. The ultrasonic signal is then sent to the hand piece where a resonator turns the waveform into linear movement.

Impedance Feedback

To help ensure a properly executed bond or staking, the instrument of the present invention may provide a positive feedback system. One way to provide user feedback is by measuring and controlling the impedance of the vibratory generator. This feedback system is based on the fact that the load placed on the end effector affects the impedance of the system. That is, the pressure put on the end effector by the object to be bonded or staked changes the impedance in the handpiece, and more particularly, of the piezo stack and associated electronic circuit.

By first transmitting a low power vibratory signal through the end effector, the impedance of the handpiece can be measured with no pressure. This establishes a baseline impedance. Then, the end effector may be subjected to known pressures, and the voltage and current may be measured to calculate the impedance for each pressure. Therefore, when a surgeon or other operator applies pressure from the end effector to a thermoplastic implant to be bonded or staked, the actual amount of pressure can be fed back to the operator because the pressure can be correlated to a known impedance. The pressure and impedance of the handpiece may be monitored throughout the thermal profile.

Alternatively, or in addition to the signal, the microprocessor can stop energy emission until the correct pressure and impedance is achieved, then the bonding may be resumed either automatically by the microprocessor or manually by the surgeon. If inadequate pressure is being exerted, the bonding instrument may operate in a pulse mode to maintain material in a near-bond state. This may allow the bonding to more rapidly continue when adequate pressure is once again being applied.

By monitoring handpiece impedance, changes to the environment, such as moisture, ambient temperature, aqueous conditions, etc., may be automatically compensated for by adjusting the drive waveform of the vibratory energy. As the impedance, Z, of the handpiece changes, the total power delivered also changes. By increasing or decreasing the drive voltage to compensate for the change in the impedance, a constant power can be delivered.

Controlled Pressure Handpiece

In accordance with the invention, a tool for producing vibratory energy is provided with a gauge positioned to respond to a differential between a pressure created by applying a force to the handle, and the physical resistance presented at the end effector. When excessive force is applied, a response is generated, operative to warn the operator and or reduce power of the vibratory signal. When insufficient force is applied, the operator is likewise warned, and or power is not yet applied to produce vibration.

In one embodiment of the invention, a series of electrical contacts are interposed between the handle grip and the end effector. Springs respond to relative movement of the handle and the end effector, to position the contacts with respect to each other, in order to open or close electrical circuits. These circuits may be connected directly to a power generator, or may pass to mechanical or electronic circuits which initiate a warning or a change in power level.

Battery Powered Vibratory Energy Generator

A handheld or portable vibratory generator has a requirement for a substantial amount of current, at high voltage. In accordance with the invention, an inverter is provided to convert a DC battery signal into a suitable sine wave signal, and a step-up transformer is provided to increase the voltage to an effective level. In one embodiment, multiple mosfet devices are used in parallel, advantageously provided in pair arrays, to provide for an adequate amount of current. A microprocessor controls power to the mosfet array pairs, alternately switching power between them, in order to produce an alternating current within a transformer. Additional control circuitry modifies the signal parameters to enable precise bonding, as described herein.

SONAR Measurement of Collapse

In another exemplary method, collapse of the fastener may be monitored, such as by the use of SONAR. Collapse is the distance a thermoplastic fastener or implant shrinks in height when vibratory energy is applied. For example, some thermoplastic fasteners have been found to shrink about 20 percent in height and increase 30 percent in width when bonded. For fasteners having two pieces, such as a cap and an anchor, the attenuation of the reflected vibratory waves changes as the two piece fastener becomes one piece. This change in attenuation may be monitored to alert the surgeon or operator when the bond or staking is complete. Furthermore, a vibratory transducer could be used in conjunction with the end effector to detect the change in acoustic impedance/attenuation of the site. This signal may be monitored by a microprocessor/controller or data signal processor (DSP) and data may be automatically interpreted to indicate whether the bond was successful.

Booster/Attenuator

In another embodiment in accordance with the invention, peak to peak motion, or amplitude of the vibratory horn is controlled using a booster or attenuator after the piezo stack. Control is further achieved by the generator through modulating the power, or amplitude, of the high frequency signal.

Thermal Staking

Staking or fastening of fastening devices of the present invention could also be performed using thermal energy. The process for thermal staking is similar to the one used for vibratory, except that it may not be necessary to tune the system. The energy signal sent to the stake can be either AC or DC. To allow for longer heater life, a pulse width modulated (PWM) signal could be used. The PWM signal allows for the energy to be rapidly switched on and off with a varying duty cycle proportional to the total system energy needed for the staking environment.

Color Change

It is also contemplated that the material being bonded or staked may change color or visible appearance as heat, vibrations, or vibratory energy is applied for a predetermined time and a predetermined frequency and wattage.

Combined Therapeutic/Diagnostic Vibratory Generator

In accordance with the invention, a vibratory generator includes circuitry and is otherwise adapted to perform diagnostic as well as therapeutic tasks. Diagnostic tasks include mapping or visualization of a target location. Information gathered during the diagnostic phase can be used by the surgical practitioner to determine optimal settings for a subsequent therapeutic use of the device, or the information may be directed to a microprocessor, which may include a DSP, which will then carry out or suggest optimal settings to the practitioner.

Diagnostic information may include the size of implant needed, as well information pertaining to the microclimate within the intended therapeutic field.

In one embodiment, diagnostic ultrasound is produced by an array of low power crystals, and therapeutic ultrasound is produced by a stack of crystals. In this manner, both structures can be packaged within a single handheld device. Accordingly, a single microprocessor may advantageously be used to control both crystal configurations based on separate algorithms for each.

Irrigation/Suction End Effector

During vibratory or ultrasonic bonding, the presence of liquid or moisture can impact the performance and quality of the bond. One approach to ensuring a consistent and reliable bond, as described in this specification, is to adjust the bonding parameters according to the amount of observed or measured moisture within the zone or area of bonding. Another approach in accordance with the invention is to remove moisture from the bonding area, by introducing an input stream of gas or liquid, or by applying suction/aspiration proximate the bonding site. In one embodiment, a tube is attached to a vibratory end effector, wherein the inlet for aspiration, or conversely the outlet for a gas or liquid stream, is positioned at a location near where bonding is to take place.

In a further embodiment, a first tube introduces an input stream of gas or liquid, and a second tube is placed proximate thereto, operative to form an output stream to collect the gas or liquid via suction, together with any debris collected and carried therein.

An advantage of the aforedescribed embodiments is the removal of debris generated during the bonding process, which may include flash formed at the bonding periphery, as well as any other material or body tissue that has vibrated loose or otherwise become loose within or near the bonding area.

The first or second tube may be fastened to the outside of the vibratory end effector, or may alternatively be formed as one or more channels or pathways within the end effector. In either embodiment, switches or controls for activating an input or output stream may be provided on the handpiece connected to the end effector, or on a foot switch or hand operated remote, or may be activated by voice control.

Radio Frequency End Effector

In another embodiment, a radio frequency transmitter is provided proximate the end effector, operative to break down or destroy contaminants within the bonding area, including moisture or particulates. Shielding is appropriately placed in order to safeguard any nearby body tissue or material which might be vulnerable to stray transmissions.

Testing

Once a fastener or other implant is vibratory bonded or staked, the surgeon can apply a quick tug on the assembly to verify the bond or staking was completed as intended. An end effector in accordance with the invention includes a post which emits vibratory energy, and which enters a bore or receptacle in a fastener. After bonding, the surgeon may actuate biasing prongs which dig slightly into the material of the fastener, so that the surgeon may now pull or tug on the instrument proximally to verify that the fastener is securely bonded or staked in place. A strain gauge may be used to measure and display to the surgeon how many pounds of pull strength is being put on the fastener.

In accordance with an embodiment of the invention, a frame is provided with an aperture through which a fastener body may pass, sized to prevent passage of a fastener head. The device may thus test the holding strength of a distally bonded connection, as well as proximal bond including a head formed with vibratory energy. A strain gauge, spring scale, or other suitable measuring device is connected to the frame, and a force is applied in a direction away from the fastened connection. The results are observed and recorded, together with the parameters under which the connection was formed and tested.

To aid in determining the exact conditions under which fastening was accomplished, an electronic circuit separately measures the power consumed in tuning the vibratory instrument, and performing the bond itself. This data is used, together with other parameters, to enable the production of a secure and reproducible bond.

Fastening Procedures

Staking

Although the above-discussion emphasizes bonding or welding, the present invention also contemplates staking in most situations as an alternative or supplement. Staking generally involves the mechanical interlock of dissimilar materials. Staking is the process of melting and reforming a piece, such as a stud, to mechanically lock a material in place. It provides an alternative to bonding when two parts to be joined are made of dissimilar materials that cannot be bonded, or simple mechanical retention of one part relative to another is adequate.

The advantages of staking include short cycle time, and the ability to perform multiple staking with one end effector. The most common staking application attaches metal to plastic. A hole in a metal part is designed to receive a plastic stud. An end effector with a contoured tip contacts the proximal end of the stud and creates localized frictional heat. As the stud melts, light pressure from the end effector reforms the head to the configuration of the end effector. When the end effector stops vibrating, the plastic solidifies and the metal and plastic parts are fastened together.

For example, a PEEK (or other polymer) anchor/fastener, or tack may be used to couple two materials together, in this case two porous metals. After staking, a proximal end assumes the shape of the end of the end effector. Additionally, the distal end of the tack is fastened to porous metal, such as may be found on an interior face of an implant, secured using vibratory energy.

Initially, the anchor is threaded or otherwise secured to the bone. A post projecting away from the bone on the proximal end of the anchor can be used to pierce soft tissue to be attached, holding it in position relative to the bone. The tip is then formed into a cap by staking, with or without an interposing element between the soft tissue and the cap formed at the proximal end of the post. If needed, the post can be trimmed (either mechanically or by shearing off with vibratory energy) before staking. In this manner, a plate or other structure can be attached using two or more tacks.

Fastening into Existing Cement/Adhesives

In an additional embodiment in accordance with the invention, a fastener is formed to embed within, and thereby become securely fastened to, previously hardened bone cement, in vivo. This method is advantageously employed, for example, to repair bone fractures, secure and resecure implants, repair periprosthetic fractures, and to secure or repair dental devices and implants. For example, a medical practitioner may observe a lucent line progressively developing as an implant loosens, indicating a separation between body tissue and the implant. In the prior art, revision surgery would be required in order to remove and or re-cement the implant. In accordance with the invention, a tack, pin, bar, rod, plate or other fastener may be inserted into the body, and fastened to cement implanted earlier, through the application of vibratory energy, said energy advantageously including ultrasonic energy. As discussed elsewhere, herein, the distal portion of the fastener is caused to resonate and vibrate in contact with the bone cement, locally heating the latter to enable adhesion to the fastener. The fastener thus may serve as an anchor point in subsequent steps to re-secure the implant.

As an anchor point, a fastener thus affixed may alternatively be used to secure soft tissue, such as a rotator cuff, collateral ligament, or joint capsule.

Fasteners securable to implanted bone cement include the materials described in this specification, including as examples PMMA, metal, metal at least partially coated with PMMA or acrylic, PEEK (polyetheretherketone), and acrylic, or can be a composite including resin, and or carbon fibers. A thin coating of PMMA or acrylic, as small as several microns, contributes to forming a secure bond with bone cement within the body. Bonds may additionally be formed between dissimilar adhesives.

An initial bore may be made in the bone cement to aid alignment, to temporarily retain the fastener, or to increase the surface area for fastening. The fastener may be placed in an intended location through, for example, intramedullary, percutaneous, or retrograde approaches.

End Effector for Fastening into Adhesives

Further, the end effector can be used as the implant itself. Specifically, in one embodiment of the invention, a metal pin, screw, or other engagement shape is inserted into a thermoplastic (e.g. PEEK) rod, the pin itself attached to an end effector. The metal pin must be firmly attached, or formed integrally with the end effector, to avoid creating arcing and sparks due to metal on metal contact between the pin and effector. For removable pins, a release mechanism is provided.

In accordance with the invention, an end effector having a distal tip formed or attached thereto is inserted into a medullary canal in a long bone, and affixed into adhesive through the use of vibratory energy, as described in this specification. The end effector is then removed from the remainder of the vibratory energy generating device, whereby connection means at a proximal end may be used to secure the end effector within the bone, or to body tissue to be attached, or to another implant.

Fastening into Implanted Device

Implants, including fastener implants, may be bonded to cement previously implanted within the body. Previously implanted intramedullary devices, secured with a substantial amount of adhesive, provided numerous points at which tacks, pins, rods or other fastener may be attached through the application of vibratory energy, as described herein. These fasteners may then serve as anchoring points for a variety of additional devices, for example plates or bands. In particular, where fasteners are affixed on opposing sides of a fracture, a plate may be used to stabilize the fracture, without a requirement for implanting screws within the bone. In this manner, more invasive or complex conventional means of repair, including cerclage, may be used to a lesser extent, or avoided.

An additional embodiment, similar to implantation of an end effector as described above, includes the implantation of a device coated over at least a portion of its surface with adhesive, or having a roughened or porous surface, or a surface with shaped regions, into or onto which a fastener may be affixed as described herein. Once the device is implanted, it may then serve as a convenient fastening point as described.

Distal Fastening/Retrograde Approach

In accordance with a further embodiment of the invention, vibratory energy is applied to cause thermal deformation distal to the site of application of the end effector. In this application, the mechanical deformation, especially in dissimilar materials, occurs at a site away from the vibratory horn or end effector. The staking or bonding can occur not at the trailing edge of the implant, but along the implant surface or at the far end of the implant where the implant can be mechanically bonded to body tissue, implanted cement, or another implant, particularly if it is a dissimilar implant. In accordance with the invention, a rough or irregular surface, or at least one surface cavity into which the fastener may deform, may be used to promote secure bonding.

Distal fastening in accordance with the invention is advantageously employed where a retrograde approach is safer or easier than direct access to a fastening site. In this manner, a fastener may be inserted at a remote location to contact a distant object, the distal end of the fastener being bonded in accordance with the invention, and the proximal end of the fastener being secured by means of the invention, or other known means, to secure the distant object within the body. An example would include bonding a fastener having distal polymeric material to an implant having a roughened or porous surface, or a surface with a gap or opening forming a shape into which the polymeric material may flow, to harden upon cooling, thereby affixing the fastener to the implant surface. In this manner, a surface of the implant positioned in fixed contact with body tissue may be fastened, while an articulating surface may remain free of fasteners.

In one embodiment, the retrograde or distally fastened fastener is additionally connected to an implanted bone augment, or bone graft, thereby providing primary and or secondary stabilization for the augment. The augment may be implanted, for example, to replace diseased or damaged bone. In this manner, an articulating surface as well as an adjoining area of bone may be secured by a single fastener, or a series of fasteners. The fastener may be distally bonded to both the augment and the device bearing the articulating surface. The fastener may also pass through the augment, as through a bore. The augment may be composed of any material or combination of materials suitable for its intended function, including metal, plastic, ceramic, alloys, moldable material including adhesives, as well as porous forms of these materials.

This retrograde approach may be facilitated through the use of a cannula, or an expanding cannula, such as is disclosed in U.S. Pat. No. 6,814,715, incorporated herein by reference, and related patents cited therein. Retrograde examples include fastening an acetabular replacement from behind the cup, fastening a tibial bearing surface replacement from a point below the bearing surface, and fastening a hip replacement implant from the femur body or distal end of the femur. Like examples are contemplated for the smaller analogs of the arm. Retrograde approaches may also be used in fastening or repairing bones of the hands, feet, skull, and spine.

It should be understood that in the case of distal fastening, as well as proximal fastening, the fastener body can be advantageously caused to enlargen. The enlarged portion may prevent staked material from separating from the fastener. Alternatively, the enlarged portion may prevent the fastener from dislocating from a target location. For example, the enlargened portion may be too large to pass through the portal or opening through which the fastener entered.

The fasteners and fastening methods of the invention are advantageously utilized for use in-vivo, reducing or avoiding tissue necrosis by minimizing exposure of tissue to heat, and may be implemented through reduced size incisions, including keyhole incisions, as may be employed in laparoscopic procedures. Fasteners may additionally be formed and fastened in accordance with the invention in the operating room, at the convenience of the surgical practitioner, when the exact configuration and dimensions needed are best understood, and thereafter implanted.

Spinal Fixation

Staking in accordance with the invention can be advantageously applied to a variety of angulated screws, typically used in spinal applications. Specifically, screws that can be placed at an angle through the plate and then staked in place. The screw and plate have a rounded mating surface, which allows some adjustability in direction. In accordance with the invention, an end effector is provided sized to matingly engage an angulated screw head, regardless of the angle of the screw head relative to a supporting structure adjacent the head. The end effector applies vibratory energy to bond bondable material of the supporting structure and or screw head to a mating surface on the supporting structure or screw head, respectively.

Locking Screw Fastening

In another embodiment of the invention, a metallic polyaxial screw/rod system, of the type typically used in spinal surgery, is modified to include holes intersecting both the saddle that holds the rod and pedicle screw head, and the locking screw used to maintain the desired angle of the pedicle screw. Into these holes, a tack is staked or bonded such that the material of the tack flows into the threads between the saddle and locking screw, effectively preventing loosening of the system.

Resecuring or Removing an Implant

As described above, vibratory energy, such as ultrasonic energy, is used to melt or liquify adhesives, including bone cement. In accordance with the invention, bone cement is melted in situ, whereupon melted cement flows to bridge or fill voids and gaps, the cement thereafter being allowed to cool in order to thus re-secure a loosened implant.

In one embodiment, a vibratory end effector is provided with a wedge or conically shaped tip, shaped to melt and displace implanted adhesive. In this manner, the adhesive is made flowable by the application of vibratory energy, and is driven by the tip into nearby bone, or the interstices between body tissue, filling voids or gaps, reengaging the bone to stabilize an attached implant. The end effector and tip could then be withdrawn, or alternatively, either or both devices may be left within the body. If the end effector is to be removed, it is decoupled from the tip, as by threading or other mechanical interlock.

In another embodiment, a rod having at least one shaped projection, for example in the form of a blade or leaf, is passed to a distal portion of a hip implant through a retrograde entry from the distal portion of the femur. The rod is passed through a space in the body, in this example through an intramedullary canal. To facilitate passage, a boring may be formed beforehand, or the rod may be hollow, for example in the form of a coring drill. As the rod and blade pass through the intramedullary canal, the blade is resiliently or mechanically maintained in a direction substantially parallel to the passage. Once the implanted adhesive is encountered, vibratory energy is transmitted through the rod to cause the blade to vibrate, and thereby melt adhesive proximate the implant. When sufficient adhesive is melted or liquified, the blade may be advanced, until a desired length of blade has been admitted. Subsequently, the rod bearing the blade may be rotated, thereby liquefying a perimeter of adhesive.

If it is desired to re-secure the implant, the blade may be withdrawn once the implant has been repositioned, if desired, and the void or gap of concern has been re-filled with melted adhesive. Alternatively, if it is desired to remove the implant, removal is accomplished before the adhesive resolidifies, such as by lifting the implant away from the adhesive, out of its current location. Multiple blades may be employed to reduce the time required to complete the removal or resecuring process.

Alternative shaped projections include cups, cones, wires, or other shapes which may pass through the body to the area where the adhesive is located, and which are advantageously formed to best fit the geometry of the adhered interface, to carry out the functions previously described.

In an alternative embodiment, the rod and blades are left within the body, embedded in the resolidified cement, to operate as a reinforcement and or attachment point for further fasteners or implants, including arthroplasty components and prosthetics, or testing or reporting apparatus attached to or embedded within the device. As an attachment point, the rod may be provided with bores or apertures, which may be threaded, into which other fasteners may be inserted, and optionally further fastened in accordance with the methods disclosed herein.

In an alternative embodiment, the shaped projection is formed of, or coated with, a bondable material, for example a polymer, which is then bonded to a roughened or porous surface, either in the operating room, or in the body. Within the body, the surface may be that of existing or implanted bone, or that of a previously or recently positioned implant. When the shaped surface is positioned in contact with the roughened surface, for example an intramedullary rod having a porous metal surface, vibratory energy is passed to the shaped projection to cause the projection to melt and bond to the roughened surface.

The issue of implant removal after bonding or staking of one or more implants is one that needs to be addressed if the clinical situation dictates. In accordance with one embodiment of the invention, a modified end effector for use with vibratory energy forms an implant removal tool. One end engages alternately a vibratory generator, and subsequently a t-handle. The other end of the end effector is provided with surface asperities, or is otherwise roughened to enhance engagement to the implant or material to be removed. In use, vibratory energy is activated to drive end effector around an implant to be removed, firmly bonding the end effector to the implant. The t-handle is then connected, and through a repeated rocking or oscillating motion of the t-handle, the bond or weld is broken and the implant may be removed.

Fastening Dissimilar Materials

It should be understood that a proximal or distal polymer to polymer connection may be made through the application of heat or vibratory energy, such as ultrasonic energy, as described herein. In this manner, fastener containing polymer may be connected to a roughened, porous or shaped surface, or to another polymeric fastener, or polymeric coating on an implant or implanted fastener. For example, an arthroplasty or prosthetic component may be at least partly covered with polymer, the polymeric surface exposed to an intended site for fastening. Moreover, a plurality of arthroplasty components may include polymeric or heat softenable material, the components being thus fastenable together in accordance with the invention.

An advantage to a polymeric containing, or polymeric coated fastener or implant is the ability to incorporate one or more therapeutic substances within the coating, whereupon the therapeutic substance may elute, or release the therapeutic substance in-vivo over time, in a predictable and useful manner. U.S. Provisional Patent Application No. 60/728,206, entitled "Drug Eluting Implant" and incorporated herein by reference, provides examples of means for delivering therapeutic agents, although those skilled in the art will appreciate that other known methods may be advantageously employed in combination with the invention.

Fastening Combinations and Applications

The fastening devices of this and other embodiments of the invention may be used in combination with fasteners in the prior art. The fastening and repair of tissue or an implant may be performed in connection with surgery of a joint, bone, muscle, ligament, tendon, cartilage, capsule, organ, skin, nerve, vessel, or other body parts. For example, tissue may be repaired during intervertebral disc surgery, knee surgery, hip surgery, organ transplant surgery, bariatric surgery, spinal surgery, anterior cruciate ligament (ACL) surgery, tendon-ligament surgery, rotator cuff surgery, capsule repair surgery, fractured bone surgery, pelvic fracture surgery, avulsion fragment surgery, shoulder surgery, hernia repair surgery, and surgery of an intrasubstance ligament tear, annulus fibrosis, fascia lata, flexor tendons, etc.

Focal Defect Correction

In accordance with the invention, areas of disease or trauma are replaced with an implant or graft, secured in situ using vibratory energy. In this manner, healthy tissue may remain undisturbed, and a focal defect corrected. Examples include replacing a portion of an articulating surface, such as a condyle, the acetabulum, or glenoid fossa, or replacing portions of bone or soft tissue that have been damaged by injury or disease.

The diseased area may be replaced by implanted tissue, including bone fragments or compressed living tissue, fabricated non-living material such as polymers or metal, or any other material a medical practitioner deems best. An interface is created between the graft and the body, and includes a quantity of bondable material there between. Advantageously, if the implant is not made entirely from bondable material, a surface of the implant contacting the bondable material of the interface is provided with a roughened or porous surface, or a surface with one or more cavities into or onto which heat softened or melted material may flow and thereby lock onto once cooled, hereafter an irregular surface. Further, the body tissue may be treated to have an irregular surface for the same purpose. In addition, an implant may be attached to the body tissue using methods or devices of the invention, or alternatively screws, adhesives, or any other known means, the implant provided with an irregular surface.

Thus, once the implanted material is in place, an interface defines a strata that includes body tissue having an irregular surface, or an implant attached to the body tissue, the implant having an irregular surface, bondable material, and implant material having an irregular surface, unless the implant is provided with bondable material at the interface.

Vibratory energy is applied proximate the interface, operative to cause the bondable material within the interface to soften or melt, thereby locking onto the irregular surface of both the body tissue or intervening implant on one side, and the implanted material on another side, whereby the implanted material is firmly attached to the body once the bondable material has cooled.

Chain of Fastening

The invention specifically contemplates a chain of fastening from bone to implant to tissue. For example, bone cement is fastened to bone, an implant is fastened to the bone cement as described herein, tissue is staked or fastened to the implant, and the end of the implant is capped or secured as described herein and in the incorporated references. Fasteners may alternatively be bonded to bone using methods described and illustrated herein and described in the incorporated references, and implants or tissue are fastened to the fastener bonded to bone, using the methods and devices of the invention.

It is contemplated that the devices and methods of the present invention be applied using minimally invasive incisions and techniques to fasten, for example, muscles, tendons, ligaments, bones, nerves, and blood vessels. A small incision(s) may be made adjacent the damaged tissue area to be repaired, and a tube, delivery catheter, sheath, cannula, or expandable cannula may be used to perform the methods of the present invention. In addition to using a cannula with the present invention, an introducer may be utilized to position implants at a specific location within the body.

The methods of the present invention may further be performed under indirect visualization, such as endoscopic guidance, computer assisted navigation, magnetic resonance imaging, CT scan, ultrasound, fluoroscopy, X-ray, or other suitable visualization technique. The implants, fasteners, fastener assemblies, and sutures of the present invention may include a radiopaque material for enhancing indirect visualization. The use of these visualization means along with minimally invasive surgery techniques permits physicians to accurately and rapidly repair, reconstruct, augment, and secure tissue or an implant within the body.

DETAILED DESCRIPTION

As detailed below, the invention provides for stabilization of implants or body structures, including fastening of a chain of implants. The invention additionally relates to removing implants fastened with bondable materials using vibratory energy, including for example ultrasonic energy. The invention further provides for locking similar or dissimilar materials together in the body by providing a surface between elements that is roughened or porous, or which has one or more cavities or projections upon which melted material may form and lock to once cooled. Additionally disclosed are devices for generating and controlling vibratory delivery, and mixing materials using vibratory energy.

The methods and devices disclosed herein may be used in conjunction with any surgical procedure of the body. The fastening and repair of tissue or an implant may be performed in connection with surgery of a joint, bone, muscle, ligament, tendon, cartilage, capsule, organ, skin, nerve, vessel, or other body parts. For example, tissue may be repaired during intervertebral disc surgery, knee surgery, hip surgery, organ transplant surgery, bariatric surgery, spinal surgery, anterior cruciate ligament (ACL) surgery, tendon-ligament surgery, rotator cuff surgery, capsule repair surgery, fractured bone surgery, pelvic fracture surgery, avulsion fragment surgery, shoulder surgery, hernia repair surgery, and surgery of an intrasubstance ligament tear, annulus fibrosis, fascia lata, flexor tendons, etc.

Also, an implant may be inserted within the body and fastened to tissue with the present invention. Such implant insertion procedures include, but are not limited to, partial or total knee replacement surgery, hip replacement surgery, shoulder replacement surgery, bone fastening surgery, etc. The implant may be an organ, partial organ grafts, tissue graft material (autogenic, allogenic, xenogenic, or synthetic), collagen, a malleable implant like a sponge, mesh, bag/sac/pouch, collagen, or gelatin, or a rigid implant made of metal, polymer, composite, or ceramic. Other implants include breast implants, biodegradable plates, porcine or bovine patches, metallic fasteners, compliant bearing for medial compartment of the knee, nucleus pulposus prosthetic, stent, suture, suture anchor, tissue graft, tissue scaffold, biodegradable collagen scaffold, and polymeric or other biocompatible scaffold. The scaffold may include fetal cells, stem cells, embryonic cells, enzymes, and proteins.

Fastening Materials

The trauma bonding and staking system and other embodiments of the present invention contemplates the use of any biocompatible material bondable and/or stakable within the human body. The materials used may include, but are not limited to, degradable, biodegradable, bioerodible, bioabsorbable, mechanically expandable, hydrophilic, bendable, deformable, malleable, riveting, threaded, toggling, barded, bubbled, laminated, coated, blocking, pneumatic, one-piece, multi-component, solid, hollow, polygon-shaped, pointed, self-introducing, and combinations thereof. Also, the devices may include, but are not limited to, metallic material, polymeric material, ceramic material, composite material, body tissue, synthetic tissue, hydrophilic material, expandable material, compressible material, bondable material, and combinations thereof.

Preferably, this material can melt with the application of energy, becoming gel-like, tacky, or soft. The energy source and the technique used to bond and/or stake the material within the body can be selected to minimize or avoid damage to surrounding body tissue. Exemplary materials that may be used may include polymers, ceramics, composites, and metals, although other materials may also be suitable for use with the invention. While the present invention contemplates the use of any of these materials in any of the following embodiments, polymeric material is used in the following examples and description simply to illustrate how the invention may be used.

Generally, there are two types of polymers: thermoset and thermoplastic. Thermoplastics may be used with the present invention because they can be softened, reheated, molded and remolded. Thermoplastics are generally classified as either amorphous or semi crystalline. Some semi crystalline polymers have some amorphous structure while other semi crystalline polymers may be more crystalline than others. Examples of amorphous polymers are poly carbonate (LEXAN), polystyrene, polysulfone (ULDALL), and acrylics polycarbonate (ABS and styrenes). Examples of semi crystalline polymers include acetyl (DELRIN), nylon, polyester, polyethylene, polyether ether ketone, poly propylene, polyvinylchloride (PVC), and Caprolactam. Biodegradable semi crystalline polymers may include polylactic acid and polyglycolic acid. Copolymers of PGA and PLA may also be used. These copolymers may vibratory bond or stake better than pure PGA and PLA. Other polymers which may be used with the present invention, either as a thermoplastic or non-thermoplastic, are polyethylene glycol (PEG)-copolymers and D,L-lactide-co-glycolide polyesters.

Some semi crystalline materials have an amorphous structure or an amorphous region within them. These materials are particularly suitable for surgical bonding and/or staking, especially vibratory bonding and staking Examples of such materials include PAEK (polyaryletherketone), including PEEK (polyetheretherketone) and PEKK (polyetherketoneketone). With these special semi crystalline materials, the amorphous content of the polymer makes the material more conducive to vibratory energy, and therefore a better bond or mechanical interlock is achieved. Also, a lower amount of energy is needed for these materials.

The semi crystalline materials without an amorphous structure or region have a rigid or fixed melting point. A high level of energy is required to breakdown the crystalline structure before the melting occurs. Once the melting starts, the material very rapidly moves through the transition area from a solid to a flowable substance, i.e. a liquid. Also, the molecular structure of semi crystalline materials absorbs vibrational energy making it more difficult to transmit the vibrational energy from an energy-producing instrument to the interface of the parts being joined. For example, polylactic acid reaches its melting point and goes through its transition region rapidly which causes it to flow in the tissue. This rapid heating and complete, or nearly complete, melting of the material weakens the overall structure and causes tissue necrosis. When this material is used in surgical screws, plates, rods, etc., care must be taken to avoid over melting and weakening of the implant. The temperature, time, and pressure must be closely monitored and controlled with semi crystalline materials or the implant will fail.

The polymers used in the present invention, such as PEEK and PLLA, have randomly arranged molecules allowing vibrational energy to pass through the material with little attenuation. As such, the material requires relatively little vibratory energy to make the material soften and become tacky. This small amount of energy or heat needed to bond or stake PEEK and PLLA helps avoid or minimize the likelihood of tissue necrosis. In fact, temperature measurements with PEEK show that the surface of the material, a distance away from the immediate bonding interface, does not exceed 37° C., and that the temperature profile trails back to ambient within 30 seconds or less, suggesting quick energy dissipation. With PLLA, temperature elevation of the surface is limited to 33° C. With these materials, the transition period is longer in duration and therefore, when applying energy, the material gradually softens, passing from a rigid state through a transition state to a rubbery state and then to a flowable gel-like state. The amorphous features of these materials make them vibratory bondable and stakable with lower temperature and better bonding points. To bond or stake these materials, the true melting point does not need to be reached or exceeded except at a limited area at the immediate bonding interface, so there is less risk to surrounding body tissue. PEEK and PLLA are also useful with the system of the present invention because it has a modulus of elasticity very close to bone.

The temperature, time, pressure, and other parameters of the energy process may be closely monitored and controlled to achieve an effective bond or staking. Also, because the material does not substantially melt (only a limited region softens and becomes tacky) the holding strength of the thermoplastic during and after application of the energy is not jeopardized. That is, a fastener made of a thermoplastic which melts, like those in the prior art, cannot maintain a compressive force against a component or implant during the bonding or staking process. This is because the material of the fastener becomes liquefied, and a fastener in liquid form cannot maintain a compressive or tension force. The present invention contemplates implants made of PHA, PEEK or PLLA which bond by softening or making tacky the polymer material at the bonding region. The remaining PHA, PEEK or PLLA material does not flow and therefore retains its ability to maintain a compression or tension force.

When bonding two thermoplastic components together, it is optimal that the components be chemically compatible to create a molecular bond. Similar thermoplastics may be compatible if their melt temperature is within about 6 degrees Celsius or if they have similar molecular structures. Generally, amorphous polymers may be bonded to each other. In the present invention, PEEK may be bonded to PEEK. Biodegradable polymers may be bonded to biodegradable polymers. Biostable polymers may be bonded to biostable polymers. Biodegradable polymers may be bonded to biostable polymers.

Sulfonation

Polymers used in methods and devices of the invention may be sulfonated to be wettable, or hydrophilic, using any of a variety of known methods, including a method of exposure to sulfur dioxide, an oxygen donating gas, and a free radical producing energy, as described in U.S. Pat. No. 6,066,286, the contents of which are hereby incorporated herein by reference. A hydrophilic surface presents the opportunity for improved biointegration of implanted devices, including an enhanced surface structure for tissue ingrowth, should that be an objective. Moreover, therapeutic substances may be readily incorporated into the sulfonated surface layer, and may more readily transfer a target therapeutic dose into the body. Through sulfonation of bioabsorbable polymers, fasteners may be formed to elute therapeutic substances, with the aforementioned desirable benefits.

Further, a wettable surface may be used to reduce friction on one or more bearing surfaces, such as articulating bearing surfaces in joints, creating a more optimal and longer lasting replacement or repair. The wettable surface can be inlaid into the bone surface, including an inlaid articular surface. One mechanism of operation for the implant containing hydrophilic materials is the formation of a molecular linkage with body fluid, thereby promoting lubrication, tissue ingrowth, and biocompatibility. It is further possible to make a device surface hydrophobic using sulfonation.

In one embodiment of the invention, a sulfonated surface improves bonding and tissue ingrowth with biological tissue introduced after the surface has been sulfonated.

Sulfonation may be used to alter an inherent characteristic of a material, for example making a non-wettable surface wettable, useful, for example, with certain polymers, including but not limited to polyurethane, polyethylene, polyglactic acid, or polylactic acid.

In another embodiment in accordance with the invention, any of the devices of the invention may be provided with a sulfonated surface, or fabricated using sulfonation, thereby conferring additional beneficial properties to the device. For example, the stents of FIGS. 91-92, or the mesh of FIG. 93, may be constructed using sulfonation, rendering the device less likely to cause thrombosis. Sulfonation may be used in a variety of ways to produce this benefit. In particular, the surface may be made more wettable, and thus smoother or more slippery. Alternatively, the surface may be treated with sulfonation to promote incorporation of antithrombotic therapeutic substances, for example Heparin, which may be released upon implantation, or gradually over time. In another alternative, the implanted device may be fabricated from two materials, for example a polymer and a metal, which are bonded together using sulfonation.

Specifically, sulfonation may be used to cause the deposition of a thin layer of metal upon a polymeric core or form. This form of metal plating may render the device harder, smoother, more biocompatible, more durable, magnetic, more receptive to wave energy, and thus heatable, or may be used to impart any other property for which metal is employed within the body. A harder, smoother surface is particularly advantageous for an articulating or load bearing surface, such as a joint. For example, a coating of cobalt chrome is plated only to the condylar surface areas of a polymeric femoral implant, thus reducing both weight and cost.

Conversely, sulfonation may be used to improve bonding of a polymer to a metallic core or form, in order to confer the metallic form with the properties of a polymer, as described further herein, and in the incorporated references.

Sulfonation is particularly advantageous for combining therapeutic substances and devices, because significant quantities may be associated with the surface of the device without the use of heat, pressure, and or time, which could have an adverse effect on the device, or on the therapeutic substance.

Metals

In accordance with the invention, metals are advantageously connected with fasteners incorporating polymeric materials. Any of a variety of metals may be used, either smooth or formed with at least portions of foam metal, or a roughened or porous surface, or formed with cavities or other shapes upon which polymeric material may mold, enter, adhere, or otherwise affix. The polymer is softened in accordance with the invention through the application of heat, including heat created using vibratory energy, to become tacky, or sufficiently softened in order to bond on a microscopic level, or a macroscopic level through adaptation to the surface structure of the metal. For use in vivo, biocompatible metals are used, including stainless steel, nitinol or other SMA (shape metal alloy), tantalum, porous tantalum, titanium, cobalt-chrome alloys, and other metals such as are known to those skilled in the art. Additional related information, including bonding polymers and metals, and polymer to polymer bonding of implant materials, may be found in U.S. Pat. No. 5,163,960 entitled "Surgical devices assembled using bondable materials", and U.S. Pat. No. 7,104,996 entitled "Method of performing surgery", the contents of each of which being incorporated herein by reference.

Therapeutic Substances

The fastening device of the present invention may include therapeutic substances to promote healing. These substances could include antibiotics, hydroxypatite, anti-inflammatory agents, steroids, antibiotics, analgesic agents, chemotherapeutic agents, bone morphogenetic protein (BMP), demineralized bone matrix, collagen, growth factors, autogenetic bone marrow, progenitor cells, calcium sulfate, immo suppressants, fibrin, osteoinductive materials, apatite compositions, germicides, fetal cells, stem cells, enzymes, proteins, hormones, cell therapy substances, gene therapy substances, and combinations thereof. These therapeutic substances may be combined with the materials used to make the device. Alternatively, the therapeutic substances may be impregnated or coated on the device. Time-released therapeutic substances and drugs may also be incorporated into or coated on the surface of the device. The therapeutic substances may also be placed in a bioabsorbable, degradable, or biodegradable polymer layer or layers.

The therapeutic agents may also be placed within one or more cavities disposed in a fastening device of the present invention. Different agents may be disposed in different cavities of the device to specifically tailor the implant for a particular patient. Dosages of the therapeutic agent may be the same or different within each of cavities as well. The cavities may include a cover which may release the agent in a controlled or timed manner. The cover may be biodegradable or bioerodible to allow the agent to release to surrounding tissue. Examples of suitable therapeutic agents include bone growth inducing material, bone morphogenic proteins, osteoinductive materials, apatite compositions with collagen, demineralized bone powder, or any agent previously listed. U.S. Provisional Patent Application No. 60/728,206 entitled "Drug Eluting Implant" discloses means for delivering therapeutic agents. The above-mentioned provisional application is incorporated by reference herein in its entirety.

The fastening devices of this and other embodiments of the invention may be used in combination with fasteners in the prior art. Examples of fasteners, implants, and their methods of employment may be found in U.S. Pat. Nos. 5,163,960; 5,403,348; 5,441,538; 5,464,426; 5,549,630; 5,593,425; 5,713,921; 5,718,717; 5,782,862; 5,814,072; 5,814,073; 5,845,645; 5,921,986; 5,948,002; 6,010,525; 6,045,551; 6,086,593; 6,099,531; 6,159,234; 6,368,343; 6,447,516; 6,475,230; 6,592,609; 6,635,073; and 6,719,765. Other fastener types are disclosed in U.S. patent application Ser. Nos. 10/102,413; 10/228,855; 10/779,978; 10/780,444; and 10/797,685. The above cited patents and patent applications are hereby incorporated by reference in their entirety.

Naturally Occurring Materials

In addition to PEEK and the other polymers described herein, the implants, devices, and methods of the present invention may use keratin, a naturally occurring polymer. Keratin may be vibratory bonded or staked to itself, to other implants, or within tissue. This may be performed in the operating room or intracorporeally. Keratin may be bonded to collagen or to other known polymers. In an exemplary application, keratin may be used to fasten tissue to bone since keratin has BMP and tissue scaffold properties. It is contemplated that any of devices and methods disclosed herein may utilize keratin alone or in combination with PEEK, polylactic acid, or other polymer. Keratin may be used to make fasteners, disc replacements, joint replacement components, stents, cell scaffolds, drug reservoirs, etc. Also, joint bearing surfaces may include keratin with or without collagen or chondrocytes. The bearing surfaces may be fastened to a joint component using PEEK or PLA fasteners.

Another polymer that can be used with the present invention is a class of natural materials, called polyhydroxyalkanoates- or PHA polymers. These polymers are synthesized in nature by numerous microorganisms, and they have been recently recognized as the fifth class of naturally occurring biopolymers (along with the polyamino acids, polynucleic acids, polysaccharides, and polyisoprenoids). Unlike the other naturally occurring biological polymers, however, the PHA polymers are thermoplastic, i.e. they can be repeatedly softened with heat and hardened with cooling. As such, these polymers can be processed much like the plastics we use today. A specific example of a PHA polymer that could be used is poly-4-hydroxybutyrate material. Such PHA polymers are available from Tepha Inc of Lexington, Mass.

Polymethylmethacrylate

Fasteners of the invention may be coated with polymethylmethacrylate (PMMA), in order to promote bonding with PMMA used in the body, or PMMA could be incorporated into polymer of the fastener, or deposited within cavities or shapes formed in the fastener surface, including threaded, roughened, porous, or nano textures. A fastener may be thus coated with PMMA, or formed entirely of PMMA, and may be heat bonded, advantageously using ultrasound, to another PMMA surface or other adhesive surface, otherwise as described herein with respect to bone cement.

Although PMMA, known generally as bone cement, and other polymers may function more as a grouting agent than a cement or adhesive, only the term "adhesive" is used throughout the specification for simplicity.

Vibratory Mixing

Figure 58:
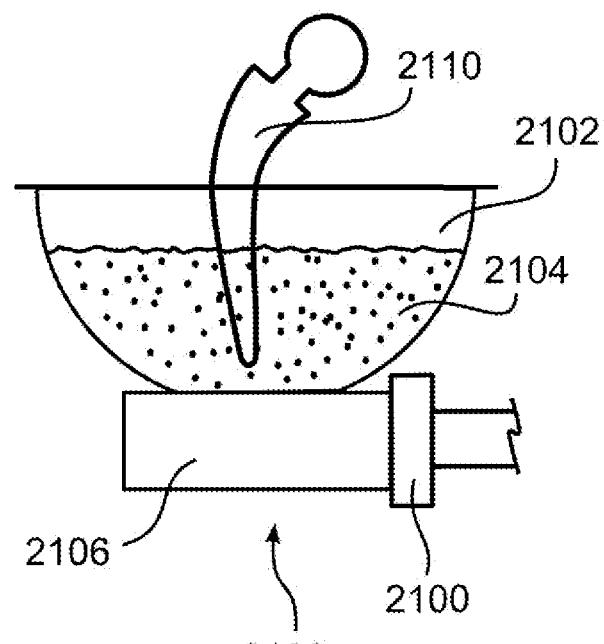
FIG. 58 illustrates vibratory mixing in accordance with the invention, and further illustrates coating an implant using vibratory energy.

With reference to FIG. 58, vibratory energy is used to mix materials 2104, for example materials to be used in formulating implants of the invention, adhesives and cements, therapeutic materials and other substances to be incorporated into implants, materials to be implanted within the body, or materials to be used during a medical procedure.

Materials 2104 may be mixed in a production or laboratory setting, or in the operating room immediately before implantation. A mixer 2108 applies vibratory energy to materials 2104, and includes a horn 2100, a mixing bowl or chamber 2102, and optionally a supporting member 2106. Vibratory energy may be applied directly to chamber 2102, or may be applied to supporting member 2104, as illustrated, in order to promote even distribution of materials 2104, possibly including the release of gases, gaps and voids, and resulting in a denser and or more even mixture. In addition, the temperature or pressure of chamber 2102 or mixture 2104, as well as other parameters, may be controlled by means known in the art, along with the application of vibratory energy, including for example ultrasonic energy, to produce an optimal resulting mixture 2104 after processing.

To improve mixing, the energy level and frequency may be tailored to the particular mix constituents. For example, low energy or longer wavelengths may be used for polymeric materials mixing, particularly amorphous polymers, and shorter wavelengths may be advantageously used for metallic materials and denser polymers, and PMMA. Other frequencies may be used, both lower and higher than the frequencies commonly used in ultrasonics, for example within the audible range, or in the megahertz range.

Polymer or adhesive, including bone cement, may be maintained or converted to a liquid or viscous form within mixer 2108. Additionally, therapeutic substances, including pharmaceuticals, may optionally be admixed. Further, an implant 2110 may be dipped into the material 2104 within chamber 2102 in order to be coated by material 2104. The dipped implant 2110 can include any material to be implanted, including metals and polymers, including porous metal or material with pores, cavities or a roughened surface, wherein material 2104 enters the pores or cavities in order to produce a stronger bond, and to increase the amount of material of the coating. It is advantageous for the dipped implant to maintain its shape until the coated polymer cools and hardens, if the polymer is heated.

In this manner, an implant such as a stent or arthroplasty component, for example implant 2110, may be coated to elute a therapeutic substance, while maintaining appropriate physical dimensions and properties. Further or alternatively, the coated implant may then be fastened within the body using the methods and devices described herein, the coating forming a substrate for proximal and or distal heat fastening, including vibratory fastening. Vibratory energy imparted to the mixing chamber during coating further serves to improve interdigitation and a close, conforming coating of the implant.

Vibratory mixing as described, advantageously combined with changes in mixing parameters, such as temperature and pressure, may be used to alter the polymerization characteristics of material 2104, for example, polymers within mixing chamber 2102. Accordingly, the resultant polymer may have properties best suited to the procedure contemplated. Properties affected may vary, but may include changes in density, porosity, flexibility, hardness, color, and smoothness.

Manufacturing with Vibratory Energy

Figure 58A:
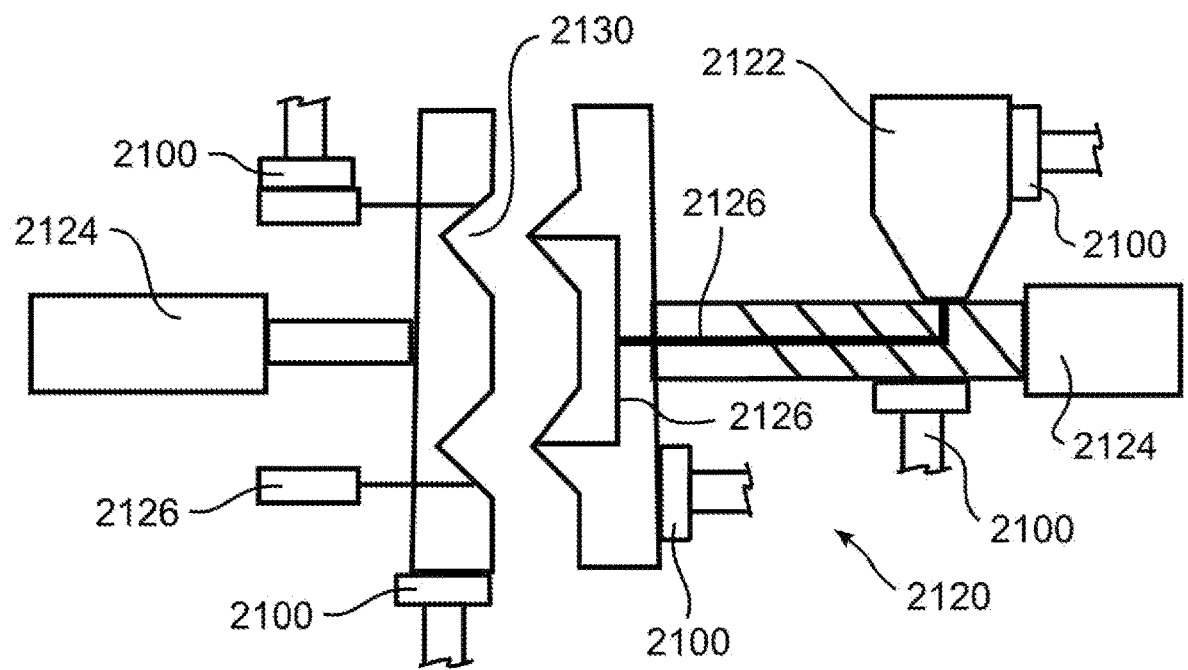
FIG. 58A illustrates the use of vibratory energy in accordance with the invention, in association with an injection molding apparatus.

With reference to FIG. 58A, in addition to mixing, as described herein, vibratory energy may be advantageously employed in manufacturing requiring a mixing step. Operating parameters such as temperature and pressure may be varied, in combination with the application of vibratory energy to mixing or staging apparatus. With respect to injection molding, in particular, vibratory energy is applied to any or all of the hoppers 2122, rams 2124, ejectors 2126, gates, sprues or runners 2128, and cavities and cores 2130 during the injection process. Vibratory horns 2100 are illustrated, connected to a source of vibratory energy (not shown) as known in the art, of sufficient power to achieve a desired affect, which may include for example improved mixing, improved flow, more uniform filling, more efficient ejection, faster injection, preheating of injected material, and increased compaction of molded material. With respect to injection molding, in particular, vibratory energy is applied to any or all of the gates, sprues, runners, cavities and cores during the injection process. In this manner, it is possible to increase the density and uniformity of the molded product, as well as to improve fracture resistance and performance of the part both during the fabrication process, and after fabrication.

Vibratory mixing and packing of the invention is particularly useful in mold filling and fabrication of precision parts requiring a tortuous fill path, having delicate structures, or having features on the nanometer scale.

In an additional manufacturing application, a biologic matrix including fibers, such as collagen fibers, can be more uniformly mixed and formed into a polymer or biologic collagen scaffold in combination with vibratory energy as described. The matrix may include cells or pharmaceutical agents, including chemotherapeutic agents, antibiotics, cell growth agents, growth inducing factors, and proteins. Moreover, manufactured or harvesting tissue, cells, or cell products may be integrated into a mixture that is molded to conform to a body surface or cavity, including epithelial surfaces, or to an implant. Manufacturing may take place, for example, in a factory, laboratory, operating room, outpatient facility, or medical office.

It should be understood that vibratory energy selected from a wide range of frequencies may be used to improve injection molding, for example vibration within the audible range, including vibratory energy of lower than 1 kHz, for example 0.3 kHz.

Bonding Parts

Figure 59:
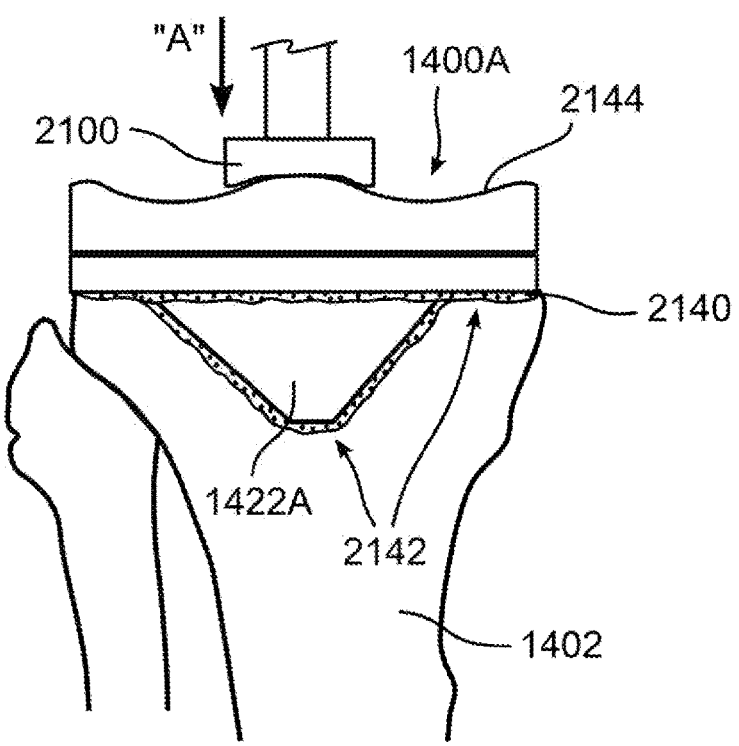
FIG. 59 illustrates vibratory energy in accordance with the invention used to distribute bondable material for bonding an implant within the body.

Referring now to FIG. 59, when bonding parts with adhesive, it can be a challenge to evenly distribute grouting agent or adhesive between the parts to be fastened. In accordance with the invention, vibratory energy, for example vibratory energy, is applied to either or both parts, and or the adhesive layer, to promote movement of the adhesive throughout the interstitial space 2142 between the parts, whereby a more uniform, reliable and predictable bond is formed.

With further reference to FIG. 59, in a medical context, it is often necessary to use an adhesive or grouting agent, for example PMMA or bone cement 2140, to secure an implant, particularly an arthroplasty component, such as tibial arthroplasty component 1400A, within the body. Implant 1400A has a projection or keel portion 1422A which enters a space within the body, for example the medullary canal of a bone 1402, or implant 1400A may simply lie upon the surface of body tissue. In either application, it is advantageous to create uniform contact in interstices 2140 between the implant, adhesive, and body tissue, in order to avoid the formation of gaps or voids, which may appear as lucencies in radiography.

In accordance with the invention, vibratory energy, advantageously vibratory energy, is applied to an implant, body tissue, or adhesive layer, for example implant 1400A, bone 1402, and adhesive layer 2140, or a combination of same, to improve movement of adhesive 2410 throughout the interface between the implant and the body tissue to be adhered. In FIG. 59, horn 2100 contacts component 1400A, connected to a vibratory energy generator (not shown). Alternatively, horn 2100 may contact the bone, or another portion of the implant 1400A. Vibratory energy is advantageously combined with pressure, applied to the interface, as by applying pressure to push the implant against a bone surface. An example includes application of force to an upper surface 2144 of tibial insert 1400A in the direction of Arrow "A", which includes insertion of an implant stem 1422A into the tibial medullary canal of bone 1402. Vibratory energy is applied to the upper portion of the tibial implant, for example near or on the bearing surface, or along the sides of the implant, as the stem is inserted into the canal. Vibratory energy may be continued for a period of time thereafter, until an even distribution of adhesive 2140 is achieved. In this example, adhesive enters the small cancellous bone interstices, as well as surface formations, including a roughened or porous implant surface, or an implant surface with one or more cavities, to improve the bond between the implant and the body.

Tissue Harvesting

In accordance with the invention, tissue is harvested by placing a harvesting tool with a holding area or chamber, such as a hollow coring drill, upon or within body tissue and applying vibratory energy to the harvesting tool, tissue, or both. Vibration, such as vibratory vibration, is applied to cause cells to become dislodged, freely mobile, or movable, whereupon they may be collected in the holding area. Cells may be further removed by applying lavage, pressure, suction, or abrasion. In a reverse process, vibratory energy aids in the implantation of cells, through modification of the body tissue surface, rendering the surface more conducive to implantation, and improves transfer of cells from the holding area to the implantation site. The use of vibratory energy is advantageously applied in the harvesting or implantation of fetal cells, for example.

The application of heat or other environmental change, or the addition of therapeutic elements, may be used to improve performance of harvesting or implantation. For example, including injectable polymers may improve bonding, the addition of nutrients may improve cell viability, or the addition of pharmaceutical agents may improve compatibility.

Fasteners

Fasteners of the invention may be configured to matingly engage other implants, being urged or locked into an advantageous orientation through a molded or otherwise formed three dimensional configuration. Alternatively, fasteners of the invention may be formed to maximize bonding surface, or to modify strength in designated locations.

Staking Fasteners

With reference to FIGS. 45 and 45A-C, in another embodiment of the invention, a tackable fastener 1100 is sized to be insertable through a stab wound, drilled portal, or other focused aperture. The body 1102 of the fastener is provided with a passageway or aperture 1104 through which another fastener may pass, for example a suture, cable, or another similar fastener. Fastener 1100 is further provided with a ramped or angled face 1106 which advantageously is provided with a constricted or pointed proximal end 1108, operative to pierce material to be held 1118 thereon. The distal end 1110 of the fastener may be secure using the distal fastening method described in this specification, or alternatively by any known means, including a press fit into a bore, attachment using the aperture described above, or adhesive. Distal end 1110 may be provided with a roughened or porous surface to promote secure attachment by adhesive. If materials are to be held on the fastener, they are passed over proximal end 1108, being pierced by the fastener if needed, and are optionally followed by a load spreading member, such as a plate or washer 1112. When all materials are held, a cap 1114 is formed on or placed upon the proximal end of the fastener, as described in this specification, and the materials are staked. In FIG. 45, an end effector or horn, for example end effector 104 and horn 120D, are applied to fastener 1102 at proximal end 1108, and upon the application of vibratory energy, melt and curl over sides 1116, thus forming cap 1114. In the example shown, pin 106 of end effector 104 enters bore or aperture 1118 at proximal end 1108, thus establishing and maintaining alignment with horn 120D at least before and during the application of vibratory energy.

Referring now to FIG. 45C, fastener 1120 is formed of at least two dissimilar materials, for example two materials 1122 and 1124 having different melting points. In the example shown, a proximal end 1108 is advantageously formed of a bondable material 1124 that may be formed using the proximal application of vibratory energy, as described above.

Distal end 1110 is advantageously fabricated with a material 1122 having a higher melting point than material 1124, and may include, for example, metal, ceramic, or a high molecular weight polymer with a higher melting point than material 1122, and may be driven into adhesive or polymer in vivo using a distal fastening method of the invention, or using other means of attachment. For example, first end 1122 may be press fit, adhered, or threaded onto another fastener.

The dissimilar materials are joined through any known means, such as extrusion, molding, press fit, threading, and adhesion. Mating segments 1126 and 1128 may be provided to promote a strong bond between the proximal and distal ends 1108 and 1110.

Embedded Bone Cement Fastener

With reference to FIGS. 32-34, anchors or embedding fasteners 800 may be embedded within previously solidified bone bondable material 802, for example PMMA or other acrylic based adhesive. In an embodiment in accordance with the invention, embedding fastener 800 is connected to end effector 804 of a vibratory energy generator 100, such as the type shown in FIG. 1. Embedding fastener 800 is adapted to enter and engage adhesive or bondable material 802 that has been locally melted by vibratory energy, through contact between embedding fastener 800 and bondable material 802 during operation of generator 100. Embedding fastener 800 is securely retained by bondable material 802 once the latter has cooled and hardened.

End effector 804 may be provided in any of a variety of shapes, one example being an elongated rod or shaft such as is shown in FIGS. 32-34, connectable to a hand piece at a proximal end 806, and operative to transmit vibratory energy at a distal end 808. While a rod shape is shown and selected for reduced manufacturing cost, end effector 804 may have the form of box or hex channel, oval or other shape, provided it communicates vibratory energy to a distal end portion, or to an attached fastener. Embedding fastener 800 is adapted to connect to distal end 808 of end effector 804 by mechanical interlocking, as by a bore 810 in embedding fastener 800, sized to receive a post 812 on end effector 804, optionally provided with internal or external threading (not shown), wherein post 812 has mating threads. Similarly, a bore or aperture may be provided in end effector 804, matable with a post or projection on embedding fastener 800. Other mechanical connections are contemplated, including twist lock configurations, friction fitting, or adhesive attachment. The mechanical connection must be operative, however, to communicate vibratory energy from end effector 804 to embedding fastener 800, as by a firm mechanical connection.

Embedding fastener 800 is adapted to be securely retained within adhesive 802, in one embodiment, by being provided with a shaped or contoured surface 814 upon which the adhesive may grip, once hardened. A roughened or porous surface (not shown) may be provided alone or in combination with shaped surface 814, the adhesive obtaining improved purchase thereupon.

Embedding fastener 800 may further be provided with a taper 816 at a leading end 818, which first enters the adhesive, as shown in FIG. 32A. Taper 816 may improves performance, for example, by promoting accurate tracking and movement of embedding fastener 800 into bondable material 802, piercing body tissue, and facilitating initial melting by concentrating vibratory energy over a smaller surface region.

Embedding fastener 800 may be provided with channels 820 operative to provide a path for molten cement 822 to be displaced, providing room for entry of embedding fastener 800. Where embedding fastener 800 is to displace a substantial amount of material, channels may be extended along the entire length of embedding fastener 800, and may further extend along end effector 804, as shown for channel 824 in FIG. 34. Channels 820 are further operative to reduce the possibility of rotation of fastener 800 within bondable material 802. Channels 820 are thus disposed to extend into bondable material 802 after insertion, and may extend to the face of embedding fastener 800. Channels 820 are additionally illustrated on embeddable end effector 3054 in FIG. 84.

Once anchored, end effector 804 and embedding fastener 800, embedded in bondable material 802, may remain connected. Alternatively, end effector 804 may be removed and another fastener of a similar or different design may be connected to an implanted embedding fastener 800, connecting by mechanical means as described, for example, by threading. In a further embodiment, a fastener such as described in the incorporated related prior patents and applications may be fastened to an implanted or installed embedding fastener 800, then secured in its respective manner. For example, a pointed polymeric fastener may pierce body tissue and enter secured embedding fastener 800, connecting by, for example, press fitting, or threading into a bore within embedding fastener 800. The additional fastener may be distally fastened into the bore using vibratory energy as detailed in this specification. Once secured within embedding fastener 800, a head portion of the polymeric fastener may then be formed to cap and secure the tissue, using a vibratory end effector, such as is described with respect to FIG. 3C or 22, for example.

An alternative method of attaching a removable embedded fastener is illustrated in FIG. 30, wherein releasable fastener 826, in this embodiment a pointed structure, is connected to end effector 104 through push and turn engagement 828 comprising a pin 832 associated with fastener 826, and an L-shaped slot 830, associated with end effector 104. Pin 832 travels through slot 830 until it rests at the end of slot 830, whereupon fastener 826 is retained upon end effector 104. To further promote retention of fastener 826, a resilient member, such as spring 834, is provided within end effector 104 to maintain tension between pin 832 and slot 830. Slot 830 may further be angled to enhance retention of pin 832. Further, it should be understood that slot 830 may be provided within fastener 826, and pin 832 may extend from end effector 104. This embodiment has the additional advantage of providing a current conducting metal to metal contact surface between end effector 104 and fastener 826, thus preventing arcing or sparking during use.

Ported Embedded Fastener

With reference to FIGS. 35-39, a locking fastener 840 is provided with one or more channels 844, accessible when locking fastener 840 is installed. A channel 844 is communicative with one or more ports 842 extending to a surface of fastener 840. In the example shown, a central bore forms channel 844, and connects with two ports 842, which emerges to the surface 846 of fastener 840, for example at threads 848. When locking fastener 840 is threaded into embedding fastener 800, described above, a heat meltable fastener 850 may be inserted within channel 844. Subsequently, vibratory energy is applied to meltable fastener 850, to soften and at least partially melt material from meltable fastener 850, at a point distally located from end effector 804. When material of the meltable fastener 850 melts, and particularly as pressure is applied to meltable fastener 850 in the direction of insertion, melted material enters one or more ports 842, flowing in a direction away from channel 844. When locking fastener 840 is installed in embedded fastener 800, an interface between both fasteners is created within bore 810 and at surface 846. Melted material of meltable fastener 850 thus flows into this interface, and adheres therein, particularly when cooled and hardened, to further secure fasteners 800 and 840. Where the interface includes shapes, such as threads 848 and mating threads 856 within bore 810, cooled material of meltable fastener 850 further forms a mechanical lock 858, in addition to or as an alternative to an adhesive lock as described.

A guide port 852 may be provided within meltable fastener 850, operative to set and maintain alignment of meltable fastener 850 with post 106, the latter disposed at the distal end of end effector 804. Meltable fastener 850 may further be provided with a tapered or pointed end 854, operative to promote initial melting of meltable fastener 850 through vibratory energy, by concentrating vibratory forces within a smaller surface area. Pointed end 854 may further serve to pierce body tissue or other materials, should that be advantageous.

With reference to FIG. 39A, in another embodiment, fastener pin 860 is sized to fit through port 842 in threads 848 or surface 846 of locking fastener 840, as previously described. Embedded fastener 800 is further provided with port 862, sized to admit passage of pin 860. When fasteners 800 and 840 are fastened, ports 842 and 862 are aligned to permit passage of pin 860 in one or both of directions "A" or "B", as convenient for the practitioner. Pin 860 may be sized to be retained with ports 842, 862 by being press fit. Alternatively, fastener pin 860 may include bondable material, heat softenable with the application of vibratory energy, whereupon pin 860 becomes tacky and or conforms to gaps or a roughened surface within ports 842 and 862, thereby locking fasteners 800 and 840 in respective fastened alignment. Alternatively, pin 860 may be retained by threading, adhesive, or other known means for retaining a pin within an aperture. Pin 860 may further be sufficiently long to pass entirely through locking fastener 840 and at least a portion of embedded fastener 800.

Offset Shaft Collar

Figure 12:
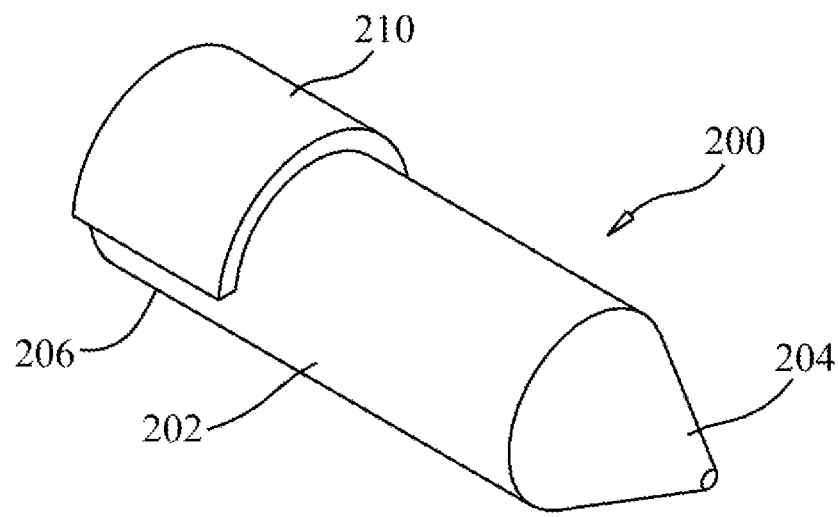
FIG. 12 shows an embodiment of a thermoplastic fastener.

FIG. 12 shows an embodiment of a fastener 200 of the present invention. Although fastener 200 is particularly well-suited for used with a spinal cage implant, it can be used for other clinical situations as well. Fastener 200 has a shaft 202, which can be threaded (not shown) or not threaded (shown). At a distal end, shaft 202 terminates in a tip 204 and at a proximal end, shaft 202 includes a head 206 that is provided with a recess 208 (FIG. 13) into which a pin of an end effector can matingly engage. Head 206 has a lip 210 that only partially extends around the circumference of shaft 202. As show, lip 210 extends about half (180°) of the circumference, but any angle can be used.

Figure 13:
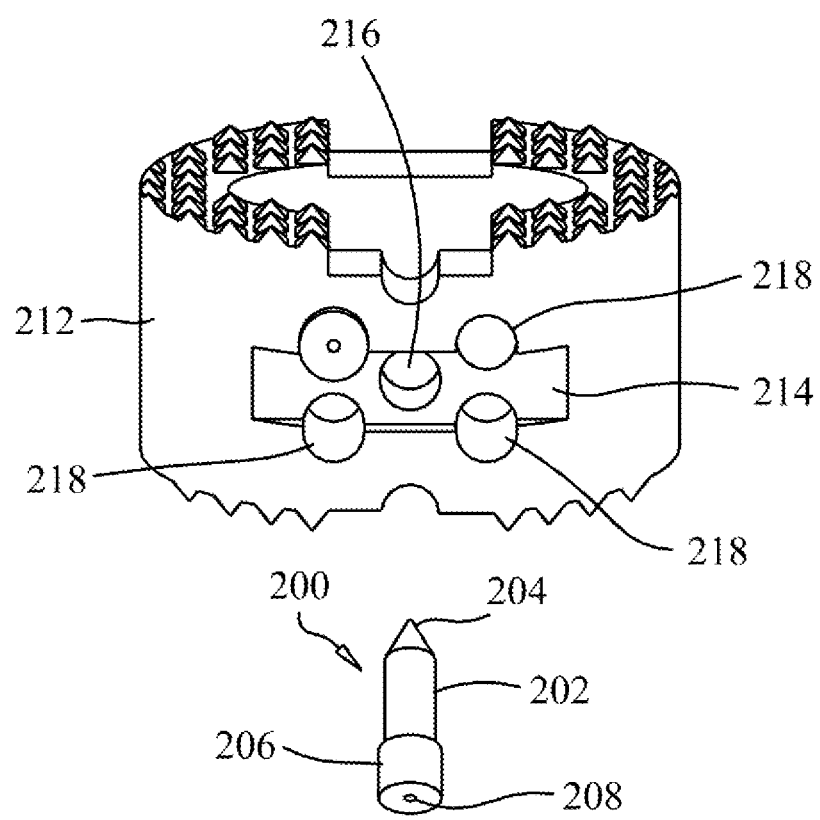
FIGS. 13 and 14 illustrate the fastener of FIG. 12 fixed to a spinal cage.
Figure 14:
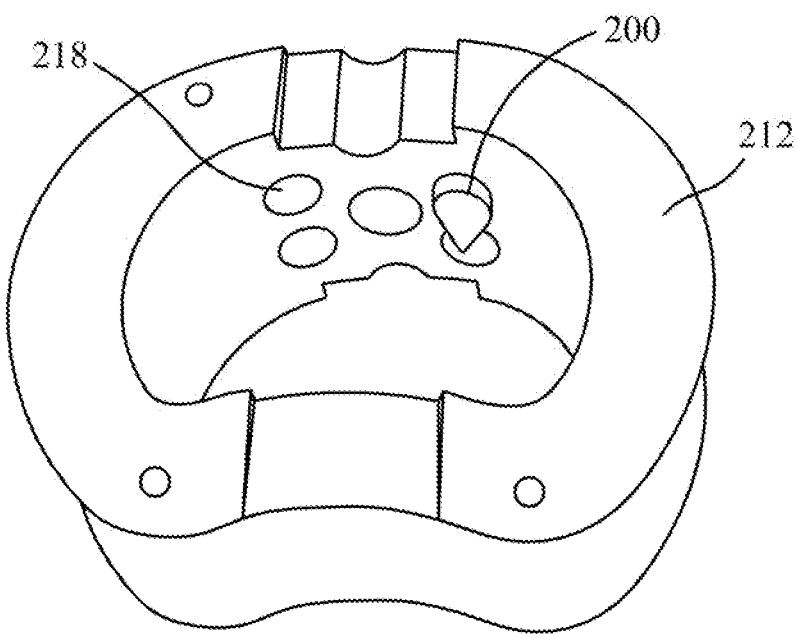
Figure 15:
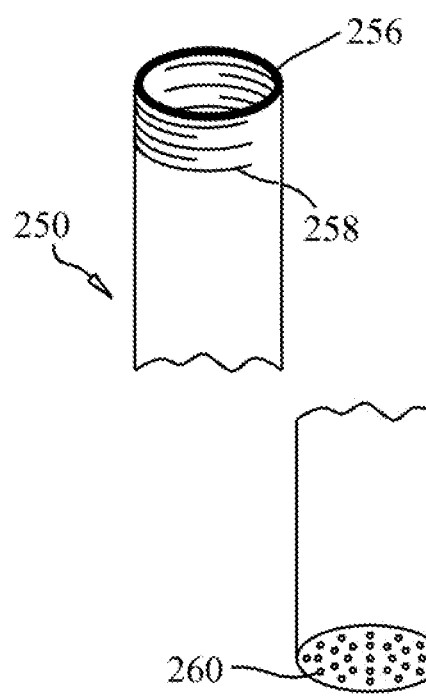
FIG. 15 shows an end effector used for implant removal.
Figure 16:
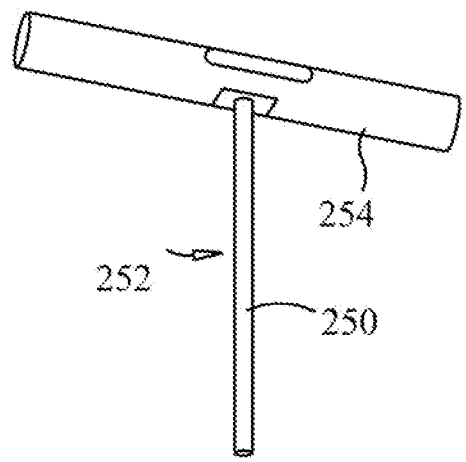
FIG. 16 shows the end effector of FIG. 15 contacted to a T handle.
Figure 17:
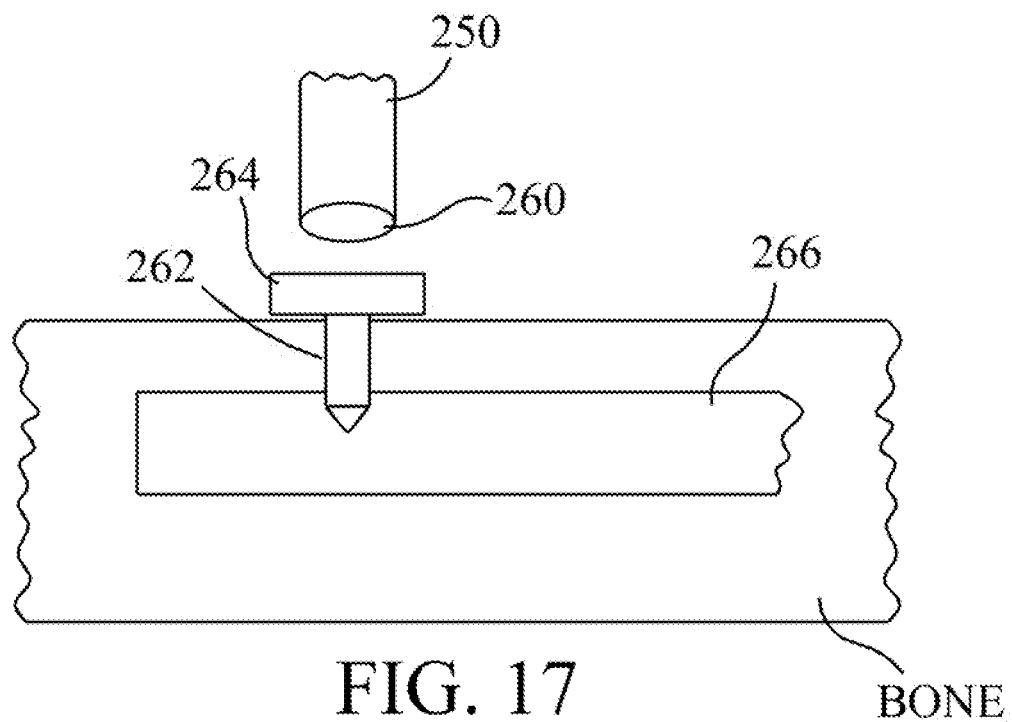
FIGS. 17 and 18 show the end effector of FIG. 15 in use to remove an implant.
Figure 18:
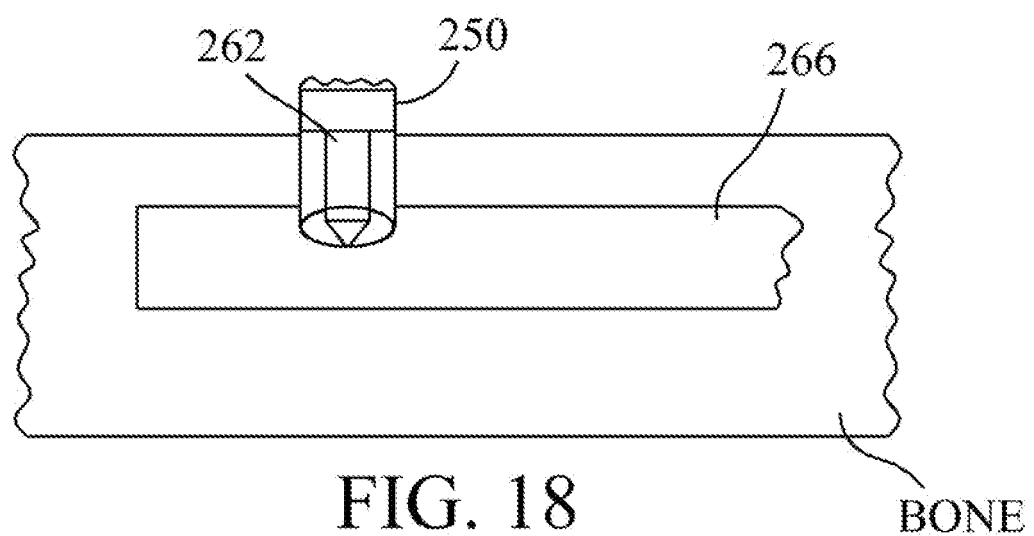
Figure 73:
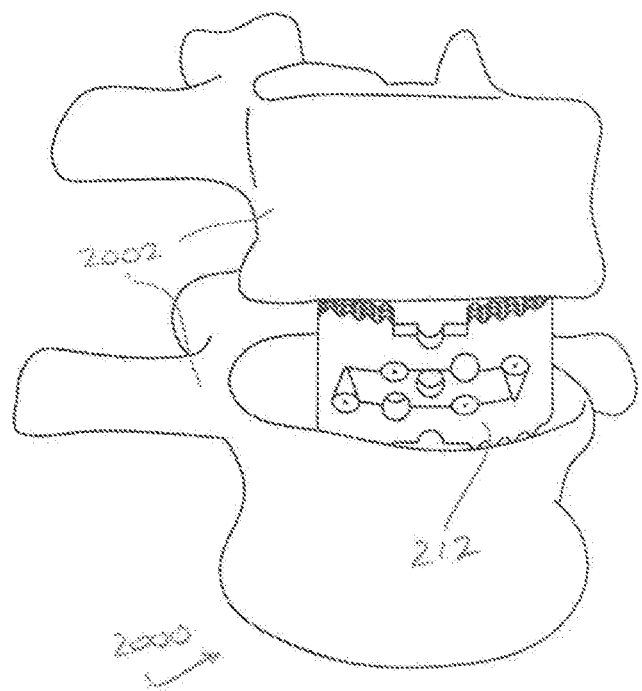
FIG. 73 illustrates a spinal cage of the invention, inserted between vertebrae, and fastened in accordance with the invention.

FIGS. 13 and 14 show fastener 200 fixed to a spinal cage 212. As is typical for these types of implants, spinal cage 212 includes a recessed area 214 configured and designed such that an inserter (which can also mate with the centrally located threaded screw hole 216) can be used to facilitate implantation. Spinal cage 212 includes a plurality of fastener holes 218 that under the prior art a traditional bone screw would be used to secure cage 212. Fastener holes 218 are located along the periphery of recessed area 214, creating a step. In order to accommodate for this step, lip 210 extends about half of the circumference. The geometry of lip 210 also facilitates the bond. With other fastener designs, the bonding occurs with the far tip of the fastener. In contrast, fastener 200 uses a shear joint with the diameter of head 206 slightly larger than hole 218. FIG. 73 illustrates fastener 212 within the spine 2000, between vertebrae 2002.

Fastener 200 and cage 212 can be made of the same material (such as PEEK) or different materials. In this regard, cage 212 can be made of a different thermoplastic material than that of fastener 200. Alternatively, cage 212 need not be made of a thermoplastic material. Where dissimilar materials are used, bonding occurs through an interlocking of bondable material between fastener 200 and cage 212, or interlocking of bondable material and the physical structure of the object to be bonded.

Knotless Suture Fastening

Figure 19:
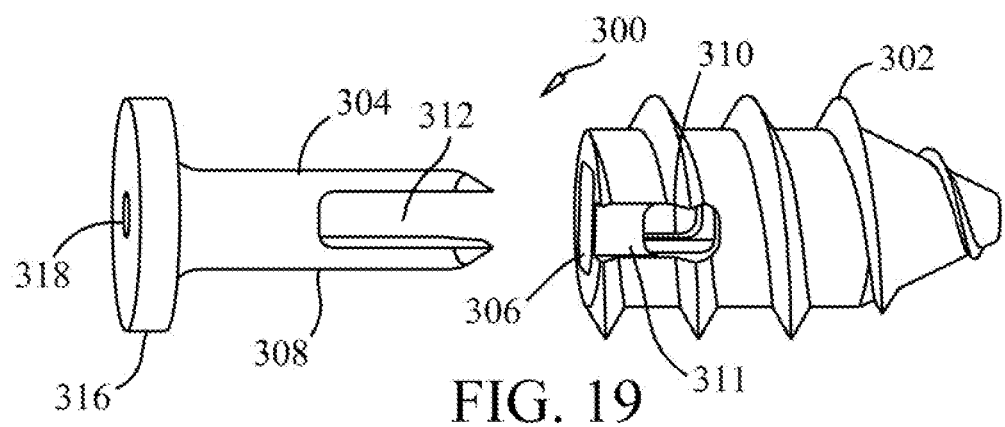
FIG. 19 shows a knotless suture fastening system.
Figure 20:
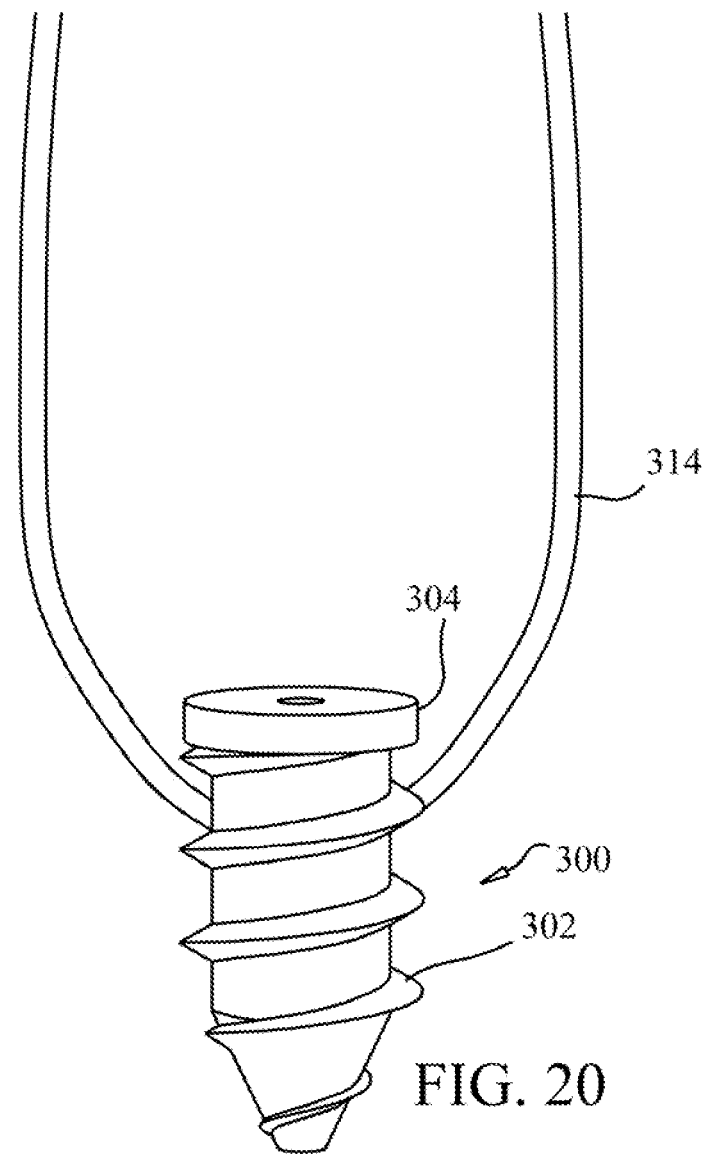
FIG. 20 shows a suture secured to the knotless suture fastening system of FIG. 19.

Although the present invention includes fastener concepts that eliminate the need for sutures (so-called "sutureless fastening"). The present invention also includes fastener concepts that use suture, but without the need for knots (so-called "knotless fastening"). FIGS. 19 and 20 show a knotless fastening system 300. System 300 includes an anchor 302 that is similar to the anchors of the inventors' prior applications and a fastener cap or tack 304 that is also similar to the fastener cap of the prior applications. In this regard, anchor 302 is shown threaded, but could be otherwise provided with protrusions or other surface features for engaging the tissue into which it is inserted. Alternatively, it could be smooth.

Anchor bore 306 is configured and dimensioned to receive shaft 308 of tack 304. Bore 306 can be substantially cylindrical or can be configured for holding an allen-type wrench. The figures illustrate an anchor bore that is square-shaped with rounded corners, although other allen-wrench shapes such as hexagonal shaped, star-shaped, pentagonal shaped, or the like may likewise be suitable to allow torque to be imparted to the anchor in order to help drive the anchor into bone, tissue, or implant material. An anchor channel 310 extends through anchor 302 and anchor 302 is also provided with slits 311 so that a suture does not become tangled during insertion and can slide when tightening.

Various methods are disclosed in U.S. Patent publication 2007/0208378 for securing sutures. With reference to FIGS. 75-77, several such methods are illustrated. However, anchors 3900, 3900A and 3900B are contacted by end effector 104 and or horns adapted to fit and communicate vibratory energy to the anchor, as shown and described for example with respect to fastener 826 of FIG. 30, and horns 2100 of FIG. 59 and 2310 of FIG. 61, whereupon the anchor may be caused to soften, melt or deform to lock suture 3902 within the anchor.

For example, a suture 3902 is passed through body tissue, and one or more strands pass through a gap or aperture in an anchor 3900, 3900A, 3900B comprising bondable material. An end effector of the invention is applied to the anchor to cause melting of the bondable material, trapping the suture strands therein.

With respect to FIGS. 75 and 76, horns 3908 are caused to contact anchor 3900 or 3902 and transmit vibratory energy into anchor 3900 or 3900A sufficient to cause softening or deformation thereof, and to thereby bind sutures 3902. Pressure may be applied in the direction of the heavy arrows within horns 3908, during and or after application of vibratory energy, to improve bonding.

With reference to FIG. 77, end effector 104 is provided with a tip 3904 adapted to fit within recess 3906 of anchor 3900C, and to transmit vibratory energy to anchor 3900C to cause softening and deformation thereof, sufficient to bind sutures 3902 within anchor 3900C. Pressure may be applied in the direction of the heavy arrow within tip 3904, during and or after application of vibratory energy, to improve bonding.

If the anchor and sutures are of the same material, the anchor and sutures may become welded. Alternatively, the anchor may be provided with a tortuous pathway for the strands, such that as vibratory energy is applied to the anchor, the anchor is deformed and the suture strands are mechanically locked within the anchor.

Further, the end effector may be driven into the anchor with vibratory energy, thus displacing material of the anchor to cause compression of the suture strands, binding the suture strands within the anchor. The end effector is thus advantageously shaped to penetrate and displace material along a predetermined path and direction. For example, fastener 826 of FIG. 30 is well adapted to penetrate a monolithic anchor, particularly where there is no established entry portal.

In an additional embodiment, more than one end effector may be applied to an anchor from opposing sides, whereupon vibratory energy and pressure caused by pinching of the anchor between the end effectors operates to compress the anchor and thereby bind one or more suture strands within the anchor. The end effectors may further be shaped to have contact the anchor along an increased surface area, improving the transmission of vibratory energy in the anchor.

A tack channel 312 (created by the forked end of shaft 308) extends through tack 304 such that one or more sutures 314 can extend through both anchor 302 and tack 304. When tack 304 is partially inserted in anchor 302, suture 314 can freely move since anchor channel 310 is aligned with tack channel 312. However, as tack 304 is further inserted in anchor 302, channels 310 and 312 misalign, trapping suture 314. When the bonding of anchor 302 and 304 occurs, knotless fastening of suture 314 is achieved. Experimental studies have shown that with anchor 302 and tack 304 made of PEEK and suture 314 made of polyethylene, knotless fastening can be achieved without any melting or degradation of the suture material. Although a single suture lead is shown in FIG. 20, there could be two leads through one side of anchor 302 and a loop of the suture for holding tissue out the other.

As discussed in connection with other embodiments, tack shaft 308 may have a cross-sectional shape corresponding to the shape of the anchor bore 306. One potential advantage of this embodiment of the invention is that it may allow the physician to apply a greater amount of torsional force to turn the anchor further into or out of the bone, tissue or implant material either before or after the anchor and tack have been bonded together. This would allow depth control of insertion and/or further control of the suture tension. Rotation of the tack can be achieved in several different ways. For example, an open-ended wrench may be used to grip the tack shaft and turned in a clockwise or counter-clockwise direction. Similarly, the tack lid 316 may be configured to receive a wrench that allows the fastener assembly to be rotated in or out of position. Tack lid 316 may include a bonding recess 318 that allows a bonding device to be aligned with and impart energy to the anchor. The bonding recess also may be configured to receive a tool either before or after bonding, or both, that allows a physician to manipulate the fastener. Thus, the shape of the bonding recess may be configured to receive an allen-type wrench, a screwdriver, or the like so that torsional forces may be exerted on the fastener. Alternatively, the outer periphery of tack lid 316 may be shaped to engage a tool, for example, while tack lid 316 is illustrated as round, it may be square, or hex shaped.

Providing features in the fastener that allow a physician to manipulate the assembly may be useful in several different ways. For instance, such a configuration may allow a physician to bond the assembly together and then rotate it to further deploy the assembly into the body. Such a configuration also may facilitate easier removal of the assembly at a later time. This configuration also may permit a physician to make one or more adjustments in the deployment or positioning of the fastener assembly, either during the initial procedure or later in time. While such benefits each have advantages, it should be noted that no embodiment of the invention requires these advantages to be realized in order to fall within the scope of the invention.

Bonding of the tack to an inside bore of an anchor may result in a collapse of the tack during the bond. As a result of this collapse, the gap distance between the anchor top surface and the underside surface of the tack may decrease. This reduction in the gap may be beneficial for further ensuring that the material disposed in the gap is more securely held in place by the fastener assembly. For instance, the bonding process may cause the gap to be reduced 1 mm or more due to bonding. This reduction may therefore cause the cap lid and top of the anchor to impinge on the tissue or implant materials disposed in between these surfaces.

In some instances, it may be desirable to fine-tune the security of the tissue and compression against the bone. As mentioned above, the fastener may be configured to receive a tool that allows manipulation of the assembly. In this manner, the fastener lid 316 may be manipulated to drive the anchor 302 and tack 304 further into the bone. This would decrease the distance between the cap lid 316 and bone, better securing a thinner tissue or implant material disposed therebetween by placing it under more compression. Alternatively, if it was thought that tissue was under too much compression the fastener cap could be turned the opposite direction increasing the gap between the bone and fastener lid. A washer may be disposed between the lower surface of the cap lid 316 and the tissue or implant material that is being fastened in place. As the cap lid is rotated or otherwise manipulated, the washer may help reduce damage to the tissue or implant material from shearing forces that may be imparted from rotation of the cap lid 316.

Additionally, such a configuration may allow the anchor placement to be adjusted even before bonding takes place. For example, the anchor may be placed in a first position. Implant material or tissue may be disposed between the anchor and a fastener. A portion of the fastener may be inserted through the implant material or tissue and into the anchor bore. If the physician then determines that the anchor position needs adjustment, the cap may be rotated to move it further into or out of the material in which it is placed. Once the anchor is in a desired position, the cap may be bonded or otherwise secured to the anchor. As noted above, further adjustments in position of the assembly may be made even after the assembly is secured together.

Bonded Flange Fastener

With reference to FIGS. 52A-B, a fastener 1700 is provided, adapted to bond an implant 1710 to body tissue 1712. Fastener 1700 includes one or more flanges 1714 or tabs projecting from implant 1710, and being formed of a bondable material. Fastener 1700 is advantageously used where the implant has the form of a shell, surface layer, or liner 1716, and where liner 1716 is advantageously formed as a smooth, continuous surface, without projecting mounting posts, or holes through which a fastener may pass. FIGS. 52A-B are cross sectional illustrations through an acetabulum, an area of roughly hemispheric shaped body tissue, and an implant 1710, having a corresponding mating shape. The discussion with respect to the acetabulum applies equally to other bearing surfaces, such as condylar surfaces, or other lined surfaces of the body.

An implant base 1714 is fastened to body tissue 1712 at a location beneath or adjacent to the intended implantation site for liner 1716. Implant base 1720 is attached to body tissue in accordance with any known manner, or in a manner disclosed herein. Implant base 1720 has mounting projections 1718 positioned to cooperate with flanges 1714 of fastener 1700. After implant base 1720 is secured, liner 1716 is positioned in the body, and flanges 1714 are attached to mounting projections 1718 using vibratory energy. Flanges 1714 and mounting projections 1718 may be provided in the form of mating flanges, flange and posts, mating posts, or any other cooperating projections which may be heat bonded together upon the application of vibratory energy. Two forms of mounting projection are illustrated, as 1718 and 1718A. Projection 1718 extends beyond a final position, and projection 1718A terminates at a final position which does not interfere with proper functioning of the body, or is potentially useful for proper body functioning.

With reference to FIG. 52B, it can be seen that projection 1718 and flange 1714 are bonded and bent to rest at a final position 1722. Bonding may occur either before or after bending. Bonding for projection 1718A differs in that only flange 1714 is bent to contact flange 1718A, and flange 1714 is then heated using vibratory energy to mold onto and bond to flange 1718A.

While two variations of an implant base projection 1718, 1718A are shown, it should be understood that a single style may be advantageously employed around the entire circumference of the union between implant base 1720 and liner 1716. However, if the style of bonding is to change, a division or seam in flange 1714, or projection 1718, may be provided to facilitate a transition.

Bonding may be improved by providing a roughened or porous surface, or at least one cavity, on projection 1718, 1718A, or on flange 1714.

In another embodiment, flange 1714 is fastened directly to bone or body tissue adjacent to the site of implantation, using vibratory energy to heat flange 1714, whereupon flange 1714 may be shaped to conform to existing body tissue structure, and may bond thereto, for example, by adhesion or mechanical interlocking Body tissue may be provided with a roughened or shaped surface to promote bonding with flange 1714.

To further secure the liner, adhesive may be applied to an inner surface of the liner before mounting and attachment.

Headless Fastener

In another embodiment of the invention, illustrated in FIG. 46G, a fastener 1240 is provided, fastenable in a manner described herein, the fastener passing, for example, through an aperture or bore. However, the fastener is not provided with a head or widened portion operative to prevent the fastener from passing completely through the aperture. For distally secured fasteners, described herein, there is a reduced possibility for the fastener to pass completely through the aperture, as the distal end of the fastener is securely fixed. Where the point of fastening is fixed relative to the location of the entry of the bore, a fastener head can be avoided. In this manner, the fastener may have an excess length, and be trimmed flush after being secured. Alternatively, the fastener may be provided with a length predetermined to lie flush with a surface through which the fastener is passed. Fastener 1240 is described further, below.

Figure 49:
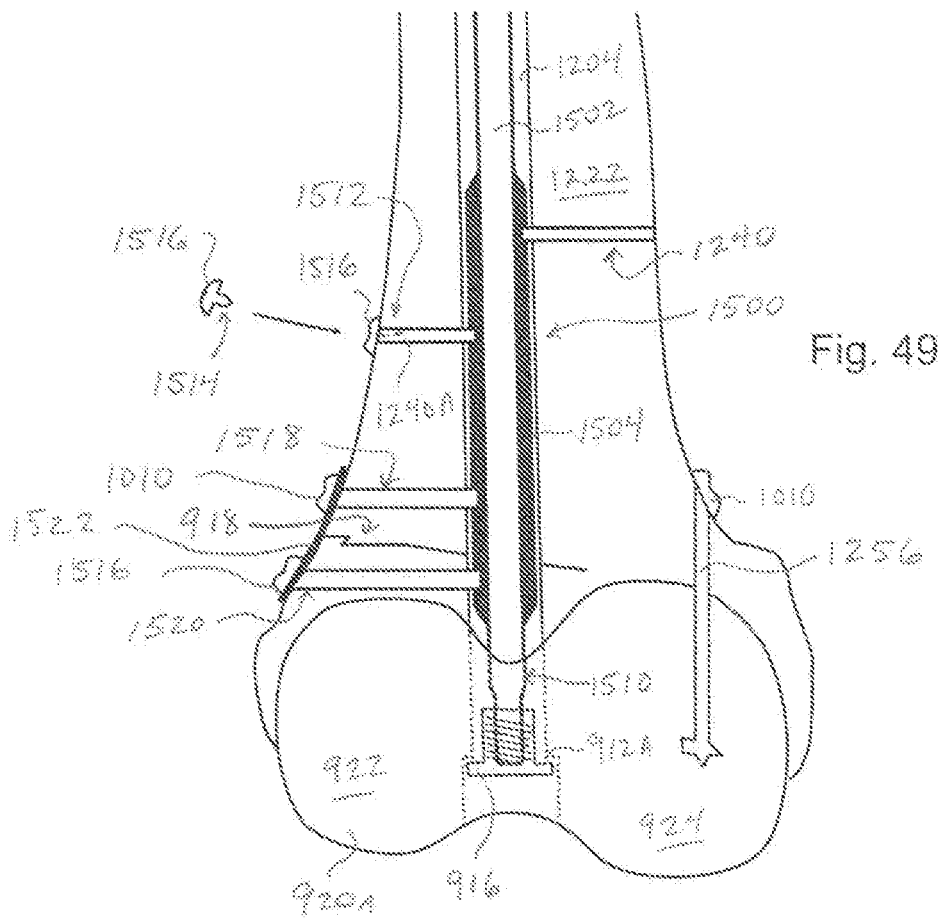
FIG. 49 illustrates the end effector of FIG. 48, deployed within the body in a partial longitudinal cross section through the center of the end effector and the bone, and further illustrates securing of a joint replacement component in accordance with the invention.

With reference to FIG. 49, in a further alternative, a head portion provided as a mountable cap 1516, may be bonded to fastener 1240 using vibratory energy, as described herein, after the fastener has been distally secured and trimmed. Reference may be had to a further discussion of FIG. 49, below.

Spacer

With reference to FIGS. 54 and 54A-C, implant 1900 may be positioned and secured in a precise location, in accordance with the invention, through the use of a progressively widening spacer. Examples include conical spacer 1902, or wedge spacer 1904. Spacers 1902, 1904 advantageously include a surface or at least partial coating of bondable material as described herein, or alternatively, fasten to one or more surfaces of implant 1900 that include bondable material. Any of fastener 1902 or 1904, implant 1900, or implant base 1906 may be provided with a roughened or porous surface, or a surface with at least one cavity, into or onto which bondable material may bond.

Due to the ramped shape of spacer 1902, 1904, a progressive insertion of the device produces a concomitant displacement of the implant to be affixed, relative to the body tissue proximate the implantation site. Spacers 1904,

1902, and 1906 are placed at different locations, so that they may cooperatively displace the implant, and offer greater strength when affixed. Spacer 1906 is of a different size than spacer 1902; a range of sizes is advantageous where gaps of differing size are required to be formed. A tool engaging structure, such as an aperture, groove, or slot 1908 may be formed in a spacer, as shown in spacers 1902 and 1906, which may be engaged by a tool to facilitate placement or removal, as by twisting.

FIG. 54C illustrates an alternative form of spacer 1910, having a spacer core 1912 which may be driven into the interior 1914 of spacer 1910 to drive outer walls 1916 apart, either before or after spacer 1910 has been implanted within the body, and then maintain outer walls at a fixed orientation. An aperture or other tool engaging structure, such as hex receiver 1918 may be provided to enable driving core 1912 into spacer 1910, as by pushing, or engaging mating threads 1920, 1922. Core 1912 may alternatively be provided as a cam structure, rotatable to push walls 1916 apart. Core 1912 may be a separate part, or attached to spacer 1910, for example by living hinge 1924 or other flexible structure.

Spacers of the invention, including spacer examples 1902 or 1904, are affixable in a predetermined location, through the use of vibratory energy. Once in position, proximal or distal vibratory fastening, as described herein, is used to bond spacer 1902 or 1904 to implant 1900, or to body tissue 1924, adjacent implant 1900.

End Effector with Cartridge Heater

Figure 2A:
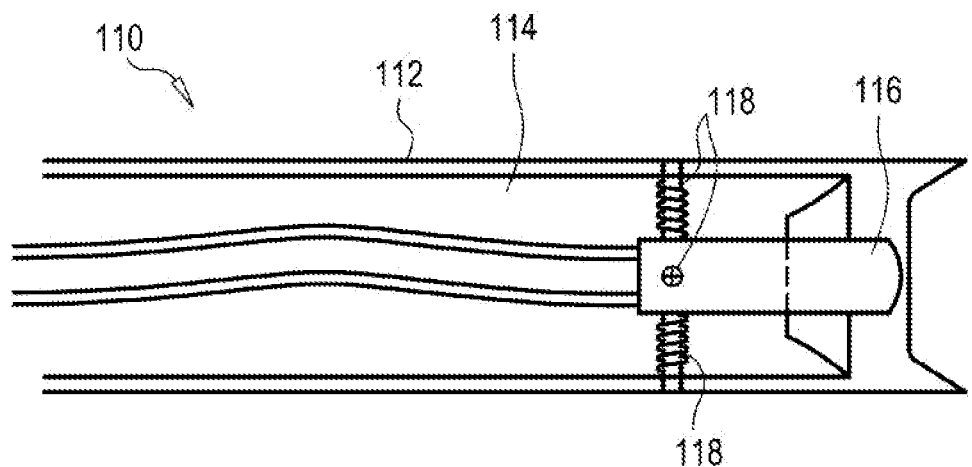
FIGS. 2A and 2B illustrate exemplary cartridge heaters of the present invention.
Figure 2B:
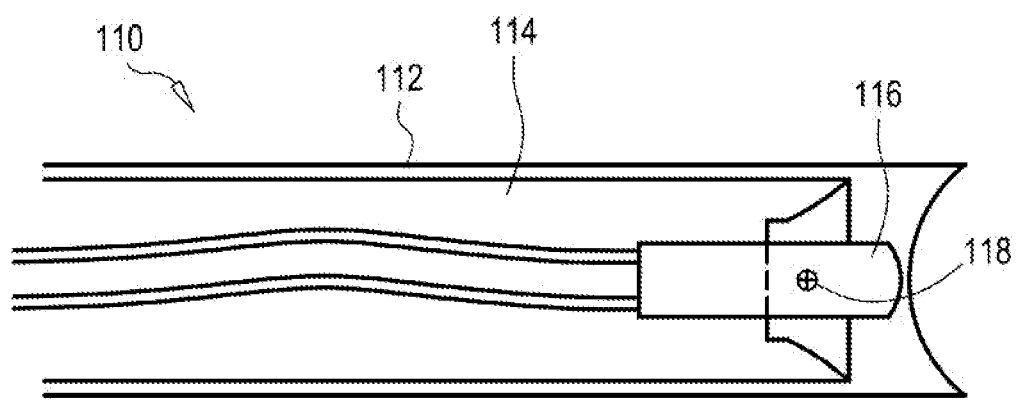

Another exemplary instrument 110 is illustrated in FIGS. 2A and 2B. A small cartridge heater 116 may be used to deliver thermal energy. Heater 116 may be a SUNROD ⅛ inch cartridge heater, for example. To prevent heat build up upon the outside shaft 112, an insulating region 114 may be formed between heater 116 and shaft 112. In FIG. 2A, four set screws 118 are used to create the insulating region 114, which in this example is an air barrier, while in FIG. 2B, a single set screw 118 is used.

Configurable End Effector Face

Figure 3A:
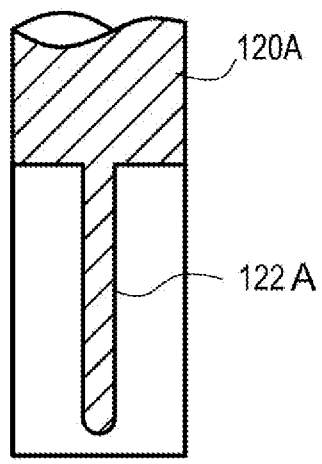
Figure 3B:
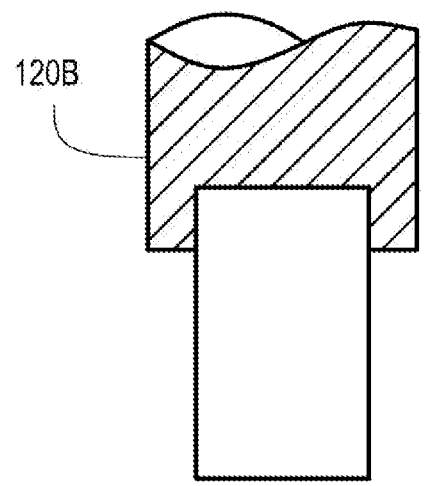
Figure 3C:
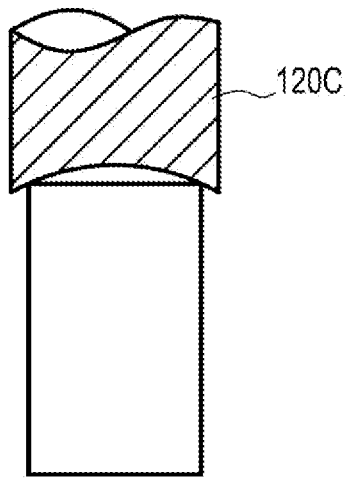
Figure 3D:
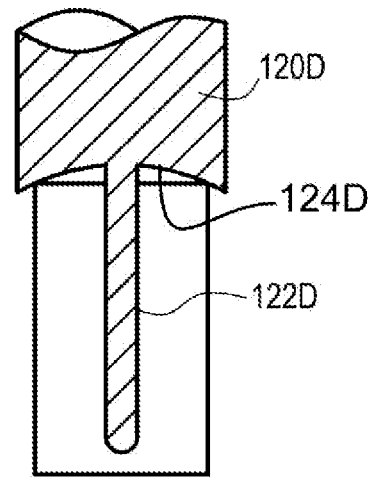
Figure 3E:
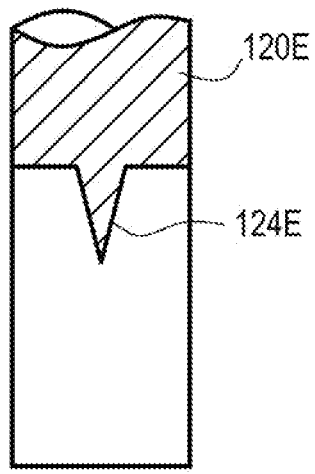
Figure 3F:
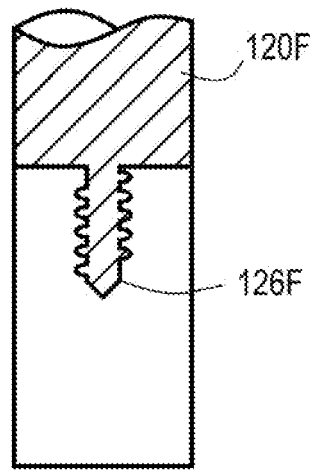
Figure 3G:
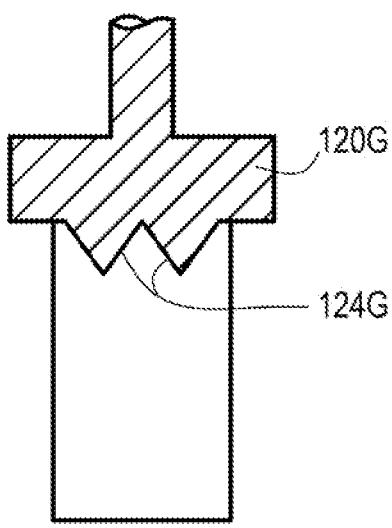
Figure 3H:
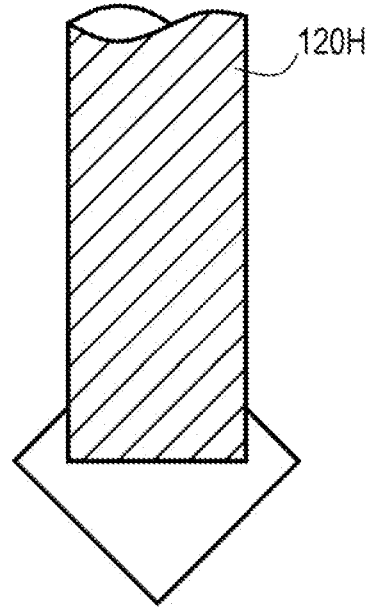

Referring to FIGS. 3A-3K, energy emitting instruments may include various horn or end effector configurations. It has been discovered that for a fixed set of parameters (energy, power, time, etc.), the bonding or bond characteristics can be varied depending on the configurations of the horn or end effector. For example, if extension 122 is made longer or the angle of the tip is changed, the stake or bond created can be adjusted. In FIG. 3A, the horn 120A emits energy to the top surface of the implant as well as the central core via an elongate extension 122A. The horn 120B of FIG. 3B is recessed to hold the thermoplastic implant during bonding or staking. In FIG. 3C, the horn 120C is concave to provide a rounded surface to the implant after bonding. As discussed below, horn 120C has been found to be particularly suitable for staking. The horn 120D of FIG. 3D is concave and includes a central extension 122D to deliver energy throughout the implant. In FIG. 3E, the horn 120E includes a spike 124E which may be disposed within an implant. The horn 120F of FIG. 3F includes a threaded pin 126F which may be received by a bore in the implant. In FIG. 3G, the horn 120G includes dual spikes 124G. The distal portion of the horn 120H of FIG. 3H may be dimensioned to fit within the thermoplastic implant. In FIG. 3I, a sleeve 128I is disposed about the horn 120I and implant. A side-bond horn 120J is shown in FIG. 3J, wherein the horn or engaging portion 128J is disposed along a side surface 130J. In FIG. 3K, a dual horn bonder 120K is used to simultaneously bond two fasteners 130. It should be noted that generation of heat through an extension such as 122A, 122D, 124E, 126F, 124G and 128J will vary with respect to that generated through the broader direct contacting surface 124D, and may be diminished.

Figure 4A:
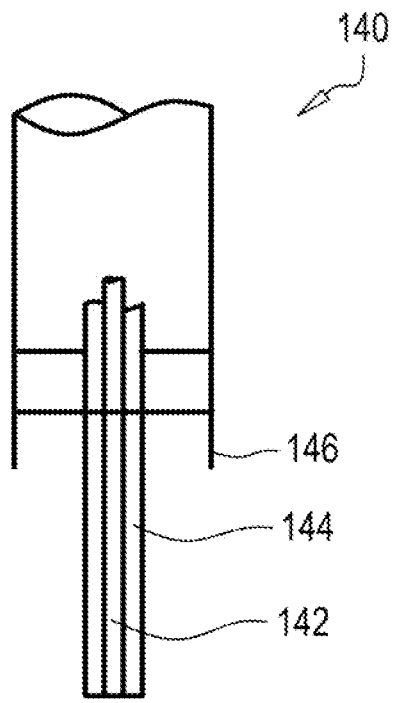
FIGS. 4A-4C illustrate a three-function bonding horn.
Figure 4B:
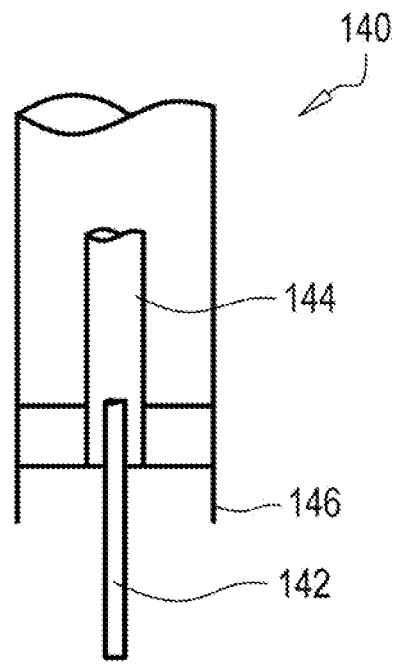
Figure 4C:
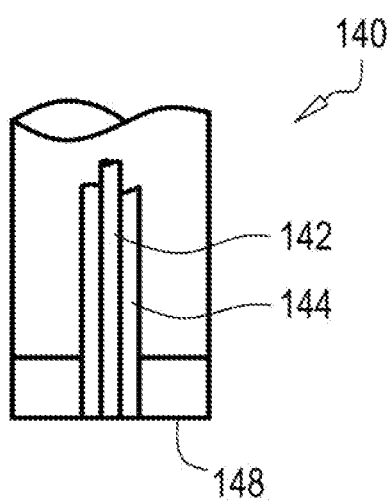

In FIGS. 4A-4C, an instrument 140 is shown which includes three different horn or end effector configurations in one design. The instrument 140 can be configured to produce a roughened or complex surface (FIG. 4A), for producing an aperture (FIG. 4B), and for flattening or contouring a surface (FIG. 4C). In FIG. 4A, a center shaft 142 is extended distally from the instrument 140, and outer shaft 144, which slides over center shaft 142, is also extended distally. This produces an outer circle and an inner circle on a surface when vibratory energy is applied to end effector 104. It should be understood that a variety of patterns could be produced in this manner, by changing the shape and relative extension of shafts 142, 144, or by adding additional shafts. In FIG. 4B the outer shaft 144 has been retracted into the bonding instrument, leaving only the center shaft 142 extended. In this position, the instrument 140 will form an aperture in bondable material, for example in preparation for adding cap 1010 (not shown), detailed elsewhere herein. Finally, FIG. 4C shows both the center and outer shafts 142 and 144 retracted into the instrument. Sheath 146, which surrounds instrument 140, has also been retracted. In this position, the instrument 140 is in a contouring horn configuration. The distal surface 148 of the contouring horn may be used to reshape a thermoplastic implant, such as the head of a fastener. A flat surface is shown, however surface 148 may be curved to produce a rounded, smooth surface after application of vibratory energy.

In use, the instrument of FIGS. 4A-4C may be reconfigured quickly by the operator as required during the procedure. In each configuration, the instrument is configured with the appropriate shafts 142, 144 and sheath 146 (if present) extended or contracted. Extended shafts 142 and or 144 may thereby come in contact with bondable material to be affected. Energy, such as vibratory energy, may be emitted from the center and outer shafts to create a roughened surface on the implant, to create an indentation or blind hole in the implant, or to create a through hole in the implant. The type of fastening desired and the intended fastener to be used will determine how deep the bonding-surface horn should be moved into the implant. With the staking/bonding surface formed, the outer shaft 144 is retracted into the instrument (FIG. 4B).

The distal portion of a fastener may be placed in or on the bonding surface of the implant, and the end effector may be placed on the fastener with the center shaft extending into a bore in the fastener. Using the desired parameters, the operator emits vibratory energy from the end effector to bond and/or mechanically interlock the fastener to the implant. Once bonded or staked, the fastener may be contoured or reshaped or resized with the contouring-horn of the instrument by retracting the center shaft and optionally retracting the sheath around the instrument (FIG. 4C).

Movement of shafts 142, 144 and or sheath 146 may be accomplished by known methods of mechanical action, for example guide shafts extending through end effector 104, or electromechanical or pneumatic actuators within the distal portion of end effector 104.

Hollow tubular outer shaft 144 may additionally be used for removing bonded implants. When used without center shaft 142, it may be used to surround an implant bonded to body tissue or another implant with a heat meltable bond, as described herein. In this application, vibratory energy is transmitted through hollow shaft 144 and the shaft is placed in contact with the melted bond. As bondable material is softened, shaft 144 is advanced, until a sufficient amount of the bond is severed by shaft 144. Combined with mechanical action applied to the handpiece, as needed, a bonded part now housed within shaft 144 may be thus loosened and removed.

Shaft 144 may be used when extended alone in the configuration shown in FIG. 4A, or may be provided in a fixed or dedicated end effector or end effector endpiece containing only shaft 144. Further, it should be understood that shaft 144 may be provided in configurations adapted to the shape and depth of the bond of specific parts to be removed.

Additionally, shaft 144 or 142 may be used to core or drill, respectively, in bondable material. In this manner, apertures may be formed for inserting or attaching additional implants, which may optionally be secured in place with vibratory energy, as described herein.

Coated Fastening Base

Figure 48:
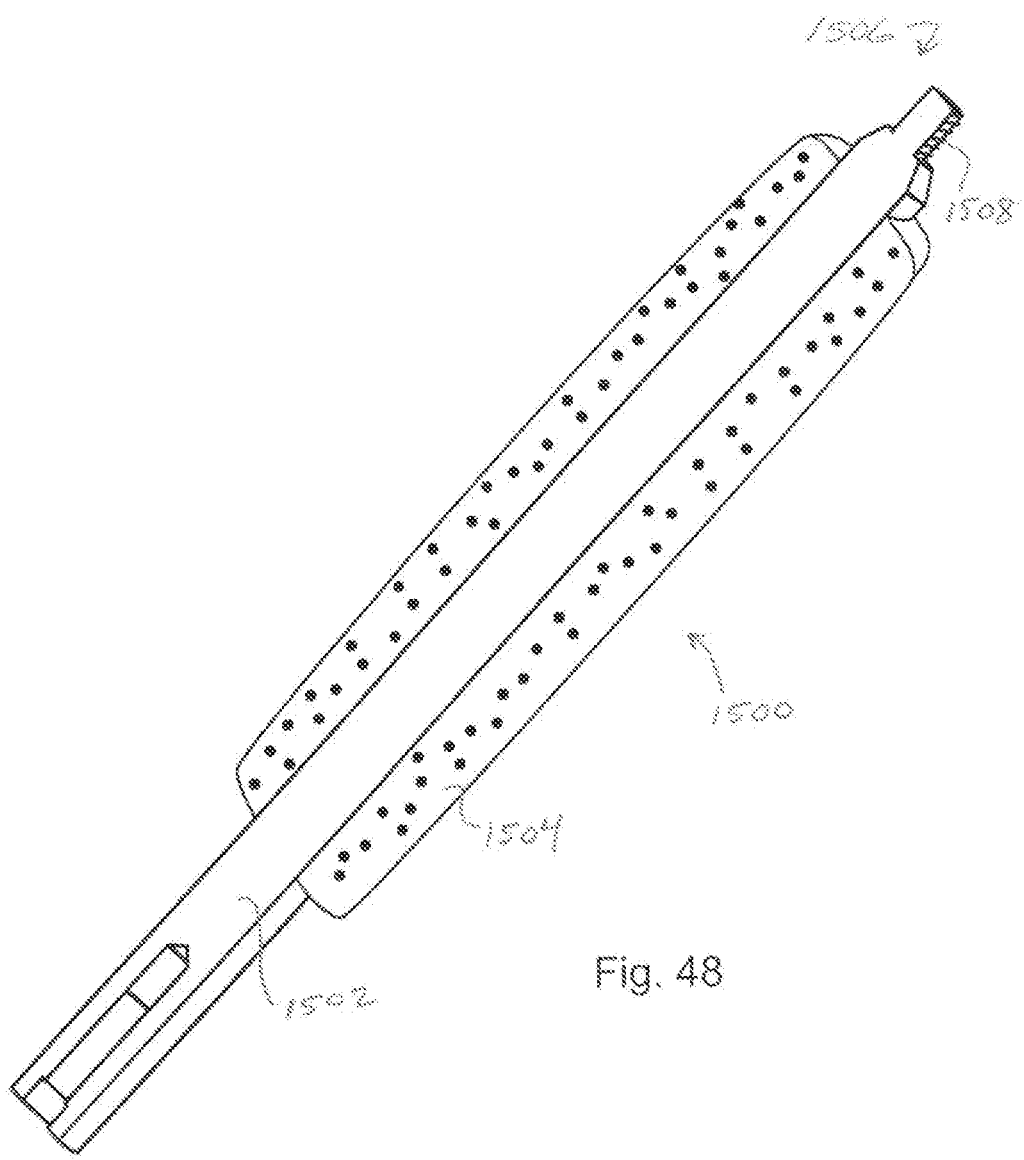
FIG. 48 illustrates an end effector coated over a portion of its exterior surface with bondable material, in accordance with the invention.

With reference to FIG. 48, a coated implant 1500, shown bisected along a longitudinal axis, includes a core 1502 and a coating 1504 of bondable material. In the embodiment shown, core 1502 is metallic, and coating 1504 is bone cement. However, the coating may be any bondable material as described herein, and core 1502 may be the same material as the coating, or any other material of suitable strength to which the coating may be securely attached, as by adhesion or mechanical attachment. The form of coated implant 1500 shown is that of a rod, sized and shaped to enter an intramedullary canal; however, a different shape may be selected to advantageously serve as a base for fastening at least one other fastener, depending upon the application and location. The coating is applied over at least a portion of the exterior surface of the core.

Coated implant 1500 is placed in the body as a point of attachment for other implants, for example any of the fasteners of the invention. The coated implant is advantageously shaped to provide a surface for attachment of numerous fasteners, or one or more fasteners at a variety of possible locations. Fasteners may be bonded to the coated implant using proximal or distal vibratory fastening, as described herein, or a combination of vibratory and mechanical fastening.

Core 1502 may be attached within the body using any means known in the art. In the embodiment shown, the distal end 1506 of core 1502 is provided with threads 1508, which may connect to mating threads of an implant previously implanted and affixed within the body, for example embedded fastener 800. In this manner, core 1502 functions as described for end effector 804.

Once secured, coated implant 1500 forms a base for fastening other fasteners, for example the fasteners illustrated in FIGS. 46D-H. With reference to FIG. 49, an elongate fastener 1240 may be seen attached to coated implant 1500 at a distal end. Coated implant 1500, in the example shown, may be attached as described with respect to fastener 900, of FIG. 43. Other means of attachment to secure coated implant 1500, as detailed herein, may alternatively be used. For example, fastener 1240 is distally bonded to coating 1504, and has been trimmed at a proximal end at the surface of bone 882. As such, fastener 1240 stabilizes coated implant 1500 by restricting motion of coated implant 1500 within intramedullary canal 1222, and particularly in a longitudinal direction.

Fastener 1240 is shown without a cap 1010, however fastener 1240A is additionally, shown, provided with a mountable cap 1516, shown both separated and attached. An optional aperture 1512 may be provided in fastener 1240, operative to receive a post 1514 projecting from mountable cap 1516. Post 1514 aligns cap 1516, and provides greater surface area for bonding of cap 1516 and fastener 1240 upon the application of vibratory energy, as described herein. It should be understood that post 1514 and aperture 1512 may be eliminated, and vibratory fastening may still be accomplished. Mountable cap 1516 prevents fastener 1240A from moving inwardly with respect to the center of the bone, and falling out of the opening in cortical bone through which it resides.

With further reference to FIG. 49, one or more fasteners 1518, 1520, of the invention are distally fastened to coated implant 1500. In this manner, the distal ends of fasteners 1518, 1520 which are embedded in coating 1504 are fixed in position relative to each other. However, the proximal ends, projecting through the outer cortical bone of bone 882, are movable with respect to each other due to a fracture 918 in bone 882. To stabilize fasteners 1518, 1520, and to secure fracture 918 in a closed configuration, plate 1522 is provided, passing over fasteners 1518, 1520, before caps 1010, 1516 are formed and attached, respectively. In this manner, both proximal and distal ends of fasteners 1518, 1520 are fixed, and thus fracture 918 is stabilized, and proper healing is facilitated.

Expanding Fastener

Figure 88:
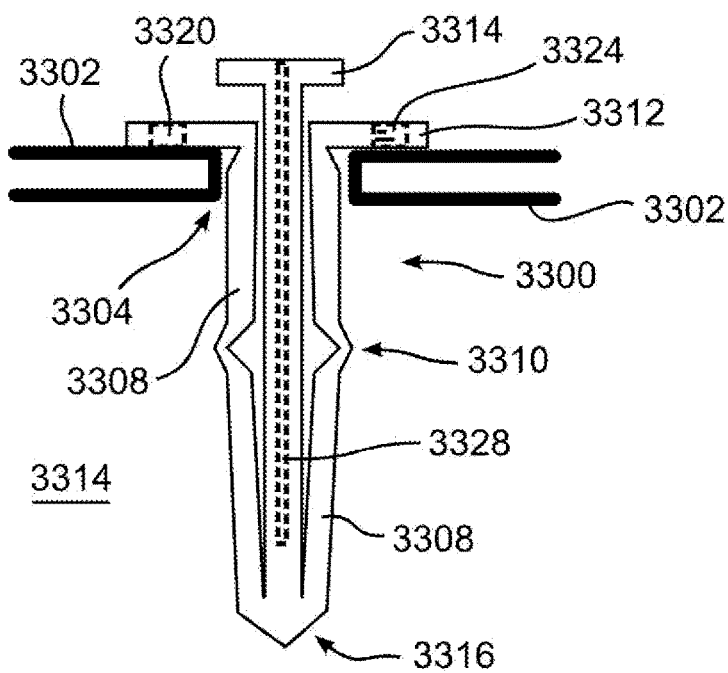
FIG. 88 illustrates a cross section through the center of a longitudinal axis of an expanding anchor in accordance with the invention.
Figure 89:
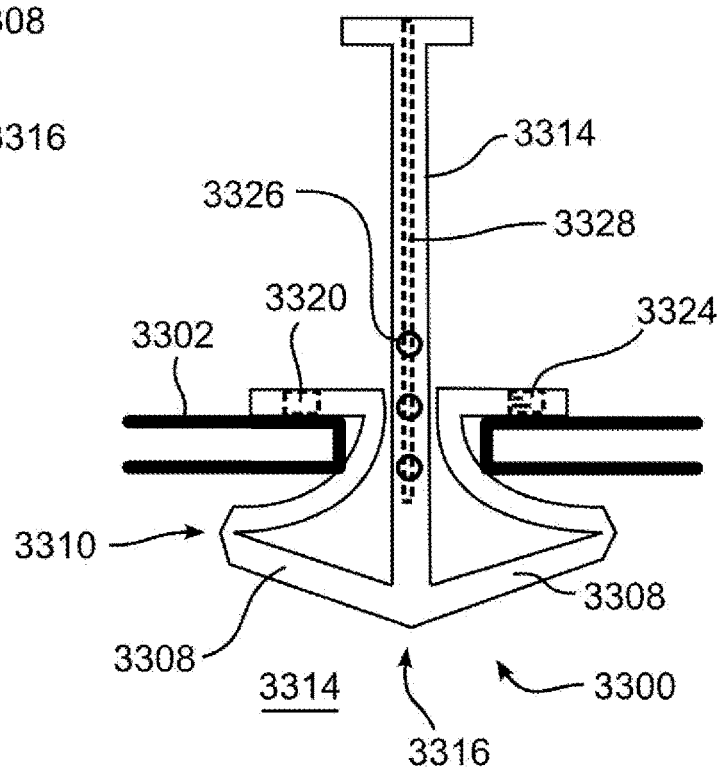
FIG. 89 illustrates the anchor of FIG. 88 expanded.
Figure 90:
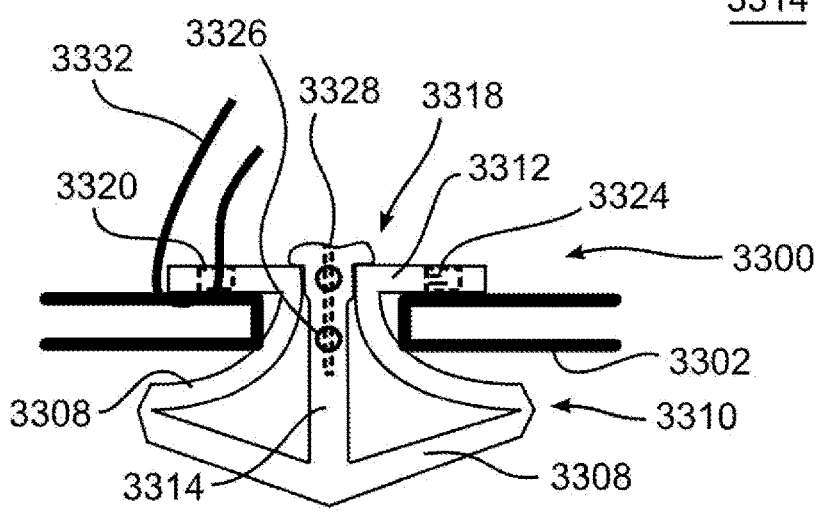
FIG. 90 illustrates the anchor of FIG. 89, fastened in an expanded state.

With reference to FIGS. 88-90, an expanding fastener 3300 is provided, adapted to pass through an opening 3304 in a wall 3302 into a hollow space 3306, and expand within hollow space 3306 thereby resisting withdrawal through opening 3304. Fastener 3300 is fastened using vibratory fastening in accordance with the invention.

In particular, fastener 3300 is provided with one or more wings 3308, which are attached to a flange 3312. Wings 3308 are passed through opening 3304, the latter sized smaller than flange 3312. In this manner, fastener 3300 is prevented from passing completely through opening 3304. Wings 3308 are adapted to fold at living hinge 3310, or alternatively, wing 3308 may resiliently bend, whereby wings 3308 expand away from opening 3304 when folded or bent, thereby creating a profile that is too large to pass through opening 3304. In the embodiment shown, a post 3314, connected to wings 3308 at a distal end 3316 thereof, passes through opening 3304, together with wings 3308. After wings 3308 and post 3314 are passed through opening 3304, post 3314 may be pulled in a direction away from hollow space 3306, thereby causing wings 3308 to expand as described, as illustrated in FIG. 89.

Fastener 3300 may be fabricated entirely from a bondable material, for example a polymer; however, in the embodiment shown, at least flange 3312 and post 3314 are coated with, or made entirely from a bondable material. In FIG. 90, post 3314 and flange 3312 have had vibratory energy applied at an area 3318, whereby material of post 3314 becomes bonded to material of flange 3312, thereby securing wings 3308 in an expanded position. Post 3314 may be cut to a desired length after fastening.

Flange 3314 may be adapted to enable attachment of body tissue or other implants, by being provided with one or more apertures 3320, operative to retain a suture 3322, or other material to be secured. Alternatively, flange 3314 may be provided with a threaded bore 3324, or other structure useful for attachment as known in the art. Alternatively, post 3314 may be provided with one or more apertures 3326, or may be provided with a central bore 3328, which may be threaded, or may be self tapped by a screw driven therein.

Fastener 3300 enables fastening through an aperture or opening 3304 where the medical practitioner does not have access to hollow space 3306 beyond opening 3304. It should be understood that hollow space 3306 may be cancellous bone or other tissue which is sufficiently soft to be displaced when wings 3308 are bent. Vibratory energy enables a fastener 3300 of simple and reliable construction, as there is no need for a threaded post and a threaded aperture at distal end 3316, as is required in prior art fasteners.

Parameters and Additives

Figure 5:
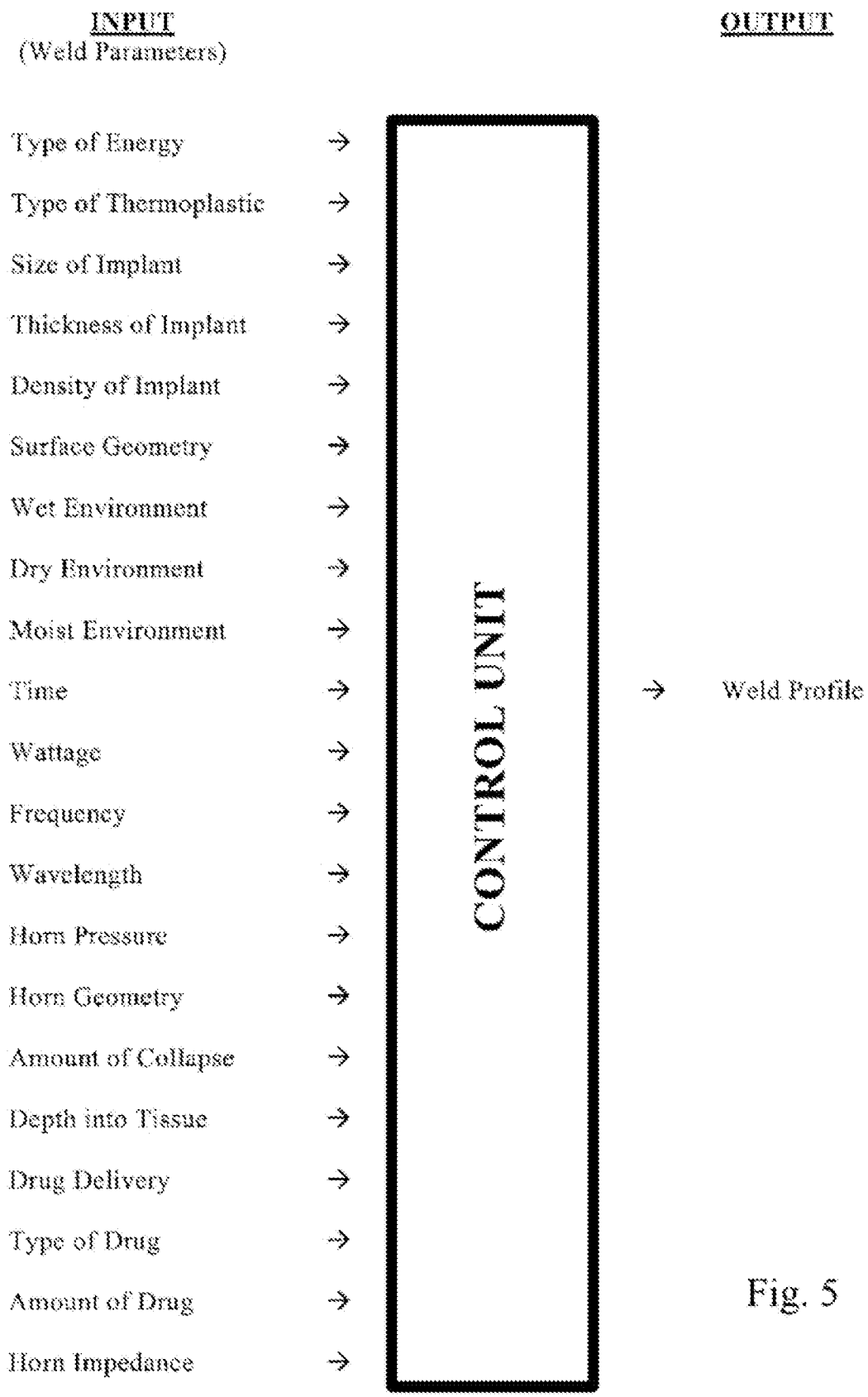
FIG. 5 shows the input parameters of a bonding control unit.

Monitoring and controlling the parameters ensures proper bonding of thermoplastics. FIG. 5 illustrates the various parameters that may be monitored and controlled for the system of the present invention. The parameters include, but are not limited to, the type of energy to emit, type of thermoplastic material, the size and configuration of the implant, the thickness of the implant, implant surface geometry, the aqueous environment, energy time, energy power, and frequency of the energy, amount of pressure applied to the implant during and after application of the energy, the geometry of the horn, the boost or attenuation of the end effector, the density of the implant, the amount of collapse of the thermoplastic material, the depth into tissue the implant is to be inserted, and the type and amount of any therapeutic agent that may be delivered.

There are several factors that effect bonding or staking of thermoplastic materials. One is hydroscopicity, the tendency of a material to absorb moisture. If too much fluid gets between the parts it can decrease the bond or create a foam which prevents proper bonding of the materials. Therefore, the bonding of thermoplastics may be performed under vacuum/suction, or a hermetic seal may be placed around the thermoplastic during the bonding process. Also, the bonding may be performed using a cannula which prevents fluid from entering the bonding area. Furthermore, pressure, such as air pressure or compression force, may be applied during bonding to prevent entry of moisture or liquid.

Additives

In addition to or in place of reducing moisture from the bonding area, certain agents can be used to aid in the bonding process. Such agents may include filler material, glass filler, glass fiber, talc, and carbon. The agents may be placed at the bond site as a temporary bonding enhancement means or may be a permanent agent to enhance the bonding. For example, the agent may be placed within the bonding region of PHA, PEEK or PLLA. The agent may be left in place to bond or could be removed. It is contemplated that any amount of agent may be used to enhance the bond strength of the thermoplastics. In an exemplary embodiment, the amount of agent may be about 10 to 20 percent.

Moisture may further be eliminated or prevented from entering the thermoplastic material through the use of desiccants. Desiccants may be added prior to or during the staking or bonding process. Also, the thermoplastic material may be stored using desiccant material to prevent change in thermal properties. It is contemplated that this moisture reducing means may be applied to any polymeric material.

Another factor which may affect bonding or staking of thermoplastic material is pigments, particularly white or black coloring. In many materials used in medical applications, white pigment is added to the polymer to make it appear sterile. Some pigments may negatively affect the bonding and staking characteristics of the material. Accordingly, pigment-free thermoplastics, such as PEEK, are advantageously used for fastening.

Mold release agents also affect the thermal properties of thermoplastics. Polymeric components are usually formed in a mold to create a desired configuration. The component is easily removed from the mold because a release agent is placed between the mold and polymer. These agents, lubricants, plasticizers, and flame retardants can negatively affect the bonding ability of the polymer. Thus, it is preferred in the present invention that PHA, PEEK, PLLA, and other thermoplastics used for bonding or staking are substantially free of these substances.

In addition to avoiding release agents, pigments, and moisture, the staking and/or bonding of thermoplastic materials may be further enhanced by adding minute metallic material to the polymer. The metallic material may be metal flakes or metal dust. Examples of such metal include iron particles, chromium, cobalt, or other suitable metals. The metal may be embedded within the polymeric material to enhance the thermal properties. Alternatively, or in addition, the metal may be applied to the surfaces of the polymeric material. Energy applied to the polymer would heat both the polymeric and metallic material providing a faster and more uniform thermal profile. It is contemplated that glass fillers, carbon fillers, talc, or combination thereof may also be used in addition with or in lieu of the metallic material, although some materials, while conferring desired properties, may adversely affect bonding, at least depending on the concentration used.

Energy Type

Other factors affecting the thermal characteristics of thermoplastics include size, thickness, surface geometry, material properties of the thermoplastic, and the type of host tissue involved in the bonding or staking, i.e. soft, hard, dry, wet, or moist tissue. These and other factors are explained in more detail with reference to FIG. 5.

Furthermore, how the thermoplastic is staked or bonded is an important characteristic of obtaining a robust mechanical interlock or thermal bond. The type of energy used is one way to control the process. As previously mentioned, various energy sources may be used to bond and/or stake polymers. In an exemplary embodiment and as used primarily throughout the invention, ultrasound energy is used to create vibrations within the polymeric material thereby exciting and heating the molecules to transition to a tacky state. Two or more different types of energy may also be used. For example, ultrasound may be used to bond a polymeric component to another component, while resistive heating may be used to contour the surface or change the geometry of the materials. The surface of the component may be smoothed out or sculpted using resistive heating.

The intensity and duration of the energy source impacts the quality of the bond or mechanical interlock. For instance, the amount of energy used affects the thermal properties. Therefore, the energy may be controlled by the operator depending on the component to be bonded or staked. A switch, dial, or other control may be placed in connection with the energy source to vary the intensity of the energy applied. For example, the amount of current supplied to the instrument may be varied or controlled. In an exemplary embodiment, the ultrasound power may be varied, for example, between 80 and 100 Watts. The amount of time the energy is applied affects the bond or staking as well. The time may be varied from milliseconds to hundredths of seconds to actual seconds depending on the desired end result. Thus, controlling the time of exposure to the energy source can be used to limit the amount and the degree of thermoplastic material which softens and becomes tacky. In an exemplary embodiment, energy may be applied from 0.1 seconds to 3 seconds, such as approximately 0.3 seconds. In case of RF and ultrasonic energy, the frequency of the energy may be varied to affect the softening or melting of the thermoplastic. It is also contemplated that the amount of time that energy is applied may be controlled not only by the operator but also via radiofrequency, optical, radiowave, etc. A computer or other microprocessor may send signals to the energy emitter to turn the energy on and off.

Pulsing of the energy source may likewise be used to intermittently apply energy to the site or to vary characteristics of the energy source over time, such as the power, frequency, or pressure, to enhance bonding or mechanical interlock and avoid tissue necrosis. That is, the energy may be emitted, then relaxed, then emitted, etc.

Pressure

Controlling the pressure applied to the thermoplastic material also may be used to affect the process. During bonding or staking, a handpiece, an anvil, a horn, end effector, or combinations thereof may be used to apply controlled force against the component. After completion, while the material is cooling, the force may continue to be applied to ensure proper bonding and/or mechanical interlock of the materials. The handpiece, anvil, horn, and end effector may be made of aluminum, titanium, or other suitable material. Also, the pressure may be varied, increased or decreased, during the process. In an exemplary embodiment, the pressure may be applied by the operator or may be applied with a spring. A sensor, spring, and/or piezoelectric device may be used to monitor and control the amount of pressure applied. In another exemplary embodiment, the bonding horn may apply ultrasound energy and pressure to a polymeric implant being attached to bone. The bone may act as the anvil eliminating the need for an anvil instrument. Also, a hard implant or another polymeric material may function as the anvil.

Furthermore, the placement of the energy source on the thermoplastic affects the bond or staking. The energy may be applied to one side of the polymer, through the center of the polymer, to two or more sides of the polymer, or to generally the outer surface of the polymer.

Collapse

Controlling collapse is another factor in achieving an effective thermoplastic bond or staking. For instance, the time and material collapse may be monitored to ensure a proper effect. A measurement of the change of the material being bonded or staked may be made to determine when complete. This may be accomplished by using microswitches to provide precise, binary control of the mold. Also, by using a linear variable displacement transducer (LVDT), the control system can monitor the bond more precisely. Because a LVDT translates position to voltage, the bond and/or staking profile can be dynamically controlled. For example, the initial energy delivered can be a higher wattage, then when the material starts to collapse the amplitude of the wave can be decreased.

By being able to monitor the position of the collapse, different bond or staking profiles can be programmed into the system. In addition, to control how far the material collapses, a combination of current and time preset in the generator control system could be used. This can also be coupled with a defined force applied during the bond or staking. Furthermore, collapse may be controlled or monitored through the use of a mechanical stop on the fastening device itself or on the instrumentation. The mechanical stop would prevent collapse after a predetermined point. It is also contemplated that the collapse could be monitored by other methods such as optics, laser, or even a hall-effect sensor.

All of the above-mentioned parameters may be monitored and controlled by a computer. The discussion relating to FIGS. 5-8, among others, illustrate instruments that may be used for controlling the parameters. Feedback may be provided by the computer to vary, start, and stop the various parameters. The feedback and control of the computer may be programmed based on the type of polymer being bonded and/or staked and the type of material the polymer is being bonded or interlocked to. For example, for PEEK to PEEK bonds, the computer may apply a set of parameters (time, power, pressure, frequency, etc.) to achieve an desired or effective bond. Other parameters may be established or preset for other polymers, other bond materials, or for staking dissimilar materials.

Without being bound by any particular theory, it is generally thought that the surgical system (either bonding or staking) of the present invention causes primarily radial deformation of the fastener. This was discussed above in the context of collapse. Because the primary deformation is collapse so that radial expansion occurs, there is little, if any, elongation in the longitudinal direction. Detailed analysis has shown that for a fastener or tack made of PEEK and having typical dimensions (head 0.180 inch; and tip 0.109 inch), there is a bond collapse of 0.050 inch for set bond parameters (111 Watts; 500 millisecond bond time; and 5-8 lbs force applied). As previously discussed, this collapse can be increased or decreased by changing the bond parameters, the geometry of the end effector and tack, and/or material of the fastener.

Instrumentation and Controls

Any known energy emitting instrument may be used with the surgical system of the present invention. The instrument may produce energy such as resistive heating, radiofrequency, ultrasound (vibratory), microwave, laser, electromagnetic, electro shockwave therapy, plasma energy (hot or cold), and other suitable energy. FIG. 1 illustrates an exemplary handpiece or instrument 100 that may be used with the present invention. The instrument 100 may be a vibratory handpiece with a sheath 102 to cover and protect the end effector 104 and hold a fastener. As will be discussed in greater detail below, the instrument may be used to bond or mechanical interlock a cap of an implanted device to an anchor, or likewise may be used to bond or mechanically interlock other components together.

The sheath 102 may have a small counter bore at its tip to cover a portion of the cap. There also may be a bushing at a nodal point of the vibratory signal to prevent the end effector 104 from contacting the sheath 102. The tip of the end effector 104 has a small post 106 sticking out of the bonding face which presses into a bore in the cap of the fastener. This can help align the fastener post into the anchor bore and keep the cap tight against the end effector face. The end effector 104 may be removable to allow it to be replaced or cleaned after use.

The post 106 on the end effector 104 may be threaded or have a Morse taper to mate with the cap. Alternatively, the end effector 104 has a bore that the top of the cap mates into. The mating of the components could also be by threads or a Morse taper along with a straight post. Furthermore, the post could be roughened on the outside surface for better adhesion.

Microprocessor Control

In accordance with the invention, A DSP simplifies additional modes for fastening control. Whether an analysis is performed by a DSP, other processor type, mechanical means, or by the practitioner, processing modes for fastening in accordance with the invention include the modes described as follows.

The phase angle differential between voltage and current is monitored during use, and changes are made to the signal to maintain a resonant frequency. For example, the drive frequency could be varied to maintain a particular phase angle differential. An optimal or target phase angle may be determined by a frequency tuning sweep, calculation, empirical means, or a combination of these methods. This is discussed further with respect to FIG. 67, below.

The output voltage may be varied while monitoring power consumption during bonding. A device using this method must adapt to the typically large variations in loading during the bonding step.

The stroke of the handpiece is measured by a sensor disposed within the handpiece or end effector. This method provides the advantage of a robust and accurate measurement of the physical displacement of the end effector.

The drive voltage is varied while monitoring the current and voltage during bonding. The minimum impedance is then calculated in real time, to adapt to variations in the environment, particularly a medical environment, during bonding.

The total power/energy applied to the bond may be calculated during bonding, and when a total predetermined amount of energy has been delivered the bonding step is terminated.

The total time during which power is applied during bonding is tracked and when power has been applied for a predetermined amount of time, bonding is complete and is stopped.

The Eddy or Foucault currents created by movement of the end effector are tracked, the movements being indicative of melting activity. As the end effector vibrates, a magnetic field is changed, creating measurable current which may be analyzed during bonding.

Collapse of the fastener is measured by a sensor within the end effector or handpiece, indicative of an amount of melting corresponding to preset levels established for correct bonding of a particular configuration.

The control methods of the invention may be combined. The methods enable adjustment of the signal for variations in the environment and loading during a surgical procedure.

The control modes described above may be combined with input or measured parameters automatically by processor control, or at the election of the surgical practitioner. In this manner a matrix for overall control is created by the selected parameters, and the selected control modality. Reference may be had to the following example parameters:

| Implant Type | 1 | 1 | 2 | 3 |
|---|---|---|---|---|
| Environment | Dry/Moist | Wet | All | All |
| Control Method | Phase Angle | Min Impedance | Min Impedance | Stroke |
| Term | Power | Energy | Energy | Collapse |

In each of the four examples above, selection of an implant triggers loading of the optimal phase angle, impedance, and or energy values. Environment values may be input by the practitioner, or measured by the system. The system may determine the type of implant based on either input from the practitioner, or by sensors or switches associated with the handpiece, whereby. For example, the particular type end effector currently connected triggers a signal to the processor regarding the appropriate type and size of fastener that will be used. Alternatively, the fastener itself indicates its presence, either by physically triggering a switch, or by other known means of signaling, for example an embedded RFID tag.

User Interface

FIG. 6 shows a manual control box 150. A surgeon determines the optimum or desired parameters and may then enter them into the control box 150 prior to or during bonding or staking. In FIG. 7, an automatic control box 152 may be provided with pre-set parameters. For example, preset 1 may be for implant A which has a known material, size, etc. to be bonded in a dry environment. Preset 2 may be for implant A in a moist environment. Preset 3 may be for implant A in a wet environment. Preset 4 may be for implant B using energy source X. Preset 5 may be for implant C using energy source Y. Preset 6 may be implant D using energy source Z. It is contemplated that any combination of bond parameters may be pre-set into the control box.

Figure 8B:
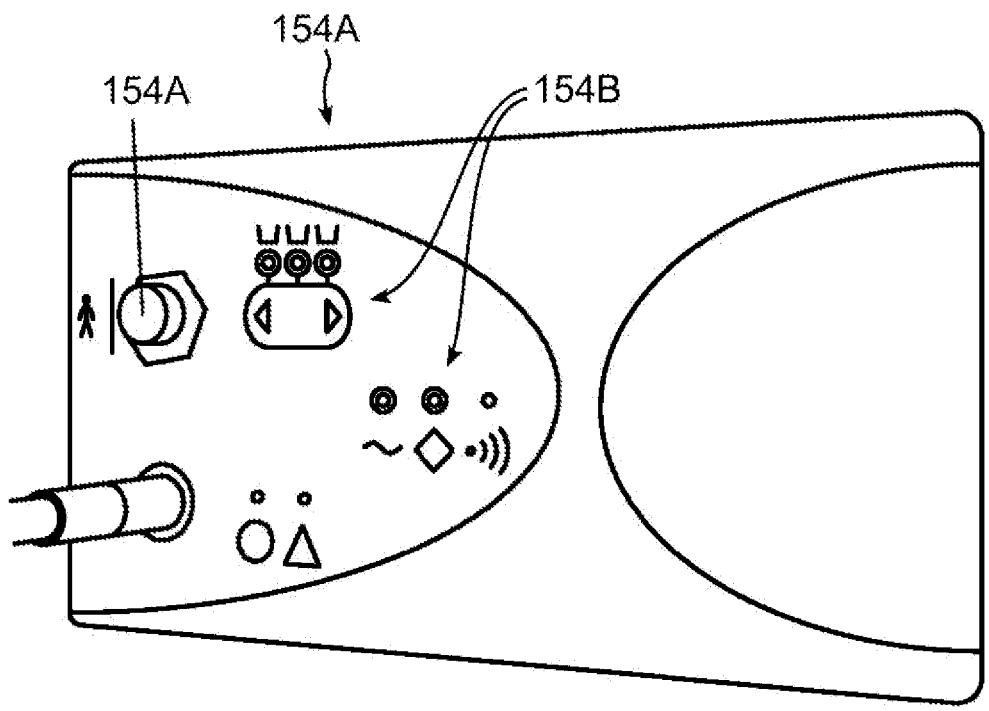
FIG. 8B is an illustration of another embodiment of bonding control unit.

The control box 154 of FIG. 8A is automatic. A sensor on the end effecter 156 determines the parameters when the horn is placed adjacent the thermoplastic material. The sensor 156 picks up material type, humidity of the environment, and any other parameter, then sends the data to the control box. The control box 154 automatically selects the time, wattage, and any other parameters. FIG. 8B illustrates a vibratory energy control box which may be used with the surgical systems of the present invention. Control box 154 includes a handpiece connector 154A, and interface controls 154B for changing bonding parameters.

Figure 8C:
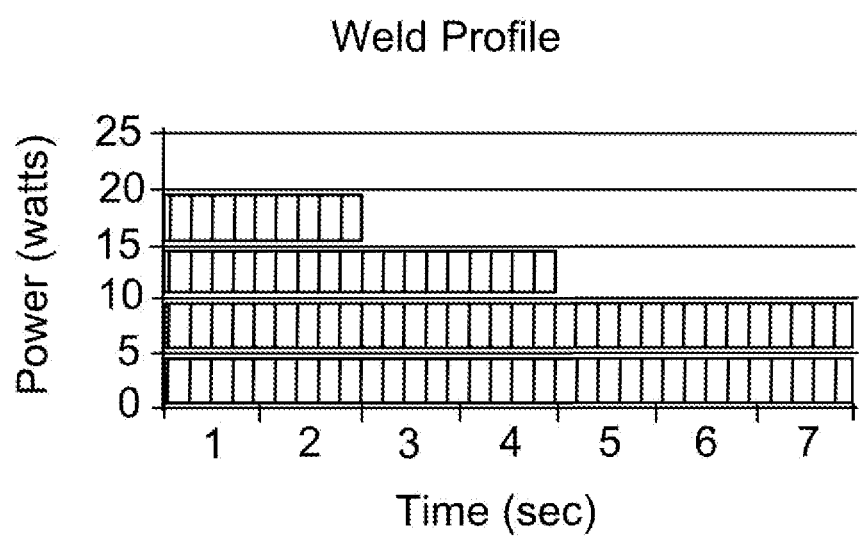
FIG. 8C is a graph showing a bonding profile having varying wattage.

The exemplary energy control units described herein may be used to select and vary any of the parameters. In FIG. 8C for example, the power or wattage of the horn is varied over time. During a first period of bonding, a large amount of energy is delivered to overcome heat sink. In the second period, the energy is reduced. In a subsequent period, the energy is maintained at an appropriate level to thermal bond or stake an implant.

Other variations of the use of a control box may likewise be used. For instance, a computer may be used to query or receive data about the surgical procedure. The physician may enter an implant manufacturer, for instance, and then select or enter an implant model, size, etc. Based on the entered information, the computer may assist the physician by instructing which energy source(s), horns, or other parameters may be recommended for the procedure. While the control box or computer may automatically select and apply a thermal profile based on expected input parameters, the control box or computer may also allow a physician to alter or override the expected input or otherwise select a different thermal profile. The ability to allow varying degrees of manual control of the instrument may also be provided.

The exemplary energy control units previously described may be used to select and vary any of the parameters. For example, the power or wattage of the horn may be varied over time. During a first period of bonding, a large amount of energy may be delivered to overcome heat sink. In the second period, the energy may be reduced. In a subsequent period, the energy may be maintained at an appropriate level to thermal bond an implant.

Figure 63:
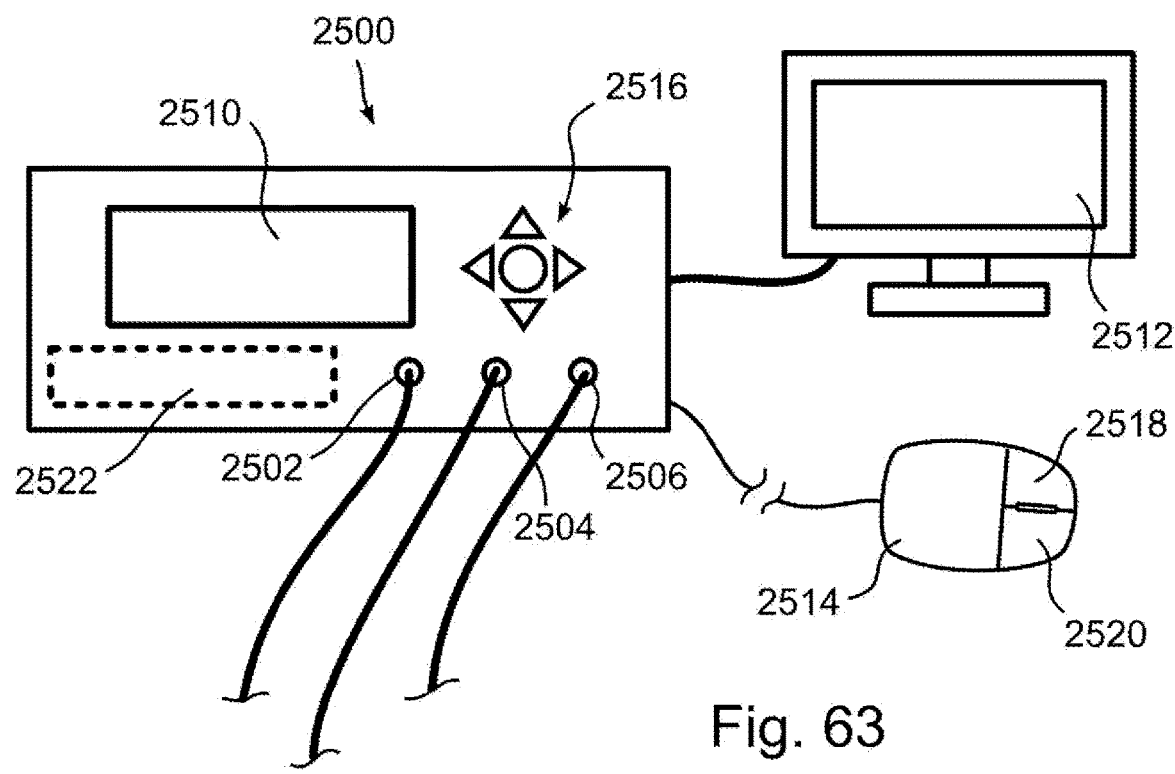
FIG. 63 illustrates a generator system in accordance with the invention, including human interface elements, and control logic.

With reference to FIG. 63, the surgeon may manually control the parameters, or the parameters may be controlled using automation, including using a microprocessor or computer. In accordance with the invention, a generator control unit 2500 is provided having connections for grounding and a signal 2502, 2504, 2506. The generator advantageously includes a user interface comprising gauges or indicators, and in one embodiment an LCD or similar output screen 2510. A user keypad 2516 is provided to move a cursor or indicator on the output screen, whereby parameters can be selected and entered. A footswitch, not shown, may be provided to enable the surgical practitioner to more easily activate the generator.

With further reference to FIG. 63, in accordance with a further embodiment of the invention, the surgical practitioner enters information pertaining to the surgical procedure through interaction with the user interface, which includes a cursor keypad 2516 and output screen 2510 on the generator 2500. It should be understood that an alternative and potentially more sophisticated and complete interface may be obtained by connecting a computer (not shown) to the generator, via a known method including USB, Bluetooth or network connection. Moreover, the generator interface may be programmed for the various types of surgeries and surgical operating parameters expected to be encountered, and the generator may thereafter be disconnected from the computer during the procedure.

Figure 72:
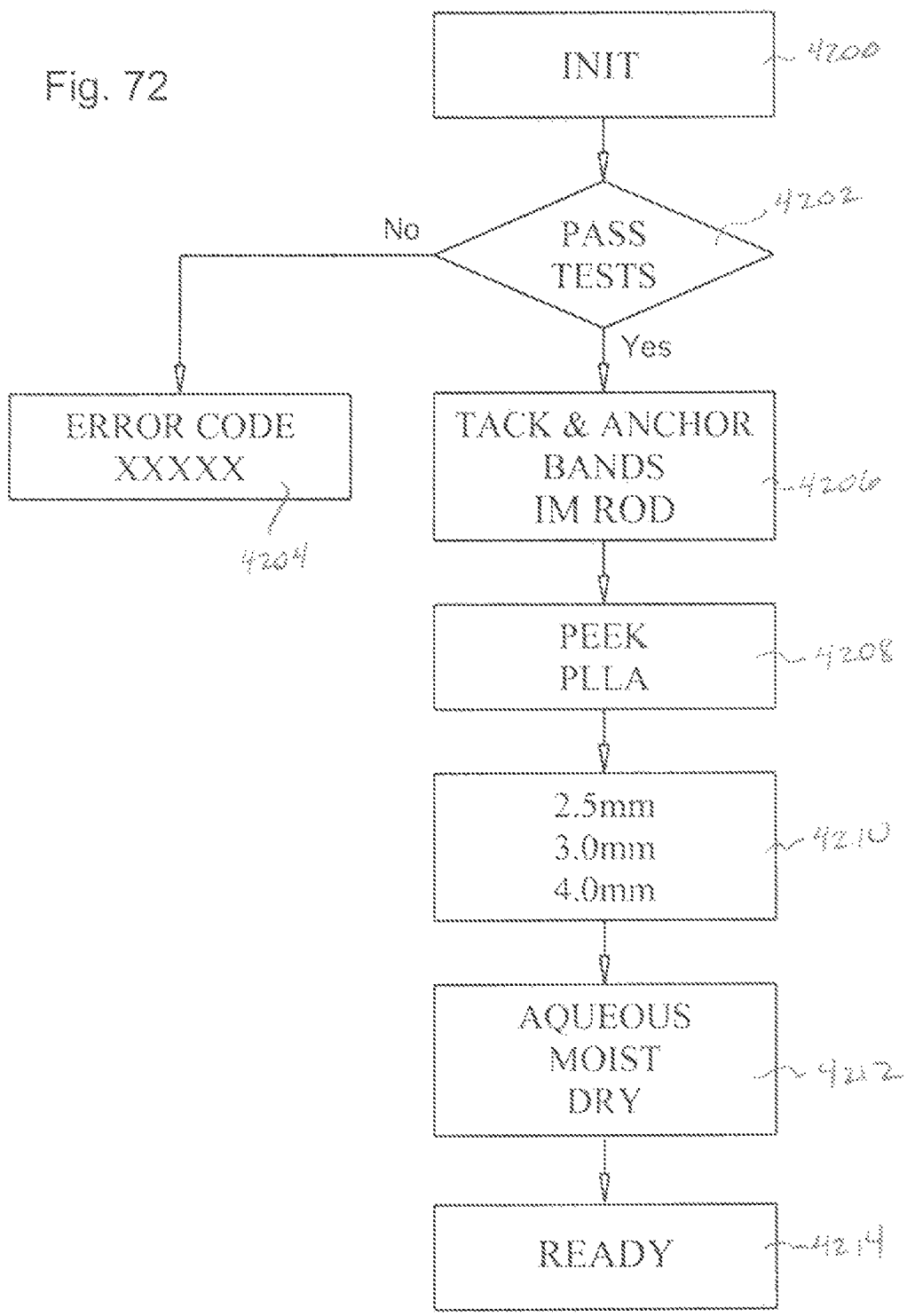
FIG. 72 illustrates an example of a sequence of steps indicated by an output screen associated with a vibratory generator in accordance with the invention.

Once programmed, output screen 2510 contains menus offering the surgical practitioner options relevant to the procedure to be performed, including the type of procedure, and any or all of the parameters described in this specification. An example of a menu is found in FIG. 72. In this example, a first screen 4200 indicates an initialization phase, after which the system performs self-tests 4202, which if unsuccessful, error codes are indicated at 4204. If self tests 4202 are passed, the practitioner is prompted at 4206 to select the type of fastener to be bonded. The practitioner makes a selection, as by pressing a button 2516 on the generator, pressing buttons 3124 (FIGS. 86-87) on the handpiece, pressing a footswitch, clicking a mouse, through voice activation, or other human interface method, and the system advances through additional parameters, in this example prompting for the material of the fastener in "PEEK PLLA" at 4208, fastener size at 4210, environmental conditions at 4212, and finally indicating a "ready" status at 4214, whereupon when ready the practitioner may start bonding.

In this manner, the practitioner has the ability to input the correct procedure and real-time parameters, in order to enable precise control in the use of the generator. Further, the generator can perform a sophisticated analysis in order to determine the correct operating parameters, including for example frequency, wattage, and pulsing, and the generator may further independently vary one or more parameters over time. Accordingly, the practitioner need not make the complex calculations necessary in order to achieve a secure and reliable fastening, and thus time is saved, and the potential for error is reduced.

Frequency Sweep Tuning

Figure 31:
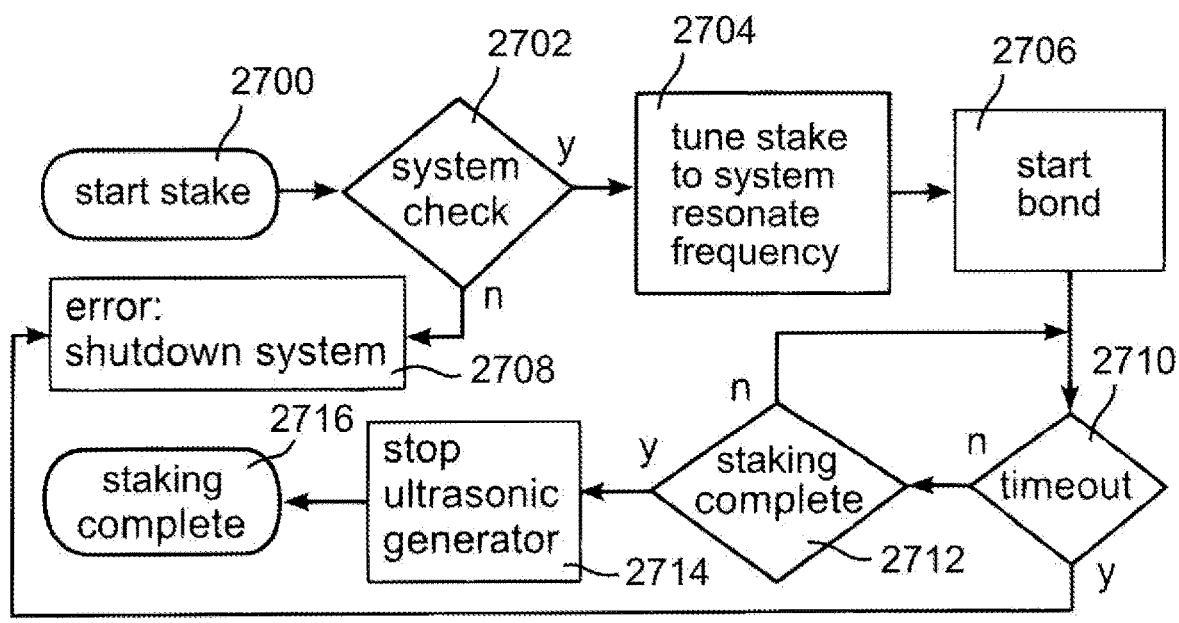
FIG. 31 illustrates an exemplary process for vibratory staking.

An exemplary process for vibratory staking is illustrated in FIG. 31. The staking process begins at "start stake" 2700 by either pushing the generator footswitch or using the control on the hand piece. Upon starting, the generator may first perform a "system check" 2702. The software may also check for proper grounding, ground offset issues, as well as other vital circuits. If there are errors with the system or the grounding, the generator can give a visual or audible indication that an error has occurred, at "error: shutdown system" 2708, and the vibratory signal generator may be disabled to prevent inadvertent use.

If no errors are detected, the system may then sweep a frequency range, such as from about 38.5 kHz to about 43.5 kHz, to tune the system, and particularly to "tune stake to system resonate frequency" 2704. Current measurements may be used to find the resonate frequency of the system, which in some embodiments may be close to 41 kHz. Next at "start bond" 2706 the vibratory or ultrasonic signal is then sent to the hand piece where a resonator turns the waveform into linear movement. A maximum bonding time is determined by the user, or by microprocessor control of the system. If an excess time is reached, a "timeout" 2710 is signaled and the system shuts down at error 2708. When bonding is complete at "staking complete" 2712, as determined by the user or by microprocessor control of the system, the generator is shut down at "stop ultrasonic generator" 2714, whereupon "staking complete" 2716 indicates bonding has been accomplished.

Impedance Feedback

To help ensure a properly executed bond or staking, the instrument of the present invention may provide a positive feedback system. One way to provide user feedback is by measuring and controlling the impedance of the vibratory generator. This feedback system is based on the fact that the load placed on the end effector affects the impedance of the system. That is, the pressure put on the end effector by the object to be bonded or staked changes the impedance within the handpiece, and specifically the piezo stack and electronics controlling the end effector. To determine the handpiece impedance, the drive voltage and current through handpiece may be monitored during the thermal process. By using Ohm's Law V=IR, the impedance, Z, may be calculated from the voltage, V, and current, I.

Figure 9:
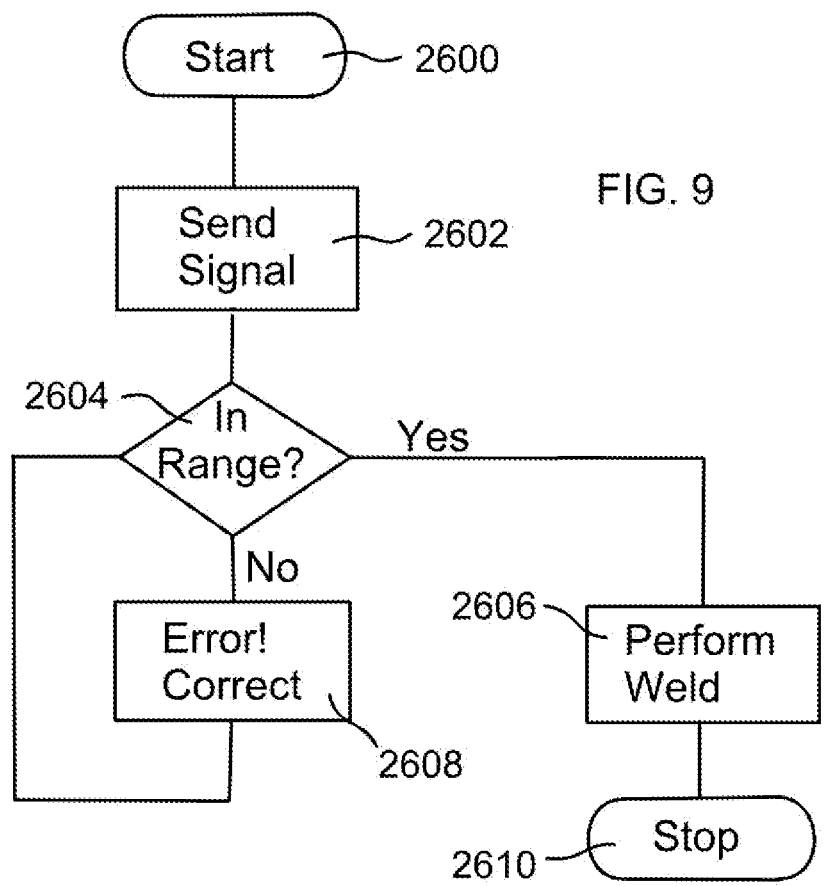
FIG. 9 is a flowchart showing the steps for adjusting the bonding device.

FIG. 9 illustrates one method of ensuring a consistent or desired bond or stake. The medical practitioner initiates a process in accordance with the invention by first transmitting a low power vibratory signal through the end effector, whereupon the impedance of the handpiece is measured with no pressure applied to the end effector. This establishes a baseline impedance. Then, the end effector may be subjected to known pressures, and the voltage and current may be measured to calculate the impedance for each pressure. Thus a set of values is known, and may be stored within a device in accordance with the invention, to be used in a subsequent bonding process, as follows.

When a surgeon or other operator applies pressure from the end effector to a thermoplastic implant to be bonded or staked, the actual amount of pressure can be fed back to the operator because the pressure can be correlated to a known impedance. Thus, "Start" 2600 corresponds to contacting the fastener in preparation for fastening, and "Send Signal" 2602 corresponds to indicating to the system that bonding should begin.

The surgeon may increase or decrease the pressure on the end effector until the desired pressure is achieved. In one embodiment, the instrument may provide audible and/or visual signals at "In Range" 2604 that tests when a surgeon is applying too much or too little pressure, whereupon a signal may be indicated at "Error! Correct" 2608, or an adequate amount of pressure is applied at "Perform Weld" 2606, whereupon the surgeon may activate the handpiece, whereupon vibratory energy is emitted in accordance with the calculated thermal profile established above. When fastening is completed, the practitioner or the system stops application of power at "Stop" 2610.

In another exemplary embodiment for providing positive feedback, the pressure and impedance of the handpiece, and more particularly the piezo stack and associated electronic circuit, may be monitored throughout the thermal profile. In the previously described method, the proper pressure based on impedance was achieved by the surgeon using a low power signal, and then the vibratory energy was emitted for bonding when an amount of pressure within a range was applied to the fastener. In this method, the pressure and impedance is measured during the bond. When pressure on the end effector is applied and the bond is started, for example by a hand control or footswitch, the current may be measured and the impedance calculated by a microprocessor. When the impedance is too high or too low or outside an acceptable range indicating an incorrect applied pressure, the microprocessor may send an audible or visual signal to the surgeon, or may alter the signal to maintain correct bonding parameters.

Alternatively, or in addition to the signal, the microprocessor can stop energy emission until the correct pressure and impedance is achieved, then the bonding may be resumed either automatically by the microprocessor or manually by the surgeon. If inadequate pressure is being exerted, the bonding instrument may operate in a pulse mode to maintain material in a near-bond state. This may allow the bonding to more rapidly continue when adequate pressure is once again being applied.

Figure 10:
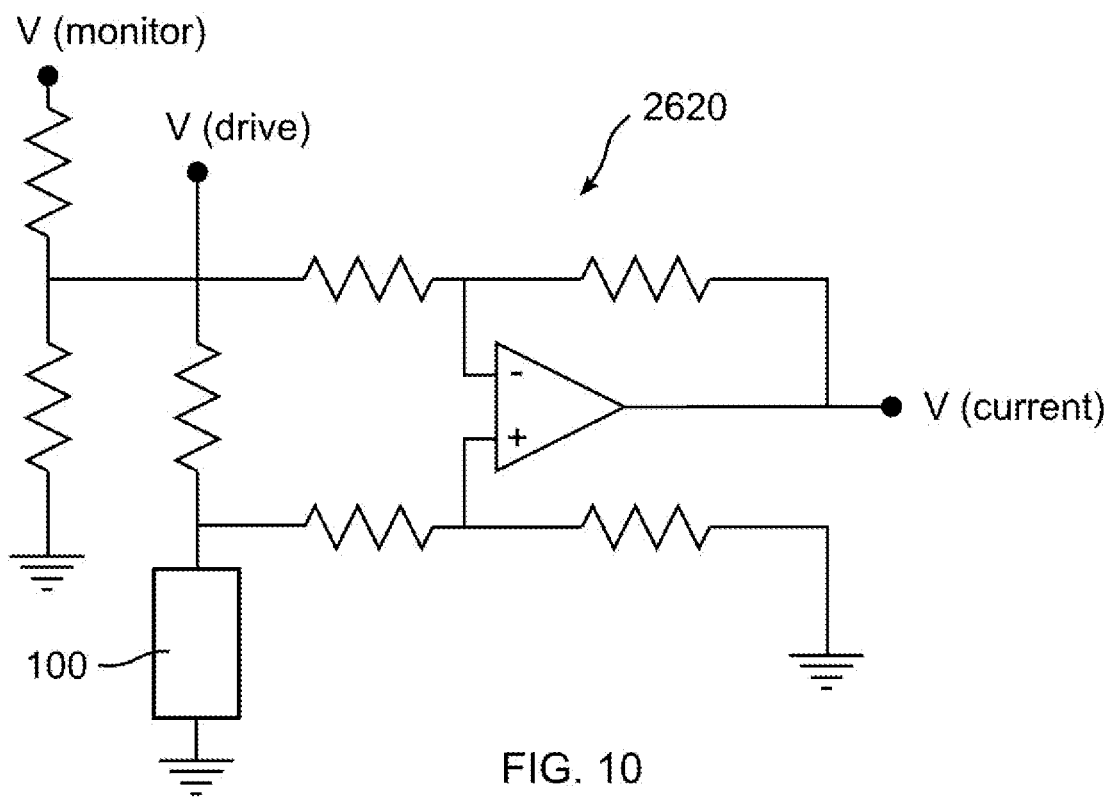
FIG. 10 is a diagram showing an electrical circuit for checking the bonding device.
Figure 70:
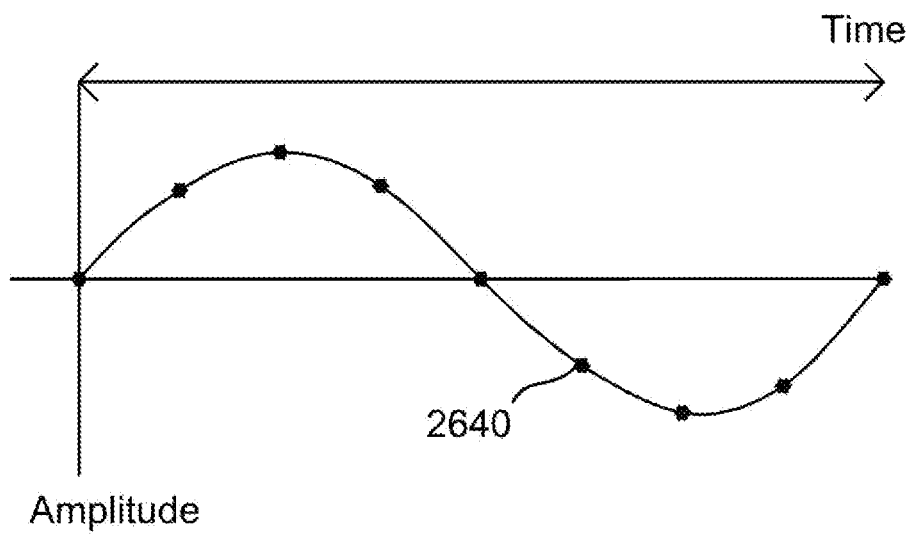
FIG. 70 is a graph illustrating sampling at node points, or data collection points useful for calculating phase shift.

Referring FIG. 10, circuit 2620 may be used to monitor power used by the handpiece. Because the drive signal for vibratory energy is sinusoidal, "V(monitor)" and "V(current)" are sampled at a rate that is advantageously at least twice the frequency of the vibratory waveform to be produced at the end effector. Reference may be had to FIG. 70, for example, where nodes, representatively illustrated by reference 2640, represent sample points. For example, if the waveform is a 41 kHz sinusoid, then samples are taken at least at 82 kHz. Further, if the resistances in circuit 2620 are known, and "V(current)" and "V(monitor)" are known, the impedance of the handpiece 100 may be calculated in a manner known in the art.

Also, by monitoring handpiece impedance, changes to the environment, such as moisture, ambient temperature, aqueous conditions, etc., may be automatically compensated for by adjusting the drive waveform of the vibratory energy. For example, if for a certain material it is determined that 80 W of power is required for a 400 ms period to achieve a consistent bond or staking, then the waveform can be adjusted to ensure that this amount of energy is constantly delivered. Power is calculated using $P=IV(\cos \varphi)$, where P is the average power, measured in watts, I is the RMS value of the sinusoidal alternating current (AC), V is the RMS value of the sinusoidal alternating voltage, and $\varphi$ is the phase angle between the voltage and the current. Because the signal from the waveform is sinusoidal, the root mean square (RMS) voltage as $V=(1/\sqrt{2})A$ must be used.

As the impedance, Z, of the handpiece changes, the total power delivered also changes. By increasing or decreasing the drive voltage to compensate for the change in the impedance, a constant power can be delivered.

Figure 71:
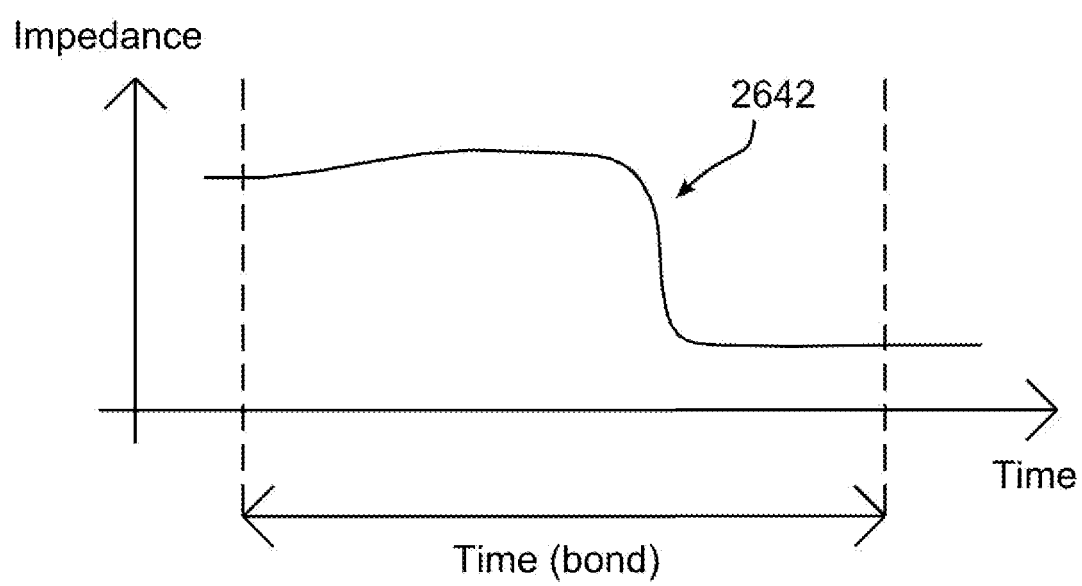
FIG. 71 is a graph illustrating a substantial change in impedance, which may be associated with an error in the bonding process.

With reference to FIG. 71, in an another embodiment of the invention, impedance during bonding is monitored over time. While bonding is taking place, during "Time (bond)", a sudden drop off in impedance, illustrated at reference 2642, can indicate that the end effector has slipped off the bond site, or some other error has occurred. This error can be communicated to the medical practitioner, and or a controlling microprocessor, so that corrective measures may be taken.

Figure 67:
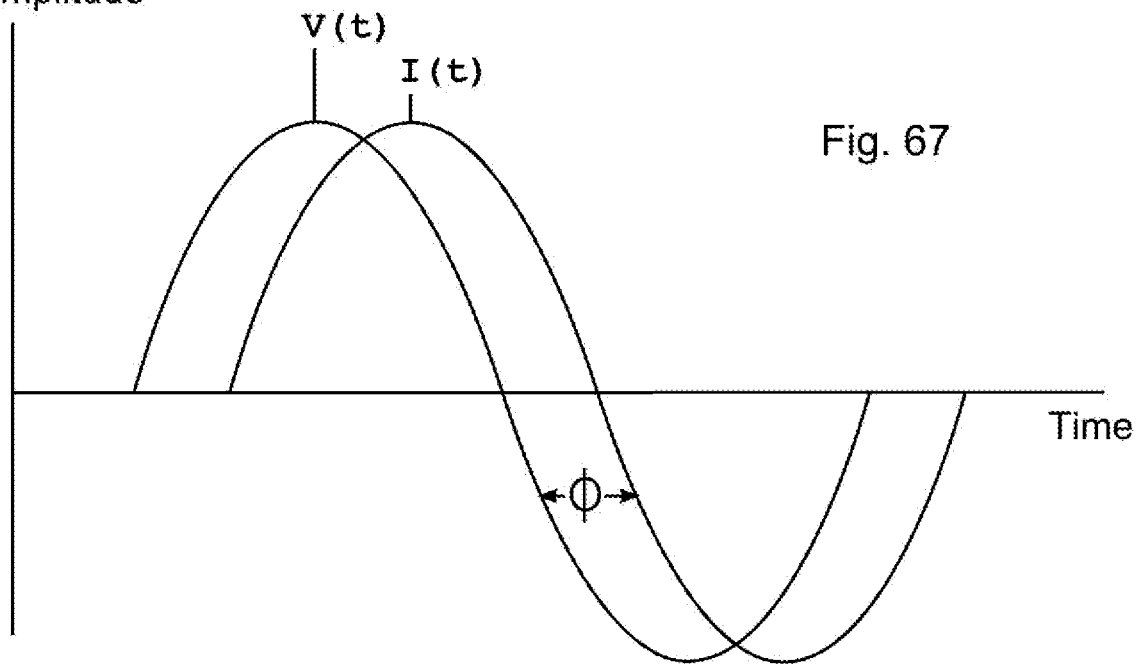
FIG. 67 is a graph illustrating a phase shift between voltage and current, generated during a bonding process in accordance with the invention.

In accordance with the invention, a phase angle differential is observed together with, or in place of, an impedance change as described herein. With reference to FIG. 67, an alternating current circuit under load is illustrated, demonstrating that the current and voltage oscillate sinusoidally. Unless the circuit is purely resistive or in resonance, the voltage and the current will be out of phase. This phase angle differential "Φ" (phi) is monitored, where current "I(t)" trails voltage "V(t)" over time, and changes are made to the signal based upon the observed phase angle differential, as well as other parameters, including the frequency, in order to maintain a resonant frequency at an area on the end effector where it is desired for bonding to take place.

More particularly, prior to bonding, the end effector is subjected to a sweep through a frequency range expected to contain an optimal resonance frequency, beginning at a frequency lower than is expected to produce resonance, and either the phase angle differential or highest and lowest impedance is observed. The optimal frequency and other parameters corresponding to the optimal frequency are recorded, for example by an electronic circuit or microprocessor, and when bonding is to be carried out, these parameters are used as initial values.

Figure 68:
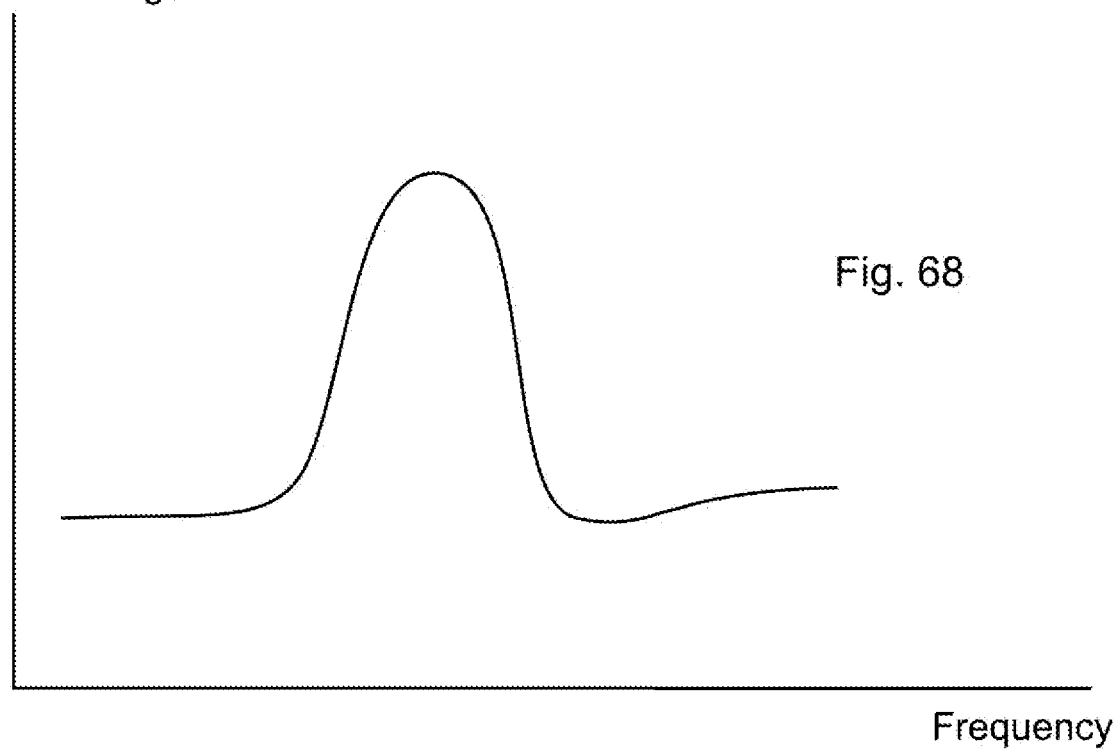
FIG. 68 illustrates a substantial change in phase shift that occurs within a particular frequency range during a bonding process in accordance with the invention.

This is further illustrated with reference to FIG. 68, wherein a particular range of frequencies generates a disproportionate change in phase angle. The change in phase angle corresponds to resonance of the end effector or horn, and thus resonance may be inferred from the phase angle differential. While resonance may be calculated under certain conditions, empirical data may additionally or alternatively be captured and used to reduce the time required for determining an optimal frequency range; the phase angle differential is one parameter that may be monitored to determine when an optimal frequency has been achieved.

A frequency likely to be close to an optimal frequency during bonding is thus determined prior to bonding, with the end effector not in contact with any other object. During bonding, an optimal frequency may change. In accordance with the invention, changes are made to one or more parameters as needed, for example the frequency, to maintain resonance of the end effector. Monitoring a phase angle differential is one of the ways in accordance with the invention of maintaining an optimal frequency during bonding. Moreover, because an optimal frequency may be maintained during bonding, the step of first determining a likely optimal frequency prior to attempting a bond may be eliminated, which is advantageous when multiple bonds are to be performed.

The foregoing methods may be used for bonding at an anti-resonant frequency as well as at a resonant frequency. An anti-resonant, or non-resonant frequency, can still be used to accomplish bonding, although it will generally result in higher impedance and a higher voltage requirement. Anti-resonant bonding is thus less efficient; however, it may result in a handpiece that is less sensitive to pressure changes, and thus determining a non-resonant frequency may be useful at least when this type of bonding is desired.

Controlled Pressure Handpiece

In accordance with the invention, a tool for producing vibratory energy is provided with a gauge positioned to respond to a differential between a pressure created by applying a force to the handle, and the physical resistance presented at the end effector. When excessive force is applied, a response is generated, operative to warn the operator and or reduce power of the vibratory signal. When insufficient force is applied, the operator is likewise warned, and or power is not yet applied to produce vibration.

In one embodiment of the invention, a series of electrical contacts are interposed between the handle grip and the end effector. Springs respond to relative movement of the handle and the end effector, to position the contacts with respect to each other, in order to open or close electrical circuits. These circuits may be connected directly to a power generator, or may pass to mechanical or electronic circuits which initiate a warning or a change in power level.

Figure 60:
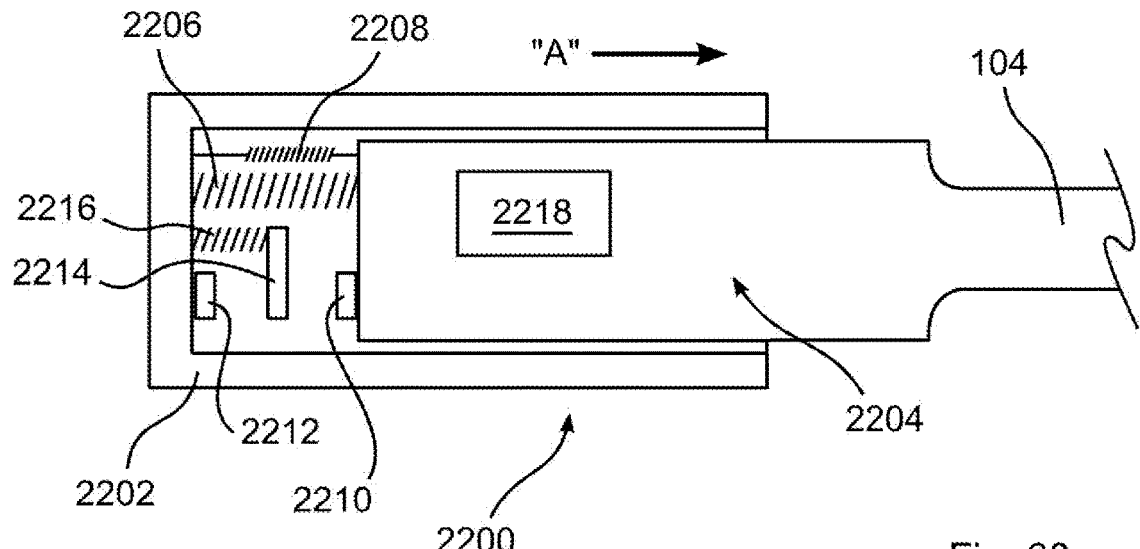
FIG. 60 illustrates a hand held device which controls production of vibratory energy based upon pressure applied to the handle of the hand held device.

With reference to FIG. 60, a handpiece 2200 is provided for transmitting vibratory energy, advantageously including ultrasonic energy, in accordance with the invention. Handpiece 2200 includes a grip sleeve 2202 sized to be conveniently held by a surgical practitioner's hand, or engageable with a haptic or robotic arm. A core body 2204 is sized to slide in engagement with sleeve 2202. While core body 2204 is illustrated to slide within sleeve 2202, it should be understood that sleeve 2202 may be disposed to slide within body 2204 without departing from the spirit and scope of the invention. Extending from core body 2204 is an end effector 104, not shown in its entirety, as described herein. Core body 2204 contains means to produce vibratory energy, as described herein, for example including a piezoelectric stack, not shown.

Extending between sleeve 2202 and body 2204 is resilient member 2206, which may have the form of a spring or other collapsible or bendable resilient element, or magnetic resistive element. End effector 104 may be pressed against a fastener of the type described herein through application of force to sleeve 2202 in the direction of Arrow "A". The application of force thus causes resilient member 2206 to compress, and sleeve 2202 to overlap core body 2204. As the application of force to sleeve 2202 is reduced, resilient member 2206 acts to restore an original relative position of sleeve 2202 and core body 2204. Resilient member 2206 may be retained within a space formed between sleeve 2202 and core body 2204, and may be attached to one or both of sleeve 2202 and core body 2204. Other means may be provided to prevent over extending or separation of sleeve 2202 and core body 2204, as is known in the art.

Associated with core body 2204 and sleeve 2202 are electrical contacts 2210, 2212, respectively. Disposed between contacts 2210, 2212 is contact 2214, attached to resilient support 2216. All contacts 2210, 2212 and 2214 are electrically connected to modifying means 2218 for enabling, disabling, or modifying the vibratory energy generated by handpiece 2200. Modifying means 2218 may be an electronic circuit contained within handpiece 2200, or in core body 2204, or alternatively may be provided external to the handpiece, connected by wired or wireless transmission means, not shown, as known in the art. Alternatively, modifying means 2218 may merely enable and disable an energizing circuit operative to power a vibratory generator within handpiece 2200. In either an electrical or electronic configuration, as sleeve 2202 is urged in a direction "A", contact 2214 will ultimately electrically connect with contact 2210, closing a circuit or sending a signal to energize a vibratory energy generating circuit. As sleeve 2202 is urged further in direction "A", contacts 2210 and 2216 remain electrically connected, contact 2214 moving in connection with resilient support 2216, which becomes compressed. As movement in direction "A" continues, contact 2212 ultimately electrically connects to contact 2214, changing the circuit previously created by contacts 2210 and 2214, opening a circuit or sending a signal to deenergize a vibratory energy generating circuit.

In this manner, if insufficient pressure is applied to a fastener of the invention by end effector 104, vibratory energy will not be applied. Moreover, as excess pressure is applied to the fastener, vibratory energy will not be applied. Thus, handpiece 2200 may be operated to reliably apply vibratory energy only while an amount of force within a predetermined range is applied. While the circuit formed between contacts 2210, 2212 and 2214 has been described to control or signal a hard limit, that is, too little or too much force, it should be understood that it is possible to reduce or increase a vibratory signal based upon excess or insufficient pressure, respectively, by using pressure sensing transducers in place of one or more of contacts 2210, 2212 or 2214, or by employing additional contacts.

It should further be understood that contacts 2210, 2212, or 2214 may be positioned along an interface formed between overlapping portions of sleeve 2202 and core body 2204. An electrical connection may be formed between sleeve 2202 and core body 2204, to convey one or more signals, and or to convey power to core body 2204, in a similar manner, or through the use of a self coiling wire 2208, as shown. Core body 2218 may alternatively obtain power through the use of an attached battery, as described further herein. Additionally, resilient support 2216 may be attached to core body 2204, as opposed to sleeve 2202, with corresponding changes to the circuit logic to achieve the aforedescribed circuit effects.

In an alternative embodiment of the invention, resilient support 2216 functions as a strain gauge, and transmits pressure information to a microprocessor or gauge. Similarly, any or all of contacts 2210, 2212 and 2214 may function as strain gauges. As such, transmitted information may cause the microprocessor to control operation of the device based upon the pressure sensed. In this manner, it may not be necessary for contacts 2210, 2212 and 2214 to establish and break contact with each other, but rather, they may resiliently contact each other throughout all or a portion of their relative movement, relaying relative pressure data.

Battery Powered Vibratory Energy Generator

Figure 62:
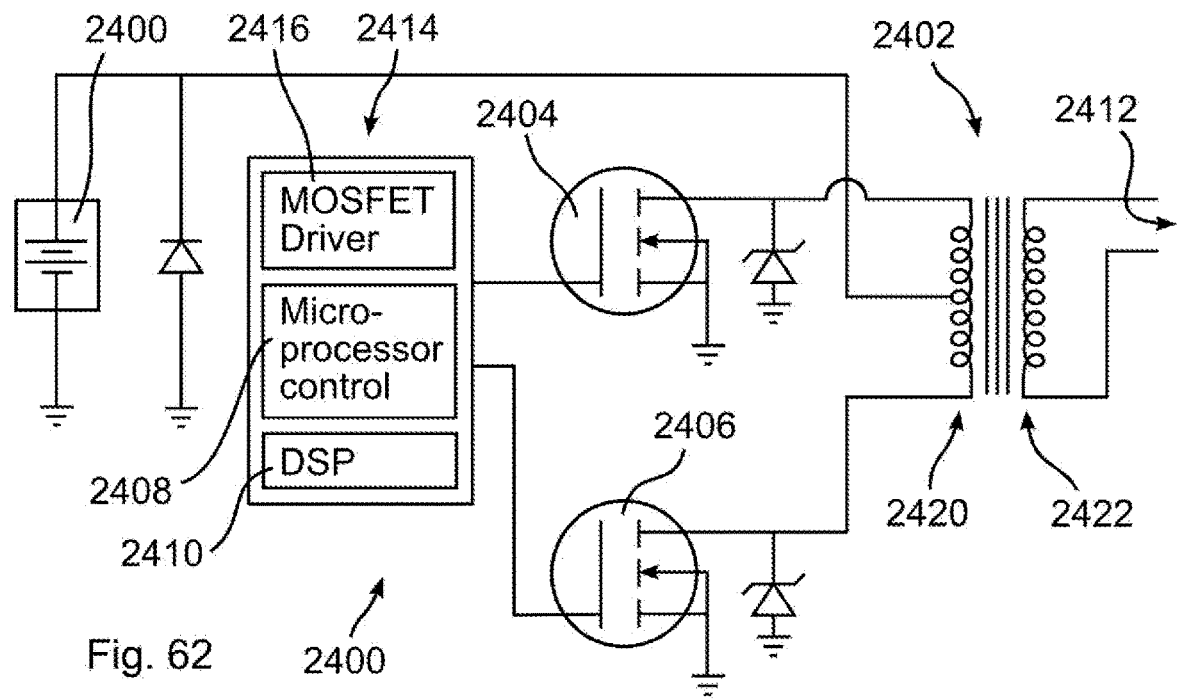
FIG. 62 illustrates a circuit operative to produce a signal suitable for generating vibratory energy, based upon a DC source provided by one or more batteries.

With reference to FIG. 62, a handheld or portable vibratory generator has a requirement for a substantial amount of current, at high voltage. In accordance with the invention, an inverter 2400 is provided to convert the signal from a direct current battery 2424 into a suitable sine wave signal, and a step-up transformer 2402 is provided to increase the voltage to an effective level.

In one embodiment multiple mosfet devices 2404, 2406 may be connected in parallel, advantageously provided in pair arrays, to provide for an adequate amount of current, wherein each pair 2404, 2406 increases the amount of current the circuit can provide. A control circuit 2414 includes a microprocessor 2408, which controls a MOSFET driver 2416, which provides power to the mosfet array pairs 2404, 2406. To convert from the direct current of battery 2418 to the alternating current required by a piezo stack or vibratory energy transducer, control circuit 2414 alternately switching power between MOSFET devices 2404 and 2406, in order to produce an alternating current within the primary windings 2420 of transformer 2402. This in turn induces an alternating magnetic field, which induces an alternating current in secondary winding 2422. Control circuit 2414, advantageously further including a digital signal processor (DSP) 2410 for further signal modification, thus creates a wave form at the proper frequency and voltage for vibratory bonding of the invention.

Additional control circuitry may be employed, as known in the art, to modify the signal parameters to enable precise bonding, as described herein, including circuitry for voltage regulation, phase control, and voltage and current detection and measurement.

Output 2412 of transformer 2402 is ultimately directed to a handpiece or piezo stack (not shown), which will transform the electrical signal into vibratory energy.

To drive the circuit with adequate power, it is advantageous to use an efficient power storage medium, such as lithium ion batteries, which at the current time are capable of sourcing up to 80 amperes at a reasonable cost.

Figure 87:
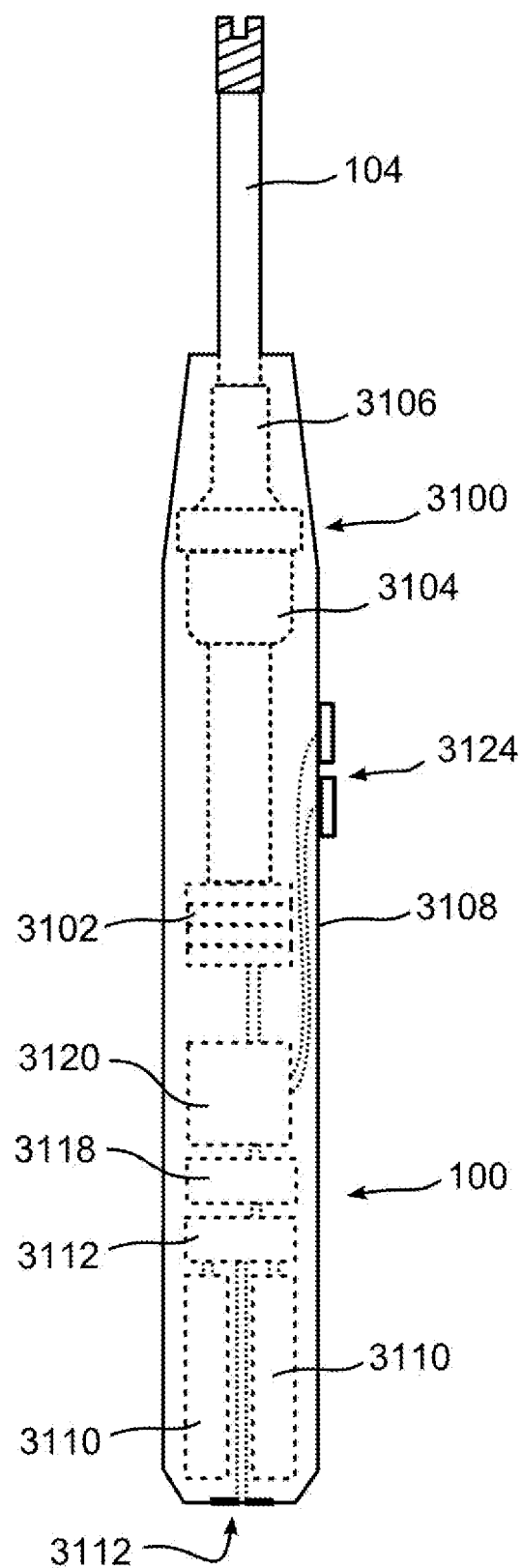
FIG. 87 illustrates the handpiece of FIG. 86, modified to incorporate a battery and signal generating circuit for converting battery power, and further illustrating a housing additionally incorporating the booster.

FIG. 87 illustrates a handpiece containing one or more batteries 3110, and an electronic circuit 3112 which may correspond to control circuit 2414.

SONAR Measurement of Collapse

In another exemplary method, collapse of the fastener may be monitored, such as by the use of SONAR. Collapse is the distance a thermoplastic fastener or implant shrinks in height when vibratory energy is applied. For example, some thermoplastic fasteners have been found to shrink about 20 percent in height and increase 30 percent in width when bonded. For fasteners having two pieces, such as a cap and an anchor, the attenuation of the reflected vibratory waves changes as the two piece fastener becomes one piece. This change in attenuation may be monitored to alert the surgeon or operator when the bond or staking is complete. Furthermore, a vibratory transducer could be used in conjunction with the end effector to detect the change in acoustic impedance/attenuation of the site. This signal may be monitored by a microprocessor/controller or data signal processor (DSP) and data may be automatically interpreted to indicate whether the bond was successful.

Another way of providing feedback of an effective bond is to monitor the Eddy currents created by the movement of the end effector. As the end effector vibrates, the linear motion creates a change in the magnetic field. By monitoring the travel of the end effector, the amount of collapse can be determined.

Booster/Attenuator

Figure 69:
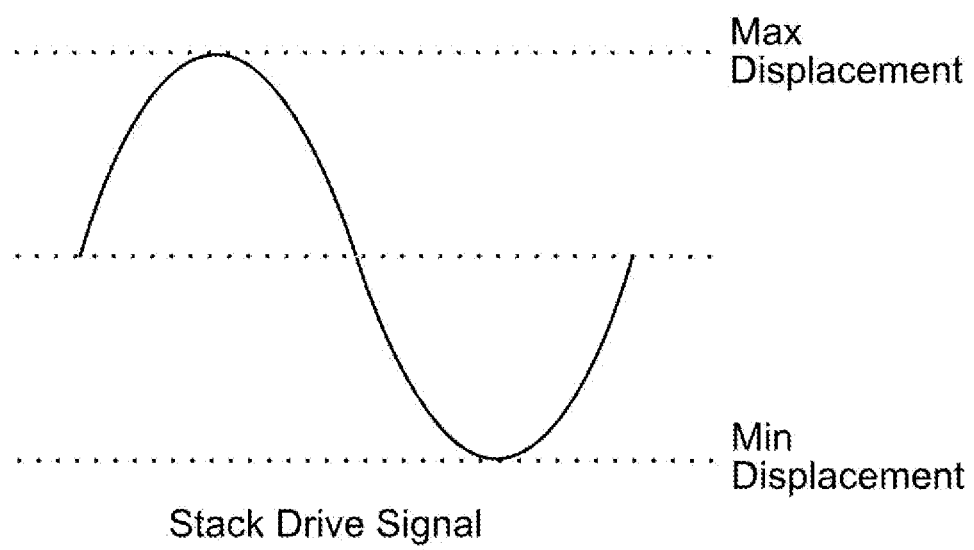
FIG. 69 illustrates end effector displacement as a function of stack drive signal, modifiable through the use of a booster or attenuator.
Figure 86:
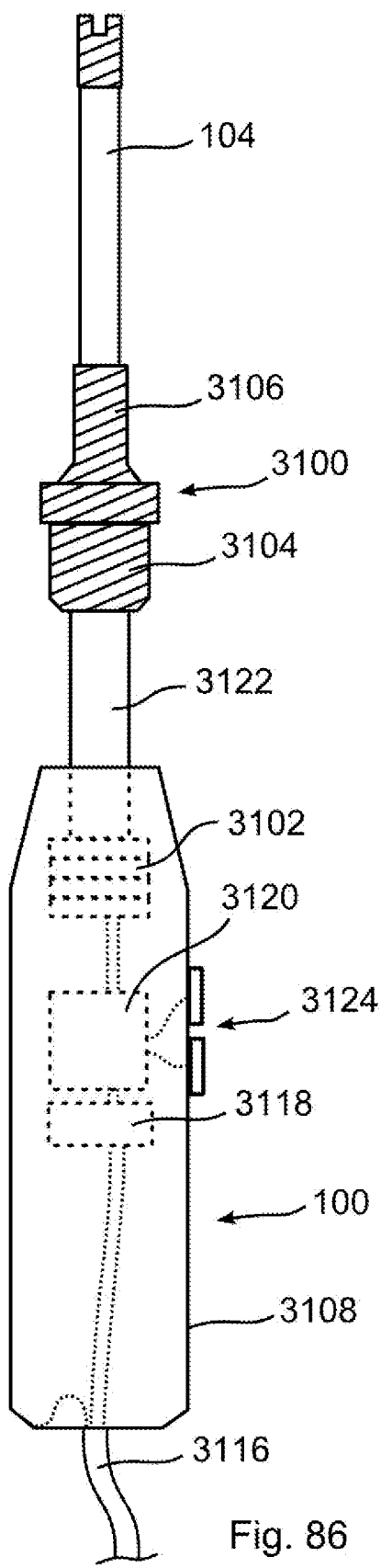
FIG. 86 illustrates a vibratory energy generating handpiece in accordance with the invention, incorporating power circuitry, logic circuitry, a piezo stack or other source of vibratory motion, a vibratory energy booster, an end effector, and a horn.

With reference to FIGS. 69 and 86-87, in another embodiment in accordance with the invention, peak to peak motion, or amplitude, of the vibratory horn or end effector 104 is controlled using an attenuator or booster 3100, positioned after the piezo stack 3102. FIG. 69 illustrates displacement varying in relationship to the stack drive signal, wherein a booster or attenuator alters the minimum and maximum displacement of the end effector. Booster 3100 comprises an input mass 3104 and an output mass 3106, sized relative to each other, with output mass 3106 of a lower mass and smaller dimension, operative to result in an increase in vibratory frequency of end effector 104. While a booster 3100 is shown, it should be understood that an attenuator, not shown, is likewise adapted as known in the art to reduce an output frequency, with an output mass larger and or larger dimension than an input mass.

FIG. 86 illustrates a booster 3100 positioned exterior to a housing 3108 of handpiece 100, whereas in FIG. 87, booster 3100 is positioned internal to housing 3108. The invention contemplates that by positioning booster 3100 within housing 3108, rigidity of booster 3108 may be reduced, as it is provided with additional support by housing 3108. In this manner, the overall weight and cost of handpiece 100 may be reduced. If the entire cost of handpiece 100 is sufficiently low, handpiece 100 may be designed for use in a single medical procedure and thereafter discarded, thereby removing a requirement that the device be sterilizable (e.g. able to withstand steam and pressure), and further reduces the potential for cross contamination between patients.

FIG. 87 further illustrates a battery powered vibratory device in accordance with the invention, containing one or more batteries 3110, and electronic circuit 3112 operative to produce the signal required for production of vibratory energy in accordance with the invention, as described elsewhere herein. Contacts 3114 enable an electrical connection for recharging the batteries. Alternatively, the batteries may be provided precharged in a single use device, wherein contacts 3114 may be eliminated. Alternatively, an inductive coil, not shown, may be used to provide power, using techniques known in the art, for charging batteries 3110, or for powering the handheld device 100 whether or not there are internal batteries 3110.

In contrast, the handpiece of FIG. 86 is provided with conductors 3116, operative to convey a required signal from a generator or control device, not shown. It should be understood that the device of FIG. 86 may also be configured as battery operated as shown for FIG. 87; however only one device is shown as such for brevity.

With reference to FIGS. 86 and 87, logic circuit 3118 is provided to carry out computational calculations as described herein, and control circuit 3120 is provided to change an input signal as required to generate a correct vibratory output at end effector 104. Alternatively, logic and control may be provided entirely by a connected generator, not shown.

In addition to booster 3100, control may further be achieved by the generator or logic circuit 3118 and or control circuit 3120 by modulating the power, or amplitude, of the high frequency signal, as described elsewhere herein. Buttons 3124 may be provided to commence bonding, stop bonding, toggle through options, or otherwise control actions of the handpiece.

Booster 3100 may be replaced, as by a threaded or other mechanical connection to end effector 104, and piezo stack output shaft 3122. To facilitate booster 3100 selection, and to reduce the incidence of error, booster 3100 may be color coded, and may further be color coded to match fasteners, handpiece 100, end effector 104, or other physical device or instruction document properly associated with the use of booster 3100. Color coding may be used elsewhere when carrying out the invention, for example between fasteners and single use handpieces, such as handpiece 100 of FIG. 87, and fasteners and end effectors and horns.

Thermal Staking

Staking of the fastening device of the present invention could also be done using thermal energy. The process for thermal staking is similar to the one used for vibratory, except that it may not be necessary to tune the system. The energy signal sent to the stake can be either AC or DC. To allow for longer heater life, a pulse width modulated (PWM) signal could be used. The PWM signal allows for the energy to be rapidly switched on and off with a varying duty cycle proportional to the total system energy needed for the staking environment.

Color Change

It is also contemplated that the material being bonded or staked may be translucent or transparent, and a visual indicator within the material could indicate when the process is complete. For example, a pigment, dye, or other substance may be impregnated into the thermoplastic which when subjected to vibratory energy the pigment or dye would be released indicating that the bond or staking is complete. However, as discussed elsewhere herein, certain pigments, particularly in high concentration, may adversely affect bonding; accordingly, appropriate testing must be carried out for each admixture. Alternatively, the material of the thermoplastic may have the characteristic of changing color as heat or vibration is applied for a predetermined time or a predetermined frequency and wattage.

Combined Therapeutic/Diagnostic Vibratory Generator

With reference to FIG. 63, in accordance with the invention, a vibratory energy generator 2500, advantageously a vibratory generator, includes power and logic circuitry 2522 for generating and controlling a signal which may be used to create vibratory energy, and is otherwise adapted to perform diagnostic as well as therapeutic tasks. Diagnostic tasks include mapping or visualization of a target location. Information gathered during the diagnostic phase can be used by the surgical practitioner to determine optimal settings for a subsequent therapeutic use of the device, specifically including vibratory fastening as described herein.

Generator 2500 may include separate connectors 2502, 2504 which are dedicated to diagnostic or therapeutic purposes, respectively, or a combined connector 2506 may be used cooperative with combination handpiece 2508, described further below. Generator 2500 may further be provided with any one or more of an integrated output display 2510, external display 2512, mouse 2514, or integrated keypad 2516. It should be understood, however, that the range of integrated and external human interface devices known in the art may be employed in combination with the invention. In one embodiment, any of the mouse controls, for example buttons 2518, 2520 may be used to switch between diagnostic or therapeutic modes, wherein a transducer is caused to output diagnostic or therapeutic vibratory energy depending upon the button pressed, advantageously in combination with a mode selected with another human input device or the circuitry within generator 2500.

The diagnostic information may further be directed to a microprocessor, either within circuitry 2522, or external (e.g. within a personal computer) to generator 2500, either of which may include a DSP, which will then carry out or suggest optimal therapeutic settings to the practitioner, which may then be communicated by output devices associated with the external microprocessor, or through human interface output devices connected to generator 2500.

Diagnostic information may include mapping information pertaining to structures in the body which are not visible, including representative images of physiological areas of interest. Additionally, diagnostic information may include information pertaining to the environment in which fastening in accordance with the invention is to take place, including microclimate information, including temperature, humidity, or information relevant to the size of implant needed. This information may be determined using calculations of the speed of travel of vibratory energy through various medium, and is particularly well understood with respect to vibratory energy.

Figure 64:
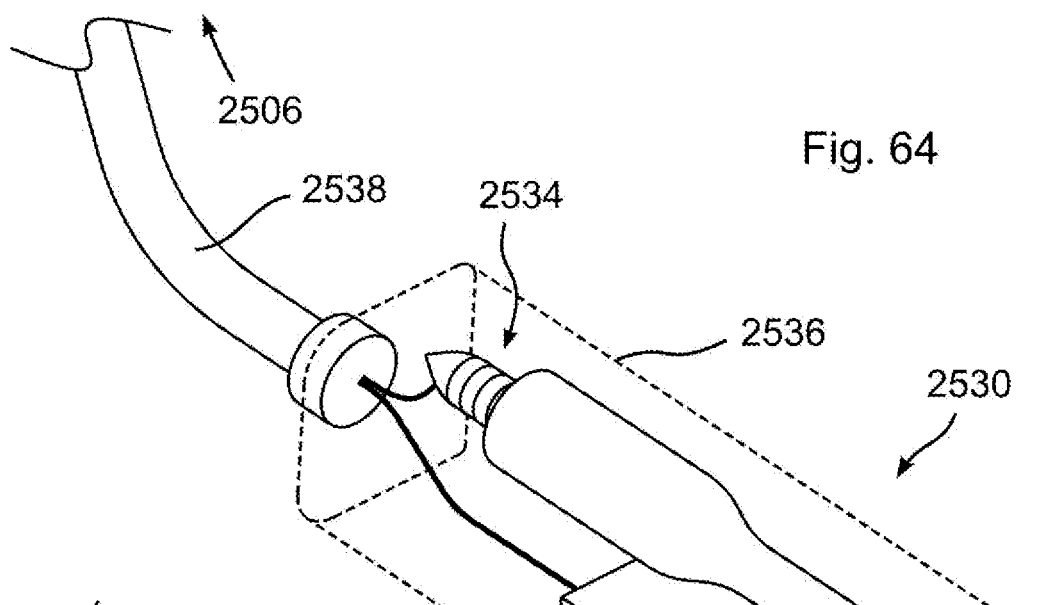
FIG. 64 is a perspective view of internal elements of a handpiece in accordance with the invention which includes an element for generating therapeutic vibratory energy, and an array of vibratory elements for diagnostic use.
Figure 65:
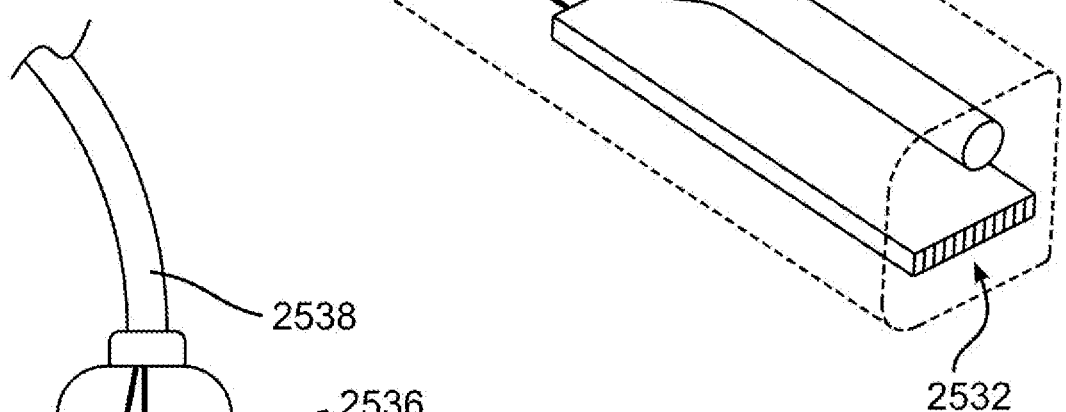
FIG. 65 is a side view of the handpiece of FIG. 64.
Figure 66:
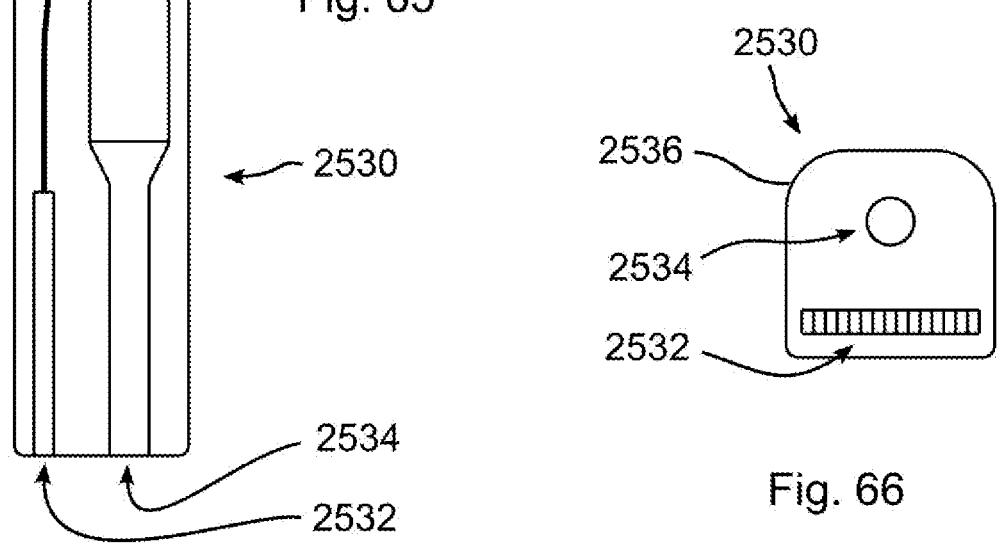
FIG. 66 is an end view of the handpiece of FIG. 64.

Referring now to FIG. 64-66, in one embodiment of the invention, a vibratory energy generator is provided in a portable or handheld device 2530, which produces vibratory energy for diagnostic purposes with an array of crystals 2532, and for therapeutic purposes by a stack of crystals 2534, within a housing 2536 incorporating both arrays.

In one embodiment of the invention, crystals 2532 and 2534 are piezoelectric crystals of ceramic with tungsten-bronze structures, but may include any crystals, or any other transducer whether or not crystalline, known in the art to generate vibratory energy from electricity, and electricity from vibratory energy.

Accordingly, a single microprocessor may advantageously be used to control both crystal configurations 2532, 2534 based on separate algorithms for each, and a medical practitioner may switch between diagnostic and therapeutic uses without switching to a different tool.

Housing 2536, shown, has a simple form, although it should be understood that housing 2536 may be ergonomically shaped to best fit the human hand, or may be shaped in the manner of a gun, and may further include buttons or other controls, not shown, useful for communicating with associated equipment, such as generator 2500. Wire 2538, extending from housing 2536 and connected to each crystal array, extends to a generator of vibratory energy, such as generator 2500. Alternatively, device 2530 may be provided with its own source of battery power, as described elsewhere herein, and may be wirelessly connected to a microprocessor or digital signal processor which conveys signal information relevant to the medical and bonding procedure undertaken.

It is advantageous to reduce the time required for most tasks during a medical procedure not only to reduce costs and the time required to complete the procedure, but also to reduce the time during which the patient is subjected to discomfort or the risks of surgery, which include prolonged anesthesia, increased bleeding, and additional exposure to microorganisms. The instant invention reduces the time required to complete a procedure by enabling rapid generation of accurate data pertaining to the physical environment, the tissue or structures to be fastened, the dimensions of a required fastener, and the bonding parameters. Once this data is available, the device enables therapeutic use of vibratory energy, including the bonding of fasteners as described herein, without a requirement to change tools.

Irrigation/Suction End Effector

With reference to FIG. 81, during vibratory bonding, the presence of liquid or moisture can impact the performance and quality of the bond. One approach to ensuring a consistent and reliable bond, as described herein, is to adjust the bonding parameters according to the amount of observed or measured moisture within the zone or area of bonding. Another approach in accordance with the invention is to remove moisture from the bonding area, by introducing an input stream of gas or liquid, or by applying suction/aspiration proximate the bonding site. In one embodiment, a tube 3000 is attached to a vibratory end effector 104, wherein tube 3000 has a distal opening 3002 which serves as the inlet for aspiration, or conversely the outlet for a gas or liquid stream, opening 3002 positioned at a location near where bonding is to take place. A fitting or coupling 3004 may be provided at a proximal opening 3008, to releasably attach tube 3000 to a source of vacuum or low pressure, not shown. Tube 3000 is attached by any means known in the art, including for example adhesive 3006, brazing or welding, or one or more resilient bands or screws. To avoid potentially damping a vibratory signal, however, it may be advantageous to alternatively attach tube 3000 to sheath 146, which surrounds end effector 104, but does not significantly inhibit vibratory motion.

In a further embodiment, an additional tube 3010 is provided, attached to end effector 104, having like components relative to tube 3000, including a coupling 3012 at proximal opening 3014, and a distal opening 3016. Tube 3000 or 3010 may be bent or shaped to direct opening 3002, 3016, respectively. For example, as illustrated at 3018, tube 3000 is bent to direct opening 3002 towards a bonding site. In an embodiment having two or more tubes, at least one of tube 3000 or 3010 introduces an input stream of gas or liquid, and a second tube is operative to form an output stream to collect the gas or liquid via suction, together with any debris collected and carried therein. While tube 3010 is illustrated as being directly connected to end effector 104, it may alternatively be connected to sheath 146, as outline above with respect to tube 3000.

An advantage of the aforedescribed embodiment is the removal of debris generated during the bonding process, which may include flash formed at the bonding periphery, as well as any other material or body tissue that has vibrated loose or otherwise has become loose within or near the bonding area.

The first or second tube 3000, 3010 may be fastened to the outside of the vibratory end effector, as described with respect to FIG. 81, or may alternatively be formed as one or more channels or pathways within the end effector, as may be seen in FIGS. 82-83, or a combination of internal and external pathways. FIG. 82 illustrates a single channel 3020, having a proximal opening 3022, a coupling 3024, and a distal opening 3026. FIG. 83 illustrates two channels 3020, 3040, channel 3040 having analogous elements including proximal opening 3042, coupling 3044, and distal opening 3046. It should be understood, however, that channels 3020 or 3040 formed within end effector 104 may impact transmission of vibratory energy, and thus tuning may result in differing parameters with respect to an end effector without channels, particularly if the channels are formed with a significant length transverse to a longitudinal axis of end effector 104.

Liquids which may be passed to the body through tube 3000, 3010, 3020 or 3040 (hereafter collectively tube 3000) include, for example, sterile saline, therapeutic substances including the substances defined herein, injectable polymer, bio-graft material, radioisotope tagged liquid, live cells, or any other material as determined by a medical practitioner to be of benefit to the patient. Similarly, gases passable through tube 3000 include oxygen, nitrogen, carbon dioxide, or any other gas determined by a medical practitioner to be of benefit to the patient. Flowable powders or particulates may also be passed through tube 3000, as determined to be of benefit.

In the embodiments of FIGS. 81-83, switches or controls for activating an input or output stream may be provided on a handpiece to which end effector 104 is connected, for example handpiece 100, or on a foot switch or hand operated remote, not shown, or the input or output stream may be activated by voice control.

Figure 85:
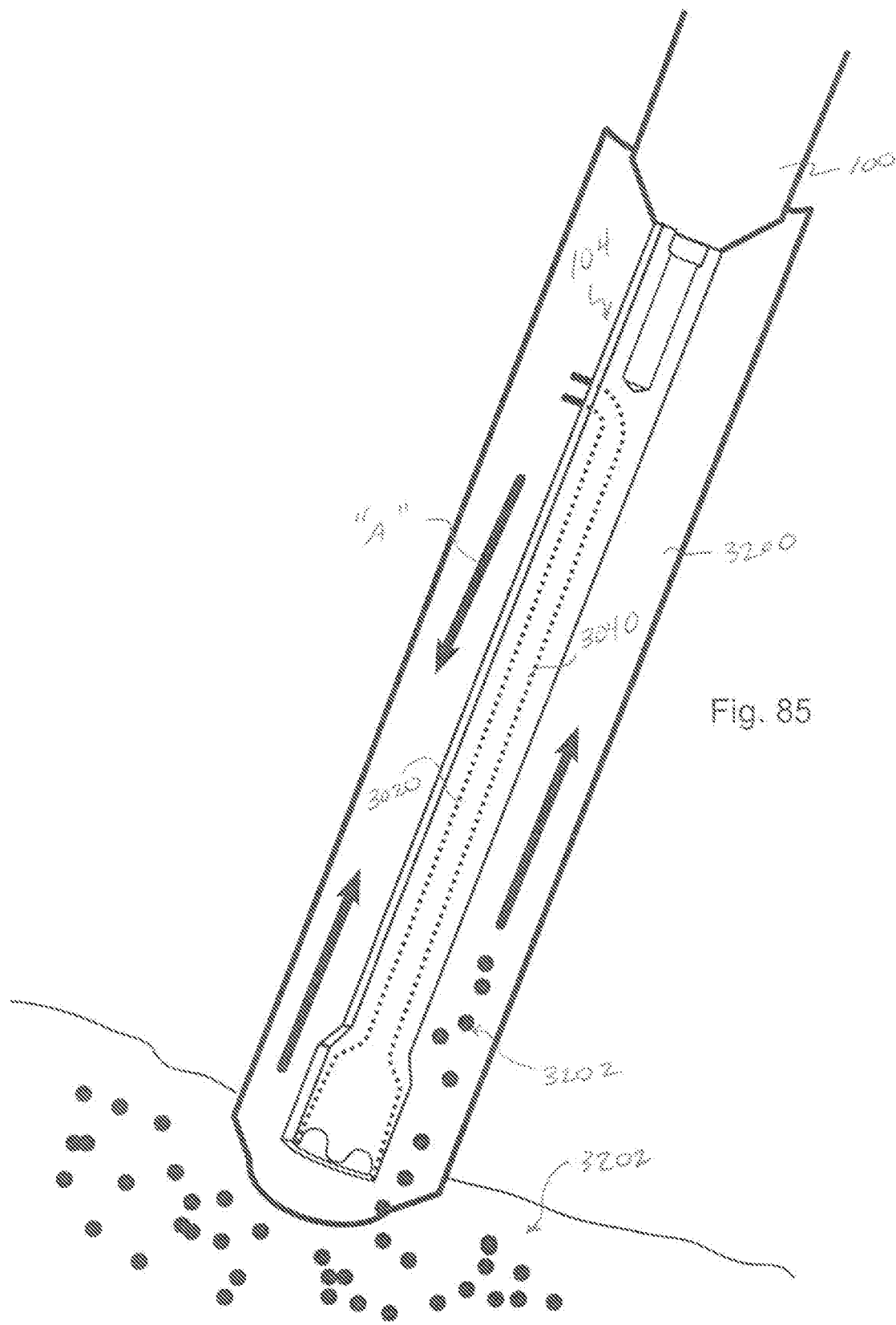
FIG. 85 illustrates, in accordance with the invention, an end effector of the invention within a cannula, operative to provide a working space, and to introduce and remove materials proximate a bonding site, including tissue to be removed.

Referring now to FIG. 85, the end effector 104 of FIG. 83 is shown disposed within a cannula 3200. In this manner, materials introduced through tube 3020 may be confined within a specific area defined by cannula 3200. Moreover, additional materials may be introduced through cannula 3200, and these materials may also be confined within cannula 3200. Thus, materials may be introduced to an area of fastening which have a reduced impact on surrounding body tissue. Additionally, benefits of a cannula, or expanding cannula, may be attained, including the maintenance of potentially intruding tissue at a distance away from a fastening site.

In one embodiment of the invention, a stream introduced through tube 3020, or alternatively through cannula 3200 (indicated by arrow "A") may dislodge tissue cells 3202 which are intended to be harvested for subsequent use, or which are harmful and are intended to be removed for the health of the patient. For harmful tissues, radio frequency may be emitted as described with respect to FIG. 84, to destroy or loosen harmful cells. Alternatively, a therapeutic substance may be used to loosen or dislodge harmful cells, the substance admitted at "A" or through tube 3000. Further, material may be admitted at "A" or through tube 3020 under pressure. In particular, material may be admitted through tube 3020, for example, at sufficiently high pressure to have a significant mechanical effect on exposed tissue, wherein firmly anchored tissue or other matter may effectively be dislodged. Moreover, vibratory energy may be applied by end effector 104 to contribute to a loosening effect. Loosened material may be removed by suction, as through tube 3040, or through a flow upwards in a direction opposite to arrow "A", to a point exterior of cannula 3200. Additionally, an aspirator, not shown, may be employed.

It should be understood that the devices of FIG. 81 or 82 may alternately be used in conjunction with cannula 3200 as described, or alternatively, any of the other devices of the invention which may advantageously be admitted to the body through a cannula.

Radio Frequency End Effector

With reference to FIG. 84, in another embodiment, one or more radio frequency transmitting antenna 3050 are provided proximate the distal end of end effector 3054, operative to break down or destroy contaminants within the bonding area, including moisture or particulates. Shielding, not shown, is appropriately placed in order to safeguard any nearby body tissue or material which might be vulnerable to stray transmissions. One or more wires 3052 connect antenna 3050 to a radio frequency signal generator, not shown. The RF embodiment of FIG. 84 may be combined with other end effector types, including those of FIGS. 81-83.

Testing

The previously described methods for providing positive feedback to the operator included the use of measurements and/or computers. Another positive feedback system is provided which relies on physical force. When two objects are fastened to each other, it is common for the technician or mechanic to pull or tug on the assembly to ensure the parts are securely fastened. This common technique may apply to the thermoplastic system of the present invention. Once a fastener or other implant is vibratory bonded or staked, the surgeon can apply a quick tug on the assembly to verify the bond or staking was completed as intended.

In accordance with an embodiment of the invention, a frame is provided with an aperture through which a fastener body may pass, sized to prevent passage of a fastener head. The device may thus test the holding strength of a distally bonded connection, as well as proximal bond including a head formed with vibratory energy. A strain gauge, spring scale, or other suitable measuring device is connected to the frame, and a force is applied in a direction away from the fastened connection. The results are observed and recorded, together with the parameters under which the connection was formed and tested.

Figure 11A:
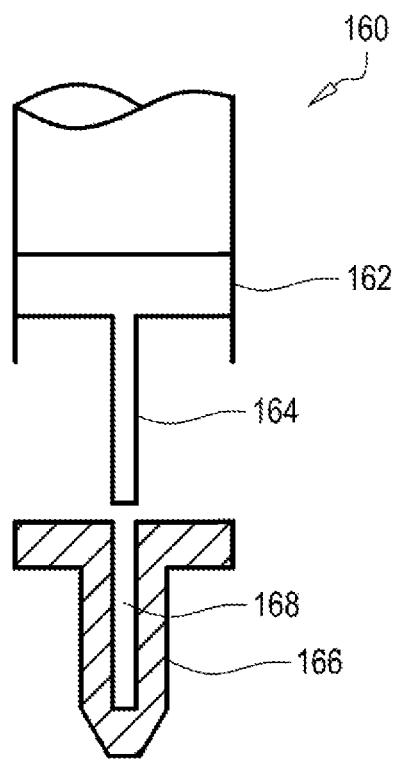
FIGS. 11A and 11B illustrate a physical positive feedback device.
Figure 11B:
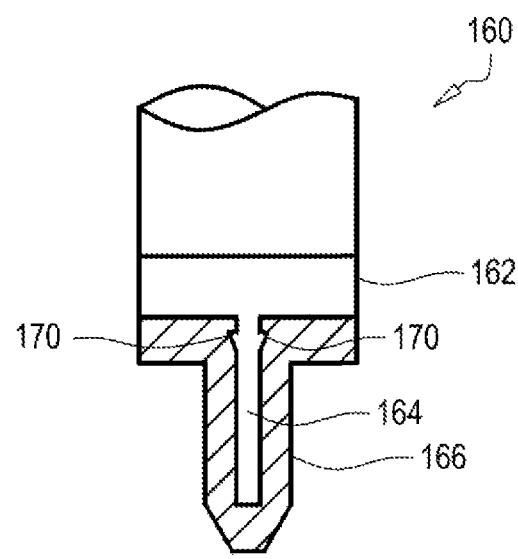

FIGS. 11A and 11B illustrate a feedback instrument 160 for performing such a physical positive feedback check. An end effector 162 includes a post 164 which emits vibratory energy. A thermoplastic fastener 166 is placed on the end effector 162 with the post 164 in a bore or receptacle 168 of the fastener 166. After emitting vibratory energy and bonding or staking the fastener to an implant or tissue, the surgeon may actuate a biasing prong or prongs 170 from the post 164 of the end effector while the post 164 is still in the fastener 166. In a stored configuration, the prongs 170 are positioned within the post 164. In a deployed configuration, the prongs 170 extend radially from the post 164 by the activation of a handle, switch, or button. The extended prongs 170 dig slightly into the material of the fastener 166 so that the surgeon may now pull or tug on the instrument 160 proximally to verify that the fastener 166 is securely bonded or staked in place. Additionally, the prongs 170 and/or post 164 may include a strain gauge or other force measuring device to measure and display to the surgeon how many pounds of pull strength is being put on the fastener.

To aid in determining the exact conditions under which fastening was accomplished, an electronic circuit separately measures the power consumed in tuning the vibratory instrument, and performing the bond itself. This data is used, together with other parameters, to enable the production of a secure and reproducible bond.

Fastening Procedures

When two dissimilar materials need to be bonded together, the bonding may be performed outside the body, such as during the manufacturing process or within the operating room. This is done to avoid damage to surrounding tissue caused by the heat required to bond the dissimilar materials to each other. Then, once implanted, further bonding may be done within the body to bond like thermoplastics creating the desired implant configuration. For example, a spacer made of PEEK may be joined to a metallic implant outside the body. The spacer and implant may be placed in the body, and the PEEK may be bonded with another PEEK element inside the body so that there is a PEEK to PEEK bond. The metal implant may be the load bearing surface or the bearing point, while the PEEK to PEEK bond provides for the fastening and stabilization of the implant.

Staking

Although the above-discussion emphasizes bonding or welding, the present invention also contemplates staking in most situations as an alternative or supplement. Staking generally involves the mechanical interlock of dissimilar materials. Staking is the process of melting and reforming a piece, such as a stud, to mechanically lock a material in place. It provides an alternative to bonding when two parts to be joined are made of dissimilar materials that cannot be bonded or simple mechanical retention of one part relative to another is adequate.

The advantages of staking include short cycle time, the ability to perform multiple staking with one end effector. The most common staking application attaches metal to plastic. A hole in a metal part is designed to receive a plastic stud. An end effector with a contoured tip contacts the proximal end and creates localized frictional heat. As the stud melts, light pressure from the end effector reforms the head to the configuration of the end effector. When the end effector stops vibrating, the plastic solidifies and the metal and plastic parts are fastened together.

Thus as set forth in the prior art, which is not in the medical field, staking using vibratory energy causes thermal deformation at the site of the end effector and the near end of a polymer. As the inventors have previously defined for bonding, vibratory bonding can be near field (less than ¼ inch from the end effector) and far field (greater than ¼ inch from the end effector). Staking, as defined in the prior art is all near field. To date, no one has performed distal or far field staking. This is where the mechanical deformation occurs at a site away from the vibratory horn or end effector. The staking can occur, not at the trailing edge of the implant, but along the implant surface, or at the far end of the implant, where the implant can be bonded to another implant mechanically, particularly if it is a dissimilar implant. The distal staking of the invention causes deforming and melting to mechanically interlock into a like or dissimilar material. In accordance with the invention, the horn does not necessarily reform or change a surface with which it comes in contact, as is disclosed in the prior art.

Figure 21:
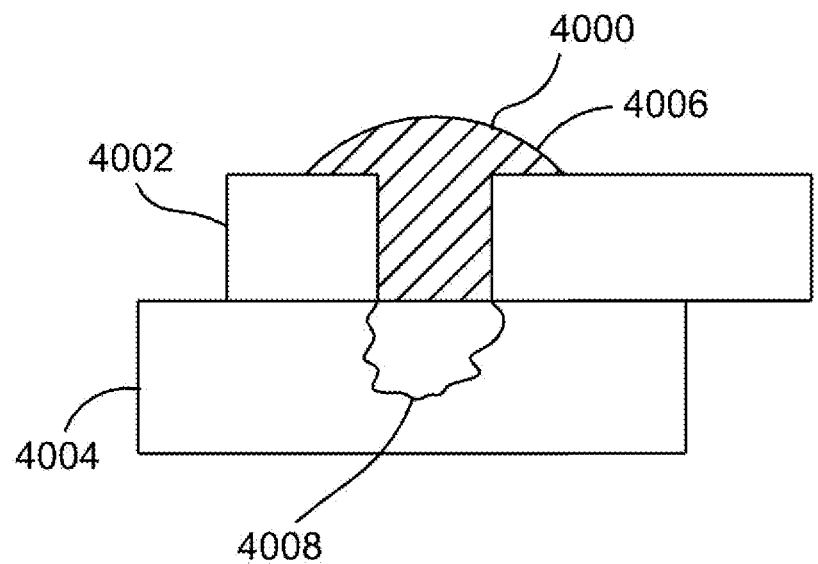
FIG. 21 shows a first staking application involving the joining of two porous materials.
Figure 22:
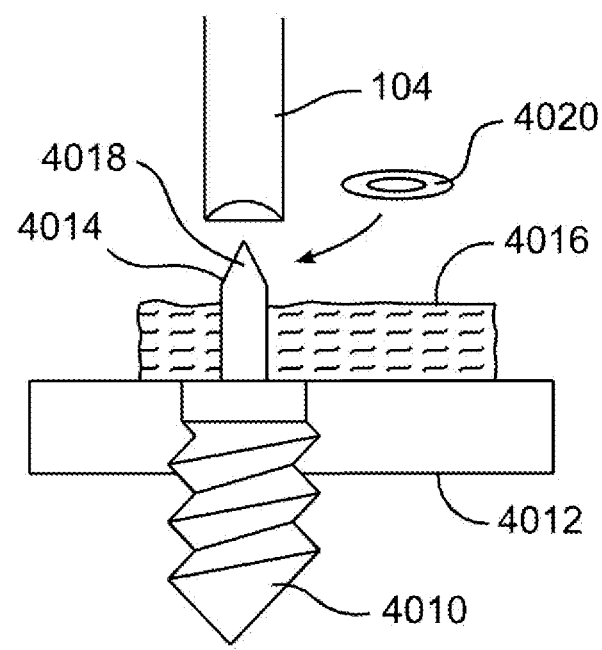
FIG. 22 shows a second staking application involving the fastening of soft tissue to bone with a polymeric anchor.

FIGS. 21-24 illustrate some uses of vibratory staking for implants and tissue fastening. In FIG. 21, a PEEK (or other polymer) tack 4000 having a proximal end similar to the anchor in FIG. 22 is used to couple two materials together, in this case two porous metals 4002, 4004. After staking, the proximal end assumes the shape 4006 of the end of the end effector. Additionally, the distal end 4008 of the tack could be secured to porous metal using vibratory energy.

FIG. 22 shows a polymeric anchor 4010 prior to staking with the domed-shape end effector. The anchor 4010 is illustrated as threaded, as a means of securing the base to the body or other implant. However, the base may be connected to the body or another implant using vibratory energy in accordance with the invention, or may otherwise be secured using means known in the art. Post 4014 on the proximal end of anchor 4010 can be used to pierce one or more objects, in this example soft tissue 4016, holding it in position relative to 4012. The objects may alternatively be bound by passing the end of post 4014 through an aperture or gap in each of the objects to be staked, or by forming the gap or aperture with post 4014. The tip 4018 is then formed by staking using end effector 104. In this example, end effector 104 is curved or dome shaped, and is operative to form a complementary dome shape on the end of post 4014. Generally, however, bondable material on the end of post 4014 will expand outwards, enlargening the end of post 4014. In this manner, the end of post 4014 becomes larger than the gap in the objects. It is desired for the end of post 4014 to expand to a size at least larger than the gap in the object closest to the end of post 4014, in order to at least secure the top-most object. As such, objects upon post 4014 are secured within the body, bounded by secured base on one side, and expanded post 4014 on the other, and are thus staked. If needed, the post can be trimmed (either mechanically or by shearing off with the vibratory energy) before staking A load bearing surface 4020 may be added before tip 4018 is formed, if additional support is deemed beneficial.

Figure 23:
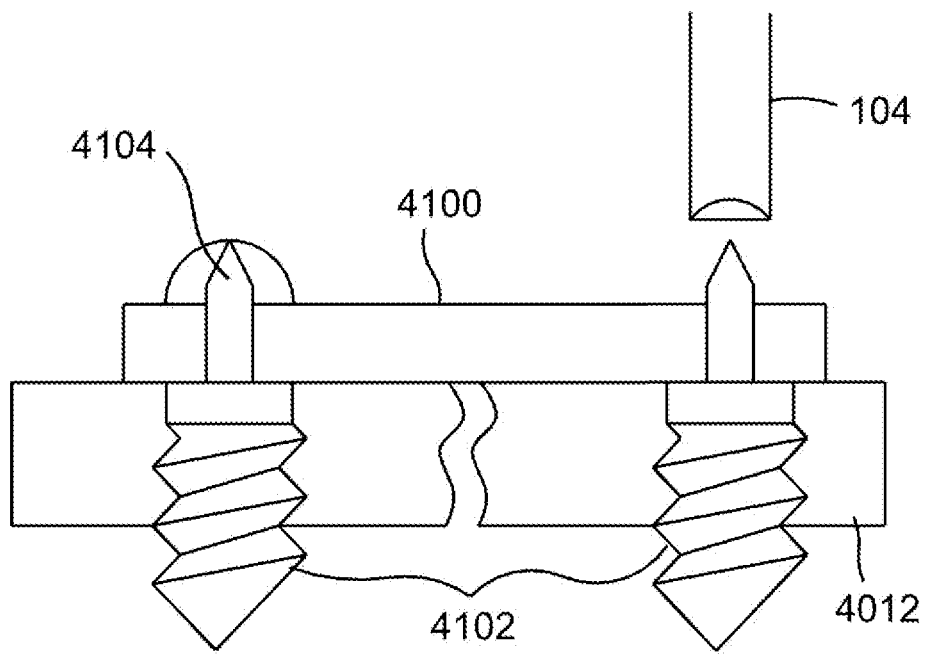
FIG. 23 shows a third staking application involving fracture fastening with a plate and bone screws.

In FIG. 23, a fracture fastening plate 4100 is secured with screws 4102 having tips 4104 projecting above the top surface of plate 4100. Screws 4102 can be placed through holes in plate 4100, and tips 4104 staked to secure plate 4100 to bone 4012. Screws 4102 can be inserted through the plate at angles other than ninety degrees. In another embodiment, screws 4102 are first threaded into bone 4012 and then plate 4100 is inserted over the proximal tip.

Figure 24:
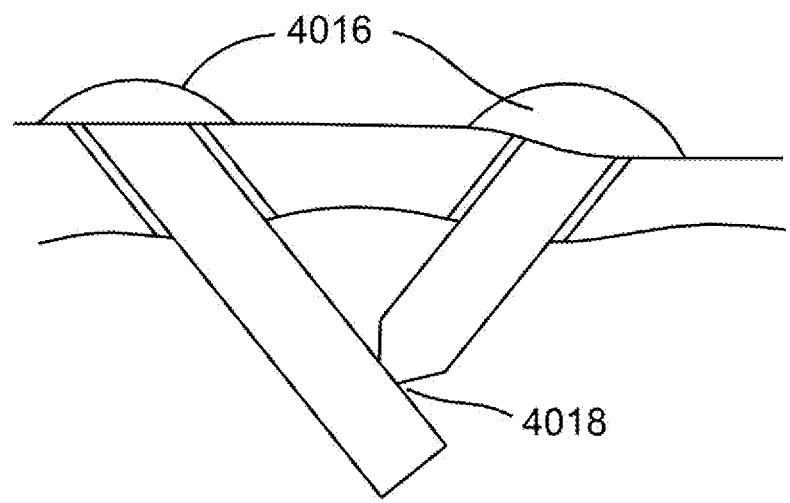
FIG. 24 shows a fourth staking application involving near field staking and far field bonding.

FIG. 24 shows that two implants can be joined with far-field bonds 4014, then formed at the end effector to seal over bone or implant. The near-field staking 4016 should not adversely damage or affect the far-field bond 4014, as each bond is tuned for the particular locus of vibration desired.

Figure 25A:
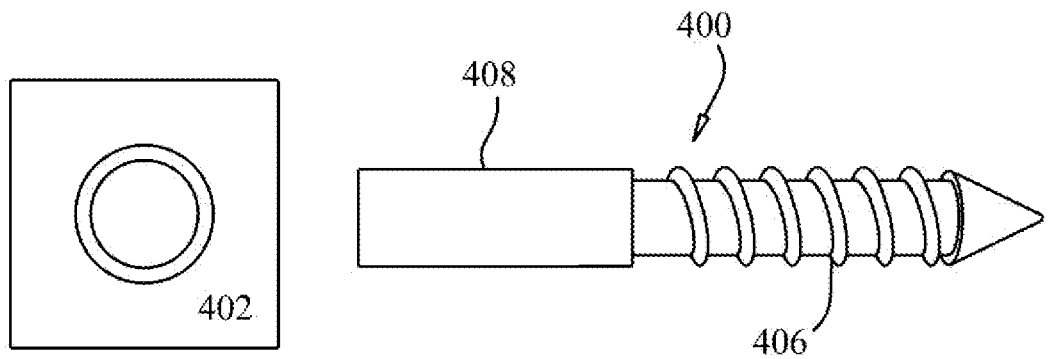
FIGS. 25A-25C show another staking application involving a bone screw and plate.
Figure 25B:
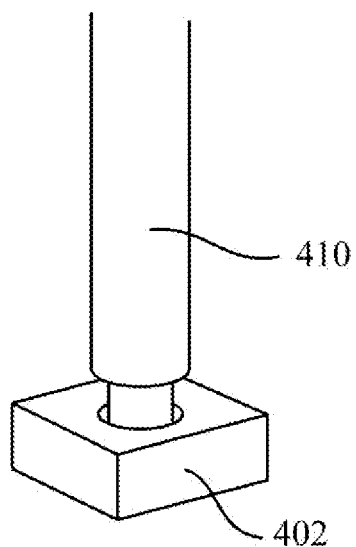
Figure 25C:
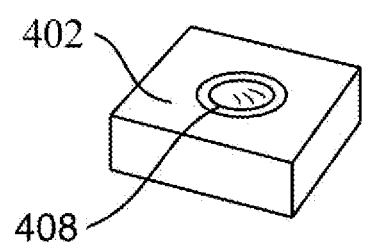

FIGS. 25A-C show another embodiment of an anchor 400 particularly well suited for staking to a plate 402. Anchor 400 has a body 404 with threads 406 for fastening to bone. As shown in the testing jig, after anchor 400 is secured to bone, the plate 402 is inserted over head 408 of anchor 400. If needed, head 408 can be trimmed or otherwise cut to size. A staking end effector 410 is placed on head 408. Upon activation of the vibratory energy, head 408 deforms to the shape of the tip of end effector 410 (in this case, domed shaped) to secure anchor 400 to plate 402.

Figure 26A:
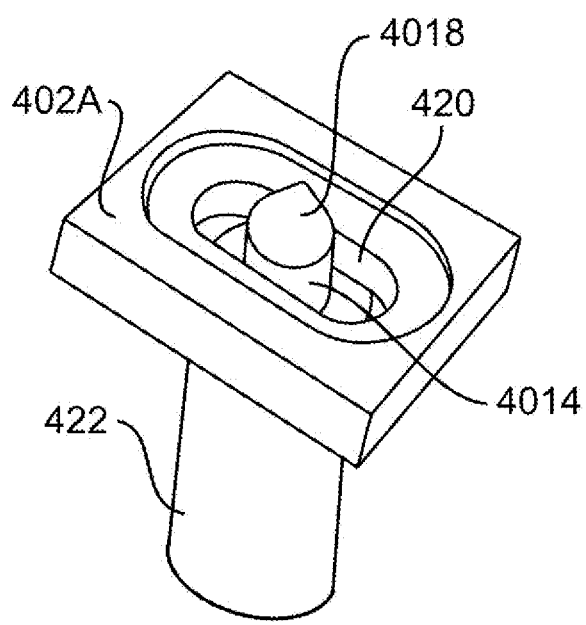
FIGS. 26A-26C show a staking application for a slotted plate and bone screw.
Figure 26B:
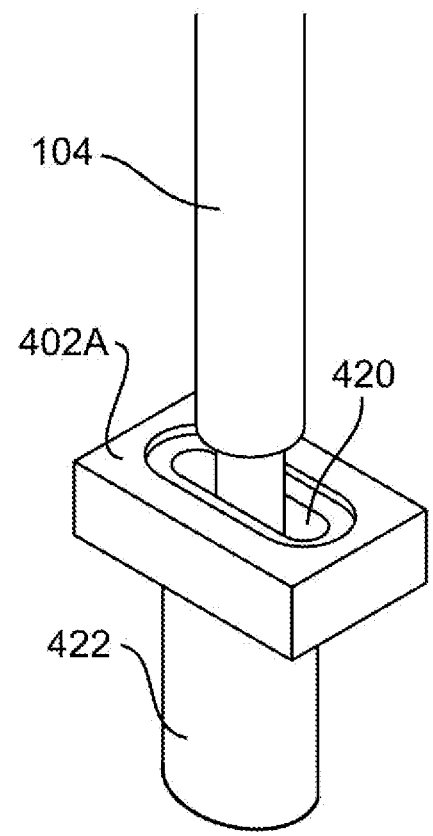
Figure 26C:
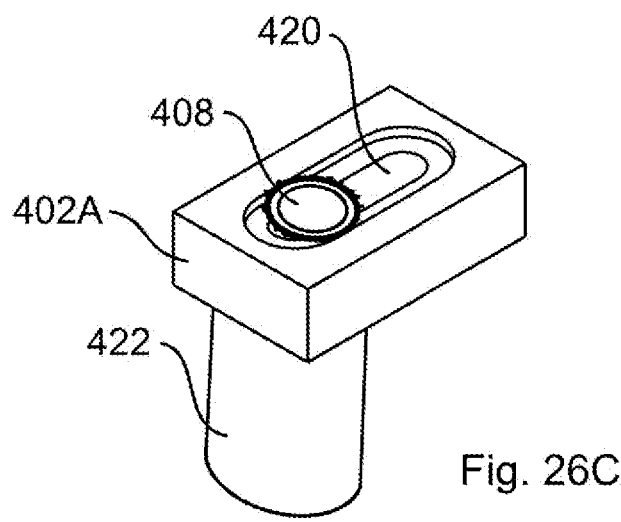

FIGS. 26A-C show an alternative anchor 422 configuration analogous to the configuration shown in FIG. 23, however plate 402A has an elongated slot 420 enabling a variety of fastening positions.

FIGS. 27A-27C show another staking application of the invention. In particular, a standard metallic polyaxial screw/rod system 4120 has been modified to include holes 4122 intersecting both the saddle 4124 that holds the rod 4126 and pedicle screw head 4130 (not visible) and the locking screw 4128 used to maintain the desired angle of the pedicle screw 4132. A tack 4134, including bondable material at least on its exterior surface, is inserted into holes 4122, and then staked or bonded using vibratory energy in accordance with the invention. In this manner, the material of tack 4134 flows into the threads 4136 between saddle 4124 and locking screw 4128, effectively preventing loosening.

FIGS. 28A-28C show that the staking concept can be applied to angulated screws, typically used in spinal applications. Specifically, screws that can be placed at an angle through the plate and then staked in place. This embodiment is discussed further within a discussion of spinal fixation, herein.

In a final staking application, FIG. 30 shows that the end effector can be used as the implant itself. Specifically, one application would be inserting a metal pin into a PEEK (or other thermoplastic material) rod. Typically, using a metal pin would create arcing and sparks due to the metal on metal contact. In order to minimize this effect, a metallic pin is rigidly attached to an end effector. Although a connection similar to a BNC connection is shown, any quick release mechanism could be used.

For example, a PEEK (or other polymer) anchor/fastener, or tack may be used to couple two materials together, in this case two porous metals. After staking, a proximal end assumes the shape of the end of the end effector. Additionally, the distal end of the tack is fastened to porous metal, such as may be found on an interior face of an implant, secured using vibratory energy.

Initially, the anchor is threaded or otherwise secured to the bone. A post projecting away from the bone on the proximal end of the anchor can be used to pierce soft tissue to be attached, holding it in position relative to the bone. The tip is then formed into a cap by staking, with or without an interposing element between the soft tissue and the cap formed at the proximal end of the post. If needed, the post can be trimmed (either mechanically or by shearing off with vibratory energy) before staking. In this manner, a plate or other structure can be attached using two or more tacks.

Fastening into Existing Cement/Adhesives

Figure 44:
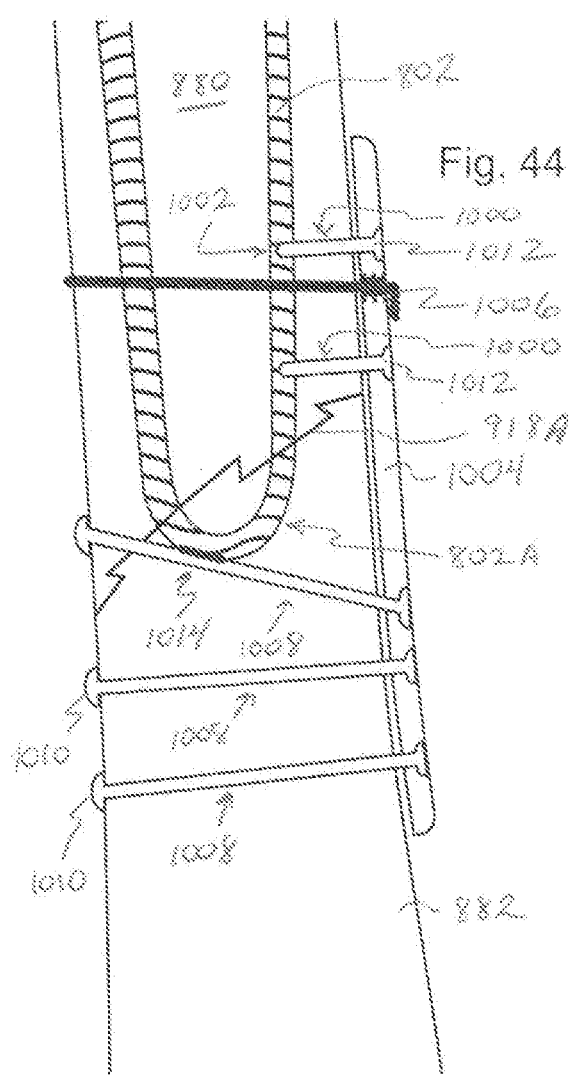
FIG. 44 illustrates fasteners and methods of fastening in accordance with the invention, including far field fastening, mid-field fastening, and near field fastening.

With reference to FIG. 44, in an additional embodiment in accordance with the invention, one or more fasteners 1000 are provided to embed within, and thereby become securely fastened to, previously hardened bondable material 802, such as bone cement, in vivo. Fastener 1000 may be any of the fasteners which may be connected to bondable material with vibratory energy, as described herein. This method is advantageously employed, for example, to repair bone fractures, secure and resecure implants, repair periprosthetic fractures, and to secure or repair dental devices and implants. For example, a medical practitioner may observe a lucent line progressively developing as an implant loosens, indicating a separation between body tissue and the implant. In the prior art, revision surgery would be required in order to remove and or re-cement the implant. In accordance with the invention, a tack, pin, bar, rod, plate or other fastener 1000 may be inserted into the body, and fastened to bondable material 802, implanted earlier, through the application of vibratory energy, said energy advantageously including ultrasonic energy. As discussed elsewhere, herein, the distal portion 1002 of the fastener is caused to resonate and vibrate in contact with the bondable material 802, locally heating the latter to enable adhesion to fastener 1000. The fastener thus may serve as an anchor point in subsequent steps to re-secure the implant.

Figure 40:
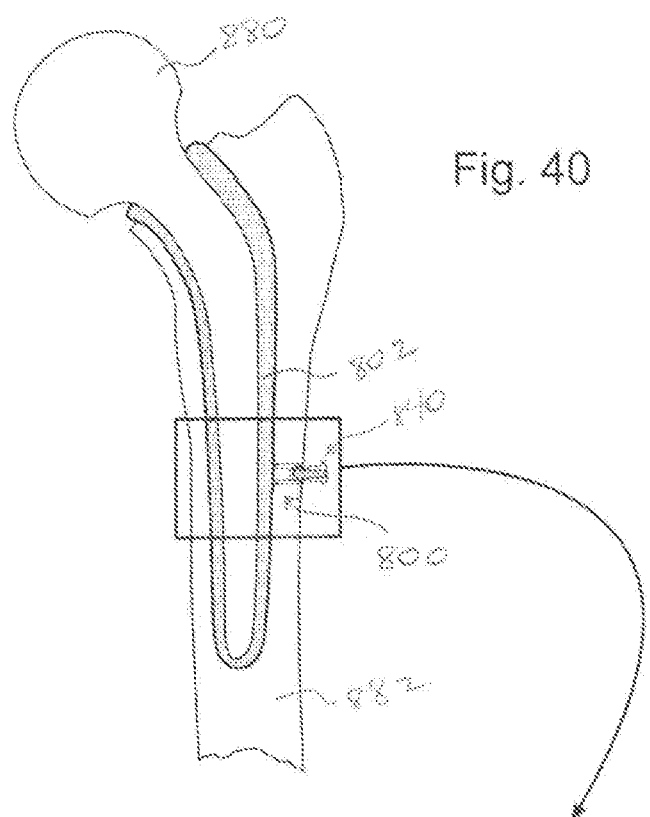
FIG. 40 illustrates an embedded fastener in accordance with FIG. 32, embedded within bondable material adjacent to an implant within the body, taken in cross section through the center of the long axis of the implant and embedded fastener.
Figure 40A:
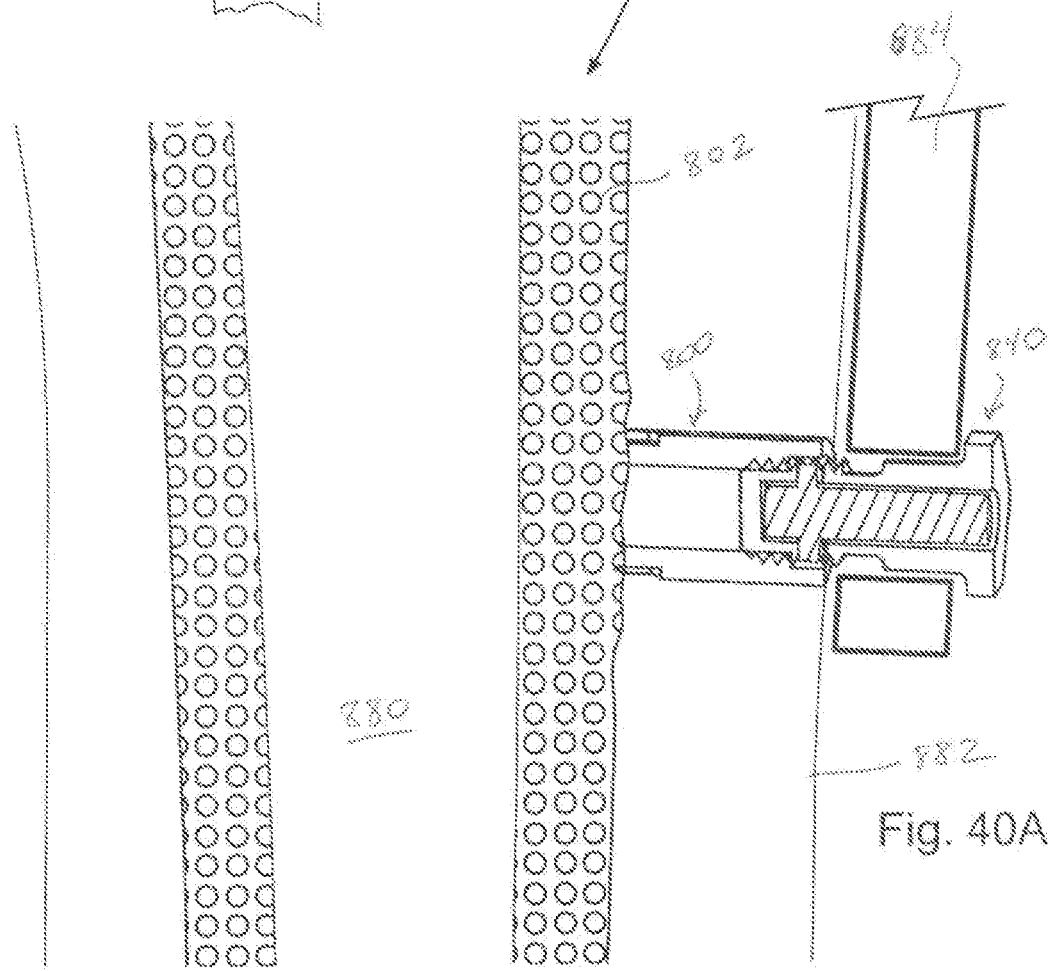
FIG. 40A is an enlarged view of the embedded fastener of FIG. 40.

With reference to FIGS. 40-41, embedded fastener 800 has been embedded within bondable material 802 within the body. As is the case with all illustrations herein, FIGS. 40-41 are not necessarily to scale, but rather drawn to simplify understanding of the invention. In the example shown, bondable material 802 is found surrounding acetabular replacement prosthetic 880, implanted within femur 882, and locking fastener 840 has been secured to embedded fastener 800. In some procedures, it may be necessary to first drill a hole or remove body tissue in order to access the implanted bondable material 802 with embedded fastener 800. Once implanted, embedded fastener 800 may serve as a convenient attachment point for further implants or fasteners, or may simply lock the adhesive and bonded prosthetic 880 in position relative to bone 882. In the example shown, locking fastener 840 attaches unsecured member 884 relative to bone 882. Unsecured member 884 may be, for example, a prosthetic, a living tendon, an allograft, or any other object a surgical practitioner may wish to secure in a specific location.

Fasteners securable to implanted bone cement include the materials described in this specification, including as examples PMMA, metal, metal at least partially coated with PMMA or acrylic, PEEK (polyetheretherketone), and acrylic, or can be a composite including resin, and or carbon fibers. A thin coating of PMMA or acrylic, as small as several microns, contributes to forming a secure bond with bone cement within the body. Bonds may additionally be formed between dissimilar adhesives.

An initial bore may be made in the bone cement to aid alignment, to temporarily retain the fastener, or to increase the surface area for fastening. The fastener may be placed in an intended location through, for example, intramedullary, percutaneous, or retrograde approaches.

With further reference to FIG. 44, a brace 1004 is positioned along bone 882. Alternatively, brace 1004 may be positioned upon the surface of the skin, or at any point between the bone surface and the skin, according to the requirements of the surgical procedure. Further, brace 1004 may be placed within the bone, for example in an intramedullary canal. Fastener 1000 is secured to bondable material 802, or a porous surface of implant 880, in a manner described herein, for example through distal vibratory fastening. A cerclage wire 1006 may be employed as known in the art, to provide further stabilization, in combination with fasteners 1000. A head portion 1012 may be provided upon fastener 1000, or may be formed using vibratory energy.

In an embodiment of the invention, one or more of fastener 1000 passes through and stabilizes brace 1004 with respect to bone 882, on a first side of bone damage 918A. Brace 1004 extends to a point distal to the first side of bone damage 918A, for example to a bone 882 portion on an opposite or second side of damage 918A. Brace 1004 is further secured on the second side of damage 918a, and the two sides of damage 918A are thus secured relative to each other, enabling healing or repair of damage 918A during a period of reduced mechanical disturbance. Fasteners 1000 may be used to stabilize brace 1004 on the second side of damage 918A if embedded bondable material is present on the second side of damage 918A, for example embedding into bondable material at 802A. Capped fasteners 1008 are shown, passing completely through both sides of bone 882. Caps or heads 1010 may be formed using vibratory energy as described in this specification, or capped fastener 1008 may be passed through 882, as by piercing bone 882 with a pointed end of the fastener, or by forming openings in bone 882 before passing the fastener through bone 882. Alternatively, capped fastener 1008 may be provided in the form of a drill bit, with caps formed before or after implantation using vibratory energy, as described in this specification.

In yet another embodiment of the invention, a fastener 1008 is passed through bone 882, contacting bondable material 802 along at least one area of shaft 1014 of fastener 1008. Through tuning, described in this specification, vibratory parameters are established which promote vibration in a contact area between shaft area 1014 and bondable material 802. Accordingly, fastener 1008 is bonded to bondable material 802 at shaft area 1014. Additional stabilization is optionally provided by passing fastener 1008 through another cortical layer of bone 882, and in the example shown, an area on an opposite side of damage 918A.

Figure 96:
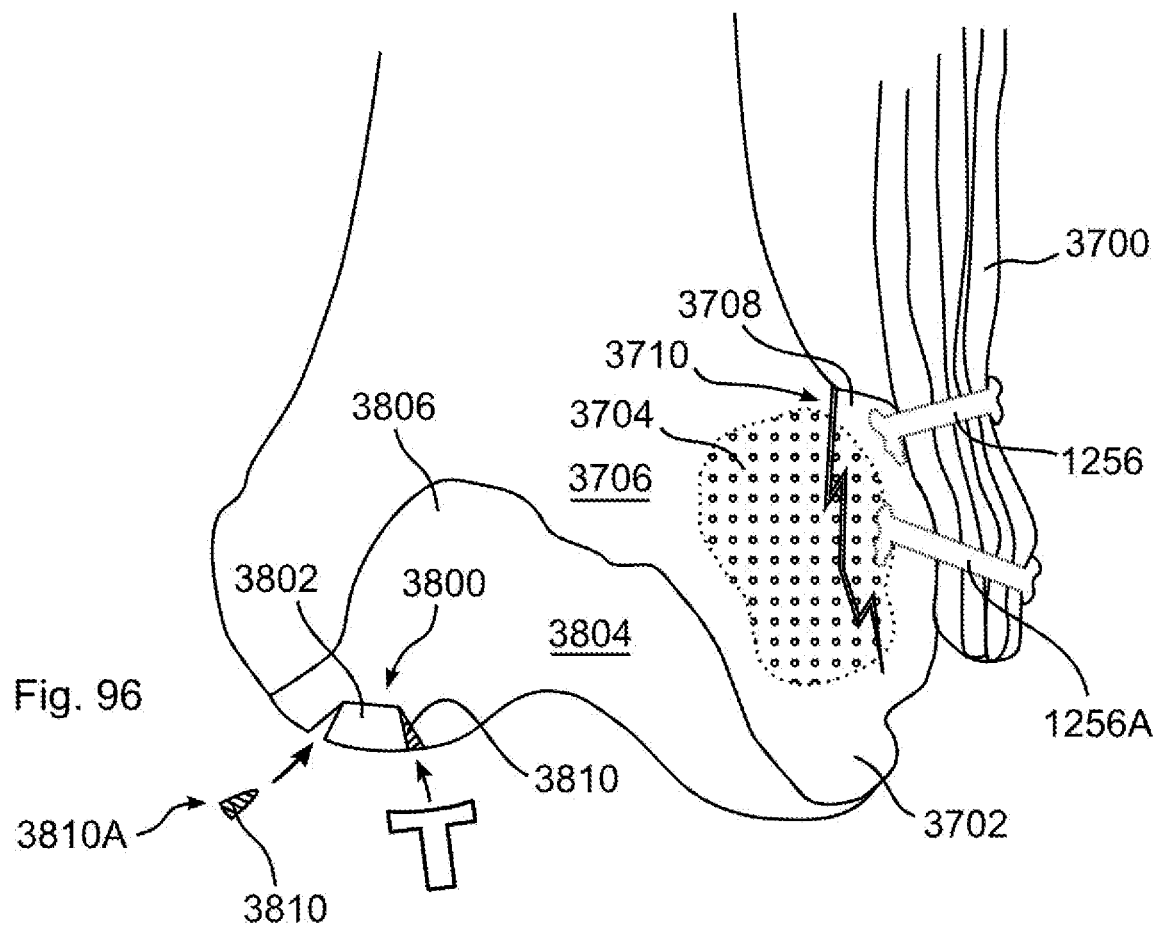
FIG. 96 illustrates fasteners of the invention fastening into an anchor of bondable material disposed within a space within the body, and further illustrates a focal defect repaired in accordance with the invention by an implant fastened with bondable material softened or melted by vibratory energy.

Referring now to FIG. 96, body tissue 3700, in the example shown, a tendon, is fastened to body tissue 3702, in the example shown, a bone, using fasteners 1256 (of FIG. 50) in accordance with the invention. While fastener 1256 is shown, other fasteners of the invention may be used, including fastener 800, or the fasteners of FIGS. 46D-46H, for example. Fastener 1256 extends through body tissue 3700, and is fastened to the surface of tissue 3702, which advantageously has been provided with a roughened or porous surface, or a surface with at least one cavity therein, in or upon which softened or melted material of fastener 1256 may attach.

Fastener 1256A penetrates body tissue 3702, either by being driven through tissue 3702, or by passing through an aperture formed within tissue 3702 in advance. Anchor 3704 of bondable material has been injected into, or otherwise been positioned within body tissue 3702, so that it is adhered within tissue 3702. Any of the bondable materials as described herein may be used, including biocompatible forms of n-butyl methacrylate, or poly-butyl-methacrylate (PBMA), of suitable strength. Anchor 3704 may further be advantageously of a biodegradable material. Fastener 1256A is thus caused to pass through tissue 3702 to contact anchor 3704, whereupon distal fastening in accordance with the invention may be carried out. In this manner, anchor 3704 serves to bind a distal side 3706 of tissue 3702 to a proximal side 3708, relative to fastener 1256A. In this manner, fracture 3710 is maintained in a position advantageous for proper healing. In the embodiment shown, fastener 1256A serves both to affix tissue 3700 and secure fracture 3710; however it should be understood that one or the other purpose may be carried out alone. For example, fastener 1256A need not pass through tissue 3700 in order to secure fracture 3710, or alternatively, may secure tissue 3700 as shown, in the absence of fracture 3710.

End Effector for Fastening into Adhesives

Further, the end effector can be used as the implant itself. Specifically, in one embodiment of the invention, a metal pin, screw, or other engagement shape is inserted into a thermoplastic (e.g. PEEK) rod, the pin itself attached to an end effector. The metal pin must be firmly attached, or formed integrally with the end effector, to avoid creating arcing and sparks due to metal on metal contact between the pin and effector. For removable pins, a release mechanism is provided.

In accordance with the invention, an end effector having a distal tip formed or attached thereto is inserted into a medullary canal in a long bone, and affixed into adhesive through the use of vibratory energy, as described in this specification. The end effector is then removed from the remainder of the vibratory energy generating device, whereby connection means at a proximal end may be used to secure the end effector within the bone, or to body tissue to be attached, or to another implant.

Figure 43:
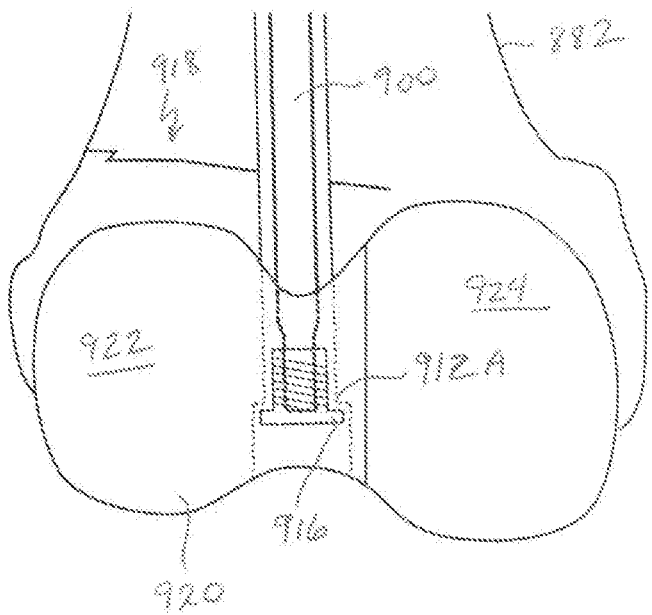
FIG. 43 illustrates a condylar replacement implant secured at least in part by the end effector of FIG. 41.

With reference to FIGS. 41-43, an end effector 900 operative to transmit vibratory energy, for example ultrasonic energy, is passed into the body, to contact a bondable material 802 within the body. The end effector may be provided with a separable distal end portion operative to transmit vibratory energy to the bondable material, such as, for example, fastener 800 of FIG. 32A. Alternatively, the end effector may be provided with a shaped distal end 902 operative to enter bondable material 802. In one embodiment, end effector 900 is replaceable and selectable by the practitioner to best pass through the body or enter bondable material. End Effector 900 may be removed or replaced, for example, at a threaded or other mechanical connection 906 proximate a handpiece 908.

With reference to FIG. 42, an end effector has been passed into the intramedullary canal of bone 882 in a body, in the example shown, a femur. It should be understood, however, that the dimensions of end effector 900, together with any attached fastener or shaped end, is selected to fit within the particular body space contemplated by the surgical procedure, which may include for example soft tissue space, or a location proximate the spine or skull. Bondable material may include any of the materials described in this specification, however in the example shown, material 802 is bone cement, previously implanted to retain hip replacement prosthetic 880.

Once end effector 900 has been secured to bondable material 802, handpiece 908 may be removed, exposing a portion of mechanical connection 906 at a proximal portion of the end effector 900. A proximal fastener 910 is then mechanically attached to mechanical connection 906, as by threading. Retaining means 912 are provided for affixing proximal fastener 910 to the body.

In the example shown, retaining means 912 comprise a flange in cortical tissue of bone 882. Proximal fastener 910 is shaped with a cooperating flange 916, sized to be retained by retaining means 912. In this manner, once a mechanical connection is made between proximal fastener 910 and mechanical connection 906, a compressive force is established between retaining means 912 and embedded shaped distal end 902, secured within bondable material 802. If proximal fastener 910 and mechanical connection 906 are threaded, the amount of compressive force is adjustable based upon the amount of threaded overlap. Retaining means 912 may alternatively include an additional implant, for example a plate or pin (not shown), or an arthroplasty component 920, having an area sized and dimensioned to engage proximal fastener 910, and to thereby transmit a force applied to fastener 910 to the body.

Compressive force may be employed, for example, to bring together portions of body tissue, such as portions separated by trauma or disease, or that have been separated in the normal course of a surgical procedure. For example, in FIG. 41, a region of bone damage 918, such as a fracture or diseased bone area, is shown prior to application of a compressive force as described, and in FIGS. 42 and 43, the fracture has been approximated by compressive force.

With further reference to FIG. 43, arthroplasty component 920, in this case the articulating surfaces of the medial and lateral condyles and the trochlear groove, are retained upon bone 882 at least by end effector 900. Mechanical connection 906 passes at least partially through a portion of component 920, and proximal fastener 910 is connected thereto at mating portion 912A to secure component 920 onto end effector 900. In the example shown, a portion 922 of component 920 containing a single condylar surface and the trochlear groove is fastened directly to end effector 900, and a remaining condylar surface portion 924 is attached to portion 922.

Fastening into Implanted Device

Figure 61:
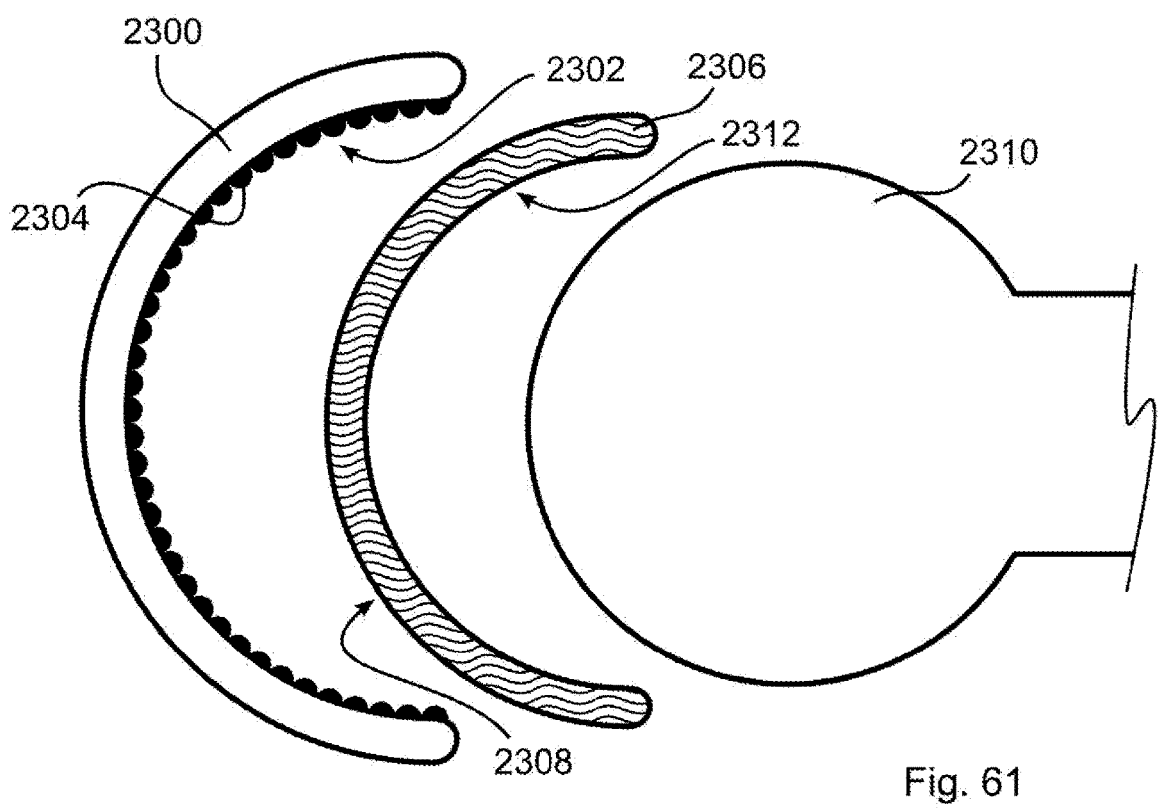
FIG. 61 illustrates a vibratory horn optimized to distribute vibratory energy throughout an area bonded by bondable material.

As described elsewhere herein, implants and fasteners in accordance with the invention are secured within the body, and then serve as attachment points for further implants or fasteners. With reference to FIG. 61, an additional embodiment of the invention includes an implant formed in parts, including a base 2300 attached within the body through connection to body tissue or another implant, using apparatus and methods of the invention, or using means known in the art. Base 2300 includes a surface 2302 that may be smooth, but in accordance with the invention, is advantageously provided with an irregular surface, such as a porous or roughened surface, or a surface having one or more cavities 2304 into which a bondable material may enter and thereby lock to the surface.

Mating portion 2306 engages base 2300 along mating surface 2308. In accordance with the invention, mating surface 2308 includes bondable material along at least a part of the surface which contacts surface 2302. Base 2300 and mating portion 2306 are placed in apposition, whereupon vibratory energy, advantageously combined with pressure, is applied to form a bond between surface 2302 and mating surface 2308, as described elsewhere herein.

In the embodiment shown in FIG. 61, however, a vibratory horn 2310 is shaped to conform to an inner surface 2312 of mating portion 2306. In one embodiment, horn 2310 is a portion or the entire implant intended to be left in the body after a surgical procedure, and is connected to a source of vibratory energy (not shown) when horn 2310 is used to bond mating portion 2306 to base 2300. In this manner, vibratory energy is uniformly distributed throughout the region of intended bonding. Moreover, if inner surface 2302 is additionally formed with bondable material, or the entire mating portion 2306 is formed of bondable material, ideal conformance may be obtained on both sides of mating surface 2308, between horn 2310 (the implant) and base 2300. This is advantageous for smooth joint replacement movement.

After application of vibratory energy, advantageously ultrasonic energy, mating surface 2308 is firmly fixed to irregular surface 2302; however, if horn 2310 and inner surface 2312 are sufficiently smooth, a gliding interface is created therebetween. Similarly, if it is a goal of having mating portion floating between horn 2310 and base 2300, a smooth surface may be provided for surface 2302. Further, it should be understood that a heat meltable surface may be additionally provided upon surface 2302, and mating surface 2308 may alternatively be provided with the irregular surface described above.

In the example shown in FIG. 61, base 2300 and mating portion 2306 are shaped to function as a replacement for an acetabulum, however it should be understood that any implanted shapes may be connected as described herein. For a hip replacement, vibratory energy may be applied to a portion of the implant proximate horn 2310, of sufficient energy to cause the required melting or softening as described above.

Distal Fastening/Retrograde Approach

In accordance with a further embodiment of the invention, vibratory energy is applied to cause thermal deformation distal to the site of application of the end effector. In this application, the mechanical deformation, especially in dissimilar materials, occurs at a site away from the vibratory horn or end effector. The staking or bonding can occur not at the trailing edge of the implant, but along the implant surface or at the far end of the implant where the implant can be mechanically bonded to body tissue, implanted cement, or another implant, particularly if it is a dissimilar implant.

Distal fastening is accomplished by reducing significant vibration at a proximal end of a fastener, and tuning for vibration at a distal end of a fastener, or alternatively, an intermediate portion of a fastener. The vibratory horn may be releasably connectable fastened to a source of vibratory energy, as by threading or twist lock engagement or other mechanical means, thereby damping vibration at a point of connection, and enabling a transfer or transmission to a distal end of the horn. The releasable connection is used, for example, where it is intended to leave the horn within the body, or simply to discard the horn after use. Alternatively, the vibratory horn may simply be in firm contact with the end effector or source of vibratory energy, in order to transmit vibratory energy at a distal end. By establishing a firm contact, it is possible to prevent generation of large quantities of heat at the point of contact. In particular, sufficient heat to substantially soften the welding horn at a point of contact can be avoided, should the welding horn contain bondable material.

In one embodiment, the end effector itself is fastened. In this embodiment, where the end effector is elongated, a point of fastening is inherently distal from a body surface, or an entry point of the end effector.

With reference to FIG. 46G, in an alternative embodiment, assembly 1240 includes an end effector 1242 comprised of or at least partially coated with a bondable material 1244. After assembly 1240 is attached using vibratory energy, end effector 1242 may be cut to a desired length. Fasteners 46D, 46G and 46H are advantageously, though not necessarily, elongated, so that they may pass through body tissue with a minimum of displacement thereof, to reach a point of fastening.

In a further embodiment, with reference to FIG. 46H, an attachable fastener 1250, which includes bondable material 1252 is secured to the end of an end effector, wherein vibration at the attachment is discouraged, as by a sufficiently firm, secure attachment, for example threading 1254 (shown in cross section), or adhesion. In this manner, vibration may be tuned to occur at a distal end 1256 of fastener 1250, and not at a point of attachment 1258 between fastener 1250 and end effector 104. Accordingly, the fastener now serves as a vibratory horn, whereupon it is used to generate heat at a distal point of contact. If the contact surface contains bondable material, that material may be softened. If the fastener includes bondable material at the point of contact, that material may also be softened by heat produced by vibration at the contact area. If the bondable material of the fastener and the contact surface are the same or sufficiently similar, welding may occur, whereupon the fastener and contact surface become bonding when the materials cool. If the materials are different, the two softened surfaces may mix, or lock to each other mechanically after cooling.

As the fastener has passed through body tissue, it is frictionally engages therewith, or may additionally be affixed using methods of the invention or prior art methods of attachment. In this manner, the contact surface is further stabilized within the body through being bonded to the fastener.

Figure 47A:
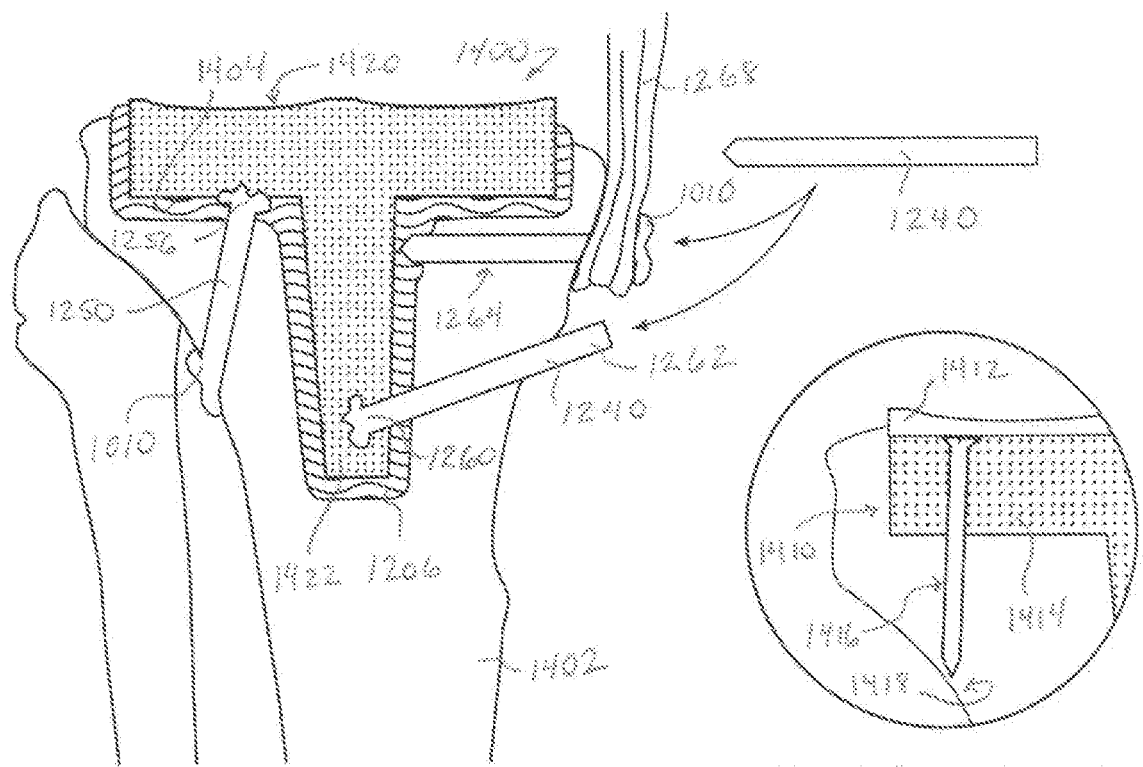
FIG. 47A illustrates a cross section through a longitudinal axis of a tibial implant and tibia, illustrating the use of fasteners in accordance with the invention.

Referring now to FIG. 47A, an implant 1400, in this example a tibial arthroplasty prosthesis, has a surface 1404 onto which a fastener including bondable material may deform and adhere, in order to form a bond therebetween. Fastener 1250 is shown extending from the underside of implant 1400, through bone 1402. Prior to forming cap or head 1010, in a manner described herein, a hole is formed in bone 1402, or fastener 1250 is driven, pushed, or drilled into bone 1402, until distal end 1256 is proximate implant 1400. In the example shown, cement, adhesive, or bondable material 1206 has been applied to the underside of implant 1400, either in a previous procedure, or in the same procedure during which fastener 1250 is affixed. If bondable material 1206 is present, it may be melted by distally applied vibratory energy, as described above, to enable distal end 1256 to reach implant 1400. Once distal end 1256 is in contact with implant 1400, vibratory energy is applied to create heat at a contact area between fastener 1400 and distal end 1256, whereby distal end 1256 deforms and flows onto a surface of implant 1400, to which it adheres.

To improve bonding, at least a portion of the surface of implant 1400 is advantageously provided with a rough, porous or irregular surface, or at least one surface cavity into which softened material of fastener 1250 may flow or be urged, as by pressure acting in the direction of the bond. Upon cooling, distal end 1256 is bonded to implant 1400, the bond strength improved due to either or both of an increased surface area of contact, or mechanical interlock with the irregular surface of fastener 1400.

Fastener 1250, in one embodiment, is sized so that sufficient material remains exposed beyond the surface of bone 1402, wherein cap 1010 may be formed, as described herein. Alternatively, fastener 1250 may be cut, as with a knife or saw, either flush with the surface of bone 1402, as may be seen for example in FIG. 47C, or may be provided with sufficient excess material to form cap 1010, as shown in FIG. 47A.

Distal fastening in accordance with the invention is advantageously employed where a retrograde approach, such as that illustrated for fastener 1250 in FIG. 47A. A retrograde approach may be the only feasible or safe approach to a fastening site, or may simply be easier than an antegrade approach. A further advantage, as can be seen in the illustration, is that a surface of the implant positioned in fixed contact with body tissue may be fastened, while an articulating surface may remain free of fasteners.

With further reference to FIG. 47A, fastener 1240 extends through bone 1402 at a downwards angle towards the interior of bone 1402, with respect to the proximate end of bone 1402. A distal end 1260 of fastener 1240 has been distally fastened as described herein. A proximal end 1262 extends from bone 1402, and may be cut at a level flush with the exterior of bone 1402, or at least a part of the extending portion may be formed into a cap 1010. Alternatively, proximal end 1262 may be used as a stake for fastening body tissue or other implants. In FIG. 47A, fastener 1264 is fastened to implant 1400, in this example embedded in bondable material 1206. Alternatively, fastener 1264 may be fastened to implant 1400, as described for fastener 1240, above, or fastener 1264 may be mechanically connected to implant 1400. Fastener 1264 is advantageously angled to promote the secure retention of staked material. In the example shown, a tendon 1268 is staked, and fastener 1264 is disposed at a neutral angle with respect to the proximal end of bone 1402. Further, a reverse angle may afford additional stability and strength of fastening, wherein fastener 1264 is angled upwards towards the interior of bone 1402 with respect to the proximal end of bone 1402. Fastener 1264 has a cap 1010 formed using the application of vibratory energy applied to the proximal end 1262 of fastener 1264, although other means of securing staked materials may be employed, such as by applying a mechanical fastener.

FIG. 47B illustrates a method of attaching an articulating surface in the prior art. Note that prior art implant 1410 must be formed in at least two parts 1412, 1414, due to the requirement of first installing a fastener 1416 through implant portion 1414 into cortical bone 1418, and then installing implant portion 1412 over fastener 1416.

In contrast, implant 1400 of the invention may be formed as a single part, or at least the articulating surface 1420 may be integrally formed with a portion 1422 which extends into bone 1402, thus presenting fewer points of potential failure, and providing a more stable and durable implant.

Figure 47C:
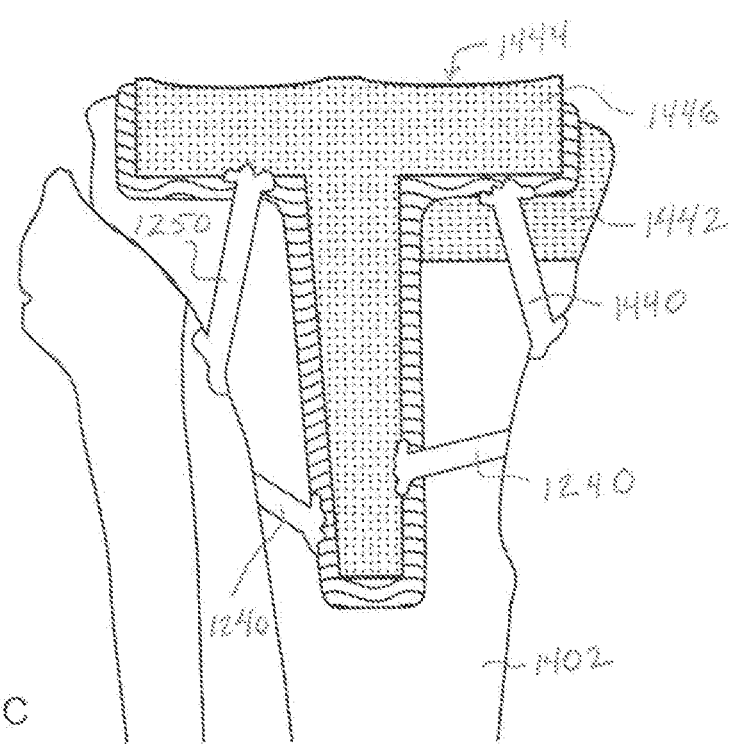
FIG. 47C illustrates fastening of a graft or augment in conjunction with the tibial insert of FIG. 47A, as well as alternative fasteners and fastening methods in accordance with the invention.

Referring now to FIG. 47C, a retrograde and distally fastened fastener 1440 is additionally connected to an implanted bone graft, or bone augment 1442, thereby providing primary and or secondary stabilization for augment 1442. Augment 1442 may be implanted, for example, to replace diseased or damaged bone. In this manner, an articulating surface 1444 as well as an adjoining bone augment 1442 may be secured by a single fastener 1440, or a series of fasteners. Fastener 1440 may be distally bonded to both augment 1442 and the device 1446 bearing articulating surface 1444. Fastener 1440 may also pass through augment 1442, for example through a bore preformed in augment 1442. Augment 1442 may be composed of any material or combination of materials suitable for its intended function, including metal, plastic, ceramic, alloys, moldable material including adhesives, as well as porous forms of these materials. Augment 1442 may additionally comprise cartilage graft material.

The retrograde approach of the invention may be facilitated through the use of a cannula, or an expanding cannula, such as is disclosed in U.S. Pat. No. 6,814,715, incorporated herein by reference, and related patents cited therein. Retrograde examples include fastening an acetabular replacement from behind the cup, fastening a tibial bearing surface replacement from a point below the bearing surface, and fastening a hip replacement implant from the femur body or distal end of the femur. Like examples are contemplated for the smaller analogs of the arm. Retrograde approaches may also be used in fastening or repairing bones of the hands, feet, skull, and spine.

Figure 47D:
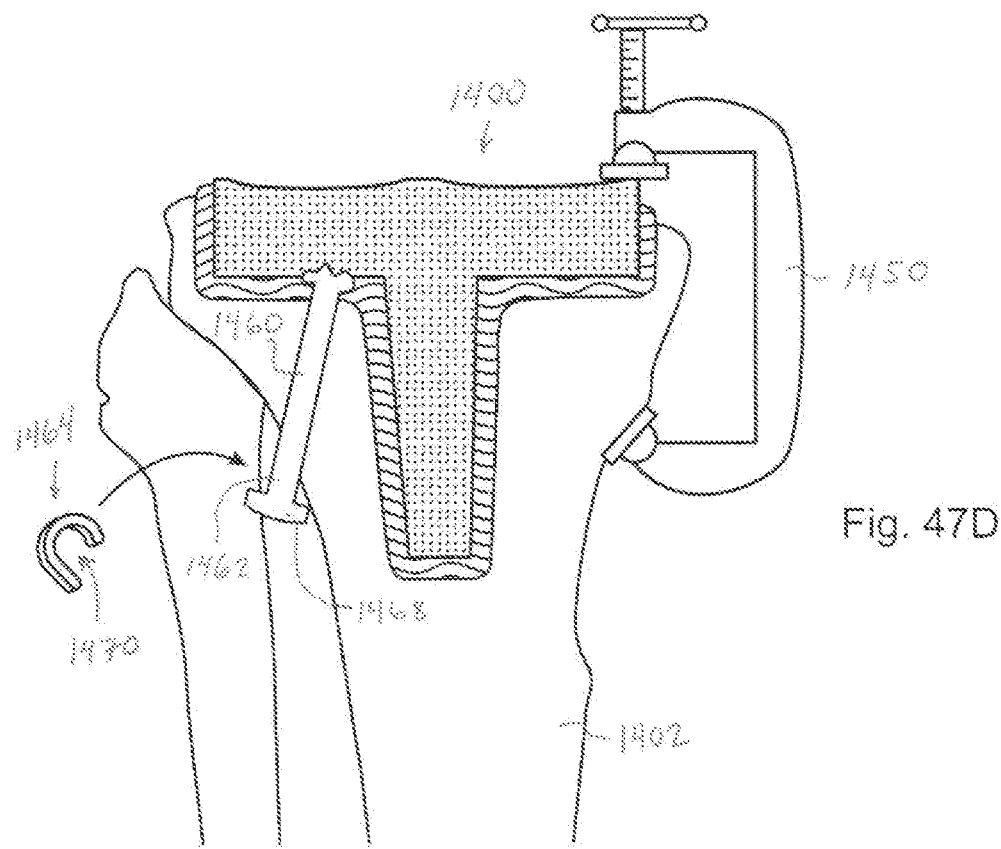
FIG. 47D illustrates the use of a clamp in conjunction with fasteners in accordance with the invention, and further illustrates the use of a spacer in accordance with the invention.
Figure 47E:
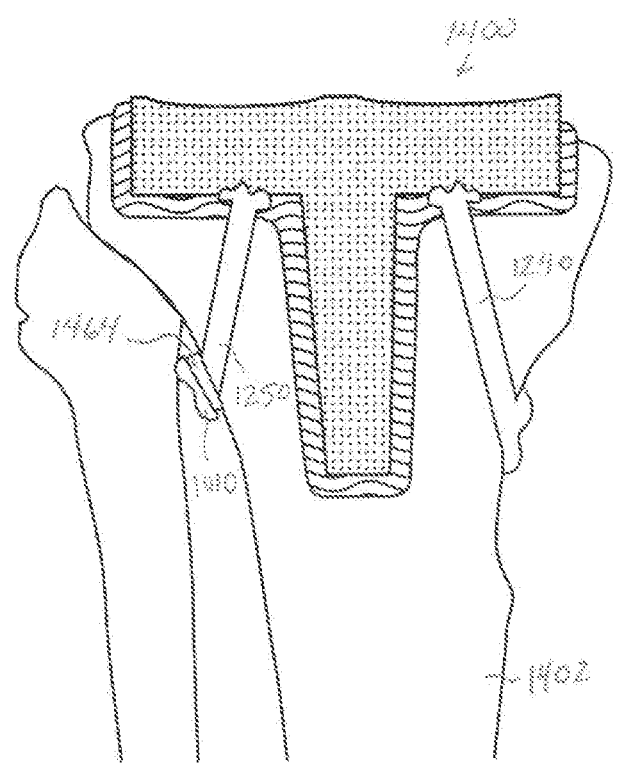
FIG. 47E illustrates the spacer of FIG. 47D, in position after fastening, as well as a fastener securing a formerly clamped region.

With reference to FIG. 47D-E, one or more of clamp 1450 may be used in accordance with the invention to position and or retain implant 1400 in a location for fastening. This is particularly advantageous where a fastener of the invention is distally fastened to implant 1400, without the use of an intervening adjustable mechanical coupling, such as that described for fastener 840, herein. In the illustration, a c-clamp type of claim 1450 is shown, however any suitable clamp may be used, provided exposure is maintained for installing a fastener of the invention, and for applying vibratory energy thereto. In FIG. 47E, fastener 1240 has been installed, and clamp 1450 has been removed.

With further reference to FIGS. 47D-E, a fastener 1460 has been distally bonded to implant 1400. Fastener 1460 is formed in a manner illustrated for fastener 1250 in FIG. 46H, however a cap 1468 is formed or attached in advance of installation. In the use of this embodiment, it may not be possible to precisely determine the length of a proximal portion 1462 extending beyond the surface of bone 1402. Accordingly, the invention provides a spacer 1464, shaped to fill a portion of a space formed between cap 1468 and bone 1402. Spacer 1464 is further formed with an opening, so that a spacer 1464 having a desired width may be selected after fastener 1460 is inserted into bone 1402. An amount of fastener collapse, described in this specification, is calculated or estimated, and a spacer 1464 is selected so that an amount of free space remains between cap 1468 and bone 1402, corresponding to the expected amount of collapse. Accordingly, after fastening, fastener 1460 transmits a force through cap 1468 and spacer 1464 to bone 1402. Further, fastener 1460 is stabilized in firm connection to bone 1402. Moreover, body tissue may not enter a space between cap 1468 and bone 1402, either through tissue ingrowth or through tissue movement. It should be understood that spacer 1464 may be employed in any fastening application in accordance with the invention where there is a space to be filled along the length of the fastener, and whether the fastener is attached to body tissue or another implant.

Figure 50:
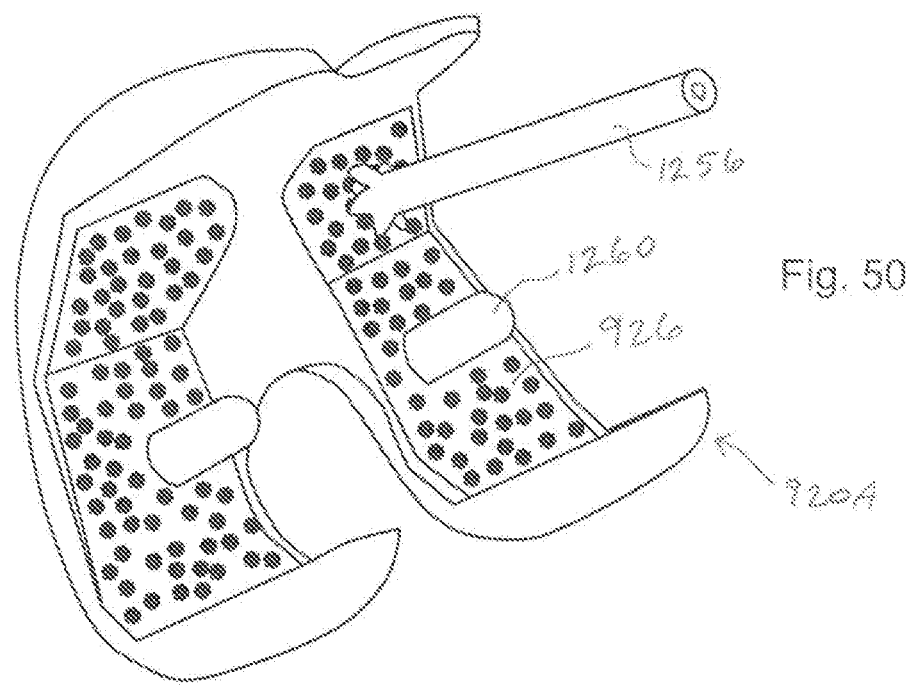
FIG. 50 illustrates bonding to a roughened or porous surface, in accordance with the invention.

FIGS. 49 and 50 illustrate distal fastening to secure a femoral arthroplasty prosthesis 920A, provided with a non-smooth surface 926, for example a surface that is roughened or porous, or has at least one cavity therein. A fastener 1256, or other fastener of the invention, for example fastener 1232 of FIG. 46D or 1240 of FIG. 46G, may be attached using distal vibratory fastening as described herein. Softened or melted material of the fastener enters into surface 926, and upon cooling, is firmly attached due to the greater surface area for adhesion presented by the irregularity of surface 926, or by an interlocking of the cooled and now hardened material into the shaped or roughened projections or cavities of surface 926. Distal fastening in accordance with the invention may be carried out upon a smooth surface, however a non-smooth surface offers the advantages described, including greater surface area, and an increased potential for mechanical interlocking A combination of known methods, such as posts 1260, affixed by bone cement, and fasteners of the invention, may be combined as determined by the practitioner to be optimal.

With reference to FIGS. 51 and 51A-B, a fastener 1600 has a plurality of tines 1610. While two tines are illustrated, it should be understood that any number of tines or projections may be employed in accordance with the invention. Fastener 1600 is contacted by an end effector 104, or may be attached to an end effector of the invention, for example as described for fastener 1250 shown if FIG. 46H, and vibratory energy is applied to produce a bond between tines 1610 and a surface 1612. Vibratory energy is tuned as described herein, to produce heat proximate the end of tines 1610 and surface 1612, whereby bondable material of either or both of tines 1610 and surface 1612 becomes softened or liquefied, whereupon a bond is formed between tines 1610 and surface 1612.

Surface 1612 may be body tissue or another implant, and is advantageously non-smooth, as described for example with respect to surface 926 of FIG. 50. Where surface 926 is body tissue, it may be roughened or otherwise provided with a non-smooth surface, as by filing, drilling, or other known means, prior to bonding.

FIG. 51A illustrates a cross section of fastener 1600, showing an aperture through which an end effector may be attached, and or through which body tissue or an additional implant may be affixed. As can be seen in FIG. 51B, a tine 1610 may be provided with one or more projections 1616 which may serve to maintain a location of fastener 1600 prior to bonding, and which may promote bonding by becoming heated and softened earlier than the remainder of the tine, thus speeding the heating of tines 1610 for rapid and reliable bonding.

Referring now to FIGS. 53 and 53A, distal fastening is illustrated in the context of an acetabular replacement implant 1800. A retrograde approach, as through illium 1806, is used to introduce a fastener of the invention. Fasteners 1240 and 1250 are illustrated, although other fasteners of the invention may be used. For fastener 1250, fastening is into a shaped cavity 1802, formed in the retrograde side of implant 1800. End effector 104, connected to fastener 1250, causes vibration at distal end 1256 while applying force in the direction indicated by arrow "A". The force urges distal end 1256 into shaped cavity 1802, generating heat sufficient to soften distal end 1256, whereby it is urged into cavity 1802, enlarging and spreading to at least partially fill cavity 1802, producing a partial shortening or collapse of the length of fastener 1250, and forming a mechanical interlock between fastener 1250 and implant 1800. After vibratory energy is discontinued, the material of distal end 1256 cools and solidifies, and end effector 104 is removed. Fastener 1250 thus prevents rotational movement of implant 1800, though engagement with a bore or aperture 1804 through which fastener 1250 passes. If aperture 1804 is tight fitting, fastener 1250 may provide additional stability with respect to a movement of implant 1800 away from contact with acetabulum 1808. A cap 1010 may additionally be bonded using vibratory energy, as described herein, to provide further.

With further reference to FIGS. 53 and 53A, fastener 1240 is introduced through a more antegrade approach than that of fastener 1250, but could be introduced through a retrograde approach as well. Rather than enter into a relatively large cavity as shown for fastener 1250, fastener 1240 bonds to a roughened or porous surface 1810, formed on the body contacting side of implant 1800, and is bonded therewith in a manner as described herein. It should be understood that while fasteners 1250 and 1240 are depicted for fastening into a cavity, and onto a porous surface, respectively, the relative roles of the fasteners could be reversed, and other fasteners of the invention could be used as described for either fastener 1240 or 1250.

It can be seen, as illustrated for fasteners 1250 and 1240 in FIGS. 53 and 53A, that in the case of distal fastening, as well as proximal fastening, the fastener body can be advantageously caused to enlarge. The enlarged portion may prevent staked material from separating from the fastener, and can prevent the fastener from detaching from a bonded location. Further, the enlarged portion may be too large to pass through the portal or opening through which the fastener entered. As examples, distal end 1256 cannot be withdrawn from cavity 1802 after cooling, and cap 1010, formed onto fastener 1240 by proximal vibratory fastening, prevents passage of fastener 1240 inwardly towards acetabulum 1808.

The fasteners and fastening methods of the invention are advantageously utilized for use in-vivo, reducing or avoiding tissue necrosis by minimizing exposure of tissue to heat, and may be implemented through reduced size incisions, including keyhole incisions, as may be employed in laparoscopic procedures. Fasteners may additionally be formed and fastened in accordance with the invention in the operating room, at the convenience of the surgical practitioner, when the exact configuration and dimensions needed are best understood, and thereafter implanted.

Spinal Fixation

Figure 57:
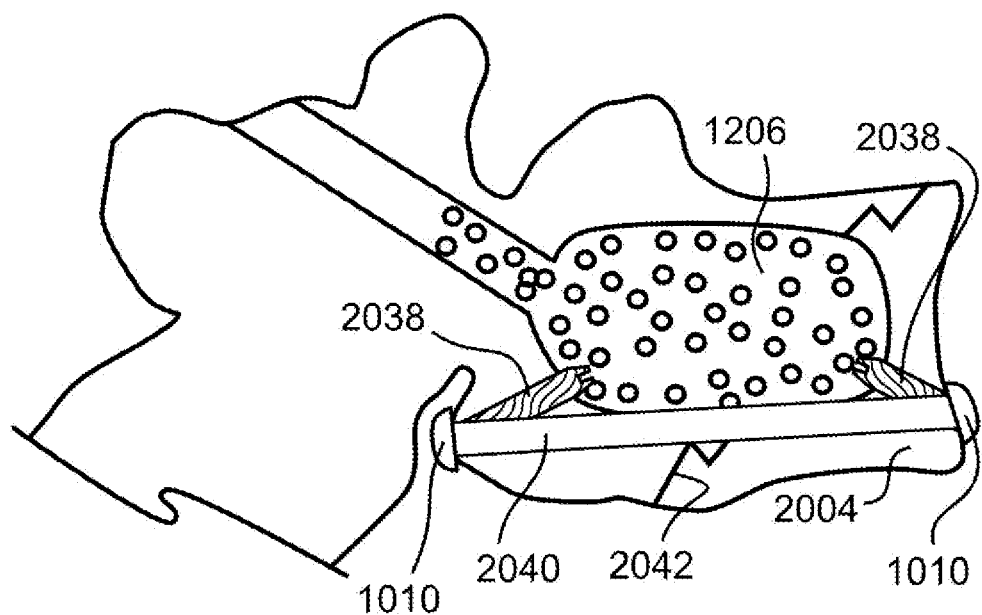
FIG. 57 illustrates a cross section through a vertebra stabilized with bondable material, the material having a fastener in accordance with the invention embedded therein, to stabilize a fracture, and further illustrating a strap secured to fasteners in accordance with the invention.

With reference to FIGS. 55-57, fastening in accordance with the invention can be advantageously applied to correction of problems of the spine 2000. In FIG. 55, a vertebra 2002 is shown, the vertebral body 2004 containing a bondable material 1206, placed using, for example, vertebroplasty or kyphoplasty. A spinal fastener 2008 has been driven into vertebral body 2004, and embedded within bondable material 1206 using vibratory energy.

With reference to FIGS. 28A-C, an angulated screw 2016 can be placed at an angle through a plate 2018, 2018A and then driven or staked in place. Screws 2016 and plates 2018, 2018A have a rounded mating surface 2020, 2022 respectively, which allows some adjustability in direction of screw 2016 relative to plate 2018, 2018A. Screw 2016 can be inserted, for example, 11 degrees off of a straight line axis through mounting holes 2024 through which they project.

With reference to FIG. 29, in accordance with one embodiment of the invention, in order to stake screw 2016, an end effector 2026 having a change in diameter 2028 can be used. An enlarged mating surface 2028 is sized to engage screw 2016 regardless of its angle within mating surface 2022. FIG. 28B shows a single hole plate 2018 with the rounded hole, and FIG. 28C shows a four hole plate 2018A with angulated screws prior to staking. In this embodiment, surface 2022 and or a portion of mating surface 2020 of fastener 2016 contains bondable material, whereby application of end effector 2026 can apply vibratory energy sufficient to bond surfaces 2020 and 2022, regardless of the angle of fastener 2016. In addition or alternatively, bondable material may be provided at a distal end 2030 of fastener 2016, and vibratory energy may be applied to bond distal end 2030 as described herein for distal fastening.

Spinal fastener 2008 may be provided with a distal end 2010 that is separable, or is otherwise shaped as described for fastener 800; however, any of the other end forms or fasteners described herein may be selected in the discretion of the practitioner. As described for example with respect to FIG. 28, spinal fastener 2008 may be provided with a head portion having a profile 2020 shaped to engage a mating support 2024, whereby spinal fastener 2008 may be secured at an angle relative to support 2018, 2018A. In this manner, a fracture may be stabilized, successive vertebrae may be maintained in a fixed relation relative to each other, or a secure fixation point may be established. In FIG. 55, two spinal fasteners 2008 are secured together by clamps 2012, which may have the form described with respect to FIGS. 27A-C. A rod 2014 is secured between clamps 2012. Alternatively, rod 2014 may be connected between clamps 2012 on different vertebrae, according to the needs of the patient.

As may further be seen in FIG. 55, a mesh pouch or bag 2016 contains a therapeutic substance, and is placed proximate a surgical site or area needing treatment over time. Bag 2016 may contain any of the therapeutic substances described herein or in the incorporated references, or other beneficial agent as known in the art, including for example antimicrobial agents, or bone healing or ingrowth agents. Formed with a mesh, bag 2016 enables the inward migration of gaseous or liquid materials from the body, or body tissue ingrowth, and the outward migration of therapeutic substances. Bag 2016 may be attached to an implanted structure, such as fastener 2008, clamp 2012, or rod 2014, by attachment means, for example by one or more sutures (not shown). Bag 2016 or attachment means may be biodegradable or bioabsorbable.

With reference to FIG. 56, in a further embodiment, a connector 2032 is fastened to heat melatable material 1206 within vertebral body 2004, using fasteners 2034. Connector 2032 is shown as an elongated bar, strip, or strap that extends between vertebrae. Fasteners 2034 may be secured to bone, or to bondable material 1206, as shown in cross section for vertebra 2036. Any of the fasteners or methods of the invention may be used to attach connector 2032 to vertebrae. Connector 2032 may be used to secure vertebrae with respect to each other, or to secure a vertebral component to any other object within the body, including other bones, soft tissue, or implant, or to a point external to the body, such as a brace or other external fixation device. Fastener 2034 may be selected from any of the fasteners described herein, depending upon, at least, the fixation medium, and the needs of the patient.

Figure 74:
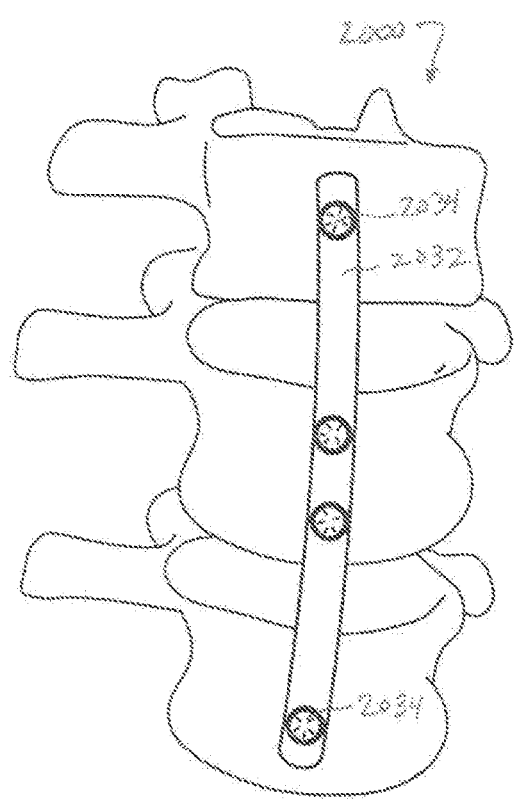
FIG. 74 illustrates a stabilizing strap fastened to vertebrae with fasteners of the invention.
Figure 74B:
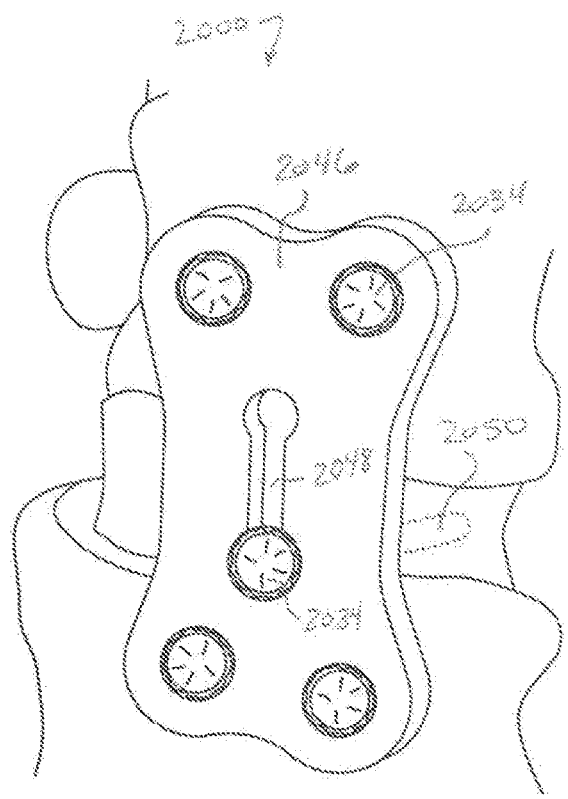
FIG. 74B illustrates a vertebral stabilizing plate having an elongated slot engagable by a fastener of the invention.

An alternative view may be found in FIG. 74B, wherein a plate 2046 is provided, for additional strength, if needed, and to provide for stabilization with movement permitted along a limited range of motion. In particular, plate 2046 is limited in movement relative to a stabilizing fastener 2050. Elongated slot 2048 enables vertical or anteroposterior motion of plate 2046 relative to fastener 2050, however fastener 2050 is secured within the disc space, and thus the disc space cannot move dorsoventrally. Elongated slot 2048 may be formed along other angles, and plate may be positioned in other locations, enabling limited range of motion along other axes, as would be understood by one skilled in the art.

Referring now to FIG. 57, one or more fasteners 2038 in accordance with the invention are embedded within bondable material 1206, disposed within a space associated with a vertebra, in this embodiment, the vertebral body 2004. fasteners 2038 may alternatively be fastened to bondable material disposed on the outside surface of the vertebra, ribs, or other bone of the body. In the embodiment shown, a strap 2040 passes from one fastener 2038 to another, and is bound to each, as by an aperture through which a portion of each fastener 2038 passes. Alternatively, strap 2040 and or fastener 2038 may include bondable material, and the elements are bonded together using vibratory energy as described herein. While two fasteners 2038 are shown, it should be understood that additional fasteners 2038 could be used, or a single fastener 2038, wherein strap 2040 passes completely around an object to fasten to fastener 2038 at more than one point along its length. To further secure strap 2040 to one or more fasteners 2038, heads or caps 1010 may be attached to fasteners 2038 as described herein, or alternatively, to strap 2040. If attachment is to strap 2040, either or both of caps 1010 or strap 2040 is fabricated with heat softenable material, and the elements are bonded using vibratory energy as described herein. In the partial cross section shown in FIG. 57, a fracture 2042 is illustrated, maintained in a position for healing by fasteners 2038 and strap 2040.

Locking Screw Fastening

In another embodiment of the invention, a metallic polyaxial screw/rod system, of the type typically used in spinal surgery, is modified to include holes intersecting both the saddle that holds the rod and pedicle screw head, and the locking screw used to maintain the desired angle of the pedicle screw. Into these holes, a tack is staked or bonded such that the material of the tack flows into the threads between the saddle and locking screw, effectively preventing loosening of the system.

Resecuring or Removing an Implant

As described above, vibratory energy, such as ultrasonic energy, is used to melt or liquify adhesives, including bone cement. In accordance with the invention, and with reference to FIGS. 46 and 46A, bone cement is melted in situ, whereupon melted cement softens or flows to bridge or cross and fill or close voids and gaps 1208 between the implant and body tissue, the cement thereafter being allowed to cool in order to thus re-secure or reduce the loosening of the implant.

With reference to FIGS. 46-47, assembly 1202 including end effector 104, is passed into a space within the body, in the example shown, intramedullary canal 1222 within bone 882. End effector 104 is provided with at least one shaped projection 1200. Projections 1200 may be threadably or otherwise mechanically connected to end effector 104, whereby the projections 1200 may be left inside the body for, as examples, future use, convenience, or further stabilization. Projections 1200 may have any convenient shape, and advantageously has a tip and at least one side edge which has a tapered profile, to facilitate passage through bondable material 1206.

To facilitate passage of end effector 104 and at least one projection 1200, a bore 1204 may be preformed within cancellous bone or tissue of intramedullary canal 1222. For other body areas, space may be made as needed, for example by retraction, insufflation, or other means known in the art. In another alternative, end effector 104 is formed as a hollow tube, as in a coring drill, to facilitate passage through body tissue.

In an alternative embodiment, projections 1200 may be formed as a continuous or substantially continuous surface, thus forming the shape of a cone, cylinder, box or shaped space, as may be seen for example in FIGS. 46D-46F. If bore 1204 is narrower than the width of projections 1200, the latter may be formed of sufficiently flexible material as to collapse while within the bore, and expand upon reaching an area of bondable material 1206.

Upon reaching bondable material, vibratory energy is generated within projections 1200, through a connection with end effector 104 attached to generator and handpiece 908, as described herein. In this manner, bondable material 1206 is made flowable by the application of vibratory energy through contact with projections 1200. Projections 1200 may then be pushed further into bondable material 1206 to a desired depth. In the example shown, projections 1200 are deflected by implant 880 and enter the interstice between body tissue and implant 880, filled with bondable material 1206. As bondable material 1206 is melted, voids or gaps, such as gap 1208, formed by a loosening of implant, may be filled, and upon cooling, the implant is restabilized. It should be understood that gap 1208 is shown above projection 1200, for clarity; however, projections 1200 are provided with a length sufficient to reach a gap of concern.

Once bondable material has been sufficiently softened, end effector 104 may be rotated to correct further defects along the path of moving projections 1200. After gaps 1208 have been corrected, end effector 104 and or projections 1200 may then be withdrawn, or alternatively, either or both devices may be left within the body. If end effector 104 is to be removed, it is first decoupled from projections 1200, for example at releasable coupling 1210.

In an alternative embodiment, a fastener 1270 or end effector 104A is passed to gap 1208 from a side entry. Fastener 1270 may be of the type shown, for example, in FIGS. 46D-H, or may be modified with an end portion 1272 having a more blunt profile, thereby increasing a contact surface. End effector 104A may similarly be provided with a widened or blunt profile 1274. Fastener 1270 or end effector 104A is caused to contact bondable material 1206 at a gapped portion 1208, either by drilling a hole to access gap 1208, or by driving or drilling fastener 1270 or end effector 104A to gap 1208. Vibratory energy may further be employed, particularly if passing through bondable material 1206 to reach gap 1208. Upon reaching gap 1208, vibratory energy is applied to remelt bondable material 1206 to cause same to soften and flow to cross and fill in gap 1208. In this manner, fastener 1270 is acting as a vibratory horn, transmitting vibratory energy from a vibratory energy generator to bondable material 1206 proximate gap 1208. In FIG. 46A, a gap 1208 is shown to extent from a point indicated at "A" to a point indicated at "B". As can be seen, regions of gap 1208 have been closed by the introduction of fastener 1270 and end effector 104A. It should be understood that, depending upon the length and width of gap 1208, that a portion or the entire gap 1208 may be remelted and corrected, depending upon the size of end portion 1272 or profile 1274, and the amount and duration of vibratory energy applied. Melting may further be caused to occur along a side portion of fastener 1270 or end effector 104A.

In addition to remelting existing implant binding material or bondable material 1206, additional material may be introduced that is associated with fastener 1270. Specifically, fastener 1270 may be fabricated from bondable material 1206, or a different bondable material, which is caused to additionally soften upon the application of vibratory energy, and to flow into and further fill gap 1208. Alternatively, fastener 1270 may be provided with bondable material at least in an area upon fastener 1270 which is intended to form a contact proximate gap 1208.

It may further be seen that, in the example shown, end effector 104A is angled in a first direction, and fastener 1272 in a contrary direction. The surgical practitioner may select an angle with respect to a vector in a direction of insertion of the implant, that best causes remelting, and that provides further stability if end effector 104A or fastener 1272 is left in the body. It may be advantageous to affix the vibratory horn, here further serving as an implanted fastener, at an obtuse angle, as measured between a line extending along the longitudinal axis of the vibratory horn, and a line extending from a point where the vibratory horn contacts the binding material 1206, extending in a direction of insertion of the implant, as may be seen for fastener 1270.

End effector 104A or fastener 1274 may be trimmed at a convenient point, for example at the surface of bone 822. Alternatively, as illustrated by dotted lines 1276, end effector 104A or fastener 1274 may extend to a more distant point, for example to the surface of the skin, or to external fixation apparatus.

With reference to FIGS. 46B-D, projections 1212 are at least partially coated with a bondable material 1214. Where the bondable material lacks sufficient strength for an intended application, one or more of projections 1200 may be included, underlying bondable material 1214. In this embodiment, projections 1212 may enter the body as described with respect to FIGS. 46 and 46A, and in particular, projections 1212 may be squeezed together, to resiliently expand after passing through a passageway. Assembly 1220 may be used to soften bondable material 1206, particularly where bondable material 1206 has the same or a lower melting point than bondable material 1204. In this manner, assembly 1220 illustrated in FIGS. 46B-D may be used in a manner similar to that described for assembly 1202 of FIGS. 46 and 46A. However, because assembly 1220 incorporates bondable material 1214, it may be used in application where there is little or no other bondable material available at a target location.

FIG. 46C illustrates assembly 1220 inserted within the body, after having been softened by the application of vibratory energy. As can be seen in the illustration, bondable material 1214 near a proximal area 1224 has flowed upwards to a distal area 1226. Bondable material 1206, if existing, is mixed with, or displaced by, bondable material 1214. After cooling, projections 1212 are affixed to bone 882, implant 880, or both. In this embodiment, although a connector 1210 may be provided, it is particularly advantageous to have end effector 104 connected, whereby it may be used to not only secure an additional implant, such as arthroplasty component 920 as illustrated in FIG. 43, but may serve to simply anchor implant 880, as illustrated in FIG. 42.

With reference to FIG. 46D, in one embodiment, an assembly 1232 includes a vibratory end effector 104 provided with a heat meltable connector 1230 having either an amorphous or defined shape, including a hollow space, for example a blob 1234, wedge, cone 1236 or tube 1238, as best adapted to the application. Connector 1230 is advantageously used where it is not necessary to resecure or separate a large region of bondable material 1206, but rather, to connect a first implant and a second implant, or a first implant to body tissue, for example to cartilage, tendon, bone, or soft tissue.

If it is desired to re-secure the implant, the blade may be withdrawn once the implant has been repositioned, if desired, and the void or gap of concern has been re-filled with melted adhesive. Alternatively, if it is desired to remove the implant, removal is accomplished before the adhesive resolidifies, such as by lifting the implant away from the adhesive, out of its current location. Multiple blades may be employed to reduce the time required to complete the removal or resecuring process.

Alternative shaped projections include cups, cones, wires, or other shapes which may pass through the body to the area where the adhesive is located, and which are advantageously formed to best fit the geometry of the adhered interface, to carry out the functions previously described.

In an alternative embodiment, the rod and blades are left within the body, embedded in the resolidified cement, to operate as a reinforcement and or attachment point for further fasteners or implants, including arthroplasty components and prosthetics, or testing or reporting apparatus attached to or embedded within the device. As an attachment point, the rod may be provided with bores or apertures, which may be threaded, into which other fasteners may be inserted, and optionally further fastened in accordance with the methods disclosed herein.

In an alternative embodiment, the shaped projection is formed of, or coated with, a bondable material, for example a polymer, which is then bonded to a roughened or porous surface, either in the operating room, or in the body. Within the body, the surface may be that of existing or implanted bone, or that of a previously or recently positioned implant. When the shaped surface is positioned in contact with the roughened surface, for example an intramedullary rod having a porous metal surface, vibratory energy is passed to the shaped projection to cause the projection to melt and bond to the roughened surface.

The issue of implant removal after bonding or staking of one or more implants is one that needs to be addressed as the clinical situation dictates.

With regard to FIGS. 46, and 46A-46D, it can be seen that while the bondable material is liquified or softened by vibratory energy, removal of an adhered object is facilitated. This is particularly useful for well fixed implants, and particularly objects within the intramedullary canal.

Referring now to FIGS. 15-18, end effector 250 is shown, which uses vibratory energy as part of an implant removal tool 252. Implant removal tool 252 includes hollow end effector 252 and a T handle 254. The proximal end of end effector 250 has an internal thread 256 that matches the threading on the hand piece of a vibratory generator. The proximal end also has an external thread 258 that matches the threading on T handle 254. T handle 254 can also be provided with a pin or other projection that extends into end effector 250 for increasing stability. Although the proximal end is shown and described as having threads 256 and 258 to mate with the hand piece and T handle, respectively, any suitable mechanism for removably connecting the end effector to the hand piece and T handle can be used. Additionally, the mechanisms for connecting to the hand piece and T handle could be reversed with the external surface used for the hand piece and the internal surface used for the end effector.

The distal end of end effector 250 is provided with surface asperities 260 or otherwise roughened to help grip the implant or material to be removed. In use (FIG. 17), end effector 250 is connected to a vibratory hand piece and is placed over an implant 262 to be removed. Head 264 can be removed (using vibratory energy or by simply shearing off) from implant 262 to help ensure end effector 250 is centered over implant 262. The vibratory energy is activated to drive end effector 250 around implant 262 and into the rod 266 to which implant 262 is bonded. In studies conducted to date, an energy level of 80 to 100 Watts with no time limit is sufficient. Average insertion time is around 2-5 seconds. Upon cooling of the material of implant 262, the material of implant 262 adheres to end effector 250.

Leaving end effector 250 around implant 262, the hand piece is removed from end effector 250 and T handle 254 is connected. Repeated rocking or oscillating motion on T handle 254 is used to break the bond or weld such that when T handle 254 is pulled back, implant 262 is removed.

The present invention also contemplates the use of end effector 250 for removing screws and other implants from bone. End effector 250 could be disposable (single use) such that removal of the cored implant would not be necessary. Alternatively, end effector 250 could be reusable.

Fastening Dissimilar Materials

It should be understood that a proximal or distal polymer to polymer connection may be made through the application of energy, such as vibratory energy, as described herein. In this manner, fastener containing polymer may be connected to a roughened, porous or shaped surface, or to another polymeric fastener, or polymeric coating on an implant or implanted fastener. For example, an arthroplasty or prosthetic component may be at least partly covered with polymer, the polymeric surface exposed to an intended site for fastening. Moreover, a plurality of arthroplasty components may include polymeric or heat softenable material, the components being thus fastenable together in accordance with the invention.

An advantage to a polymeric containing, or polymeric coated fastener or implant is the ability to incorporate one or more therapeutic substances within the coating, whereupon the therapeutic substance may elute, or release the therapeutic substance in-vivo over time, in a predictable and useful manner. U.S. Provisional Patent Application No. 60/728,206, entitled "Drug Eluting Implant" and incorporated herein by reference, provides examples of means for delivering therapeutic agents, although those skilled in the art will appreciate that other known methods may be advantageously employed in combination with the invention.

Fastening Combinations and Applications

It is contemplated the surgical system of the present invention may be used with and integrated with the methods and devices disclosed in U.S. Provisional Application No. 60/765,857 entitled "Surgical Fastening Device" filed on Feb. 7, 2006. In the '857 document, various thermoplastic fastening devices are disclosed. The fastening devices may be, but are not limited to, degradable, biodegradable, bioerodible, bioabsorbable, mechanically expandable, hydrophilic, bendable, deformable, malleable, riveting, threaded, toggling, barded, bubbled, laminated, coated, blocking, pneumatic, one-piece, multi-component, solid, hollow, polygon-shaped, pointed, self-introducing, and combinations thereof. Also, the devices may include, but are not limited to, metallic material, polymeric material, ceramic material, composite material, body tissue, synthetic tissue, hydrophilic material, expandable material, compressible material, bondable material, and combinations thereof.

The methods and devices disclosed in the '857 document may be used in conjunction with any surgical procedure of the body. The fastening and repair of tissue or an implant may be performed in connection with surgery of a joint, bone, muscle, ligament, tendon, cartilage, capsule, organ, skin, nerve, vessel, or other body parts. For example, tissue may be repaired during intervertebral disc surgery, knee surgery, hip surgery, organ transplant surgery, bariatric surgery, spinal surgery, anterior cruciate ligament (ACL) surgery, tendon-ligament surgery, rotator cuff surgery, capsule repair surgery, fractured bone surgery, pelvic fracture surgery, avulsion fragment surgery, shoulder surgery, hernia repair surgery, and surgery of an intrasubstance ligament tear, annulus fibrosis, fascia lata, flexor tendons, etc.

It is contemplated that the devices and methods of the present invention be applied using minimally invasive incisions and techniques to fasten muscles, tendons, ligaments, bones, nerves, and blood vessels. A small incision(s) may be made adjacent the damaged tissue area to be repaired, and a tube, delivery catheter, sheath, cannula, or expandable cannula may be used to perform the methods of the present invention. U.S. Pat. No. 5,320,611 entitled "Expandable Cannula Having Longitudinal Wire and Method of Use" discloses cannulas for surgical and medical use expandable along their entire lengths. The cannulas are inserted through tissue when in an unexpanded condition and with a small diameter. The cannulas are then expanded radially outwardly to give a full-size instrument passage. Expansion of the cannulas occurs against the viscoelastic resistance of the surrounding tissue. The expandable cannulas do not require a full depth incision, or at most require only a needle-size entrance opening.

U.S. Pat. Nos. 5,674,240; 5,961,499; and 6,338,730 also disclose cannulas for surgical and medical use expandable along their lengths. The cannula can be provided with a pointed end portion and can include wires having cores which are enclosed by jackets. The jackets are integrally formed as one piece with a sheath of the cannula. The cannula may be expanded by inserting members or by fluid pressure. An expandable chamber may be provided at the distal end of the cannula. The above mentioned patents are hereby incorporated by reference.

In addition to using a cannula with the present invention, an introducer may be utilized to position implants at a specific location within the body. U.S. Pat. No. 5,948,002 entitled "Apparatus and Method for Use in Positioning a Suture Anchor" discloses devices for controlling the placement depth of a fastener. Also, U.S. patent application Ser. No. 10/102,413 discloses methods of securing body tissue with a robotic mechanism. The above-mentioned patent and application are hereby incorporated by reference. Another introducer or cannula which may be used with the present invention is the VersaStep® System by Tyco® Healthcare.

The present invention may also be utilized with minimally invasive surgery techniques disclosed in U.S. patent application Ser. No. 10/191,751 and U.S. Pat. Nos. 6,702,821 and 6,770,078. These patent documents disclose, inter alia, apparatus and methods for minimally invasive joint replacement. The femoral, tibial, and/or patellar components of a knee replacement may be fastened or locked to each other and to adjacent tissue using fastening devices disclosed herein and incorporated by reference. Furthermore, the methods and devices of the present invention may be utilized for repairing, reconstructing, augmenting, and securing tissue or implants during and "on the way out" of a knee replacement procedure. For example, the anterior cruciate ligament and other ligaments may be repaired or reconstructed; quadriceps mechanisms and other muscles may be repaired; a damaged rotator cuff may be mended. The patent documents mentioned above are hereby incorporated by reference.

Furthermore, it is contemplated that the present invention may be used with bariatric surgery, colorectal surgery, plastic surgery, gastroesophageal reflex disease (GERD) surgery, or for repairing hernias. A band, mesh, or cage of synthetic material or body tissue may be placed around an intestine or other tubular body member. The band may seal the intestine. This method may be performed over a balloon or bladder so that anastomosis is maintained. The inner diameter of the tubular body part is maintained by the balloon. The outer diameter of the body part is then closed or wrapped with a band, mesh, or patch. The inner diameter of the tubular body member may be narrowed or restricted by the band. The band may be secured to the tubular body part or surrounding tissue with the devices and methods described herein and incorporated by reference.

It is further contemplated that the present invention may be used in conjunction with the devices and methods disclosed in U.S. Pat. No. 5,329,846 entitled "Tissue Press and System" and U.S. Pat. No. 5,269,785 entitled "Apparatus and Method for Tissue Removal." For example, an implant secured within the body using the present invention may include tissue harvested, configured, and implanted as described in the patents. The above-mentioned patents are hereby incorporated by reference.

Additionally, it is contemplated that the devices and methods of the present invention may be used with bondable materials as disclosed in U.S. Pat. No. 5,593,425 entitled "Surgical Devices Assembled Using bondable materials." For example, the implants of the present invention may include bondable material. The material may be deformed to secure tissue or hold a suture or cable. The fasteners made of bondable material may be mechanically crimped, plastically crimped, or may be bonded to a suture or cable with RF (Bovie devices), laser, ultrasound, electromagnet, ultraviolet, infrared, electro-shockwave, or other known energy. The bonding may be performed in an aqueous, dry, or moist environment. The bonding device may be disposable, sterilizable, single-use, and/or battery-operated. The above-mentioned patent is hereby incorporated by reference.

Furthermore, the methods of the present invention may be performed under indirect visualization, such as endoscopic guidance, computer assisted navigation, magnetic resonance imaging, CT scan, ultrasound, fluoroscopy, X-ray, or other suitable visualization technique. The implants, fasteners, fastener assemblies, and sutures of the present invention may include a radiopaque material for enhancing indirect visualization. The use of these visualization means along with minimally invasive surgery techniques permits physicians to accurately and rapidly repair, reconstruct, augment, and secure tissue or an implant within the body. U.S. Pat. Nos. 5,329,924; 5,349,956; and 5,542,423 disclose apparatus and methods for use in medical imaging. Also, the present invention may be performed using robotics, such as haptic arms or similar apparatus. The above-mentioned patents are hereby incorporated by reference.

Moreover, the devices and methods of the present invention may be used for the repair and reconstruction of a tubular pathway like a blood vessel, intestine, urinary tract, esophagus, or other similar body parts. For example, a blood vessel may be intentionally severed during a surgical operation, or the blood vessel may be damaged or torn as a result of an injury. Flexible fastening of the vessel would permit the vessel to function properly and also compress and stabilize the vessel for enhanced healing. To facilitate the repair or reconstruction of a body lumen, a balloon may be inserted into the lumen and expanded so the damaged, severed, or torn portion of the vessel is positioned against the outer surface of the inflated balloon. In this configuration, the implants and methods described and incorporated herein may be used to approximate the damaged portion of the vessel.

It should further be understood that vibratory energy, and particularly ultrasonic energy, may be created within the body, through a barrier such as skin or other body tissue. This is described more particularly in pending U.S. application Ser. No. 10/945,331 (Publication 2006/0064082), of common inventor P. Bonutti, the contents of which are hereby incorporated herein by reference.

Focal Defect Correction

Figure 96B:
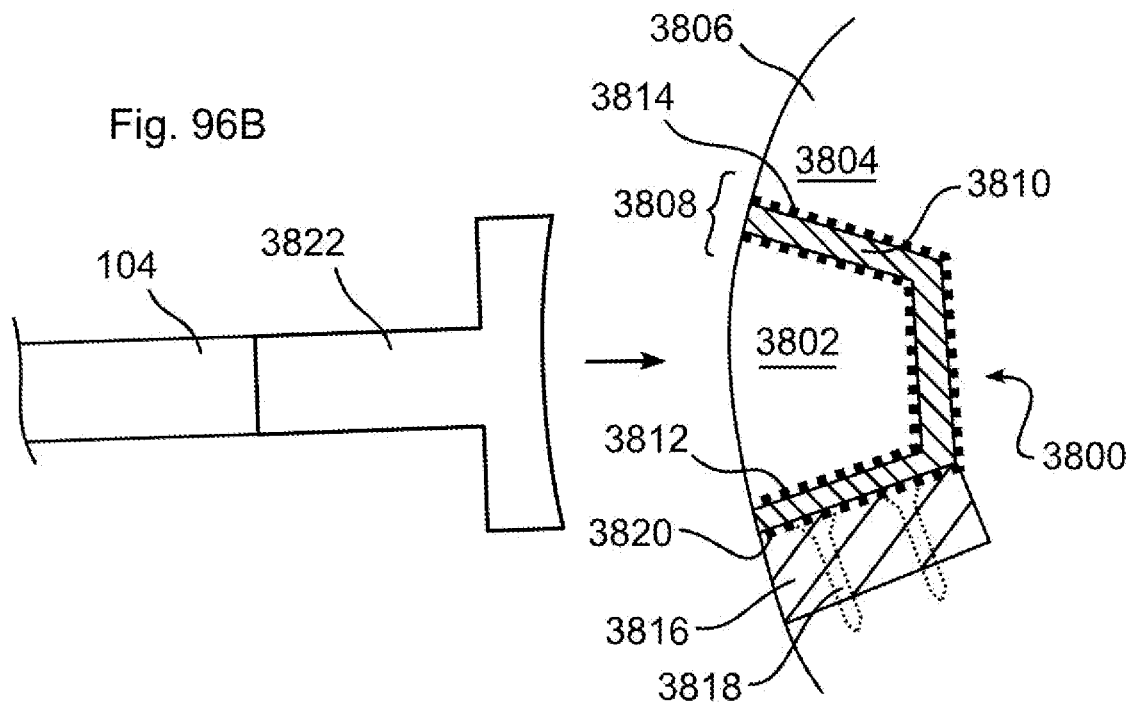
FIG. 96B illustrates a focal defect repaired in accordance with the invention using bondable material melted or softened by vibratory energy provided by a conforming horn in accordance with the invention.

With reference to FIGS. 96-96B, in accordance with the invention, areas of disease or trauma representing a focused or focal defect 3800 are replaced with an implant or graft 3802, secured in situ using vibratory energy. In this manner, healthy tissue 3804 may remain undisturbed, and defect 3800 is corrected. Examples include replacing a portion of an articulating surface, such as a condyle 3806, acetabulum, or glenoid fossa, or replacing portions of bone or soft tissue that have been damaged by injury or disease.

The diseased area is replaced by, for example, implanted tissue, including bone fragments or compressed living tissue, fabricated non-living material such as polymers or metal, or any other material a medical practitioner deems best. An interface 3808 is created between graft 3802 and body tissue 3804, and includes a quantity of bondable material 3810 therebetween. Advantageously, if the implant is not made entirely from bondable material, a surface 3812 of the implant contacting the bondable material of the interface is provided with a roughened or porous surface, or a surface with one or more cavities into or onto which heat softened or melted material may flow and thereby lock onto once cooled, hereafter an irregular surface. Similarly, the body tissue 3804 may be treated to have an irregular surface 3814 for purpose of improving a bond between body tissue 3804 and bondable material 3810. In addition, an implant 3816 may be attached to body tissue 3804 using methods or devices of the invention, or alternatively screws 3818, adhesives, or any other known means, and the implant may be provided with an irregular surface 3820 for the purpose of improving a bond between implant 3816 and bondable material 3810.

Thus, once graft 3802 is in place, interface 3808 defines a strata that includes body tissue 3804 having an irregular surface 3814, or an implant 3816 attached to body tissue 3804, implant 3816 having an irregular surface 3820, bondable material 3810, and graft 3802 having an irregular surface 3812, unless the implant is provided with bondable material at interface 3808. If a bond of satisfactory strength may be made without irregular surface at 3812, 3814 or 3820, the irregular surface need not be formed or provided.

Vibratory energy is applied proximate the interface by an end effector 104, and horn 3822, operative to cause bondable material 3810 within interface 3808 and within graft 3802, if present, to soften or melt, thereby locking onto the irregular surface of both body tissue 3804 or intervening implant 3816, if present, and graft 3802, whereby graft 3802 is firmly attached to the body once bondable material 3810 has cooled. Horn 3822 is advantageously provided with a shape which improves transfer of vibratory energy either directly to interface 3808, or to graft 3802, which may be caused to vibrate to heat interface 3808.

bondable material 3810 may be provided in the form of a wedge 3810A, which may be driven into a gap between graft 3802 and body tissue 3804, whereby a tight and secure connection is formed, operative to maintain graft 3802 in a desired position during bonding, and to improve the transfer of vibratory energy throughout interface 3808.

Chain of Fastening

The invention specifically contemplates a chain of fastening from bone to implant to tissue. For example, bone cement is fastened to bone, an implant is fastened to the bone cement as described herein, tissue is staked or fastened to the implant, and the end of the implant is capped or secured as described herein and in the incorporated references. Fasteners may alternatively be bonded to bone using methods described and illustrated herein and described in the incorporated references, and implants or tissue are fastened to the fastener bonded to bone, using the methods and devices of the invention.

Figure 91:
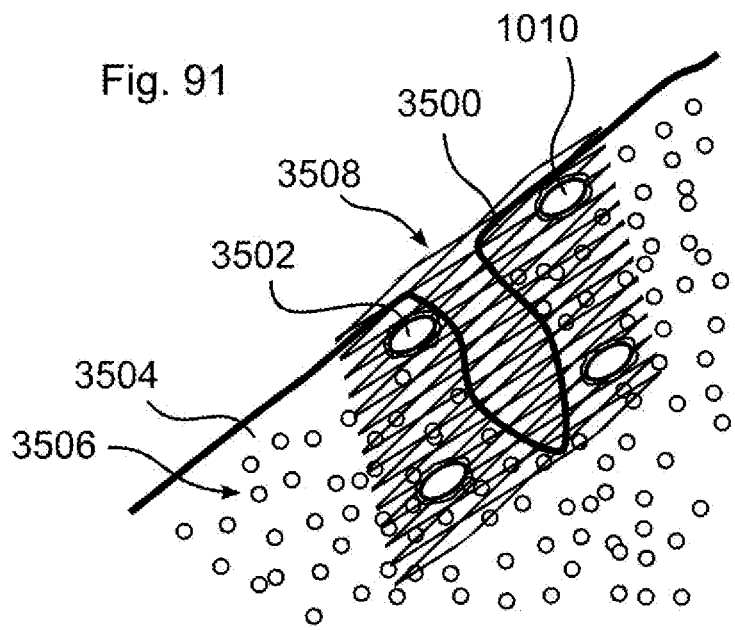
FIG. 91 illustrates a mesh in accordance with the invention, fastened within the body using fasteners of the invention, the mesh operative, for example, to promote tissue ingrowth.

Examples of chains of fastening have been provided elsewhere herein, and FIG. 91 illustrates a further example. Specifically, a mesh 3400 is fastened within the body by one or more fasteners 3502 in accordance with the invention. In the example of FIG. 91, fastener 3502 is selected from fasteners of the invention which enable the formation of cap 1010. Further, an embedded fastener 800 (not shown) may be used to secure fastener 3502 within body tissue 3504. In the example illustrated, mesh 3502 is operative to promote the growth of cells, shown symbolically as circles 3506, and may also be used to close, bridge or secure a fissure or tissue gap 3508 from further expansion, until tissue growth closes tissue gap 3508. Mesh 3500 may incorporate therapeutic substances as described elsewhere herein, in any of the manners described elsewhere herein. For example, mesh 3500 may be coated with a bondable material incorporating a tissue ingrowth agent. The aperture size of mesh 3500 may be selected to promote the type of tissue ingrowth desired; for example, bone ingrowth is favored by an aperture size of 100-400 microns, whereas soft tissue growth is favored by an aperture size of 50-150 microns.

Mesh 3500 is advantageously coated with, or fabricated from, a bondable material. As such, as caps 1010 are formed as described elsewhere herein, caps and associated fasteners 3502 are additionally fastened to bondable material of mesh 3500 by vibratory fastening in accordance with the invention. Accordingly, mesh 3500 is secured to body tissue 3504 with greater strength and reliability.

The invention further contemplates connecting implants together using vibratory energy. Examples have been given elsewhere herein, and additional examples are provided in FIGS. 92-93A. Specifically, with reference to FIG. 92, a first stent 3500 is disposed within a tubular body vessel 3502, for example a blood vessel, within a patient, and a second stent 3504 is positioned within a branching blood vessel 3506. A connecting fastener 3508 in accordance with the invention is positioned between stent 3500 and stent 3504, and is connected to both stents 3500, 3504, at regions 3510, 3512, respectively. Connecting fastener 3508 includes a bondable material at least upon its surface, and may be fabricated entirely of a bondable material.

When connecting fastener 3508 is positioned in overlapping contact with stent 3500, vibratory energy may be applied along a portion or the entire overlapping region of connecting fastener 3506, in order to cause bondable material of connecting fastener to soften and form around material of stent 3500 and 3504, wherein upon cooling, connecting fastener is firmly attached to stent 3500 and 3504.

In accordance with the invention, vibratory energy may be provided inside blood vessel 3502 or 3506, or other confined space, by an end effector 104 disposed at the end of a catheter or laparoscopic shaft 3514. Vibratory energy is generated at piezo stack 3516, supplied with a suitable signal through wires (not shown) extending within shaft 3516. Visualization may be carried out using fluoroscopy or other known method. Alternatively, connecting fastener 3508 is fabricated with metal, and is caused to vibrate to produce heat using a source of ultrasonic vibration produced outside the body and directed at connecting fastener 3508, to cause the latter to vibrate resonantly, as described for example in copending U.S. patent application Ser. No. 10/945,331, the contents of which are incorporated herein by reference.

Stent 3500 and or 3504 (hereafter referred to as stent 3500) may be fabricated partially or entirely with bondable material. In this manner, vibratory energy applied at a region of overlap between stent 3500 and connecting fastener 3508 may operate to cause melting of bondable material of connecting fastener 3508 and stent 3500, whereby bonding is potentially improved by integration of bondable material of both connecting fastener 3508 and stent 3500. Alternatively, or in addition to connecting fastener 3508 containing metal, stent 3500 may be fabricated with metal and caused to vibrate and produce heat sufficient for softening bondable material of stent 3500, or bonding with bondable material of connecting fastener 3508.

Additionally, vibratory energy may be applied to stent 3500 to soften same, facilitating expansion. Stent 3500 is generally transferred to an implantation site in an unexpanded state, typically surrounding a balloon catheter, as known in the art. An unexpanded stent is illustrated, for example, in FIG. 93. A heated stent 3500 may be easier to expand, particularly if coated with bondable material, and more particularly if there are multiple layers of material, possibly including therapeutic substances.

It should be understood that stent 3500 and connecting fastener may be formed of biodegradable material. It should further be understood that other expandable devices, or alternatively filtration devices, or any other such device adapted to reside within a space in the body may be adapted as described for stent 3500, and may be bonded within the body, operating room, or other setting, in accordance with the invention.

Referring now to FIG. 93-93A, stent 3500 and 3500B are bonded together within tubular body tissue 3502A at connection area 3520, shown at a possibly enlarged size for clarity, comprising bondable material of either stent 3500 or 3500B or both, melted by vibratory energy applied as described above. In this embodiment, there is no requirement for a separate connector, such as connecting fastener 3508.

With further reference to FIGS. 93-93A, a collapsed or non-expanded stent 3500A is positioned within the body using known means, positioned to be overlapped by another stent 3500 along a portion of its length. Stent 3500A is then expanded, possibly softened using vibratory energy as described above, whereby portions of stent 3500A contact portions of stent 3500B. Bonding may then take place, representatively illustrated at 3522. In addition to extending a length of body tissue supported by a stent, this embodiment enables a second stent 3500A to be securely fixed with respect to a first stent 3500. Moreover, if tissue ingrowth has occurred within the first stent 3500, second stent 3500A may then be used to increase an occluded diameter of first stent 3500 by being expanded within first stent 3500.

An alternative approach is further illustrated in FIGS. 93-93A, wherein stent 3500C is bonded to a side surface of stent 3500B, the bonding illustrated at 3524, gaining access through tubular body tissue 3502B. Stent 3500C may abut stent 3500B, or alternatively, stent 3500 B may be provided with an aperture into which stent 3500C is sized to fit. In either event, bonding is accomplished as described above.

With reference to FIG. 94, two tubular body tissue members 3604, 3608 are joined in a surgical anastomosis procedure of the invention. A supporting frame 3610 is provided to maintain segments 3604, 3608 in an open, flowing configuration, should tubular body tissue 3604, 3608 require additional support. Other methods of supporting tissue during anastomosis are disclosed in U.S. Pat. No. 5,254,113 to Wilk, the contents of which are incorporated herein by reference. One or more bands 3600 is positioned to encircle one or more segments 3604, 3608, overlapping supporting frame 3610. Band 3600 comprises bondable material along at least one end portion 3602 of an exterior surface. Where bondable material is provided on only one end portion, a joining portion 3602A is advantageously provided with a roughened or porous surface, or a surface having one or more cavities therein. Accordingly, vibratory energy may be applied to one or more end portions 3602, 3602A, to cause bondable material thereof to soften or melt in accordance with the invention. If both ends 3602, 3602A contain bondable material, the respective material will become bonded at 3616, and upon cooling, band 3600 will be secured in place. If one end of 3602 or 3602A contains bondable material, bonding takes place between the ends by mechanical interlock, improved by the roughened surface of the other end. Band 3600 advantageously comprises material which shrinks when warmed, whereby heat imparted by application of vibratory energy causes ends 3602, 3602A to not only bond together, but causes band 3600 to shrink in order to improve a seal between band 3600, body tissue 3604, 3608, and supporting frame 3610.

With reference to FIG. 95, a band 3612 is provided, sufficiently wide to overlap at least a portion of both body tissue 3604 and 3608. Band 3612 is fastened, and optionally heat shrunk, as described for bands 3600. If supporting frame 3610 is required to maintain body tissue 3604, 3608 open and flowing, it is provided as described with respect to FIG. 94.

In a further embodiment of the invention, vibratory energy is applied to at least a portion 3614 of band 3612 which is in overlapping contact with supporting frame 3610. In this manner, if contacting surfaces of supporting frame 3614 and band 3612 contain bondable material, they may become bonded, rendering the union of body tissue 3604 and 3608 more durable, and potentially improving a seal between band 3612, body tissue 3604, 3608, and supporting frame 3614.

Figure 92:
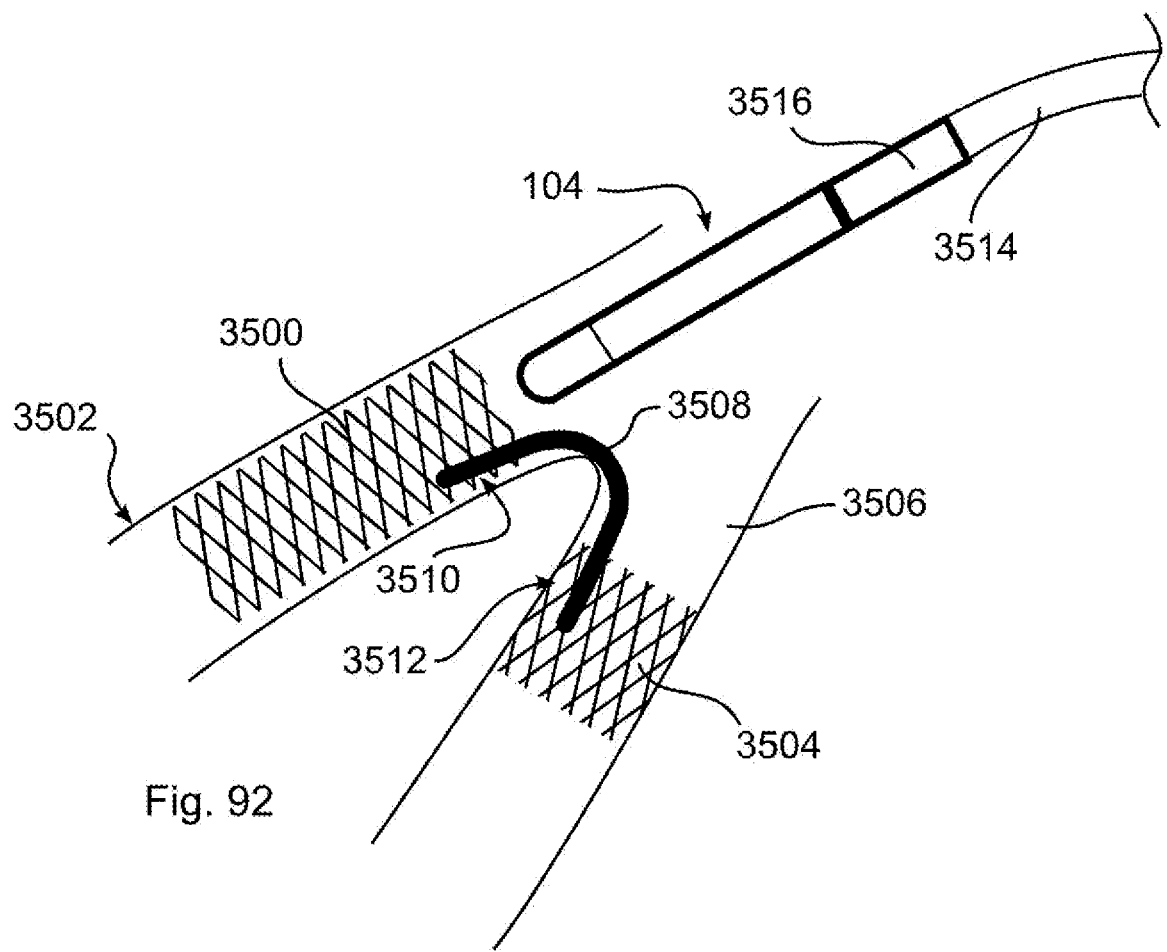
FIG. 92 illustrates vibratory fastening within a tubular structure within the body, vibratory fastening of at least one stent, and further illustrating an end effector disposed upon the end of a catheter or laparoscopic instrument.

It should be understood that while various methods of bonding are illustrated together in FIGS. 92-94, and throughout the specification, any or all methods may be combined as deemed best by the medical practitioner.

Figure 78:
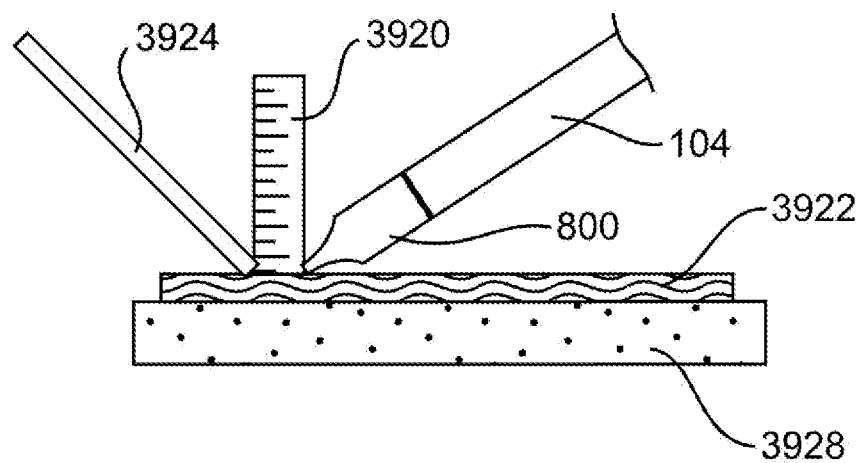
FIG. 78 illustrates a shaped end effector applying vibratory energy to a therapeutic component, with the introduction of bondable material.
Figure 79:
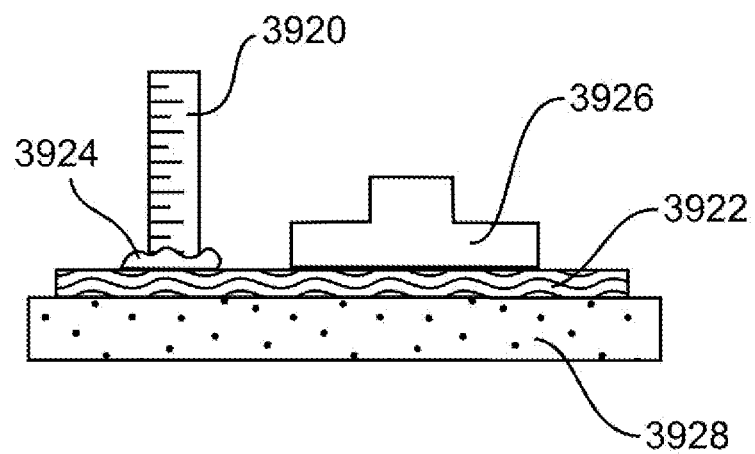
FIG. 79 illustrates the bondable material of FIG. 78 applied to the union of two therapeutic components to secure their relative positions.
Figure 80:
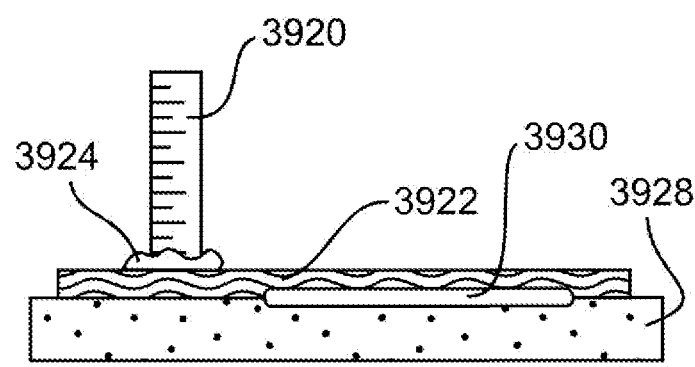
FIG. 80 illustrates two layers secured in relative apposition through the application of vibratory energy in accordance with the invention.

Referring now to FIGS. 78-80, methods of the invention may be combined to construct prostheses or other implants. In FIG. 78, end effector 104 and horn 800 of FIG. 32A apply vibratory energy to a threaded post 3920 projecting from an upper base layer 3922. A supply of bondable material 3924 is introduced proximate a point of heating caused by the application of vibratory energy, whereupon bondable material 3924 is caused to melt and bond to post 3920 and upper layer 3922, operative to secure post 3920 and layer 3922 relative to each other, as may be seen in FIG. 79.

With further reference to FIG. 79, a horn 3926, connected to an end effector (not shown), is applied to upper layer 3922. Lower layer 3928 contains bondable material, or alternatively, bondable material is placed between layers 3922 and 3928. Upon application of vibratory energy through horn 3926, layers 3922 and 3928 are caused to vibrate relative to each other along at least an area underlying horn 3926, causing bondable material 3930 of layer 3928 to soften or melt and bond to the underside of layer 3922, as may be seen in FIG. 80. A variety of permutations are possible for binding layers 3922 and 3928, including providing bondable material attached to the underside of layer 3922, and providing a separate layer of bondable material between layers 3922 and 3928.

FIGS. 78-80 thus illustrate several of the many ways in which methods and devices of the invention may be used to construct a wide variety of structures useful for therapeutic purposes.

It is contemplated that the devices and methods of the present invention be applied using minimally invasive incisions and techniques to fasten, for example, muscles, tendons, ligaments, bones, nerves, and blood vessels. A small incision(s) may be made adjacent the damaged tissue area to be repaired, and a tube, delivery catheter, sheath, cannula, or expandable cannula may be used to perform the methods of the present invention. In addition to using a cannula with the present invention, an introducer may be utilized to position implants at a specific location within the body.

The methods of the present invention may further be performed under indirect visualization, such as endoscopic guidance, computer assisted navigation, magnetic resonance imaging, CT scan, ultrasound, fluoroscopy, X-ray, or other suitable visualization technique. The implants, fasteners, fastener assemblies, and sutures of the present invention may include a radiopaque material for enhancing indirect visualization. The use of these visualization means along with minimally invasive surgery techniques permits physicians to accurately and rapidly repair, reconstruct, augment, and secure tissue or an implant within the body.

All references cited herein are expressly incorporated by reference in their entirety. In addition, unless mention was made above to the contrary, it should be noted that all of the accompanying drawings are not to scale.

There are many different features to the present invention and it is contemplated that these features may be used together or separately. Thus, the invention should not be limited to any particular combination of features or to a particular application of the invention. Further, it should be understood that variations and modifications within the spirit and scope of the invention might occur to those skilled in the art to which the invention pertains. Accordingly, all expedient modifications readily attainable by one versed in the art from the disclosure set forth herein that are within the scope and spirit of the present invention are to be included as further embodiments of the present invention.

What is claimed is:

1. A method comprising:
    embedding an anchor into a bone in a body, the anchor defining a blind bore that is unthreaded and terminates at a bottom surface, wherein the anchor has a leading end, a trailing end, a length extending between the leading and trailing ends, a tapered leading portion an entirety of which tapers to the leading end, and a constant outer cross-sectional size and shape extending from the tapered leading end portion to the trailing end;
    providing a fastener configured to transmit vibratory energy to the anchor, the fastener having a fully unthreaded external surface, and a shaft, wherein the shaft terminating at a leading tip;
    inserting the leading tip of the shaft of the fastener into the blind bore of the anchor embedded in the bone in the body; and
    applying vibratory energy through the fastener to the anchor to join the leading tip of the shaft of the fastener to the bottom surface of the blind bore in the anchor, wherein the anchor is configured to retain the fastener within the anchor.

2. The method of claim 1, wherein at least one of the fastener and the anchor includes a bondable material.

3. The method of claim 1, wherein at least one of a portion of the fastener and a portion of the anchor is configured to be softened by heat produced by relative vibration between the fastener and the anchor during the application of vibratory energy.

4. The method of claim 1, wherein the anchor includes at least one of a rough, porous, and irregular surface.

5. The method of claim 1, further comprising providing an end effector configured to connect to and apply the vibratory energy to the fastener.

6. The method of claim 4, further comprising positioning the end effector with a robotic mechanism.

7. The method of claim 1, wherein the fastener includes a polymeric material and the anchor includes a metallic material.

8. The method of claim 1, wherein the anchor includes at least one cavity into which softened material of the fastener may flow during the application of vibratory energy.

9. The method of claim 7, wherein the fastener is configured to mechanically interlock with the anchor when a portion of the fastener is softened during the application of vibratory energy.

10. The method of claim 1, further comprising controlling an amount of pressure applied to the fastener with at least one of a sensor, spring, and piezoelectric device.

11. A method comprising:
    securing an anchor, wherein the anchor has a leading end, a trailing end, a length extending between the leading and trailing ends, a tapered leading portion an entirety of which tapers to the leading end, and a constant outer cross-sectional size and shape extending from the tapered leading end portion to the trailing end;
    providing a fastener having a fully unthreaded external surface configured to transmit vibratory energy, the fastener comprised of a shaft terminating in a leading end tip;
    contacting the leading end tip of the shaft of the fastener against the anchor; and
    applying vibratory energy to the fastener to join the leading end tip of the shaft of the fastener directly to the outer surface of the anchor.

12. The method of claim 11, wherein at least one of the fastener and the anchor includes a bondable material.

13. The method of claim 11, further comprising connecting the fastener to an end effector and applying the vibratory energy to the fastener with the end effector.

14. The method of claim 11, further comprising securing the anchor in a bone in a body.

15. The method of claim 13, further comprising positioning the end effector with a robotic mechanism.

16. The method of claim 11, wherein the fastener includes a polymeric material and the anchor includes a metallic material.

17. The method of claim 11, wherein at least a portion of the anchor includes at least one cavity into which softened material of the fastener may flow during the application of vibratory energy.

18. The method of claim 16, wherein the fastener is configured to mechanically interlock with the anchor when the fastener is softened during the application of vibratory energy.

19. The method of claim 11, further comprising controlling an amount of pressure applied to the fastener with at least one of a sensor, spring, and piezoelectric device.

20. A method comprising:

providing an anchoring component having an unthreaded bore terminating at a bottom surface, wherein the bottom surface is comprised at least in part of a bondable material;

providing a fastening component having a leading tip, wherein at least the leading tip of the fastening component is comprised at least in part of the same bondable material;

providing an end effector connected to a device configured to produce vibratory energy, connecting the fastening component to the end effector;

positioning the end effector with a robotic mechanism; and applying vibratory energy to the fastening component with the end effector, thereby causing at least the leading tip of the fastening component to join to the bottom surface of the anchoring component, wherein the anchoring component is configured to retain the fastening component within the anchoring component.

21. The method of claim 20, further comprising controlling an amount of pressure applied to the fastening component with at least one of a sensor, spring, and piezoelectric device.

* * * * *

UNITED STATES PATENT AND TRADEMARK OFFICE
CERTIFICATE OF CORRECTION

| | |
|---|---|
| PATENT NO. | : 11,129,645 B2 |
| APPLICATION NO. | : 13/953652 |
| DATED | : September 28, 2021 |
| INVENTOR(S) | : Peter M. Bonutti et al. |

It is certified that error appears in the above-identified patent and that said Letters Patent is hereby corrected as shown below:

In the Claims

Column 95 Lines 55- Column 98 Line 17:
Claims 1-21 should be replaced with the following Claims 1-21:
1. A method comprising:
    providing an anchoring component;
    providing a fastening component having a leading contacting feature;
    providing an end effector operatively connected to a device configured to produce vibratory energy;
    contacting the fastening component with the end effector;
    engaging the leading contacting feature of the fastening component against the anchoring component;
    monitoring an amount of pressure applied to the fastening component from the end effector with a pressure sensor; and
    applying vibratory energy to the fastening component with the end effector to join the leading contacting feature of the fastening component to the anchoring component.
2. The method of claim 1, wherein at least one of the contacting feature of the fastening component and the anchoring component includes a bondable material configured to be softened by heat produced by relative vibration between the fastening component and the anchoring component during the application of vibratory energy.
3. The method of claim 1, further comprising controlling the vibratory energy produced by the device and applied by the end effector to the fastening component by monitoring and changing weld parameters.
4. The method of claim 1, further comprising physically attaching the fastening component to the end effector.
5. The method of claim 3, wherein the weld parameters include at least one of pressure applied to the fastener by the end effector, displacement of the end effector, phase angle differential, output voltage, drive voltage, current, total energy, total power, time, and collapse of the contacting feature of the fastening component.

Signed and Sealed this
Thirtieth Day of August, 2022

Katherine Kelly Vidal
*Director of the United States Patent and Trademark Office*

6. The method of claim 1, wherein the anchoring component includes at least one of a cavity and a bonding region comprising at least one of a rough, porous, and irregular surface into which softened material of the contacting feature of the fastening component may flow and be retained to secure the fastening component to the anchoring component during and after the application of vibratory energy.

7. The method of claim 1, further comprising positioning the end effector with a robotic mechanism.

8. The method of claim 1, wherein the contacting feature of the fastening component includes a polymeric material configured to be softened during the application of vibratory energy and the anchoring component includes a metallic material.

9. The method of claim 1, wherein the fastening component is multiple fastening components each having a leading contacting feature configured to be engaged against the anchoring component with the end effector, wherein the end effector is configured to contact and join the multiple fastening components.

10. The method of claim 1, wherein the anchoring component has a bore terminating at a bottom surface, wherein the leading end contacting feature of the fastening component is positioned into the bore, and wherein the leading end contacting feature of the fastening component is retained in the bore during and after the application of vibratory energy.

11. A method comprising:
   providing an anchor;
   providing a fastener having a leading contacting feature;
   providing an end effector operatively connected to a device configured to produce vibratory energy;
   contacting the fastener with the end effector;
   contacting the leading contacting feature of the fastener against the anchor;
   applying vibratory energy and pressure to the fastener from the end effector to join the leading contacting feature of the fastener directly to the anchor; and
   monitoring and controlling the amount of collapse of the contacting feature of the fastener during the application of vibratory and pressure.

12. The method of claim 11, wherein at least one of the contacting feature of the fastener and the anchor includes a bondable material configured to be softened by heat produced by relative vibration between the fastening component and the anchoring component during the application of vibratory energy.

13. The method of claim 11, further comprising physically attaching the fastener to the end effector.

14. The method of claim 11, further comprising controlling the vibratory energy produced by the device and applied by the end effector to the fastening component by monitoring and changing weld parameters, wherein the weld parameters include at least one of pressure applied to the fastener by the end effector, displacement of the end effector, phase angle differential, output voltage, drive voltage, current, total energy, total power, time, and collapse of the contacting feature of the fastening component.

15. The method of claim 11, wherein the anchor includes at least one cavity and a bonding region comprising at least one of a rough, porous, and irregular surface into which softened material of the contacting feature of the fastener may flow and be retained to secure the fastening component to the anchoring component during and after the application of vibratory energy.

16. The method of claim 11, further comprising positioning the end effector with a robotic mechanism.

17. The method of claim 11, wherein the contacting feature of the fastener includes a polymeric material configured to be softened during the application of vibratory energy and the anchor includes a metallic material.

18. The method of claim 11, wherein the fastener is multiple fasteners each having a leading contacting feature configured to be engaged against the anchor with the end effector, wherein the end effector is configured to contact and join the multiple fasteners.

19. The method of claim 11, wherein the monitoring and controlling the amount of collapse of the contacting feature of the fastener is performed by measuring with at least one of a micro-switch and a linear variable displacement transducer (LVDT).

20. A method comprising:

providing an anchoring component having an unthreaded bore terminating at a bottom surface, wherein the bottom surface is comprised at least in part of a bondable material;

providing a fastening component having a leading tip, wherein at least the leading tip of the fastening component is comprised at least in part of the same bondable material;

providing an end effector connected to a device configured to produce vibratory energy;

connecting the fastening component to the end effector;

positioning the end effector with a robotic mechanism; and applying vibratory energy to the fastening component with the end effector, thereby causing at least the leading tip of the fastening component to join to the bottom surface of the anchoring component, wherein the anchoring component is configured to retain the fastening component within the anchoring component.

21. The method of claim 20, further comprising controlling an amount of pressure applied to the fastening component with at least one of a sensor, spring, and piezoelectric device.